US010280207B2

(12) United States Patent
Kim et al.

(10) Patent No.: US 10,280,207 B2
(45) Date of Patent: May 7, 2019

(54) FCRN-SPECIFIC HUMAN ANTIBODY AND COMPOSITION FOR TREATMENT OF AUTOIMMUNE DISEASES

(71) Applicant: Hanall Biopharma Co., Ltd., Daejeon (KR)

(72) Inventors: Sung Wuk Kim, Gyeonggi-do (KR); Seung Kook Park, Seoul (KR); Jae Kap Jeong, Gyeonggi-do (KR); Min Sun Kim, Gyeonggi-do (KR); Eun Sun Kim, Gyeonggi-do (KR); Jeong Haing Heo, Gyeonggi-do (KR); Yeon Jung Song, Gyeonggi-do (KR); Hae-Young Yong, Gyeonggi-do (KR); Dongok Shin, Gyeonggi-do (KR)

(73) Assignee: HANALL BIOPHARMA CO., LTD., Daejeon (KR)

( * ) Notice: Subject to any disclaimer, the term of this patent is extended or adjusted under 35 U.S.C. 154(b) by 378 days.

(21) Appl. No.: 14/899,554

(22) PCT Filed: Jun. 20, 2014

(86) PCT No.: PCT/KR2014/005495
§ 371 (c)(1),
(2) Date: Dec. 17, 2015

(87) PCT Pub. No.: WO2014/204280
PCT Pub. Date: Dec. 24, 2014

(65) Prior Publication Data
US 2016/0137713 A1     May 19, 2016

(30) Foreign Application Priority Data

Jun. 20, 2013   (KR) .................. 10-2013-0071185

(51) Int. Cl.
*C07K 16/00* (2006.01)
*C12P 21/08* (2006.01)
*A61K 39/395* (2006.01)
*A61K 39/40* (2006.01)
*A61K 49/00* (2006.01)
*C07K 16/28* (2006.01)
*G01N 33/566* (2006.01)
*C07K 14/705* (2006.01)

(52) U.S. Cl.
CPC ........ *C07K 14/705* (2013.01); *A61K 49/0004* (2013.01); *C07K 16/283* (2013.01); *G01N 33/566* (2013.01); *C07K 2317/21* (2013.01); *C07K 2317/33* (2013.01); *C07K 2317/565* (2013.01); *C07K 2317/622* (2013.01); *C07K 2317/76* (2013.01); *C07K 2317/92* (2013.01); *G01N 2333/70535* (2013.01)

(58) Field of Classification Search
None
See application file for complete search history.

(56) References Cited

U.S. PATENT DOCUMENTS

| 5,977,322 | A | 11/1999 | Marks et al. |
| 5,994,511 | A | 11/1999 | Lowman et al. |
| 6,172,197 | B1 | 1/2001 | McCafferty et al. |
| 6,218,149 | B1 | 4/2001 | Morrison et al. |
| 7,063,943 | B1 | 6/2006 | McCafferty et al. |
| 9,657,102 | B2 * | 5/2017 | Smith ............... C07K 16/2809 |
| 2002/0138863 | A1 | 11/2002 | Roopenian |
| 2007/0092507 | A1 | 4/2007 | Balthasar et al. |

FOREIGN PATENT DOCUMENTS

| WO | 0243658 A2 | 6/2002 | |
| WO | WO-2006120230 A2 * | 11/2006 | ......... C07K 16/1081 |

OTHER PUBLICATIONS

Janeway et al., Immunology Third Edition, Garland Publishing Inc. 1997, Chapter 3, Structure of the Antibody Molecule and Immunoglobulin Genes, pp. 3:1-3:31 (Year: 1997).*
Rudikoff et al., PNAS. 1982 vol. 79 p. 1979-83 (Year: 1982).*
Casset et al. (BBRC(2003) 307, 198-205. (Year: 2003).*
Arnson, Y., et al., "Intravenous immunoglobulin therapy for autoimmune diseases", Autoimmunity, Sep. 9, 2009, pp. 553-560, vol. 42, No. 6.
Burmeister, W., et al., "Crystal structure at 2.2 Å resolution of the MHC-related neonatal Fc receptor", Nature, Nov. 24, 1994, pp. 336-343, vol. 372.
Burmeister, W., et al., "Crystal structure of the complex of rat neonatal Fc receptor with Fc", Nature, Nov. 24, 1994, pp. 379-383, vol. 372.
Christianson, G., et al., "Monoclonal antibodies directed against human FcRn and their applications", mAbs, Mar. 1, 2012, pp. 208-216, vol. 4, No. 2.
Li, N., et al., "Complete FcRn dependence for intravenous Ig therapy in autoimmune skin blistering disease", The Journal of Clinical Investigation, Dec. 2005, pp. 3440-3450, vol. 115, No. 12.
Praetor, A., et al., "β2-microglobulin is important for cell surface expression and pH-dependent IgG binding of human FcRn", Journal of Cell Science, Jun. 1, 2002, pp. 2389-2397, vol. 115.

(Continued)

*Primary Examiner* — Chun W Dahle
(74) *Attorney, Agent, or Firm* — Hultquist, PLLC; Steven J. Hultquist

(57) ABSTRACT

The present invention relates to a human antibody specific for FcRn that is a receptor with a high affinity for IgG, a production method thereof, a composition for treating autoimmune disease, which comprises the antibody, and a method of treating and diagnosing autoimmune disease using the same. The FcRn-specific antibody according to the present invention can bind to FcRn non-competitively with IgG or the like to reduce serum auto-antibody levels, and thus can be used for the treatment of autoimmune diseases.

5 Claims, 6 Drawing Sheets

Specification includes a Sequence Listing.

(56) References Cited

OTHER PUBLICATIONS

Rath, T., et al., "The Immunologic Functions of the Neonatal Fc Receptor for IgG", Journal of Clinical Immunology: Author Manuscript, Sep. 5, 2012, Page(s) (Supplement 1, pp. S9-S17), vol. 33.
Roopenian, D., et al., "The MHC Class I-Like IgG Receptor Controls Perinatal IgG Transport, IgG Homeostasis, and Fate of IgG-Fc-Coupled Drugs", The Journal of Immunology, Apr. 1, 2003, pp. 3528-3533, vol. 170.
Schwab, I., et al., "Intravenous immunoglobulin therapy: how does IgC modulate the immune system?", Nature Reviews: Immunology, Feb. 15, 2013, pp. 176-189, vol. 13.

\* cited by examiner

| HL161 Hit Ab | 250nM | 500nM | 1000nM |
|---|---|---|---|
| hIgG1 | 87.4% | 69.9% | 69.1% |
| 1A | 40.0% | 34.4% | 41.5% |
| 2A | 77.1% | 64.1% | 63.3% |
| 2D | 101.2% | 87.4% | 82.4% |
| 6C | 88.2% | 84.7% | 81.1% |
| 9F | 88.6% | 92.5% | 83.2% |
| 10E | 101.4% | 76.8% | 81.0% |
| 11G | 58.4% | 44.7% | 50.8% |
| 11H | 75.4% | 60.4% | 51.8% |

SEQUENCE LISTING

<160> NUMBER OF SEQ ID NOS: 435

<210> SEQ ID NO 1
<211> LENGTH: 345
<212> TYPE: DNA
<213> ORGANISM: Artificial Sequence
<220> FEATURE:
<223> OTHER INFORMATION: HL161-1A heavy

<400> SEQUENCE: 1

```
caggtgcagc tggtgcagtc tgggggaggc ttggtacagc ctggcaggtc cctgagactc      60
tcctgtgcag cctctggttt cagttttggt gaatatggca tgcactgggt ccggcaagct     120
ccagggaagg gcctggagtg ggtctcaggt gttagttgga acagtggtag cattgcctat     180
gcggactctg tgaggggccg attcaccatc tccagagaca acagcaaaaa ctccctgtat     240
ctgcaaatga acagtctgag agccgaggac acggccgtgt attactgtgc gagaggtaga     300
agtatggacg tctggggcca agggaccacg gtcaccgtct cctca                     345
```

<210> SEQ ID NO 2
<211> LENGTH: 115
<212> TYPE: PRT
<213> ORGANISM: Artificial Sequence
<220> FEATURE:
<223> OTHER INFORMATION: HL161-1A heavy

<400> SEQUENCE: 2

```
Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Ser Phe Gly Glu Tyr
            20                  25                  30

Gly Met His Trp Val Arg Gln Ala Pro Gly Lys Gly Leu Glu Trp Val
        35                  40                  45

Ser Gly Val Ser Trp Asn Ser Gly Ser Ile Ala Tyr Ala Asp Ser Val
    50                  55                  60

Arg Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Met Asp Val Trp Gly Gln Gly Thr Thr Val Thr
            100                 105                 110

Val Ser Ser
        115
```

<210> SEQ ID NO 3
<211> LENGTH: 348
<212> TYPE: DNA
<213> ORGANISM: Artificial Sequence
<220> FEATURE:
<223> OTHER INFORMATION: HL161-2A heavy

<400> SEQUENCE: 3

```
cagatgcagc tggtgcagtc tgggctgag gtgaagaagc ctgggtcctc ggtgaaggtc       60
tcctgcaagg cttctggagg caccttcaac aactatgctg tcagctgggt gcgacaggcc     120
cctggacaag gcttgagtg gatgggaagg atcatcccta tccttggtat agcaaactac     180
gcacagacat tccagggcag agtcacgatt accgcggaca aatccacgac cacagcctac     240
atggagctga gcagcctgag atctgaggac acggccgtgt attactgtgc aagagatcgt     300
tacggtatgg acgtctgggg ccaagggacc acggtcaccg tctcctca                  348
```

<210> SEQ ID NO 4
<211> LENGTH: 116
<212> TYPE: PRT
<213> ORGANISM: Artificial Sequence
<220> FEATURE:
<223> OTHER INFORMATION: HL161-2A heavy

<400> SEQUENCE: 4

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Tyr
            20                  25                  30

Ala Val Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Thr Phe
    50                  55                  60

Gln Gly Arg Val Thr Ile Thr Ala Asp Lys Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Tyr Gly Met Asp Val Trp Gly Gln Gly Thr Thr Val
            100                 105                 110

Thr Val Ser Ser
        115

<210> SEQ ID NO 5
<211> LENGTH: 369
<212> TYPE: DNA
<213> ORGANISM: Artificial Sequence
<220> FEATURE:
<223> OTHER INFORMATION: HL161-2D heavy

<400> SEQUENCE: 5
caggtgcagc tggtggagtc tgggggaggc ttggtacagc cagggcggtc cctgagactc      60
tcctgtacag cttctggatt cacctttggt gattatgcta tgagctgggt ccgccaggct     120
ccagggaagg ggctggagtg ggtaggtttc attagaagca aagcttatgg tgggacaaca     180
gaatacgccg cgtctgtgaa aggcagattc accatctcaa gagatgattc aaaagcatc     240 gcctatctgc aaatgaacag tctgagagcc gaggacacgg ccgtgtatta ctgtgcgaga     300
gaggggctgt cctgcccct gggaggtttt gatttatggg cctagggac aatggtcacc      360 gtctcctca                                                             369

<210> SEQ ID NO 6
<211> LENGTH: 123
<212> TYPE: PRT
<213> ORGANISM: Artificial Sequence
<220> FEATURE:
<223> OTHER INFORMATION: HL161-2D heavy

<400> SEQUENCE: 6

Gln Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Val Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala

```
                    50                  55                  60
Ser Val Lys Gly Arg Phe Thr Ile Ser Arg Asp Asp Ser Lys Ser Ile
 65                  70                  75                  80

Ala Tyr Leu Gln Met Asn Ser Leu Arg Ala Glu Asp Thr Ala Val Tyr
                     85                  90                  95

Tyr Cys Ala Arg Glu Gly Leu Phe Leu Pro Leu Gly Gly Phe Asp Leu
            100                 105                 110

Trp Gly Leu Gly Thr Met Val Thr Val Ser Ser
        115                 120

<210> SEQ ID NO 7
<211> LENGTH: 348
<212> TYPE: DNA
<213> ORGANISM: Artificial Sequence
<220> FEATURE:
<223> OTHER INFORMATION: HL161-6C heavy

<400> SEQUENCE: 7
caggtgcagc tggtggagtc tggggctgag gtgaagaagc ctggggcctc agtgaaggtt    60
tcctgcaagg catctggata caccttcacc agctactata tgcactgggt gcgacaggcc   120
cctggacaag gcttgagtg gatgggaata atcaaccccta gtggtggtag cacaagctac   180
gcacagaagt tccagggcag agtcaccatg accagggaca cgtccacgag cacagtctac   240
atggagctga gcagcctgag atctgaggac acggccgtgt attactgtgc aagagggggg   300
ggggcttttg atatctgggg ccaagggaca atggtcaccg tctcctca                348

<210> SEQ ID NO 8
<211> LENGTH: 116
<212> TYPE: PRT
<213> ORGANISM: Artificial Sequence
<220> FEATURE:
<223> OTHER INFORMATION: HL161-6C heavy

<400> SEQUENCE: 8

Gln Val Gln Leu Val Glu Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Gly Gly Ala Phe Asp Ile Trp Gly Gln Gly Thr Met Val
            100                 105                 110

Thr Val Ser Ser
        115

<210> SEQ ID NO 9
<211> LENGTH: 369
<212> TYPE: DNA
<213> ORGANISM: Artificial Sequence
<220> FEATURE:
<223> OTHER INFORMATION: HL161-9F heavy

<400> SEQUENCE: 9
```

```
caggtgcagc tggtggagtc tgggggaggc ttggtacagt cagggcggtc cctgagactc    60
tcctgtacag cttctggatt cacctttggt gattatgcta tgagctgggt ccgccaggct   120
ccagggaagg ggctggagtg ggtaggtttc attagaagca aagcttatgg tgggacaaca   180
gaatacgccg cgtctgtgaa aggcagattc accatctcaa gagatgattc caaaagcatc   240
gcctatctgc aaatgaacag tctgagagcc gaggacacgg ccgtgtatta ctgtgcgaga   300 gagggctgt tcctgcccct gggaggtttt gatttatggg gcctagggac aatggtcacc   360
gtctcctca                                                          369

<210> SEQ ID NO 10
<211> LENGTH: 123
<212> TYPE: PRT
<213> ORGANISM: Artificial Sequence
<220> FEATURE:
<223> OTHER INFORMATION: HL161-9F heavy

<400> SEQUENCE: 10

Gln Val Gln Leu Val Glu Ser Gly Gly Gly Leu Val Gln Ser Gly Arg
1               5                   10                  15

Ser Leu Arg Leu Ser Cys Thr Ala Ser Gly Phe Thr Phe Gly Asp Tyr
            20                  25                  30

Ala Met Ser Trp Val Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Arg Ala Glu Asp Thr Ala Val Tyr
                85                  90                  95

Tyr Cys Ala Arg Glu Gly Leu Phe Leu Pro Leu Gly Gly Phe Asp Leu
            100                 105                 110

Trp Gly Leu Gly Thr Met Val Thr Val Ser Ser
        115                 120

<210> SEQ ID NO 11
<211> LENGTH: 363
<212> TYPE: DNA
<213> ORGANISM: Artificial Sequence
<220> FEATURE:
<223> OTHER INFORMATION: HL161 10E heavy

<400> SEQUENCE: 11
caggtgcagc tggtggagtc tgggggaggc ttagtacagc ctgggggtc cctgagactc    60 tcctgtgcag cctctggctt cagattcagc aactttgcca tgacctgggt ccgccaggct   120
ccagggaagg ggctggagtg ggtctcaact cttagtggta gtggtggtag tatacaccac   180
gcagactccg tgaagggccg attcaccatc tccagagaca attccaagaa cacgctgtat   240
ctgcaaatga acagtctgag agccgaggac acggccgtgt attactgtgc gaagggccc   300 ttgaggggac agccggccta ccttgacccc tggggccagg gaaccctggt caccgtctcc   360
tca                                                                363

<210> SEQ ID NO 12
<211> LENGTH: 121
<212> TYPE: PRT
<213> ORGANISM: Artificial Sequence
<220> FEATURE:
```

<223> OTHER INFORMATION: HL161 10E heavy

<400> SEQUENCE: 12

```
Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Arg Phe Ser Asn Phe
            20                  25                  30
Ala Met Thr Trp Val Arg Gln Ala Pro Gly Lys Gly Leu Glu Trp Val
        35                  40                  45
Ser Thr Leu Ser Gly Ser Gly Gly Ser Ile His His Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Gly Pro Leu Arg Gly Gln Pro Ala Tyr Leu Asp Pro Trp Gly
            100                 105                 110
Gln Gly Thr Leu Val Thr Val Ser Ser
        115                 120
```

<210> SEQ ID NO 13
<211> LENGTH: 345
<212> TYPE: DNA
<213> ORGANISM: Artificial Sequence
<220> FEATURE:
<223> OTHER INFORMATION: HL161-11G heavy

<400> SEQUENCE: 13

```
cagatgcagc tggtggagtc ggggggaggc gtggtccagc ctgggaggtc tctgagactc    60
tcctgtgtag gtctggatt caacttcaac agttatggca tacactgggt ccgccaggct   120
ccaggcaagg gctggagtg gtgggagga atattttatg atggaagtca agtaaagtat   180
gcagactccg tgaagggccg agtctccatc tatgccatga attccaagaa cacagcgtat   240
ctgcaaatga acagtctgag agccgaggac acggccgtgt attactgtgc gcgacgaaac   300
ctcctggact actggggcca gggaacggtg gtcaccgtct cctca                   345
```

<210> SEQ ID NO 14
<211> LENGTH: 115
<212> TYPE: PRT
<213> ORGANISM: Artificial Sequence
<220> FEATURE:
<223> OTHER INFORMATION: HL161-11G heavy

<400> SEQUENCE: 14

```
Gln Met Gln Leu Val Glu Ser Gly Gly Gly Val Val Gln Pro Gly Arg
1               5                   10                  15
Ser Leu Arg Leu Ser Cys Val Gly Ser Gly Phe Asn Phe Asn Ser Tyr
            20                  25                  30
Gly Ile His Trp Val Arg Gln Ala Pro Gly Lys Gly Leu Glu Trp Val
        35                  40                  45
Gly Gly Ile Phe Tyr Asp Gly Ser Gln Val Lys Tyr Ala Asp Ser Val
    50                  55                  60
Lys Gly Arg Val Ser Ile Ser Arg Asp Asn Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Arg Asn Leu Leu Asp Tyr Trp Gly Gln Gly Thr Val Val Thr
```

Val Ser Ser
     115

<210> SEQ ID NO 15
<211> LENGTH: 357
<212> TYPE: DNA
<213> ORGANISM: Artificial Sequence
<220> FEATURE:
<223> OTHER INFORMATION: HL161-11H heavy

<400> SEQUENCE: 15
cagatgcagc tggtagagtc tggggggaggt ttggtacagc cgggcaggtc cctgagactc      60
tcctgtgcag cctctggatt caccttcagt agctatgcta tgcactgggt ccgccaggct     120
ccaggcaagg gctggagtg gtggcagtt atatcatatg atggaagcaa taaatactac     180
gcagactccg tgaagggccg attcaccatc tccagagaca attccaagaa cacgctgtat     240
ctgcaaatga acagcctgag atctgaggac acggccgtgt attactgtgc gagaggtagt     300
ggtggtcgtg acgcttttga tgtctggggc caaggaacaa tgatcaccgt ctcctca      357

<210> SEQ ID NO 16
<211> LENGTH: 119
<212> TYPE: PRT
<213> ORGANISM: Artificial Sequence
<220> FEATURE:
<223> OTHER INFORMATION: HL161-11h heavy

<400> SEQUENCE: 16

Gln Met Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Glu Asp Thr Ala Val Tyr Tyr Cys
                85                  90                  95

Ser Arg Gly Ser Gly Gly Arg Asp Ala Phe Asp Val Trp Gly Gln Gly
            100                 105                 110

Thr Met Ile Thr Val Ser Ser
        115

<210> SEQ ID NO 17
<211> LENGTH: 345
<212> TYPE: DNA
<213> ORGANISM: Artificial Sequence
<220> FEATURE:
<223> OTHER INFORMATION: A11-C07 heavy

<400> SEQUENCE: 17
gaagtgcagc tggtcgagag tgggggaggc ttggtacaac ctggaagatc ccttagactc      60
tcttgcgcag caagcgggtt caccttttgac gaatatggca tgcactgggt gagacaggct     120
ccagggaagg gtctggagtg gtgtctggc gtttcatgga attctggtag cattgcgtac     180
gctgactctg tgagaggcag attcactatc tccagagata acgccaaaaa cagcttatac     240

```
ctgcagatga attcactgag agccgaggac acagccctgt actattgtgc tagaggaaga      300
tattcggatg tgtggggcca gggaactaca gttaccgtct cctca                      345
```

<210> SEQ ID NO 18
<211> LENGTH: 115
<212> TYPE: PRT
<213> ORGANISM: Artificial Sequence
<220> FEATURE:
<223> OTHER INFORMATION: A11-C07 heavy

<400> SEQUENCE: 18

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Glu Tyr
            20                  25                  30

Gly Met His Trp Val Arg Gln Ala Pro Gly Lys Gly Leu Glu Trp Val
        35                  40                  45

Ser Gly Val Ser Trp Asn Ser Gly Ser Ile Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Tyr Ser Asp Val Trp Gly Gln Gly Thr Thr Val Thr
            100                 105                 110

Val Ser Ser
        115
```

<210> SEQ ID NO 19
<211> LENGTH: 345
<212> TYPE: DNA
<213> ORGANISM: Artificial Sequence
<220> FEATURE:
<223> OTHER INFORMATION: A11-G06 heavy

<400> SEQUENCE: 19

```
gaagtgcagc tggtcgagag tgggggaggc ttggtacaac ctggaagatc ccttagactc       60
tcttgcgcag caagcgggtt cacctttgac gaatatggca tgcactgggt gagacaggct      120
ccagggaagg gtctggagtg ggtgtctggc gtttcatgga attctggtag cattgcgtac      180
gctgactctg tgagaggcag attcactatc tccagagata cgccaaaaa cagcttatac       240 ctgcagatga attcactgag agccgaggac acagccctgt actattgtgc taaaggaaga      300
atgttggatg tgtggggcca gggaactaca gttaccgtct cctca                      345
```

<210> SEQ ID NO 20
<211> LENGTH: 115
<212> TYPE: PRT
<213> ORGANISM: Artificial Sequence
<220> FEATURE:
<223> OTHER INFORMATION: A11-G06 heavy

<400> SEQUENCE: 20

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Glu Tyr
            20                  25                  30

Gly Met His Trp Val Arg Gln Ala Pro Gly Lys Gly Leu Glu Trp Val
        35                  40                  45
```

```
Ser Gly Val Ser Trp Asn Ser Gly Ser Ile Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Leu Met Asp Val Trp Gly Gln Gly Thr Thr Val Thr
            100                 105                 110

Val Ser Ser
        115

<210> SEQ ID NO 21
<211> LENGTH: 345
<212> TYPE: DNA
<213> ORGANISM: Artificial Sequence
<220> FEATURE:
<223> OTHER INFORMATION: A12-C09 heavy

<400> SEQUENCE: 21
gaagtgcagc tggtcgagag tgggggaggc ttggtacaac ctggaagatc ccttagactc     60
tcttgcgcag caagcgggtt cacctttgac gaatatggca tgcactgggt gagacaggct    120
ccagggaagg gtctggagtg ggtgtctggc gtttcatgga attctggtag cattgcgtac    180
gctgactctg tgagaggcag attcactatc tccagagata cgccaaaaa cagcttatac     240 ctgcagatga attcactgag agccgaggac acagccctgt actattgtgc taaaggaaga    300
acgatggatg tgtggggcca gggaactaca gttaccgtct cctca                    345

<210> SEQ ID NO 22
<211> LENGTH: 115
<212> TYPE: PRT
<213> ORGANISM: Artificial Sequence
<220> FEATURE:
<223> OTHER INFORMATION: A12-C09 heavy

<400> SEQUENCE: 22

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Glu Tyr
            20                  25                  30

Gly Met His Trp Val Arg Gln Ala Pro Gly Lys Gly Leu Glu Trp Val
        35                  40                  45

Ser Gly Val Ser Trp Asn Ser Gly Ser Ile Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Thr Met Asp Val Trp Gly Gln Gly Thr Thr Val Thr
            100                 105                 110

Val Ser Ser
        115

<210> SEQ ID NO 23
<211> LENGTH: 345
<212> TYPE: DNA
<213> ORGANISM: Artificial Sequence
<220> FEATURE:
<223> OTHER INFORMATION: A12-D55 heavy
```

<400> SEQUENCE: 23

```
gaagtgcagc tggtcgagag tgggggaggc ttggtacaac ctggaagatc ccttagactc      60
tcttgcgcag caagcgggtt cacctttgac gaatatggca tgcactgggt gagacaggct     120
ccagggaagg gtctggagtg ggtgtctggc gtttcatgga attctggtag cattgcgtac     180
gctgactctg tgagaggcag attcactatc tccagagata cgccaaaaa cagcttatac      240
ctgcagatga attcactgag agccgaggac acagccctgt actattgtgc tagaggaaga     300
atgatcgatg tgtggggcca gggaactaca gttaccgtct cctca                     345
```

<210> SEQ ID NO 24
<211> LENGTH: 115
<212> TYPE: PRT
<213> ORGANISM: Artificial Sequence
<220> FEATURE:
<223> OTHER INFORMATION: A12-D55 heavy

<400> SEQUENCE: 24

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Glu Tyr
            20                  25                  30

Gly Met His Trp Val Arg Gln Ala Pro Gly Lys Gly Leu Glu Trp Val
        35                  40                  45

Ser Gly Val Ser Trp Asn Ser Gly Ser Ile Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Ile Leu Asp Val Trp Gly Gln Gly Thr Thr Val Thr
            100                 105                 110

Val Ser Ser
        115

<210> SEQ ID NO 25
<211> LENGTH: 345
<212> TYPE: DNA
<213> ORGANISM: Artificial Sequence
<220> FEATURE:
<223> OTHER INFORMATION: A12-E01 heavy

<400> SEQUENCE: 25

```
gaagtgcagc tggtcgagag tgggggaggc ttggtacaac ctgcaagatc ccttagactc      60
tcttgcgcag caagcgggtt cacctttgac gaatatggca tgcactgggt gagacaggct     120
ccagggaagg gtctggagtg ggtgtctggc gtttcatgga attctggtag cattgcgtac     180
gctgactctg tgagaggcag attcactatc tccagagata cgccaaaaa cagcttatac      240
ctgcagatga attcactgag agccgaggac acagccctgt actattgtgc taaaggaaga     300
cttttggatg tgtggggcca gggaactaca gttaccgtct cctca                     345
```

<210> SEQ ID NO 26
<211> LENGTH: 115
<212> TYPE: PRT
<213> ORGANISM: Artificial Sequence
<220> FEATURE:
<223> OTHER INFORMATION: A12-E01 heavy

<400> SEQUENCE: 26

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Glu Tyr
            20                  25                  30

Gly Met His Trp Val Arg Gln Ala Pro Gly Lys Gly Leu Glu Trp Val
        35                  40                  45

Ser Gly Val Ser Trp Asn Ser Gly Ser Ile Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ser Arg Ser Met Asp Val Trp Gly Gln Gly Thr Thr Val Thr
            100                 105                 110

Val Ser Ser
        115

<210> SEQ ID NO 27
<211> LENGTH: 345
<212> TYPE: DNA
<213> ORGANISM: Artificial Sequence
<220> FEATURE:
<223> OTHER INFORMATION: A12-E04 heavy

<400> SEQUENCE: 27
gaagtgcagc tggtcgagag tgggggaggc ttggtacaac ctggaagatc ccttagactc     60
tcttgcgcag caagcgggtt caccttttgac gaatatggca tgcactgggt gagacaggct   120
ccagggaagg gtctggagtg gtgtctggc gtttcatgga attctggtag cattgcgtac    180
gctgactctg tgagaggcag attcactatc tccagagata acgccaaaaa cagcttatac   240
ctgcagatga attcactgag agccgaggac acagccctgt actattgtgc taaaggaaga   300
atgatggatg tgtggggcca gggaactaca gttaccgtct cctca                   345

<210> SEQ ID NO 28
<211> LENGTH: 115
<212> TYPE: PRT
<213> ORGANISM: Artificial Sequence
<220> FEATURE:
<223> OTHER INFORMATION: A12-E04 heavy

<400> SEQUENCE: 28

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Glu Tyr
            20                  25                  30

Gly Met His Trp Val Arg Gln Ala Pro Gly Lys Gly Leu Glu Trp Val
        35                  40                  45

Ser Gly Val Ser Trp Asn Ser Gly Ser Ile Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Leu Phe Asp Val Trp Gly Gln Gly Thr Thr Val Thr
            100                 105                 110

Val Ser Ser

<210> SEQ ID NO 29
<211> LENGTH: 345
<212> TYPE: DNA
<213> ORGANISM: Artificial Sequence
<220> FEATURE:
<223> OTHER INFORMATION: A12-F02 heavy

<400> SEQUENCE: 29

```
gaagtgcagc tggtcgagag tggggaggc ttggtacaac ctggaagatc ccttagactc      60
tcttgcgcag caagcgggtt cacctttgac gaatatggca tgcactgggt gagacaggct    120
ccagggaagg gtctggagtg ggtgtctggc gtttcatgga attctggtag cattgcgtac    180
gctgactctg tgagaggcag attcactatc tccagagata cgccaaaaa cagcttatac     240
ctgcagatga attcactgag agccgaggac acagccctgt actattgtgc taaaggaaga    300
tatttggatg tgtggggcca gggaactaca gttaccgtct cctca                    345
```

<210> SEQ ID NO 30
<211> LENGTH: 115
<212> TYPE: PRT
<213> ORGANISM: Artificial Sequence
<220> FEATURE:
<223> OTHER INFORMATION: A12-F02 heavy

<400> SEQUENCE: 30

```
Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Glu Tyr
            20                  25                  30
Gly Met His Trp Val Arg Gln Ala Pro Gly Lys Gly Leu Glu Trp Val
        35                  40                  45
Ser Gly Val Ser Trp Asn Ser Gly Ser Ile Ala Tyr Ala Asp Ser Val
    50                  55                  60
Arg Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Leu Tyr Tyr Cys
                85                  90                  95
Ala Lys Gly Arg Tyr Leu Asp Val Trp Gly Gln Gly Thr Thr Val Thr
            100                 105                 110
Val Ser Ser
        115
```

<210> SEQ ID NO 31
<211> LENGTH: 345
<212> TYPE: DNA
<213> ORGANISM: Artificial Sequence
<220> FEATURE:
<223> OTHER INFORMATION: A12-H04 heavy

<400> SEQUENCE: 31

```
gaagtgcagc tggtcgagag tggggaggc ttggtacaac ctggaagatc ccttagactc      60
tcttgcgcag caagcgggtt cacctttgac gaatatggca tgcactgggt gagacaggct    120
ccagggaagg gtctggagtg ggtgtctggc gtttcatgga attctggtag cattgcgtac    180
gctgactctg tgagaggcag attcactatc tccagagata cgccaaaaa cagcttatac     240
ctgcagatga attcactgag agccgaggac acagccctgt actattgtgc taaaggaaga    300
cttttggatg tgtggggcca gggaactaca gttaccgtct cctca                    345
```

-continued

<210> SEQ ID NO 32
<211> LENGTH: 115
<212> TYPE: PRT
<213> ORGANISM: Artificial Sequence
<220> FEATURE:
<223> OTHER INFORMATION: A12-H04 heavy

<400> SEQUENCE: 32

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Glu Tyr
            20                  25                  30

Gly Met His Trp Val Arg Gln Ala Pro Gly Lys Gly Leu Glu Trp Val
        35                  40                  45

Ser Gly Val Ser Trp Asn Ser Gly Ser Ile Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Leu Leu Asp Val Trp Gly Gln Gly Thr Thr Val Thr
            100                 105                 110

Val Ser Ser
        115

<210> SEQ ID NO 33
<211> LENGTH: 345
<212> TYPE: DNA
<213> ORGANISM: Artificial Sequence
<220> FEATURE:
<223> OTHER INFORMATION: A23-3H04 heavy

<400> SEQUENCE: 33
gaagtgcagc tggtcgagag tggggggaggc ttggtacaac ctggaagatc ccttagactc    60
tcttgcgcag caagcgggtt cacctttgac acctatggga tgaactgggt gagacaggct   120
ccagggaagg gtctggagtg ggtgtctggc atttcatata tggtggtac cacagcgtac   180 gctgactctg tgagaggcag attcactatc tccagagata cgccaaaaa cagcttatac   240 ctgcagatga attcactgag agccgaggac acagccctgt actattgtgc tagaggaaga   300
tattcggatg tgtggggcca gggaactaca gttaccgtct cctca                   345

<210> SEQ ID NO 34
<211> LENGTH: 115
<212> TYPE: PRT
<213> ORGANISM: Artificial Sequence
<220> FEATURE:
<223> OTHER INFORMATION: A23-3H04 heavy

<400> SEQUENCE: 34

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Thr Tyr
            20                  25                  30

Gly Met Asn Trp Val Arg Gln Ala Pro Gly Lys Gly Leu Glu Trp Val
        35                  40                  45

Ser Gly Ile Ser Tyr Asn Gly Gly Thr Thr Ala Tyr Ala Asp Ser Val
    50                  55                  60

```
Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Gly Arg Tyr Ser Asp Val Trp Gly Gln Gly Thr Thr Val Thr
            100                 105                 110

Val Ser Ser
        115

<210> SEQ ID NO 35
<211> LENGTH: 345
<212> TYPE: DNA
<213> ORGANISM: Artificial Sequence
<220> FEATURE:
<223> OTHER INFORMATION: A21-4C03 heavy

<400> SEQUENCE: 35
gaagtgcagc tggtcgagag tggggggaggc ttggtacaac ctggaagatc ccttagactc      60
tcttgcgcag caagcgggtt cacctttgac gcatatggga tgaactgggt gagacaggct     120
ccagggaagg gtctgagtg ggtgtctggc atttcatata attctggtac catagcgtac     180
gctgactctg tgaaaggcag attcactatc tccagagata cgccaaaaa cagcttatac     240 ctgcagatga attcactgag agccgaggac acagccctgt actattgtgc tagaggaaga     300
tattcggatg tgtggggcca gggaactaca gttaccgtct cctca                     345

<210> SEQ ID NO 36
<211> LENGTH: 115
<212> TYPE: PRT
<213> ORGANISM: Artificial Sequence
<220> FEATURE:
<223> OTHER INFORMATION: A21-4C03 heavy

<400> SEQUENCE: 36

Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Ala Tyr
                 20                  25                  30

Gly Met Asn Trp Val Arg Gln Ala Pro Gly Lys Gly Leu Glu Trp Val
             35                  40                  45

Ser Gly Ile Ser Tyr Asn Ser Gly Thr Ile Ala Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Gly Arg Ser Met Asp Val Trp Gly Gln Gly Thr Thr Val Thr
            100                 105                 110

Val Ser Ser
        115

<210> SEQ ID NO 37
<211> LENGTH: 345
<212> TYPE: DNA
<213> ORGANISM: Artificial Sequence
<220> FEATURE:
<223> OTHER INFORMATION: A24-1G10 heavy

<400> SEQUENCE: 37
gaagtgcagc tggtcgagag tggggggaggc ttggtacaac ctggaagatc ccttagactc      60
```

```
tcttgcgcag caagcgggtt cacctttgac gcctatggga tgcactgggt gagacaggct      120
ccagggaagg gtctggagtg ggtgtctggc atttcatata attctggtac caaagcgtac      180
gctgactctg tgaaaggcag attcactatc tccagagata cgccaaaaa cagcttatac       240 ctgcagatga attcactgag agccgaggac acagccctgt actattgtgc tagaggaaga      300
tattcggatg tgtggggcca gggaactaca gttaccgtct cctca                     345
```

<210> SEQ ID NO 38
<211> LENGTH: 115
<212> TYPE: PRT
<213> ORGANISM: Artificial Sequence
<220> FEATURE:
<223> OTHER INFORMATION: A24-1G10 heavy

<400> SEQUENCE: 38

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
            20                  25                  30

Gly Met His Trp Val Arg Gln Ala Pro Gly Lys Gly Leu Glu Trp Val
        35                  40                  45

Ser Gly Ile Ser Tyr Asn Ser Gly Thr Lys Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115
```

<210> SEQ ID NO 39
<211> LENGTH: 345
<212> TYPE: DNA
<213> ORGANISM: Artificial Sequence
<220> FEATURE:
<223> OTHER INFORMATION: A24-1F07 heavy

<400> SEQUENCE: 39

```
gaagtgcagc tggtcgagag tggggagggc ttggtacaac ctggaagatc ccttagactc       60
tcttgcgcag caagcgggtt cacctttgac gcctatggga tgcactgggt gagacaggct      120
ccagggaagg gtctggagtg ggtgtctggc gtttcatata attctggtac cacagcgtac      180
gctgactctg tgagaggcag attcactatc tccagagata cgccaaaaa cagcttatac       240 ctgcagatga attcactgag agccgaggac acagccctgt actattgtgc tagaggaaga      300
tattcggatg tgtggggcca gggaactaca gttaccgtct cctca                     345
```

<210> SEQ ID NO 40
<211> LENGTH: 115
<212> TYPE: PRT
<213> ORGANISM: Artificial Sequence
<220> FEATURE:
<223> OTHER INFORMATION: A24-1F07 heavy

<400> SEQUENCE: 40

```
Glu Val Gln Leu Val Glu Ser Gly Gly Gly Leu Val Gln Pro Gly Arg
1               5                   10                  15
```

```
Ser Leu Arg Leu Ser Cys Ala Ala Ser Gly Phe Thr Phe Asp Ala Tyr
        20                  25                  30

Gly Met His Trp Val Arg Gln Ala Pro Gly Lys Gly Leu Glu Trp Val
        35                  40                  45

Ser Gly Val Ser Tyr Asn Ser Gly Thr Thr Ala Tyr Ala Asp Ser Val
 50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115

<210> SEQ ID NO 41
<211> LENGTH: 345
<212> TYPE: DNA
<213> ORGANISM: Artificial Sequence
<220> FEATURE:
<223> OTHER INFORMATION: A21-4B10 heavy

<400> SEQUENCE: 41
gaagtgcagc tggtcgagag tgggggaggc ttggtacaac ctggaagatc ccttagactc     60
tcttgcgcag caagcgggtt cacctttgac gaatatggga tgcactgggt gagacaggct    120
ccagggaagg gtctggagtg ggtgtctggc atttcatata attctggtaa caaagcgtac    180
gctgactctg tgagaggcag attcactatc tccagagata cgccaaaaa cagcttatac     240 ctgcagatga attcactgag agccgaggac acagccctgt actattgtgc tagaggaaga    300
tattcggatg tgtggggcca gggaactaca gttaccgtct cctca                    345

<210> SEQ ID NO 42
<211> LENGTH: 115
<212> TYPE: PRT
<213> ORGANISM: Artificial Sequence
<220> FEATURE:
<223> OTHER INFORMATION: A21-4B10 heavy

<400> SEQUENCE: 42

Glu Val Gln Leu Val Glu Ser Gly Gly Gly Leu Val Gln Pro Gly Arg
 1                   5                  10                  15

Ser Leu Arg Leu Ser Cys Ala Ala Ser Gly Phe Thr Phe Asp Glu Tyr
            20                  25                  30

Gly Met His Trp Val Arg Gln Ala Pro Gly Lys Gly Leu Glu Trp Val
        35                  40                  45

Ser Gly Ile Ser Tyr Asn Ser Gly Asn Lys Ala Tyr Ala Asp Ser Val
 50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115
```

<210> SEQ ID NO 43
<211> LENGTH: 345
<212> TYPE: DNA
<213> ORGANISM: Artificial Sequence
<220> FEATURE:
<223> OTHER INFORMATION: A21-4G04 heavy

<400> SEQUENCE: 43

```
gaagtgcagc tggtcgagag tgggggaggc ttggtacaac ctggaagatc ccttagactc      60
tcttgcgcag caagcgggtt cacctttgac agctatggga tgcactgggt gagacaggct     120
ccagggaagg gtctggagtg ggtgtctggc atttcatata atggtggtaa cacagcgtac     180
gctgactctg tgagaggcag attcactatc tccagagata cgccaaaaa cagcttatac      240 ctgcagatga attcactgag agccgaggac acagccctgt actattgtgc tagaggaaga     300
tattcggatg tgtggggcca gggaactaca gttaccgtct cttca                    345
```

<210> SEQ ID NO 44
<211> LENGTH: 115
<212> TYPE: PRT
<213> ORGANISM: Artificial Sequence
<220> FEATURE:
<223> OTHER INFORMATION: A21-4G04 heavy

<400> SEQUENCE: 44

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ser Tyr
            20                  25                  30

Gly Met His Trp Val Arg Gln Ala Pro Gly Lys Gly Leu Glu Trp Val
        35                  40                  45

Ser Gly Ile Ser Tyr Asn Gly Gly Asn Thr Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115
```

<210> SEQ ID NO 45
<211> LENGTH: 345
<212> TYPE: DNA
<213> ORGANISM: Artificial Sequence
<220> FEATURE:
<223> OTHER INFORMATION: A23-3H05 heavy

<400> SEQUENCE: 45

```
gaagtgcagc tggtcgagag tgggggaggc ttggtacaac ctggaagatc ccttagactc      60
tcttgcgcag caagcgggtt cacctttgac gcatatggga tgaactgggt gagacaggct     120
ccagggaagg gtctggagtg ggtgtctggc atttcatata attctggtac catagcgtac     180
gctgactctg tgaaaggcag attcactatc tccagagata cgccaaaaa cagcttatac      240 ctgcagatga attcactgag agccgaggac acagccctgt actattgtgc tagaggaaga     300
tattcggatg tgtggggcca gggaactaca gttaccgtct cctca                    345
```

<210> SEQ ID NO 46

```
<211> LENGTH: 115
<212> TYPE: PRT
<213> ORGANISM: Artificial Sequence
<220> FEATURE:
<223> OTHER INFORMATION: A23-3H05 heavy

<400> SEQUENCE: 46
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
            20                  25                  30

Gly Met Asn Trp Val Arg Gln Ala Pro Gly Lys Gly Leu Glu Trp Val
        35                  40                  45

Ser Gly Ile Ser Tyr Asn Ser Gly Thr Ile Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115

```
<210> SEQ ID NO 47
<211> LENGTH: 345
<212> TYPE: DNA
<213> ORGANISM: Artificial Sequence
<220> FEATURE:
<223> OTHER INFORMATION: A21-3A09 heavy

<400> SEQUENCE: 47
gaagtgcagc tggtcgagag tggggggaggc ttggtacaac ctggaagatc ccttagactc      60
tcttgcgcag caagcgggtt cacctttgac aactatggga tgaactgggt gagacaggct     120
ccagggaagg gtctggagtg ggtgtctggc atttcatata attctggtac caaagcgtac     180
gctgactctg tgaaaggcag attcactatc tccagagata cgccaaaaaa cagcttatac     240
ctgcagatga attcactgag agccgaggac acagccctgt actattgtgc tagaggaaga     300
tattcggatg tgtggggcca gggaactaca gttaccgtct cctca                     345

<210> SEQ ID NO 48
<211> LENGTH: 115
<212> TYPE: PRT
<213> ORGANISM: Artificial Sequence
<220> FEATURE:
<223> OTHER INFORMATION: A21-3A09 heavy

<400> SEQUENCE: 48
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asn Tyr
            20                  25                  30

Gly Met Asn Trp Val Arg Gln Ala Pro Gly Lys Gly Leu Glu Trp Val
        35                  40                  45

Ser Gly Ile Ser Tyr Asn Ser Gly Thr Lys Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115

<210> SEQ ID NO 49
<211> LENGTH: 345
<212> TYPE: DNA
<213> ORGANISM: Artificial Sequence
<220> FEATURE:
<223> OTHER INFORMATION: A21-4B06 heavy

<400> SEQUENCE: 49
gaagtgcagc tggtcgagag tgggggaggc ttggtacaac ctggaagatc ccttagactc    60
tcttgcgcag caagcgggtt cacctttgac agctatggga tgcactgggt gagacaggct   120
ccagggaagg gtctggagtg ggtgtctggc atttcatata atggtggtag caaagcgtac   180
gctgactctg tgagaggcag attcactatc tccagagata cgccaaaaa cagcttatac    240 ctgcagatga attcactgag agccgaggac acagccctgt actattgtgc tagaggaaga   300
tattcggatg tgtgggccca gggaactaca gttaccgtct cctca                  345

<210> SEQ ID NO 50
<211> LENGTH: 115
<212> TYPE: PRT
<213> ORGANISM: Artificial Sequence
<220> FEATURE:
<223> OTHER INFORMATION: A21-4B06 heavy

<400> SEQUENCE: 50

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ser Tyr
            20                  25                  30

Gly Met His Trp Val Arg Gln Ala Pro Gly Lys Gly Leu Glu Trp Val
        35                  40                  45

Ser Gly Ile Ser Tyr Asn Gly Gly Ser Lys Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115

<210> SEQ ID NO 51
<211> LENGTH: 345
<212> TYPE: DNA
<213> ORGANISM: Artificial Sequence
<220> FEATURE:
<223> OTHER INFORMATION: A24-1B05 heavy

<400> SEQUENCE: 51
gaagtgcagc tggtcgagag tgggggaggc ttggtacaac ctggaagatc ccttagactc    60
tcttgcgcag caagcgggtt cacctttgac aaatatggga tgaactgggt gagacaggct   120

```
ccagggaagg gtctggagtg ggtgtctggc atttcatata attctggtaa cacagcgtac    180
gctgactctg tgagaggcag attcactatc tccagagata acgccaaaaa cagcttatac    240
ctgcagatga attcactgag agccgaggac acagccctgt actattgtgc tagaggaaga    300
tattcggatg tgtggggcca gggaactaca gttaccgtct cctca                    345
```

<210> SEQ ID NO 52
<211> LENGTH: 115
<212> TYPE: PRT
<213> ORGANISM: Artificial Sequence
<220> FEATURE:
<223> OTHER INFORMATION: A24-1B05 heavy

<400> SEQUENCE: 52

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Lys Tyr
            20                  25                  30

Gly Met Asn Trp Val Arg Gln Ala Pro Gly Lys Gly Leu Glu Trp Val
        35                  40                  45

Ser Gly Ile Ser Tyr Asn Ser Gly Asn Thr Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115
```

<210> SEQ ID NO 53
<211> LENGTH: 345
<212> TYPE: DNA
<213> ORGANISM: Artificial Sequence
<220> FEATURE:
<223> OTHER INFORMATION: A23-3A08 heavy

<400> SEQUENCE: 53

```
gaagtgcagc tggtcgagag tggggggaggc ttggtacaac ctggaagatc ccttagactc    60
tcttgcgcag caagcgggtt cacctttgac gcatatggga tgcactgggt gagacaggct   120
ccagggaagg gtctggagtg ggtgtctggc atttcatata attctggtac cacagcgtac   180
gctgactctg tgaaaggcag attcactatc tccagagata acgccaaaaa cagcttatac   240
ctgcagatga attcactgag agccgaggac acagccctgt actattgtgc tagaggaaga   300
tattcggatg tgtggggcca gggaactaca gttaccgtct cctca                    345
```

<210> SEQ ID NO 54
<211> LENGTH: 115
<212> TYPE: PRT
<213> ORGANISM: Artificial Sequence
<220> FEATURE:
<223> OTHER INFORMATION: A23-3A08 heavy

<400> SEQUENCE: 54

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
            20                  25                  30
```

Gly Met His Trp Val Arg Gln Ala Pro Gly Lys Gly Leu Glu Trp Val
        35                  40                  45

Ser Gly Ile Ser Tyr Asn Ser Gly Thr Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115

<210> SEQ ID NO 55
<211> LENGTH: 345
<212> TYPE: DNA
<213> ORGANISM: Artificial Sequence
<220> FEATURE:
<223> OTHER INFORMATION: A21-4C08 heavy

<400> SEQUENCE: 55
gaagtgcagc tggtcgagag tgggggaggc ttggtacaac tggaagatc ccttagactc      60 tcttgcgcag caagcgggtt cacctttgac acatatggga tgcactgggt gagacaggct     120
ccagggaagg gtctggagtg ggtgtctggc atttcatata atgccggtaa caaagcgtac     180
gctgactctg tgagaggcag attcactatc tccagagata cgccaaaaa cagcttatac      240 ctgcagatga attcactgag agccgaggac acagccctgt actattgtgc tagaggaaga     300
tattcggatg tgtggggcca gggaactaca gttaccgtct cctca                    345

<210> SEQ ID NO 56
<211> LENGTH: 115
<212> TYPE: PRT
<213> ORGANISM: Artificial Sequence
<220> FEATURE:
<223> OTHER INFORMATION: A21-4C08 heavy

<400> SEQUENCE: 56

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Thr Tyr
            20                  25                  30

Gly Met His Trp Val Arg Gln Ala Pro Gly Lys Gly Leu Glu Trp Val
        35                  40                  45

Ser Gly Ile Ser Tyr Asn Ala Gly Asn Lys Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115

<210> SEQ ID NO 57
<211> LENGTH: 345
<212> TYPE: DNA

<213> ORGANISM: Artificial Sequence
<220> FEATURE:
<223> OTHER INFORMATION: A23-4D09 heavy

<400> SEQUENCE: 57

```
gaagtgcagc tggtcgagag tggggggaggc ttggtacaac ctggaagatc ccttagactc    60
tcttgcgcag caagcgggtt cacctttgac gcctatggga tgcactgggt gagacaggct   120
ccagggaagg gtctggagtg ggtgtctggc gtttcatatg atgctggtaa cacagcgtac   180
gctgactctg tgagaggcag attcactatc tccagagata atgccaaaaa cagcttatac   240
ctgcagatga attcactgag agccgaggac acagccctgt actattgtgc tagaggaaga   300
tattcggatg tgtggggcca gggaactaca gttaccgtct cctca                   345
```

<210> SEQ ID NO 58
<211> LENGTH: 115
<212> TYPE: PRT
<213> ORGANISM: Artificial Sequence
<220> FEATURE:
<223> OTHER INFORMATION: A23-4D09 heavy

<400> SEQUENCE: 58

```
Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Ala Tyr
            20                  25                  30
Gly Met His Trp Val Arg Gln Ala Pro Gly Lys Gly Leu Glu Trp Val
        35                  40                  45
Ser Gly Val Ser Tyr Asp Ala Gly Asn Thr Ala Tyr Ala Asp Ser Val
    50                  55                  60
Arg Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Leu Tyr Tyr Cys
                85                  90                  95
Ala Arg Gly Arg Tyr Ser Asp Val Trp Gly Gln Gly Thr Thr Val Thr
            100                 105                 110
Val Ser Ser
        115
```

<210> SEQ ID NO 59
<211> LENGTH: 345
<212> TYPE: DNA
<213> ORGANISM: Artificial Sequence
<220> FEATURE:
<223> OTHER INFORMATION: A23-3D03heavy

<400> SEQUENCE: 59

```
gaagtgcagc tggtcgagag tggggggaggc ttggtacaac ctggaagatc ccttagactc    60
tcttgcgcag caagcgggtt cacctttgac gcatatggga tgaactgggt gagacaggct   120
ccagggaagg gtctggagtg ggtgtctggc atttcatata atgctggtag cacagcgtac   180
gctgactctg tgagaggcag attcactatc tccagagata acgccaaaaa cagcttatac   240
ctgcagatga attcactgag agccgaggac acagccctgt actattgtgc tagaggaaga   300
tattcggatg tgtggggcca gggaactaca gttaccgtct cctca                   345
```

<210> SEQ ID NO 60
<211> LENGTH: 115
<212> TYPE: PRT
<213> ORGANISM: Artificial Sequence
<220> FEATURE:
<223> OTHER INFORMATION: A23-3D03 heavy

<400> SEQUENCE: 60

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
            20                  25                  30

Gly Met Asn Trp Val Arg Gln Ala Pro Gly Lys Gly Leu Glu Trp Val
        35                  40                  45

Ser Gly Ile Ser Tyr Asn Ala Gly Ser Thr Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115

<210> SEQ ID NO 61
<211> LENGTH: 345
<212> TYPE: DNA
<213> ORGANISM: Artificial Sequence
<220> FEATURE:
<223> OTHER INFORMATION: A21-4B03 heavy

<400> SEQUENCE: 61
gaagtgcagc tggtcgagag tgggggaggc ttggtacaac ctggaagatc ccttagactc      60
tcttgcgcag caagcgggtt cacctttgac gcatatggga tgaactgggt gagacaggct     120
ccagggaagg gtctggagtg ggtgtctggc atttcatata atgctggtaa caaagcgtac     180
gctgactctg tgagaggcag attcactatc tccagagata cgccaaaaa cagcttatac      240 ctgcagatga attcactgag agccgaggac acagccctgt actattgtgc tagaggaaga     300
tattcggatg tgtggggcca gggaactaca gttaccgtct cctca                     345

<210> SEQ ID NO 62
<211> LENGTH: 115
<212> TYPE: PRT
<213> ORGANISM: Artificial Sequence
<220> FEATURE:
<223> OTHER INFORMATION: A21-4B03 heavy

<400> SEQUENCE: 62

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
            20                  25                  30

Gly Met Asn Trp Val Arg Gln Ala Pro Gly Lys Gly Leu Glu Trp Val
        35                  40                  45

Ser Gly Ile Ser Tyr Asn Ala Gly Asn Lys Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115

<210> SEQ ID NO 63
<211> LENGTH: 345
<212> TYPE: DNA
<213> ORGANISM: Artificial Sequence
<220> FEATURE:
<223> OTHER INFORMATION: A21-3D10 heavy

<400> SEQUENCE: 63
gaagtgcagc tggtcgagag tgggggaggc ttggtacaac ctggaagatc ccttagactc    60
tcttgcgcag caagcgggtt cacctttgac aactatggga tgcactgggt gagacaggct   120
ccagggaagg gtctggagtg ggtgtctggc atttcatatg atgctggtac cacagcgtac   180
gctgactctg tgaaaggcag attcactatc tccagagata cgccaaaaa cagcttatac    240 ctgcagatga attcactgag agccgaggac acagccctgt actattgtgc taaaggaaga   300
tattcggatg tgtggggcca gggaactaca gttaccgtct cctca                   345

<210> SEQ ID NO 64
<211> LENGTH: 115
<212> TYPE: PRT
<213> ORGANISM: Artificial Sequence
<220> FEATURE:
<223> OTHER INFORMATION: A21-3D10 heavy

<400> SEQUENCE: 64

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asn Tyr
            20                  25                  30

Gly Met His Trp Val Arg Gln Ala Pro Gly Lys Gly Leu Glu Trp Val
        35                  40                  45

Ser Gly Ile Ser Tyr Asp Ala Gly Thr Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Tyr Ser Asp Val Trp Gly Gln Gly Thr Thr Val Thr
            100                 105                 110

Val Ser Ser
        115

<210> SEQ ID NO 65
<211> LENGTH: 345
<212> TYPE: DNA
<213> ORGANISM: Artificial Sequence
<220> FEATURE:
<223> OTHER INFORMATION: A21-3A10 heavy

<400> SEQUENCE: 65
gaagtgcagc tggtcgagag tgggggaggc ttggtacaac ctggaagatc ccttagactc    60
tcttgcgcag caagcgggtt cacctttgac gcatatggga tgcactgggt gagacaggct   120
ccagggaagg gtctggagtg ggtgtctggc atttcatata atgctggtaa caaagcgtac   180
gctgactctg tgagaggcag attcactatc tccagagata cgccaaaaa cagcttatac    240

```
ctgcagatga attcactgag agccgaggac acagccctgt actattgtgc tagaggaaga    300
tattcggatg tgtggggcca gggaactaca gttaccgtct cctca                   345
```

<210> SEQ ID NO 66
<211> LENGTH: 115
<212> TYPE: PRT
<213> ORGANISM: Artificial Sequence
<220> FEATURE:
<223> OTHER INFORMATION: A21-3A10 heavy

<400> SEQUENCE: 66

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
            20                  25                  30

Gly Met His Trp Val Arg Gln Ala Pro Gly Lys Gly Leu Glu Trp Val
        35                  40                  45

Ser Gly Ile Ser Tyr Asn Ala Gly Asn Lys Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115
```

<210> SEQ ID NO 67
<211> LENGTH: 345
<212> TYPE: DNA
<213> ORGANISM: Artificial Sequence
<220> FEATURE:
<223> OTHER INFORMATION: A21-4H04 heavy

<400> SEQUENCE: 67

```
gaagtgcagc tggtcgagag tgggggaggc ttggtacaac tggaagatcc cttagactc     60 tcttgcgcag caagcgggtt cacctttgac agctatggga tgcactgggt gagacaggct   120
ccagggaagg gtctggagtg ggtgtccggc atttcatata attctggtaa caaagcgtac   180
gctgactctg tgaaaggcag attcactatc tccagagata cgccaaaaa cagcttatac    240 ctgcagatga attcactgag agccgaggac acagccctgt actattgtgc tagaggaaga   300
tattcggatg tgtggggcca gggaactaca gttaccgtct cctca                   345
```

<210> SEQ ID NO 68
<211> LENGTH: 115
<212> TYPE: PRT
<213> ORGANISM: Artificial Sequence
<220> FEATURE:
<223> OTHER INFORMATION: A21-4H04 heavy

<400> SEQUENCE: 68

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ser Tyr
            20                  25                  30

Gly Met His Trp Val Arg Gln Ala Pro Gly Lys Gly Leu Glu Trp Val
        35                  40                  45
```

```
Ser Gly Ile Ser Tyr Asn Ser Gly Asn Lys Ala Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
    115

<210> SEQ ID NO 69
<211> LENGTH: 345
<212> TYPE: DNA
<213> ORGANISM: Artificial Sequence
<220> FEATURE:
<223> OTHER INFORMATION: A21-4F11 heavy

<400> SEQUENCE: 69
gaagtgcagc tggtcgagag tggggggaggc ttggtacaac ctggaagatc ccttagactc      60
tcttgcgcag caagcgggtt cacctttgac gcatatggga tgaactgggt gagacaggct     120
ccagggaagg gtctggagtg ggtgtctggc atttcatata atggtggtac caaagcgtac     180
gctgactctg tgagaggcag attcactatc tccagagata cgccaaaaa cagcttatac      240 ctgcagatga attcactgag agccgaggat acagccctgt actattgtgc tagaggaaga     300
tattcggatg tgtggggcca gggaactaca gttaccgtct cctca                    345

<210> SEQ ID NO 70
<211> LENGTH: 115
<212> TYPE: PRT
<213> ORGANISM: Artificial Sequence
<220> FEATURE:
<223> OTHER INFORMATION: A21-4F11 heavy

<400> SEQUENCE: 70

Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Ala Tyr
             20                  25                  30

Gly Met Asn Trp Val Arg Gln Ala Pro Gly Lys Gly Leu Glu Trp Val
            35                  40                  45

Ser Gly Ile Ser Tyr Asn Gly Gly Thr Lys Ala Tyr Ala Asp Ser Val
    50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
    115

<210> SEQ ID NO 71
<211> LENGTH: 345
<212> TYPE: DNA
<213> ORGANISM: Artificial Sequence
<220> FEATURE:
<223> OTHER INFORMATION: A23-3G05 heavy
```

<400> SEQUENCE: 71

```
gaagtgcagc tggtcgagag tggggggaggc ttggtacaac ctggaagatc ccttagactc    60
tcttgcgcag caagcgggtt cacctttgac acatatggga tgcactgggt gagacaggct   120
ccagggaagg gtctggagtg ggtgtctggc atttcatata attctggtac catagcgtac   180
gctgactctg tgagaggcag attcactatc tccagagata cgccaaaaa cagcttatac    240
ctgcagatga attcactgag agccgaggac acagccctgt actattgtgc tagaggaaga   300
tattcggatg tgtggggcca gggaactaca gttaccgtct cctca                   345
```

<210> SEQ ID NO 72
<211> LENGTH: 115
<212> TYPE: PRT
<213> ORGANISM: Artificial Sequence
<220> FEATURE:
<223> OTHER INFORMATION: A23-3G05 heavy

<400> SEQUENCE: 72

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Thr Tyr
            20                  25                  30

Gly Met His Trp Val Arg Gln Ala Pro Gly Lys Gly Leu Glu Trp Val
        35                  40                  45

Ser Gly Ile Ser Tyr Asn Ser Gly Thr Ile Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115
```

<210> SEQ ID NO 73
<211> LENGTH: 345
<212> TYPE: DNA
<213> ORGANISM: Artificial Sequence
<220> FEATURE:
<223> OTHER INFORMATION: A23-3A10 heavy

<400> SEQUENCE: 73

```
gaagtgcagc tggtcgagag tggggggaggc ttggtacaac ctggaagatc ccttagactc    60
tcttgcgcag caagcgggtt cacctttgac aaatatggga tgcactgggt gagacaggct   120
ccagggaagg gtctggagtg ggtgtctggc atttcatata atgctggtag caaagcgtac   180
gctgactctg tgaaaggcag attcactatc tccagagata cgccaaaaa cagcttatac    240
ctgcagatga attcactgag agccgaggac acagccctgt actattgtgc tagaggaaga   300
tattcggatg tgtggggcca gggaactaca gttaccgtct cctca                   345
```

<210> SEQ ID NO 74
<211> LENGTH: 115
<212> TYPE: PRT
<213> ORGANISM: Artificial Sequence
<220> FEATURE:
<223> OTHER INFORMATION: A23-3A10 heavy

<400> SEQUENCE: 74

| Glu | Val | Gln | Leu | Val | Glu | Ser | Gly | Gly | Gly | Leu | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Asp | Lys | Tyr |
|---|---|---|---|---|---|---|---|---|---|---|---|---|---|---|---|
| | | | 20 | | | | | 25 | | | | | 30 | | |

| Gly | Met | His | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Gly | Ile | Ser | Tyr | Asn | Ala | Gly | Ser | Lys | Ala | Tyr | Ala | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ala | Lys | Asn | Ser | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Leu | Tyr | Tyr | Cys |
|---|---|---|---|---|---|---|---|---|---|---|---|---|---|---|---|
| | | | | 85 | | | | | 90 | | | | | 95 | |

| Ala | Arg | Gly | Arg | Tyr | Ser | Asp | Val | Trp | Gly | Gln | Gly | Thr | Thr | Val | Thr |
|---|---|---|---|---|---|---|---|---|---|---|---|---|---|---|---|
| | | 100 | | | | | 105 | | | | | 110 | | | |

| Val | Ser | Ser |
|---|---|---|
| | | 115 |

<210> SEQ ID NO 75
<211> LENGTH: 345
<212> TYPE: DNA
<213> ORGANISM: Artificial Sequence
<220> FEATURE:
<223> OTHER INFORMATION: A25-1H04 heavy

<400> SEQUENCE: 75

```
gaagtgcagc tggtcgagag tgggggaggc ttggtacaac ctggaagatc ccttagactc      60
tcttgcgcag caagcgggtt cacctttgac gcatatggga tgaactgggt gagacaggct     120
ccagggaagg gtctggagtg ggtgtctggc atttcatata attctggtaa cacagcgtac     180
gctgactctg tgagaggcag attcactatc tccagagata cgccaaaaa cagcttatac      240
ctgcagatga attcactgag agccgaggac acagccctgt actattgtgc tagaggaaga     300
tattcggatg tgtggggcca gggaactaca gttaccgtct cctca                     345
```

<210> SEQ ID NO 76
<211> LENGTH: 115
<212> TYPE: PRT
<213> ORGANISM: Artificial Sequence
<220> FEATURE:
<223> OTHER INFORMATION: A25-1H04 heavy

<400> SEQUENCE: 76

| Glu | Val | Gln | Leu | Val | Glu | Ser | Gly | Gly | Gly | Leu | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Asp | Ala | Tyr |
|---|---|---|---|---|---|---|---|---|---|---|---|---|---|---|---|
| | | | 20 | | | | | 25 | | | | | 30 | | |

| Gly | Met | Asn | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Gly | Ile | Ser | Tyr | Asn | Ser | Gly | Asn | Thr | Ala | Tyr | Ala | Asp | Ser | Val |
|---|---|---|---|---|---|---|---|---|---|---|---|---|---|---|---|
| 50 | | | | | 55 | | | | | 60 | | | | | |

| Arg | Gly | Arg | Phe | Thr | Ile | Ser | Arg | Asp | Asn | Ala | Lys | Asn | Ser | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Leu | Tyr | Tyr | Cys |
|---|---|---|---|---|---|---|---|---|---|---|---|---|---|---|---|
| | | | | 85 | | | | | 90 | | | | | 95 | |

| Ala | Arg | Gly | Arg | Tyr | Ser | Asp | Val | Trp | Gly | Gln | Gly | Thr | Thr | Val | Thr |
|---|---|---|---|---|---|---|---|---|---|---|---|---|---|---|---|
| | | 100 | | | | | 105 | | | | | 110 | | | |

Val Ser Ser
       115

<210> SEQ ID NO 77
<211> LENGTH: 345
<212> TYPE: DNA
<213> ORGANISM: Artificial Sequence
<220> FEATURE:
<223> OTHER INFORMATION: A23-3B06 heavy

<400> SEQUENCE: 77

```
gaagtgcagc tggtcgagag tgggggaggc ttggtacaac ctggaagatc ccttagactc    60
tcttgcgcag caagcgggtt cacctttgac gcctatggga tgcactgggt gagacaggct   120
ccagggaagg gtctggagtg ggtgtctggc atttcatata attctggtag caaagcgtac   180
gctgactctg tgaaaggcag attcactatc tccagagata cgccaaaaaa cagcttatac   240
ctgcagatga attcactgag agccgaggac acagccctgt actattgtgc tagaggaaga   300
tattcggatg tgtggggcca gggaactaca gttaccgtct cctca                   345
```

<210> SEQ ID NO 78
<211> LENGTH: 115
<212> TYPE: PRT
<213> ORGANISM: Artificial Sequence
<220> FEATURE:
<223> OTHER INFORMATION: A23-3B06 heavy

<400> SEQUENCE: 78

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
            20                  25                  30

Gly Met His Trp Val Arg Gln Ala Pro Gly Lys Gly Leu Glu Trp Val
        35                  40                  45

Ser Gly Ile Ser Tyr Asn Ser Gly Ser Lys Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
       115

<210> SEQ ID NO 79
<211> LENGTH: 345
<212> TYPE: DNA
<213> ORGANISM: Artificial Sequence
<220> FEATURE:
<223> OTHER INFORMATION: A23-4A09 heavy

<400> SEQUENCE: 79

```
gaagtgcagc tggtcgagag tgggggaggc ttggtacaac ctggaagatc ccttagactc    60
tcttgcgcag caagcgggtt cacctttgac aactatggga tgaactgggt gagacaggct   120
ccagggaagg gtctggagtg ggtgtctggc atttcatatg attctggtaa caaagcgtac   180
gctgactctg tgaaaggcag attcactatc tccagagata cgccaaaaaa cagcttatac   240
ctgcagatga attcactgag agccgaggac acagccctgt actattgtgc tagaggaaga   300
```
tattcggatg tgtgggggcca gggaactaca gttaccgtct cctca    345

<210> SEQ ID NO 80
<211> LENGTH: 115
<212> TYPE: PRT
<213> ORGANISM: Artificial Sequence
<220> FEATURE:
<223> OTHER INFORMATION: A23-4A09 heavy

<400> SEQUENCE: 80

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asn Tyr
            20                  25                  30

Gly Met Asn Trp Val Arg Gln Ala Pro Gly Lys Gly Leu Glu Trp Val
        35                  40                  45

Ser Gly Ile Ser Tyr Asp Ser Gly Asn Lys Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115

<210> SEQ ID NO 81
<211> LENGTH: 345
<212> TYPE: DNA
<213> ORGANISM: Artificial Sequence
<220> FEATURE:
<223> OTHER INFORMATION: A25-1D09 heavy

<400> SEQUENCE: 81
gaagtgcagc tggtcgagag tggggggaggc ttggtacaac ctggaagatc ccttagactc    60
tcttgcgcag caagcgggtt cacctttac gcatatggga tgcactgggt gagacaggct    120
ccagggaagg gtctggagtg ggtgtctggc atttcatata atggtggtac catagcgtac    180
gctgactctg tgaaaggcag attcactatc tccagagata cgccaaaaaa cagcttatac    240
ctgcagatga attcactgag agccgaggac acagccctgt actattgtgc tagaggaaga    300
tattcggatg tgtgggggcca gggaactaca gttaccgtct cctca    345

<210> SEQ ID NO 82
<211> LENGTH: 115
<212> TYPE: PRT
<213> ORGANISM: Artificial Sequence
<220> FEATURE:
<223> OTHER INFORMATION: A25-1D09 heavy

<400> SEQUENCE: 82

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Tyr Ala Tyr
            20                  25                  30

Gly Met His Trp Val Arg Gln Ala Pro Gly Lys Gly Leu Glu Trp Val
        35                  40                  45

Ser Gly Ile Ser Tyr Asn Gly Gly Thr Ile Ala Tyr Ala Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Gly Arg Tyr Ser Asp Val Trp Gly Gln Gly Thr Thr Val Thr
            100                 105                 110

Val Ser Ser
        115

<210> SEQ ID NO 83
<211> LENGTH: 345
<212> TYPE: DNA
<213> ORGANISM: Artificial Sequence
<220> FEATURE:
<223> OTHER INFORMATION: A21-4E10 heavy

<400> SEQUENCE: 83
gaagtgcagc tggtcgagag tggggggaggc ttggtacaac ctggaagatc ccttagactc    60
tcttgcgcag caagcgggtt cacctttgac gcctatggga tgaactgggt gagacaggct   120
ccagggaagg gtctggagtg ggtgtctggc gtttcatata acgctggtaa caaagcgtac   180
gctgactctg tgagaggcag attcactatc tccagagata cgccaaaaa cagcttatac    240 ctgcagatga attcactgag agccgaggac acagccctgt actattgtgc tagaggaaga   300
tattcggatg tgtggggcca gggaactaca gttaccgtct cctca                   345

<210> SEQ ID NO 84
<211> LENGTH: 115
<212> TYPE: PRT
<213> ORGANISM: Artificial Sequence
<220> FEATURE:
<223> OTHER INFORMATION: A21-4E10 heavy

<400> SEQUENCE: 84

Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Ala Tyr
                 20                  25                  30

Gly Met Asn Trp Val Arg Gln Ala Pro Gly Lys Gly Leu Glu Trp Val
            35                  40                  45

Ser Gly Val Ser Tyr Asn Ala Gly Asn Lys Ala Tyr Ala Asp Ser Val
     50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Gly Arg Tyr Ser Asp Val Trp Gly Gln Gly Thr Thr Val Thr
            100                 105                 110

Val Ser Ser
        115

<210> SEQ ID NO 85
<211> LENGTH: 345
<212> TYPE: DNA
<213> ORGANISM: Artificial Sequence
<220> FEATURE:
<223> OTHER INFORMATION: A23-3C04 heavy

<400> SEQUENCE: 85
```

```
gaagtgcagc tggtcgagag tggggggaggc ttggtacaac ctggaagatc ccttagactc    60
tcttgcgcag caagcgggtt cacctttgac acatatggga tgcactgggt gagacaggct   120
ccagggaagg gtctggagtg ggtgtctggc atttcatatg attctggtac cacagcgtac   180
gctgactctg tgaaaggcag attcactatc tccagagata acgccaaaaa cagcttatac   240
ctgcagatga attcactgag agccgaggac acagccctgt actattgtgc tagaggaaga   300
tattcggatg tgtggggcca gggaactaca gttaccgtct cctca                   345
```

<210> SEQ ID NO 86
<211> LENGTH: 115
<212> TYPE: PRT
<213> ORGANISM: Artificial Sequence
<220> FEATURE:
<223> OTHER INFORMATION: A23-3C04 heavy

<400> SEQUENCE: 86

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Thr Tyr
            20                  25                  30

Gly Met His Trp Val Arg Gln Ala Pro Gly Lys Gly Leu Glu Trp Val
        35                  40                  45

Ser Gly Ile Ser Tyr Asp Ser Gly Thr Thr Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115
```

<210> SEQ ID NO 87
<211> LENGTH: 345
<212> TYPE: DNA
<213> ORGANISM: Artificial Sequence
<220> FEATURE:
<223> OTHER INFORMATION: A23-3G06 heavy

<400> SEQUENCE: 87

```
gaagtgcagc tggtcgagag tggggggaggc ttggtacaac ctggaagatc ccttagactc    60
tcttgcgcag caagcgggtt cacctttgac gcatatggga tgaactgggt gagacaggct   120
ccagggaagg gtctggagtg ggtgtctggc atttcatata attctggtaa catagcgtac   180
gctgactctg tgagaggcag attcactatc tccagagata acgccaaaaa cagcttatac   240
ctgcagatga attcactgag agccgaggac acagccctgt actattgtgc tagaggaaga   300
tattcggatg tgtggggcca gggaactaca gttaccgtct cctca                   345
```

<210> SEQ ID NO 88
<211> LENGTH: 115
<212> TYPE: PRT
<213> ORGANISM: Artificial Sequence
<220> FEATURE:
<223> OTHER INFORMATION: A23-3G06 heavy

<400> SEQUENCE: 88

```
Glu Val Gln Leu Val Glu Ser Gly Gly Gly Leu Val Gln Pro Gly Arg
```

```
1               5                   10                  15
Ser Leu Arg Leu Ser Cys Ala Ala Ser Gly Phe Thr Phe Asp Ala Tyr
            20                  25                  30

Gly Met Asn Trp Val Arg Gln Ala Pro Gly Lys Gly Leu Glu Trp Val
            35                  40                  45

Ser Gly Ile Ser Tyr Asn Ser Gly Asn Ile Ala Tyr Ala Asp Ser Val
            50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115
```

<210> SEQ ID NO 89
<211> LENGTH: 345
<212> TYPE: DNA
<213> ORGANISM: Artificial Sequence
<220> FEATURE:
<223> OTHER INFORMATION: A24-1E09 heavy

<400> SEQUENCE: 89

```
gaagtgcagc tggtcgagag tgggggaggc ttggtacaac ctggaagatc ccttagactc    60
tcttgcgcag caagcgggtt cacctttgac aaatatggga tgcactgggt gagacaggct   120
ccagggaagg gtctggagtg ggtgtctggc gtttcatata atgctggtac cacagcgtac   180
gctgactctg tgagaggcag attcactatc tccagagata cgccaaaaaa cagcttatac   240
ctgcagatga attcactgag agccgaggac acagccctgt actattgtgc tagaggaaga   300
tattcggatg tgtggggcca gggaactaca gttaccgtct cctca                   345
```

<210> SEQ ID NO 90
<211> LENGTH: 115
<212> TYPE: PRT
<213> ORGANISM: Artificial Sequence
<220> FEATURE:
<223> OTHER INFORMATION: A24-1E09 heavy

<400> SEQUENCE: 90

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Lys Tyr
            20                  25                  30

Gly Met His Trp Val Arg Gln Ala Pro Gly Lys Gly Leu Glu Trp Val
            35                  40                  45

Ser Gly Val Ser Tyr Asn Ala Gly Thr Thr Ala Tyr Ala Asp Ser Val
            50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115
```

<210> SEQ ID NO 91
<211> LENGTH: 345
<212> TYPE: DNA
<213> ORGANISM: Artificial Sequence
<220> FEATURE:
<223> OTHER INFORMATION: A23-3F03 heavy

<400> SEQUENCE: 91

```
gaagtgcagc tggtcgagag tgggggaggc ttggtacaac ctggaagatc ccttagactc    60
tcttgcgcag caagcgggtt cacctttgac acatatggga tgcactgggt gagacaggct   120
ccagggaagg gtctggagtg ggtgtctggc atttcatata attctggtaa catagcgtac   180
gctgactctg tgaaaggcag attcactatc tccagagata cgccaaaaa cagcttatac    240 ctgcagatga attcactgag agccgaggac acagccctgt actattgtgc tagaggaaga   300
tattcggatg tgtggggcca gggaactaca gttaccgtct cctca                   345
```

<210> SEQ ID NO 92
<211> LENGTH: 115
<212> TYPE: PRT
<213> ORGANISM: Artificial Sequence
<220> FEATURE:
<223> OTHER INFORMATION: A23-3F03 heavy

<400> SEQUENCE: 92

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Thr Tyr
            20                  25                  30

Gly Met His Trp Val Arg Gln Ala Pro Gly Lys Gly Leu Glu Trp Val
        35                  40                  45

Ser Gly Ile Ser Tyr Asn Ser Gly Asn Ile Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115

<210> SEQ ID NO 93
<211> LENGTH: 345
<212> TYPE: DNA
<213> ORGANISM: Artificial Sequence
<220> FEATURE:
<223> OTHER INFORMATION: A21-4F07 heavy

<400> SEQUENCE: 93

```
gaagtgcagc tggtcgagag tgggggaggc ttggtacaac ctggaagatc ccttagactc    60
tcttgcgcag caagcgggtt cacctttgac gcctatggga tgaactgggt gagacaggct   120
ccagggaagg gtctggagtg ggtgtctggc atttcatata atgctggtaa caaagcgtac   180
gctgactctg tgaaaggcag attcactatc tccagagata cgccaaaaa cagcttatac    240 ctgcagatga attcactgag agccgaggac acagccctgt actattgtgc tagaggaaga   300
tattcggatg tgtggggcca gggaactaca gttaccgtct cctca                   345
```

<210> SEQ ID NO 94
<211> LENGTH: 115
<212> TYPE: PRT
<213> ORGANISM: Artificial Sequence
<220> FEATURE:
<223> OTHER INFORMATION: A21-4F07 heavy

<400> SEQUENCE: 94

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
                20                  25                  30

Gly Met Asn Trp Val Arg Gln Ala Pro Gly Lys Gly Leu Glu Trp Val
            35                  40                  45

Ser Gly Ile Ser Tyr Asn Ala Gly Asn Lys Ala Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115
```

<210> SEQ ID NO 95
<211> LENGTH: 345
<212> TYPE: DNA
<213> ORGANISM: Artificial Sequence
<220> FEATURE:
<223> OTHER INFORMATION: A24-1A03 heavy

<400> SEQUENCE: 95

```
gaagtgcagc tggtcgagag tgggggaggc ttggtacaac ctggaagatc ccttagactc    60
tcttgcgcag caagcgggtt cacctttgac gcatatggga tgaactgggt gagacaggct   120
ccagggaagg gtctggagtg ggtgtctggc atttcatata atgctggtaa cacagcgtac   180
gctgactctg tgaaaggcag attcactatc tccagagata cgccaaaaaa cagcttatac   240
ctgcagatga attcactgag agccgaggac acagccctgt actattgtgc tagaggaaga   300
tattcggatg tgtggggcca gggaactaca gttaccgtct cctca                   345
```

<210> SEQ ID NO 96
<211> LENGTH: 115
<212> TYPE: PRT
<213> ORGANISM: Artificial Sequence
<220> FEATURE:
<223> OTHER INFORMATION: A24-1A03 heavy

<400> SEQUENCE: 96

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
                20                  25                  30

Gly Met Asn Trp Val Arg Gln Ala Pro Gly Lys Gly Leu Glu Trp Val
            35                  40                  45

Ser Gly Ile Ser Tyr Asn Ala Gly Asn Thr Ala Tyr Ala Asp Ser Val
        50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Leu Tyr Tyr Cys
            85                  90                  95

Ala Arg Gly Arg Tyr Ser Asp Val Trp Gly Gln Gly Thr Thr Val Thr
            100                 105                 110

Val Ser Ser
        115

<210> SEQ ID NO 97
<211> LENGTH: 345
<212> TYPE: DNA
<213> ORGANISM: Artificial Sequence
<220> FEATURE:
<223> OTHER INFORMATION: A24-1H11 heavy

<400> SEQUENCE: 97
gaagtgcagc tggtcgagag tgggggaggc ttggtacaac ctggaagatc ccttagactc     60
tcttgcgcag caagcgggtt cacctttgac gcatatggga tgcactgggt gagacaggct    120
ccagggaagg gtctggagtg ggtgtctggc atttcatata attctggtac cacagcgtac    180
gctgactctg tgagaggcag attcactatc tccagagata cgccaaaaa cagcttatac     240 ctgcagatga attcactgag agccgaggac acagccctgt actattgtgc tagaggaaga    300
tattcggatg tgtggggcca gggaactaca gttaccgtct cctca                    345

<210> SEQ ID NO 98
<211> LENGTH: 115
<212> TYPE: PRT
<213> ORGANISM: Artificial Sequence
<220> FEATURE:
<223> OTHER INFORMATION: A24-1H11 heavy

<400> SEQUENCE: 98

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
            20                  25                  30

Gly Met His Trp Val Arg Gln Ala Pro Gly Lys Gly Leu Glu Trp Val
        35                  40                  45

Ser Gly Ile Ser Tyr Asn Ser Gly Thr Thr Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Arg Gly Arg Tyr Ser Asp Val Trp Gly Gln Gly Thr Thr Val Thr
            100                 105                 110

Val Ser Ser
        115

<210> SEQ ID NO 99
<211> LENGTH: 345
<212> TYPE: DNA
<213> ORGANISM: Artificial Sequence
<220> FEATURE:
<223> OTHER INFORMATION: A21-3D09 heavy

<400> SEQUENCE: 99
gaagtgcagc tggtcgagag tgggggaggc ttggtacaac ctggaagatc ccttagactc     60
tcttgcgcag caagcgggtt cacctttgac aactatggga tgaactgggt gagacaggct    120
```

```
ccagggaagg gtctggagtg ggtgtctggc atttcatata attctggtac caaagcgtac    180
gctgactctg tgaaaggcag attcactatc tccagagata acgccaaaaa cagcttatac    240
ctgcagatga attcactgag agccgaggac acagccctgt actattgtgc tagaggaaga    300
tattcggatg tgtggggcca gggaactaca gttaccgtct cctca                    345
```

<210> SEQ ID NO 100
<211> LENGTH: 115
<212> TYPE: PRT
<213> ORGANISM: Artificial Sequence
<220> FEATURE:
<223> OTHER INFORMATION: A21-3D09 heavy

<400> SEQUENCE: 100

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asn Tyr
            20                  25                  30

Gly Met Asn Trp Val Arg Gln Ala Pro Gly Lys Gly Leu Glu Trp Val
        35                  40                  45

Ser Gly Ile Ser Tyr Asn Ser Gly Thr Lys Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115
```

<210> SEQ ID NO 101
<211> LENGTH: 345
<212> TYPE: DNA
<213> ORGANISM: Artificial Sequence
<220> FEATURE:
<223> OTHER INFORMATION: A24-1D10 heavy

<400> SEQUENCE: 101

```
gaagtgcagc tggtcgagag tggggggaggc ttggtacaac ctggaagatc ccttagactc     60
tcttgcgcag caagcgggtt cacctttgac aactatggga tgcactgggt gagacaggct    120
ccagggaagg gtctggagtg ggtgtctggc atttcatata attctggtaa caaagcgtac    180
gctgactctg tgaaaggcag attcactatc tccagagata acgccaaaaa cagcttatac    240
ctgcagatga attcactgag agccgaggac acagccctgt actattgtgc tagaggaaga    300
tattcggatg tgtggggcca gggaactaca gttaccgtct cctca                    345
```

<210> SEQ ID NO 102
<211> LENGTH: 115
<212> TYPE: PRT
<213> ORGANISM: Artificial Sequence
<220> FEATURE:
<223> OTHER INFORMATION: A24-1D10 heavy

<400> SEQUENCE: 102

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asn Tyr
```

|  |  | 20 |  |  |  | 25 |  |  |  | 30 |  |  |
|---|---|---|---|---|---|---|---|---|---|---|---|---|

Gly Met His Trp Val Arg Gln Ala Pro Gly Lys Gly Leu Glu Trp Val
         35                      40                     45

Ser Gly Ile Ser Tyr Asn Ser Gly Asn Lys Ala Tyr Ala Asp Ser Val
         50                      55                     60

Lys Gly Arg Phe Thr Ile Ser Arg Asp Asn Ala Lys Asn Ser Leu Tyr
65                      70                     75                    80

Leu Gln Met Asn Ser Leu Arg Ala Glu Asp Thr Ala Leu Tyr Tyr Cys
                 85                      90                     95

Ala Arg Gly Arg Tyr Ser Asp Val Trp Gly Gln Gly Thr Thr Val Thr
                100                     105                    110

Val Ser Ser
         115

<210> SEQ ID NO 103
<211> LENGTH: 345
<212> TYPE: DNA
<213> ORGANISM: Artificial Sequence
<220> FEATURE:
<223> OTHER INFORMATION: A21-4B04 heavy

<400> SEQUENCE: 103
gaagtgcagc tggtcgagag tgggggaggc ttggtacaac ctggaagatc ccttagactc    60
tcttgcgcag caagcgggtt cacctttgac gcctatggga tgcactgggt gagacaggct   120
ccagggaagg gtctggagtg ggtgtctggc atttcatatg atgctggtaa catagcgtac   180
gctgactctg tgagaggcag attcactatc tccagagata cgccaaaaaa cagcttatac   240
ctgcagatga attcactgag agccgaggac acagccctgt actattgtgc tagaggaaga   300
tattcggatg tgtggggcca gggaactaca gttaccgtct cctca               345

<210> SEQ ID NO 104
<211> LENGTH: 115
<212> TYPE: PRT
<213> ORGANISM: Artificial Sequence
<220> FEATURE:
<223> OTHER INFORMATION: A21-4B04 heavy

<400> SEQUENCE: 104

Glu Val Gln Leu Val Glu Ser Gly Gly Gly Leu Val Gln Pro Gly Arg
1               5                       10                      15

Ser Leu Arg Leu Ser Cys Ala Ala Ser Gly Phe Thr Phe Asp Ala Tyr
                 20                      25                     30

Gly Met His Trp Val Arg Gln Ala Pro Gly Lys Gly Leu Glu Trp Val
         35                      40                     45

Ser Gly Ile Ser Tyr Asp Ala Gly Asn Ile Ala Tyr Ala Asp Ser Val
         50                      55                     60

Arg Gly Arg Phe Thr Ile Ser Arg Asp Asn Ala Lys Asn Ser Leu Tyr
65                      70                     75                    80

Leu Gln Met Asn Ser Leu Arg Ala Glu Asp Thr Ala Leu Tyr Tyr Cys
                 85                      90                     95

Ala Arg Gly Arg Tyr Ser Asp Val Trp Gly Gln Gly Thr Thr Val Thr
                100                     105                    110

Val Ser Ser
         115

<210> SEQ ID NO 105
<211> LENGTH: 345

```
<212> TYPE: DNA
<213> ORGANISM: Artificial Sequence
<220> FEATURE:
<223> OTHER INFORMATION: A23-4C12 heavy

<400> SEQUENCE: 105
gaagtgcagc tggtcgagag tgggggaggc ttggtacaac ctggaagatc ccttagactc     60
tcttgcgcag caagcgggtt cacctttgac gcatatggga tgaactgggt gagacaggct    120
ccagggaagg gtctggagtg ggtgtctggc gtttcatata attctggtaa caaagcgtac    180
gctgactctg tgagaggcag attcactatc tccagagata cgccaaaaa cagcttatac     240 ctgcagatga attcactgag agccgaggac acagccctgt actattgtgc tagaggaaga    300
tattcggatg tgtggggcca gggaactaca gttaccgtct cctca                    345

<210> SEQ ID NO 106
<211> LENGTH: 115
<212> TYPE: PRT
<213> ORGANISM: Artificial Sequence
<220> FEATURE:
<223> OTHER INFORMATION: A23-4C12 heavy

<400> SEQUENCE: 106

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
            20                  25                  30

Gly Met Asn Trp Val Arg Gln Ala Pro Gly Lys Gly Leu Glu Trp Val
        35                  40                  45

Ser Gly Val Ser Tyr Asn Ser Gly Asn Lys Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115

<210> SEQ ID NO 107
<211> LENGTH: 345
<212> TYPE: DNA
<213> ORGANISM: Artificial Sequence
<220> FEATURE:
<223> OTHER INFORMATION: A21-4G06 heavy

<400> SEQUENCE: 107
gaagtgcagc tggtcgagag tgggggaggc ttggtacaac ctggaagatc ccttagactc     60
tcttgcgcag caagcgggtt cacctttgac acatatggga tgaactgggt gagacaggct    120
ccagggaagg gtctggagtg ggtgtctggc atttcatata atgctggtac caaagcgtac    180
gctgactctg tgagaggcag attcactatc tccagagata cgccaaaaa cagcttatac     240 ctgcagatga attcactgag agccgaggac acagccctgt actattgtgc tagaggaaga    300
tattcggatg tgtggggcca gggaactaca gttaccgtct cctca                    345

<210> SEQ ID NO 108
<211> LENGTH: 115
<212> TYPE: PRT
```

<213> ORGANISM: Artificial Sequence
<220> FEATURE:
<223> OTHER INFORMATION: A21-4G06 heavy

<400> SEQUENCE: 108

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Arg |
| 1 | | | | 5 | | | | | 10 | | | | | 15 | |
| Ser | Leu | Arg | Leu | Ser | Cys | Ala | Ala | Ser | Gly | Phe | Thr | Phe | Asp | Thr | Tyr |
| | | | 20 | | | | | 25 | | | | | 30 | | |
| Gly | Met | Asn | Trp | Val | Arg | Gln | Ala | Pro | Gly | Lys | Gly | Leu | Glu | Trp | Val |
| | | 35 | | | | | 40 | | | | | 45 | | | |
| Ser | Gly | Ile | Ser | Tyr | Asn | Ala | Gly | Thr | Lys | Ala | Tyr | Ala | Asp | Ser | Val |
| | 50 | | | | | 55 | | | | | 60 | | | | |
| Arg | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Leu | Tyr | Tyr | Cys |
| | | | | 85 | | | | | 90 | | | | | 95 | |
| Ala | Arg | Gly | Arg | Tyr | Ser | Asp | Val | Trp | Gly | Gln | Gly | Thr | Thr | Val | Thr |
| | | | 100 | | | | | 105 | | | | | 110 | | |
| Val | Ser | Ser | | | | | | | | | | | | | |
| | | 115 | | | | | | | | | | | | | |

<210> SEQ ID NO 109
<211> LENGTH: 345
<212> TYPE: DNA
<213> ORGANISM: Artificial Sequence
<220> FEATURE:
<223> OTHER INFORMATION: A23-3E04 heavy

<400> SEQUENCE: 109

```
gaagtgcagc tggtcgagag tgggggaggc ttggtacaac ctggaagatc ccttagactc      60
tcttgcgcag caagcgggtt cacctttgac aaatatggga tgcactgggt gagacaggct     120
ccagggaagg gtctggagtg gtgtctggc atttcatata atgctggtac cacagcgtac     180
gctgactctg tgaaaggcag attcactatc tccagagata cgccaaaaa cagcttatac     240
ctgcagatga attcactgag agccgaggac acagccctgt actattgtgc tagaggaaga    300
tattcggatg tgtggggcca gggaactaca gttaccgtct cctca                     345
```

<210> SEQ ID NO 110
<211> LENGTH: 115
<212> TYPE: PRT
<213> ORGANISM: Artificial Sequence
<220> FEATURE:
<223> OTHER INFORMATION: A23-3E04 heavy

<400> SEQUENCE: 110

| | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Arg |
| 1 | | | | 5 | | | | | 10 | | | | | 15 | |
| Ser | Leu | Arg | Leu | Ser | Cys | Ala | Ala | Ser | Gly | Phe | Thr | Phe | Asp | Lys | Tyr |
| | | | 20 | | | | | 25 | | | | | 30 | | |
| Gly | Met | His | Trp | Val | Arg | Gln | Ala | Pro | Gly | Lys | Gly | Leu | Glu | Trp | Val |
| | | 35 | | | | | 40 | | | | | 45 | | | |
| Ser | Gly | Ile | Ser | Tyr | Asn | Ala | Gly | Thr | Thr | Ala | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Leu | Tyr | Tyr | Cys |
| | | | | 85 | | | | | 90 | | | | | 95 | |

Ala Arg Gly Arg Tyr Ser Asp Val Trp Gly Gln Gly Thr Thr Val Thr
            100                 105                 110

Val Ser Ser
        115

<210> SEQ ID NO 111
<211> LENGTH: 345
<212> TYPE: DNA
<213> ORGANISM: Artificial Sequence
<220> FEATURE:
<223> OTHER INFORMATION: A24-1C09 heavy

<400> SEQUENCE: 111
gaagtgcagc tggtcgagag tgggggaggc ttggtacaac ctggaagatc ccttagactc      60
tcttgcgcag caagcgggtt cacctttgac gcatatggga tgaactgggt gagacaggct     120
ccagggaagg gtctggagtg ggtgtctggc atttcatata atggtggtaa caaagcgtac     180
gctgactctg tgagaggcag attcactatc tccagagata cgccaaaaa cagcttatac      240 ctgcagatga attcactgag agccgaggac acagccctgt actattgtgc tagaggaaga     300
tattcggatg tgtggggcca gggaactaca gttaccgtct cctca                     345

<210> SEQ ID NO 112
<211> LENGTH: 115
<212> TYPE: PRT
<213> ORGANISM: Artificial Sequence
<220> FEATURE:
<223> OTHER INFORMATION: A24-1C09 heavy

<400> SEQUENCE: 112

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
            20                  25                  30

Gly Met Asn Trp Val Arg Gln Ala Pro Gly Lys Gly Leu Glu Trp Val
        35                  40                  45

Ser Gly Ile Ser Tyr Asn Gly Gly Asn Lys Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115

<210> SEQ ID NO 113
<211> LENGTH: 345
<212> TYPE: DNA
<213> ORGANISM: Artificial Sequence
<220> FEATURE:
<223> OTHER INFORMATION: A24-1C04 heavy

<400> SEQUENCE: 113
gaagtgcagc tggtcgagag tgggggaggc ttggtacaac ctggaagatc ccttagactc      60
tcttgcgcag caagcgggtt cacctttgac ggatatggga tgcactgggt gagacaggct     120
ccagggaagg gtctggagtg ggtgtctggc atttcatata attctggtag cacagcgtac     180

```
gctgactctg tgagaggcag attcactatc tccagagata cgccaaaaa cagcttatac    240 ctgcagatga attcactgag agccgaggac acagccctgt actattgtgc tagaggaaga    300
tattcggatg tgtggggcca gggaactaca gttaccgtct cctca                   345
```

<210> SEQ ID NO 114
<211> LENGTH: 115
<212> TYPE: PRT
<213> ORGANISM: Artificial Sequence
<220> FEATURE:
<223> OTHER INFORMATION: A24-1C04 heavy

<400> SEQUENCE: 114

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Gly Tyr
            20                  25                  30

Gly Met His Trp Val Arg Gln Ala Pro Gly Lys Gly Leu Glu Trp Val
        35                  40                  45

Ser Gly Ile Ser Tyr Asn Ser Gly Ser Thr Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115
```

<210> SEQ ID NO 115
<211> LENGTH: 345
<212> TYPE: DNA
<213> ORGANISM: Artificial Sequence
<220> FEATURE:
<223> OTHER INFORMATION: A25-1H10 heavy

<400> SEQUENCE: 115

```
gaagtgcagc tggtcgagag tgggggaggc ttggtacaac ctggaagatc ccttagactc    60
tcttgcgcag caagcgggtt cacctttgac gcctatggga tgcactgggt gagacaggct    120
ccagggaagg gtctggagtg gtgtctggc gtttcatata atgctggtac cacagcgtac    180
gctgactctg tgagaggcag attcactatc tccagagata cgccaaaaa cagcttatac    240 ctgcagatga attcactgag agccgaggac acagccctgt actattgtgc tagaggaaga    300
tattcggatg tgtggggcca gggaactaca gttaccgtct cctca                   345
```

<210> SEQ ID NO 116
<211> LENGTH: 115
<212> TYPE: PRT
<213> ORGANISM: Artificial Sequence
<220> FEATURE:
<223> OTHER INFORMATION: A25-1H10 heavy

<400> SEQUENCE: 116

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
            20                  25                  30

Gly Met His Trp Val Arg Gln Ala Pro Gly Lys Gly Leu Glu Trp Val
```

```
                35                  40                  45
Ser Gly Val Ser Tyr Asn Ala Gly Thr Thr Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115

<210> SEQ ID NO 117
<211> LENGTH: 345
<212> TYPE: DNA
<213> ORGANISM: Artificial Sequence
<220> FEATURE:
<223> OTHER INFORMATION: A21-4D08 heavy

<400> SEQUENCE: 117
gaagtgcagc tggtcgagag tgggggaggc ttggtacaac ctggaagatc ccttagactc      60
tcttgcgcag caagcgggtt cacctttgac acatatggga tgcactgggt gagacaggct     120
ccagggaagg gtctggagtg ggtgtctggc gtttcatata attctggtaa caaagcgtac     180
gctgactctg tgaaaggcag attcactatc tccagagata cgccaaaaa cagcttatac      240 ctgcagatga attcactgag agccgaggac acagccctgt actattgtgc tagaggaaga     300
tattcggatg tgtggggcca gggaactaca gttaccgtct cctca                     345

<210> SEQ ID NO 118
<211> LENGTH: 115
<212> TYPE: PRT
<213> ORGANISM: Artificial Sequence
<220> FEATURE:
<223> OTHER INFORMATION: A21-4D08 heavy

<400> SEQUENCE: 118

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Thr Tyr
            20                  25                  30

Gly Met His Trp Val Arg Gln Ala Pro Gly Lys Gly Leu Glu Trp Val
        35                  40                  45

Ser Gly Val Ser Tyr Asn Ser Gly Asn Lys Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115

<210> SEQ ID NO 119
<211> LENGTH: 345
<212> TYPE: DNA
<213> ORGANISM: Artificial Sequence
<220> FEATURE:
```

<223> OTHER INFORMATION: A24-1D08 heavy

<400> SEQUENCE: 119

```
gaagtgcagc tggtcgagag tgggggaggc ttggtacaac ctggaagatc ccttagactc    60
tcttgcgcag caagcgggtt cacctttgac aactatggga tgcactgggt gagacaggct   120
ccagggaagg gtctggagtg ggtgtctggc atttcatata attctggtaa cacagggtac   180
gctgactctg tgagaggcag attcactatc tccagagata cgccaaaaa cagcttatac    240
ctgcagatga attcactgag agccgaggac acagccctgt actattgtgc tagaggaaga   300
tattcggatg tgtggggcca gggaactaca gttaccgtct cctca                   345
```

<210> SEQ ID NO 120
<211> LENGTH: 115
<212> TYPE: PRT
<213> ORGANISM: Artificial Sequence
<220> FEATURE:
<223> OTHER INFORMATION: A24-1D08 heavy

<400> SEQUENCE: 120

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asn Tyr
            20                  25                  30

Gly Met His Trp Val Arg Gln Ala Pro Gly Lys Gly Leu Glu Trp Val
        35                  40                  45

Ser Gly Ile Ser Tyr Asn Ser Gly Asn Thr Gly Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115
```

<210> SEQ ID NO 121
<211> LENGTH: 345
<212> TYPE: DNA
<213> ORGANISM: Artificial Sequence
<220> FEATURE:
<223> OTHER INFORMATION: A24-1A08 heavy

<400> SEQUENCE: 121

```
gaagtgcagc tggtcgagag tgggggaggc ttggtacaac ctggaagatc ccttagactc    60
tcttgcgcag caagcgggtt cacctttgac gcatatggga tgcactgggt gagacaggct   120
ccagggaagg gtctggagtg ggtgtctggc atttcatatg atgctggtaa cacagcgtac   180
gctgactctg tgagaggcag attcactatc tccagagata cgccaaaaa cagcttatac    240
ctgcagatga attcactgag agccgaggac acagccctgt actattgtgc tagaggaaga   300
tattcggatg tgtggggcca gggaactaca gttaccgtct cctca                   345
```

<210> SEQ ID NO 122
<211> LENGTH: 115
<212> TYPE: PRT
<213> ORGANISM: Artificial Sequence
<220> FEATURE:
<223> OTHER INFORMATION: A24-1A08 heavy

<400> SEQUENCE: 122

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
            20                  25                  30

Gly Met His Trp Val Arg Gln Ala Pro Gly Lys Gly Leu Glu Trp Val
        35                  40                  45

Ser Gly Ile Ser Tyr Asp Ala Gly Asn Thr Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
        115

<210> SEQ ID NO 123
<211> LENGTH: 345
<212> TYPE: DNA
<213> ORGANISM: Artificial Sequence
<220> FEATURE:
<223> OTHER INFORMATION: A21-4A07 heavy

<400> SEQUENCE: 123
gaagtgcagc tggtcgagag tgggggaggc ttggtacaac ctggaagatc ccttagactc      60
tcttgcgcag caagcgggtt cacctttgac acctatggga tgcactgggt gagacaggct     120
ccagggaagg gtctggagtg ggtgtctggc gtttcatata attctggtag caaagcgtac     180
gctgactctg tgaaaggcag attcactatc tccagagata cgccaaaaa cagcttatac      240
ctgcagatga attcactgag agccgaggac acagccctgt actattgtgc tagaggaaga     300
tattcggatg tgtggggcca gggaactaca gttaccgtct cctca                     345

<210> SEQ ID NO 124
<211> LENGTH: 115
<212> TYPE: PRT
<213> ORGANISM: Artificial Sequence
<220> FEATURE:
<223> OTHER INFORMATION: A21-4A07 heavy

<400> SEQUENCE: 124

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Thr Tyr
            20                  25                  30

Gly Met His Trp Val Arg Gln Ala Pro Gly Lys Gly Leu Glu Trp Val
        35                  40                  45

Ser Gly Val Ser Tyr Asn Ser Gly Ser Lys Ala Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Arg Tyr Ser Asp Val Trp Gly Gln Gly Thr Thr Val Thr
            100                 105                 110

Val Ser Ser
    115

<210> SEQ ID NO 125
<211> LENGTH: 345
<212> TYPE: DNA
<213> ORGANISM: Artificial Sequence
<220> FEATURE:
<223> OTHER INFORMATION: A24-1B09 heavy

<400> SEQUENCE: 125
gaagtgcagc tggtcgagag tgggggaggc ttggtacaac ctggaagatc ccttagactc    60
tcttgcgcag caagcgggtt cacctttgac agatatggga tgcactgggt gagacaggct   120
ccagggaagg gtctgagtg gtgtctggc gtttcatatg atggtggtac cacagcgtac     180
gctgactctg tgagaggcag attcactatc tccagagata cgccaaaaa cagcttatac    240 ctgcagatga attcactgag agccgaggac acagccctgt actattgtgc tagaggaaga   300
tattcggatg tgtggggcca gggaactaca gttaccgtct cctca                   345

<210> SEQ ID NO 126
<211> LENGTH: 115
<212> TYPE: PRT
<213> ORGANISM: Artificial Sequence
<220> FEATURE:
<223> OTHER INFORMATION: A24-1B09 heavy

<400> SEQUENCE: 126

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Arg Tyr
            20                  25                  30

Gly Met His Trp Val Arg Gln Ala Pro Gly Lys Gly Leu Glu Trp Val
        35                  40                  45

Ser Gly Val Ser Tyr Asp Gly Gly Thr Thr Ala Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Arg Gly Arg Tyr Ser Asp Val Trp Gly Gln Gly Thr Thr Val Thr
        100                 105                 110

Val Ser Ser
    115

<210> SEQ ID NO 127
<211> LENGTH: 345
<212> TYPE: DNA
<213> ORGANISM: Artificial Sequence
<220> FEATURE:
<223> OTHER INFORMATION: A24-1E07 heavy

<400> SEQUENCE: 127
gaagtgcagc tggtcgagag tgggggaggc ttggtacaac ctggaagatc ccttagactc    60
tcttgcgcag caagcgggtt cacctttgac gaatatggga tgcactgggt gagacaggct   120
ccagggaagg gtctgagtg gtgtctggc atttcatatg atgctggtag cacagcgtac     180
gctgactctg tgagaggcag attcactatc tccagagata cgccaaaaa cagcttatac    240 ctgcagatga attcactgag agccgaggac acagccctgt actattgtgc tagaggaaga   300

```
tattcggatg tgtggggcca gggaactaca gttaccgtct cctca              345
```

```
<210> SEQ ID NO 128
<211> LENGTH: 115
<212> TYPE: PRT
<213> ORGANISM: Artificial Sequence
<220> FEATURE:
<223> OTHER INFORMATION: A24-1E07 heavy

<400> SEQUENCE: 128
```

| Glu | Val | Gln | Leu | Val | Glu | Ser | Gly | Gly | Gly | Leu | Val | Gln | Pro | Gly | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Ala | Ala | Ser | Gly | Phe | Thr | Phe | Asp | Glu | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Met | His | Trp | Val | Arg | Gln | Ala | Pro | Gly | Lys | Gly | Leu | Glu | Trp | Val |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ser | Gly | Ile | Ser | Tyr | Asp | Ala | Gly | Ser | Thr | Ala | Tyr | Ala | Asp | Ser | Val |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Arg | Gly | Arg | Phe | Thr | Ile | Ser | Arg | Asp | Asn | Ala | Lys | Asn | Ser | Leu | Tyr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Leu | Gln | Met | Asn | Ser | Leu | Arg | Ala | Glu | Asp | Thr | Ala | Leu | Tyr | Tyr | Cys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ala | Arg | Gly | Arg | Tyr | Ser | Asp | Val | Trp | Gly | Gln | Gly | Thr | Thr | Val | Thr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Val | Ser | Ser |
|-----|-----|-----|
|     |     | 115 |

```
<210> SEQ ID NO 129
<211> LENGTH: 357
<212> TYPE: DNA
<213> ORGANISM: Artificial Sequence
<220> FEATURE:
<223> OTHER INFORMATION: H21-3A07 heavy

<400> SEQUENCE: 129
caagtgcagc tggtggagtc tggcggaggt gtggtccaac ccggtaagtc tctgagactc    60
tcctgcgcag cctctggctt acattcagt aactactaca tgaattgggt cagacaggct    120
ccaggaaaag gcttggagtg ggtggccact gtttcttacg atagcggcaa caaatactat   180
gcagattctg tgaagggcg attcaccatt tccagagaca actctaagaa cactctttat    240
ctgcagatga atagcctgag agctgaagac actgccgttt actattgtgc gagggggagt   300
tgaagacggg atgcttttga cgtgtggggc cagggcacaa tggtcaccgt atcatca     357
```

```
<210> SEQ ID NO 130
<211> LENGTH: 118
<212> TYPE: PRT
<213> ORGANISM: Artificial Sequence
<220> FEATURE:
<223> OTHER INFORMATION: H21-3A07 heavy

<400> SEQUENCE: 130
```

| Gln | Val | Gln | Leu | Val | Glu | Ser | Gly | Gly | Gly | Val | Val | Gln | Pro | Gly | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Ala | Ala | Ser | Gly | Phe | Thr | Phe | Ser | Asn | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Met | Asn | Trp | Val | Arg | Gln | Ala | Pro | Gly | Lys | Gly | Leu | Glu | Trp | Val |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Thr | Val | Ser | Tyr | Asp | Ser | Gly | Asn | Lys | Tyr | Tyr | Ala | Asp | Ser | Val | Lys |
|-----|-----|-----|-----|-----|-----|-----|-----|-----|-----|-----|-----|-----|-----|-----|-----|

```
                50                  55                  60
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Ser Arg Arg Asp Ala Phe Asp Val Trp Gly Gln Gly Thr Met
                100                 105                 110

Val Thr Val Ser Ser Ala
            115

<210> SEQ ID NO 131
<211> LENGTH: 357
<212> TYPE: DNA
<213> ORGANISM: Artificial Sequence
<220> FEATURE:
<223> OTHER INFORMATION: H21-4D11 heavy

<400> SEQUENCE: 131
caagtgcagc tggtggagtc tggcggaggt gtggtccaac tggaaggtc tctgagactc    60 tcctgcgcag cctctggatt tacattcagt aactacgcca tgaattgggt cagacaggct   120
ccaggaaaag gcttggagtg ggtggccatt atttcttacg atagcagcag caaatactat   180
gcagattctg tgaaagggcg attcaccatt ccagagaca actctaagaa cactctttat    240
ctgcagatga atagcctgag agctgaagac actgccgttt actattgtgc gagggggagt   300
gggaagcggg atgcttttga cgtgtggggc cagggcacaa tggtcaccgt atcatca     357

<210> SEQ ID NO 132
<211> LENGTH: 119
<212> TYPE: PRT
<213> ORGANISM: Artificial Sequence
<220> FEATURE:
<223> OTHER INFORMATION: H21-4D11 heavy

<400> SEQUENCE: 132

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
                20                  25                  30

Ala Met Asn Trp Val Arg Gln Ala Pro Gly Lys Gly Leu Glu Trp Val
             35                  40                  45

Ile Ile Ser Tyr Asp Ser Ser Lys Tyr Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Ser Gly Lys Arg Asp Ala Phe Asp Val Trp Gly Gln Gly Thr
                100                 105                 110

Met Val Thr Val Ser Ser Ala
            115

<210> SEQ ID NO 133
<211> LENGTH: 357
<212> TYPE: DNA
<213> ORGANISM: Artificial Sequence
<220> FEATURE:
<223> OTHER INFORMATION: H21-3C11 heavy

<400> SEQUENCE: 133
```

```
caagtgcagc tggtggagtc tggcggaggt gtggtccaac ctggaaggtc tctgagactc    60
tcctgcgcag cctctggctt tacattcagt aactacgcca tgcattgggt cagacaggct   120
ccaggaaaag gcttggagtg ggtggccgtt gtttcttacg atggcggcaa catatactat   180
gcagattctg tgaaagggcg attcaccatt ccagacaca actctaagaa cactcttat    240 ctgcagatga atagcctgag agctgaagac actgccgttt actattgtgc gaggggagt   300 gggcggcggg atgcttttga cgtgtggggc cagggcacaa tggtcaccgt atcatca     357
```

<210> SEQ ID NO 134
<211> LENGTH: 119
<212> TYPE: PRT
<213> ORGANISM: Artificial Sequence
<220> FEATURE:
<223> OTHER INFORMATION: H21-3C11 heavy

<400> SEQUENCE: 134

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Val Val Ser Tyr Asp Gly Gly Asn Ile Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Gly Arg Arg Asp Ala Phe Asp Val Trp Gly Gln Gly Thr
            100                 105                 110

Met Val Thr Val Ser Ser Ala
        115
```

<210> SEQ ID NO 135
<211> LENGTH: 357
<212> TYPE: DNA
<213> ORGANISM: Artificial Sequence
<220> FEATURE:
<223> OTHER INFORMATION: H21-3A09 heavy

<400> SEQUENCE: 135

```
caagtgcagc tggtggagtc tggcggaggt gtggtccaac ctggaaggtc tctgagactc    60
tcctgcgcag cctctggctt tacattcagt aactacgaca ttcattgggt cagacaggct   120
ccaggaaaaa gcttggagtg ggtggccgtt gtttcttacg atggcagcaa cacatactat   180
gcagattctg tgaaagggcg attcaccatt ccagacaca actctaagaa cactcttat    240 ctgcagatga atagcctgag agctgaagac actgccgttt actattgtgc gaggggagt   300 gggaagcggg atgcttttga cgtgtggggc cagggcacaa tggtcaccgt atcatca     357
```

<210> SEQ ID NO 136
<211> LENGTH: 119
<212> TYPE: PRT
<213> ORGANISM: Artificial Sequence
<220> FEATURE:
<223> OTHER INFORMATION: H21-3A09 heavy

<400> SEQUENCE: 136

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Asp Ile His Trp Val Arg Gln Ala Pro Gly Lys Gly Leu Glu Trp Val
        35                  40                  45

Val Val Ser Tyr Asp Gly Ser Asn Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Gly Lys Arg Asp Ala Phe Asp Val Trp Gly Gln Gly Thr
            100                 105                 110

Met Val Thr Val Ser Ser Ala
            115

<210> SEQ ID NO 137
<211> LENGTH: 358
<212> TYPE: DNA
<213> ORGANISM: Artificial Sequence
<220> FEATURE:
<223> OTHER INFORMATION: H21-4H04 heavy

<400> SEQUENCE: 137
caagtgcagc tggtggagtc tggcggaggt gtggtccaac ccgtttaagt ctctgagact     60
ctcctgcgca gcctctggct ttacacttag tagctacgcc attcattggg tcagacaggc    120
tccaggaaaa ggcttggagt gggtggccgt tgtttcttac gatggcggca gcaaatacta    180
tgcagattct gtgaaaggc gattcaccat ttccagagac aactctaaga acactcttta    240
tctgcagatg aatagcctga gctgaagaga cactgccgtt tactattgtg cgaggggag    300
tgggaggcgg gatgcttttg acgtgtgggg ccagggcaca atggtcaccg tatcatca     358

<210> SEQ ID NO 138
<211> LENGTH: 119
<212> TYPE: PRT
<213> ORGANISM: Artificial Sequence
<220> FEATURE:
<223> OTHER INFORMATION: H21-4H04 heavy

<400> SEQUENCE: 138

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Ile His Trp Val Arg Gln Ala Pro Gly Lys Gly Leu Glu Trp Val
        35                  40                  45

Val Val Ser Tyr Asp Gly Gly Ser Lys Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Gly Arg Arg Asp Ala Phe Asp Val Trp Gly Gln Gly Thr
            100                 105                 110

Met Val Thr Val Ser Ser Ala
            115

<210> SEQ ID NO 139
<211> LENGTH: 357
<212> TYPE: DNA
<213> ORGANISM: Artificial Sequence
<220> FEATURE:
<223> OTHER INFORMATION: H23-3D08 heavy

<400> SEQUENCE: 139

```
caagtgcagc tggtggagtc tggcggaggt gtggtccaac ctggaaggtc tctgagactc      60
tcctgcgcag actctggctt tacattcagt gactacgaca tgcattgggt cagacaggct     120
ccaggaaaag gcttggagtg gtggccgtt atttcttacg atggcggcag caaatactat      180
gcagattctg tgaaagggcg attcaccatt ccagagaca actctaagaa cactctttat      240
ctgcagatga atagcctgag agctgaagac actgccgttt actattgtgc gagggggagt     300
gggcagcggg atgcttttga cgtgtggggc cagggcacaa tggtcaccgt atcatca       357
```

<210> SEQ ID NO 140
<211> LENGTH: 119
<212> TYPE: PRT
<213> ORGANISM: Artificial Sequence
<220> FEATURE:
<223> OTHER INFORMATION: H23-3D08 heavy

<400> SEQUENCE: 140

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Asp Met His Trp Val Arg Gln Ala Pro Gly Lys Gly Leu Glu Trp Val
        35                  40                  45

Val Ile Ser Tyr Asp Gly Gly Ser Lys Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Gly Gln Arg Asp Ala Phe Asp Val Trp Gly Gln Gly Thr
            100                 105                 110

Met Val Thr Val Ser Ser Ala
        115
```

<210> SEQ ID NO 141
<211> LENGTH: 357
<212> TYPE: DNA
<213> ORGANISM: Artificial Sequence
<220> FEATURE:
<223> OTHER INFORMATION: H21-4D09 heavy

<400> SEQUENCE: 141

```
caagtgcagc tggtggagtc tggcggaggt gtggtccaac ctggaaggtc tctgagactc      60
tcctgcgcag cctctggctt tacattcagt aactactaca ttaattgggt cagacaggct     120
ccaggaaaag gcttggagtg gtggccagt gtttcttacg atggcggcag catatactat      180
gcagattctg tgaaagggcg attcaccatt ccagagaca actctaagaa cactctttat      240
ctgcagatga atagcctgag agctgaagac actgccgttt actattgtgc gagggggagt     300
gggaggcggg atgcttttga cgtgtggggc cagggcacaa tggtcaccgt atcatca       357
```

<210> SEQ ID NO 142
<211> LENGTH: 119
<212> TYPE: PRT
<213> ORGANISM: Artificial Sequence
<220> FEATURE:
<223> OTHER INFORMATION: H21-4D09 heavy

<400> SEQUENCE: 142

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Tyr Ile Asn Trp Val Arg Gln Ala Pro Gly Lys Gly Leu Glu Trp Val
        35                  40                  45

Ser Val Ser Tyr Asp Gly Gly Ser Ile Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Gly Arg Arg Asp Ala Phe Asp Val Trp Gly Gln Gly Thr
            100                 105                 110

Met Val Thr Val Ser Ser Ala
        115

<210> SEQ ID NO 143
<211> LENGTH: 357
<212> TYPE: DNA
<213> ORGANISM: Artificial Sequence
<220> FEATURE:
<223> OTHER INFORMATION: H24-1D11 heavy

<400> SEQUENCE: 143
caagtgcagc tggtggagtc tggcggaggt gtggtccaac ctggaaggtc tctgagactc      60
tcctgcgcag cctctggctt acattcagt agctacgcca tgcactgggt cagacaggct     120
ccaggaaaag gcttggagtg ggtggccgtt atctcttacg atggtagcaa taagtactat     180
gcagattctg tgaaagggcg attcaccatt tccagagaca actctaagaa cactctttat     240
ctgcagatga atagcctgag agctgaagac actgccgttt actattgtgc gaggggagt     300 gggggacggg atgcttttga cgtgtgggc cagggcacaa tggtcaccgt atcatca       357

<210> SEQ ID NO 144
<211> LENGTH: 120
<212> TYPE: PRT
<213> ORGANISM: Artificial Sequence
<220> FEATURE:
<223> OTHER INFORMATION: H24-1D11 heavy

<400> SEQUENCE: 144

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                        85                  90                  95

Ala Arg Gly Ser Gly Gly Arg Asp Ala Phe Asp Val Trp Gly Gln Gly
            100                 105                 110

Thr Met Val Thr Val Ser Ser Ala
            115                 120

<210> SEQ ID NO 145
<211> LENGTH: 330
<212> TYPE: DNA
<213> ORGANISM: Artificial Sequence
<220> FEATURE:
<223> OTHER INFORMATION: HL161-1A light

<400> SEQUENCE: 145
aattttatgc tgactcagcc cgcctccgtg tctgggtctc ctggacagac gatcaccatc     60
tcctgcactg gaagcagcag cgacgttggt ggttataact atgtctcctg gtaccaacag    120
cacccaggca agccccccca actcatcatt tatgatgtca ctaagcggcc ctcaggggtt    180
tctaatcgct tctccggctc caagtctggc aactcggcct ccctgaccat ctctggactc    240
caggctgagg acgaggctga ttattactgc agctcataca gcagcagcac ttttttacgtc   300 ttcggaactg ggaccaaggt caccgtccta                                     330

<210> SEQ ID NO 146
<211> LENGTH: 110
<212> TYPE: PRT
<213> ORGANISM: Artificial Sequence
<220> FEATURE:
<223> OTHER INFORMATION: HL161-1A light

<400> SEQUENCE: 146

Asn Phe Met Leu Thr Gln Pro Ala Ser Val Ser Gly Ser Pro Gly Gln
1               5                   10                  15

Thr Ile Thr Ile Ser Cys Thr Gly Ser Ser Ser Asp Val Gly Gly Tyr
            20                  25                  30

Asn Tyr Val Ser Trp Tyr Gln Gln His Pro Gly Lys Ala Pro Gln Leu
        35                  40                  45

Ile Ile Tyr Asp Val Thr Lys Arg Pro Ser Gly Val Ser Asn Arg Phe
    50                  55                  60

Ser Gly Ser Lys Ser Gly Asn Ser Ala Ser Leu Thr Ile Ser Gly Leu
65                  70                  75                  80

Gln Ala Glu Asp Glu Ala Asp Tyr Tyr Cys Ser Ser Tyr Ser Ser Ser
                85                  90                  95

Thr Phe Tyr Val Phe Gly Thr Gly Thr Lys Val Thr Val Leu
            100                 105                 110

<210> SEQ ID NO 147
<211> LENGTH: 330
<212> TYPE: DNA
<213> ORGANISM: Artificial Sequence
<220> FEATURE:
<223> OTHER INFORMATION: HL161-2A light

<400> SEQUENCE: 147
cagctcgtgc tgactcagcc accctcaacg tctgagaccc ccgggcagag ggtcaccatc     60
tcttgttctg gaagcagctc caacatcgga agtaattatg tatactggta ccagcaactc    120
ccaggaacgg cccccaaact cctcatctat aggaataatc agcggccctc agggtccct    180
```

```
gaccgattct ctggctccaa gtctggcact tcagcctccc tggccatcag tgggctccgg    240
tccgaggatg aggctgatta ttactgtgca tcatgggatg acagcctgag tggtgtggtt    300
ttcggcggag ggaccaagct gaccgtccta                                    330
```

<210> SEQ ID NO 148
<211> LENGTH: 110
<212> TYPE: PRT
<213> ORGANISM: Artificial Sequence
<220> FEATURE:
<223> OTHER INFORMATION: HL161-2A light

<400> SEQUENCE: 148

```
Gln Leu Val Leu Thr Gln Pro Pro Ser Thr Ser Glu Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Gly Val Val Phe Gly Gly Gly Thr Lys Leu Thr Val Leu
            100                 105                 110
```

<210> SEQ ID NO 149
<211> LENGTH: 330
<212> TYPE: DNA
<213> ORGANISM: Artificial Sequence
<220> FEATURE:
<223> OTHER INFORMATION: HL161-2D light

<400> SEQUENCE: 149

```
aattttatgc tgactcagcc ccactctgtg tcggagtctc cggggaagac ggtcaccatc     60
tcctgcaccc gcagcagtgg cagcattgcc gccaactatg tgcactggta ccaacagcgc    120
ccgggcagtc cccccaccac tgtcatctat aacgataacc aaagaccctc tggagtccct    180
gatcggttct ctgggtccat cgacaggtcc tccaactctg cctccctcac catctctgga    240
ctgaagactg aggacgaggc tgactactac tgtcagtcct acgatagtac cacttatgca    300
ttcggcggag ggaccaagct gaccgtccta                                    330
```

<210> SEQ ID NO 150
<211> LENGTH: 110
<212> TYPE: PRT
<213> ORGANISM: Artificial Sequence
<220> FEATURE:
<223> OTHER INFORMATION: HL161-2D light

<400> SEQUENCE: 150

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ala Asn
            20                  25                  30

Tyr Val His Trp Tyr Gln Gln Arg Pro Gly Ser Pro Pro Thr Thr Val
        35                  40                  45
```

Ile Tyr Asn Asp Asn Gln Arg Pro Ser Gly Val Pro Asp Arg Phe Ser
 50                  55                  60

Gly Ser Ile Asp Arg Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Thr Thr Tyr Ala Phe Gly Gly Gly Thr Lys Leu Thr Val Leu
            100                 105                 110

<210> SEQ ID NO 151
<211> LENGTH: 321
<212> TYPE: DNA
<213> ORGANISM: Artificial Sequence
<220> FEATURE:
<223> OTHER INFORMATION: HL161-6C light

<400> SEQUENCE: 151
gacatccaga tgacccagtc tccatcttcc gtgtctgcat ctgtaggaga cagagtcacc        60
atcacttgtc gggcgagtca gggtatcagc aactgggtag cctggtatca gcagaaacca       120
ggcaaagccc ctaagctcct gatctatgct gcatccagtt tgcaaagtgg ggtcccatca       180
aggttcagcg gcagtggatc tgggacagac ttcactctca ccatcagcag cctgcagcct       240
gaagattttg caatttacta ttgtcaacag ggtcacagtt tcccgtacac ttttggccaa       300
gggaccaagg tggaaatcaa a                                                 321

<210> SEQ ID NO 152
<211> LENGTH: 107
<212> TYPE: PRT
<213> ORGANISM: Artificial Sequence
<220> FEATURE:
<223> OTHER INFORMATION: HL161-6C light

<400> SEQUENCE: 152

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Asn Trp
                 20                  25                  30

Val Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Ile Tyr Tyr Cys Gln Gln Gly His Ser Phe Pro Tyr
                 85                  90                  95

Thr Phe Gly Gln Gly Thr Lys Val Glu Ile Lys
            100                 105

<210> SEQ ID NO 153
<211> LENGTH: 330
<212> TYPE: DNA
<213> ORGANISM: Artificial Sequence
<220> FEATURE:
<223> OTHER INFORMATION: HL161-6C light

<400> SEQUENCE: 153
aattttatgc tgactcagcc ccactctgtg tcggagtctc cggggaagac ggtcaccatc        60
tcctgcaccc gcagcagtgg cagcattgcc gccaactatg tgcactggta ccaacagcgc       120

```
ccgggcagtc cccccaccac tgtcatctat aacgataacc aaagaccctc tggagtccct    180
gatcggttct ctgggtccat cgacaggtcc tccaactctg cctccctcac catctctgga    240
ctgaagactg aggacgaggc tgactactac tgtcagtcct acgatagtac cacttatgca    300
ttcggcggag ggaccaagct gaccgtccta                                     330
```

<210> SEQ ID NO 154
<211> LENGTH: 110
<212> TYPE: PRT
<213> ORGANISM: Artificial Sequence
<220> FEATURE:
<223> OTHER INFORMATION: HL161-6C light

<400> SEQUENCE: 154

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ala Asn
            20                  25                  30

Tyr Val His Trp Tyr Gln Gln Arg Pro Gly Ser Pro Pro Thr Thr Val
        35                  40                  45

Ile Tyr Asn Asp Asn Gln Arg Pro Ser Gly Val Pro Asp Arg Phe Ser
    50                  55                  60

Gly Ser Ile Asp Arg Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Thr Thr Tyr Ala Phe Gly Gly Gly Thr Lys Leu Thr Val Leu
            100                 105                 110
```

<210> SEQ ID NO 155
<211> LENGTH: 327
<212> TYPE: DNA
<213> ORGANISM: Artificial Sequence
<220> FEATURE:
<223> OTHER INFORMATION: HL161 10E light

<400> SEQUENCE: 155

```
tcctatgagc tgacacagcc actctcggtg tcaatgtccc caggacaaac ggccaggatc     60
acctgttctg gagatgcttt gtcaaagcaa tatgcttctt ggtaccagct gaagccaggc    120
caggcccctg tggtggtgat gtataaagac actgagaggc cctcagggat ccctgaccga    180
ttctctggct ccagctccgg gacaacagtc acgttgacca tcagtggagt ccaggcagaa    240
gacgaggctg attattactg tcaatcaata acagacaaga gtggtactga tgtgatcttc    300
ggcggaggga ccaagctgac cgtccta                                        327
```

<210> SEQ ID NO 156
<211> LENGTH: 109
<212> TYPE: PRT
<213> ORGANISM: Artificial Sequence
<220> FEATURE:
<223> OTHER INFORMATION: HL161 10E light

<400> SEQUENCE: 156

```
Ser Tyr Glu Leu Thr Gln Pro Leu Ser Val Ser Met Ser Pro Gly Gln
1               5                   10                  15

Thr Ala Arg Ile Thr Cys Ser Gly Asp Ala Leu Ser Lys Gln Tyr Ala
            20                  25                  30

Ser Trp Tyr Gln Leu Lys Pro Gly Gln Ala Pro Val Val Val Met Tyr
        35                  40                  45
```

```
Lys Asp Thr Glu Arg Pro Ser Gly Ile Pro Asp Arg Phe Ser Gly Ser
        50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ile Thr Asp Lys Ser Gly Thr
                85                  90                  95

Asp Val Ile Phe Gly Gly Gly Thr Lys Leu Thr Val Leu
            100                 105
```

<210> SEQ ID NO 157
<211> LENGTH: 330
<212> TYPE: DNA
<213> ORGANISM: Artificial Sequence
<220> FEATURE:
<223> OTHER INFORMATION: HL161-11G light

<400> SEQUENCE: 157

```
aattttatgc tgactcagcc cgcctccgtg tctgggtccc ctggacagtc gatcaccatc    60
tcctgcactg gaagcagcag cgacgttggt ggttataact atgtctcctg gtaccaacag   120
cacccaggca aagccccccca actcatcatt tatgatgtca ctaagcggcc ctcagggggtt  180 tctaatcgat tctccggctc caagtctggc aactcggcct ccctgaccat ctctggactc   240
caggctgagg acgaggctga ttattactgc agctcataca gcagcagcac ttttacgtc   300 ttcggaactg ggaccaaggt caccgtccta                                     330
```

<210> SEQ ID NO 158
<211> LENGTH: 110
<212> TYPE: PRT
<213> ORGANISM: Artificial Sequence
<220> FEATURE:
<223> OTHER INFORMATION: HL161-11G light

<400> SEQUENCE: 158

```
Asn Phe Met Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
            20                  25                  30

Asn Tyr Val Ser Trp Tyr Gln Gln His Pro Gly Lys Ala Pro Gln Leu
        35                  40                  45

Ile Ile Tyr Asp Val Thr Lys Arg Pro Ser Gly Val Ser Asn Arg Phe
    50                  55                  60

Ser Gly Ser Lys Ser Gly Asn Ser Ala Ser Leu Thr Ile Ser Gly Leu
65                  70                  75                  80

Gln Ala Glu Asp Glu Ala Asp Tyr Tyr Cys Ser Ser Tyr Ser Ser Ser
                85                  90                  95

Thr Phe Tyr Val Phe Gly Thr Gly Thr Lys Val Thr Val Leu
            100                 105                 110
```

<210> SEQ ID NO 159
<211> LENGTH: 321
<212> TYPE: DNA
<213> ORGANISM: Artificial Sequence
<220> FEATURE:
<223> OTHER INFORMATION: HL161-11H light

<400> SEQUENCE: 159

```
gacatccaga tgacccagtc tcctccacc ctgtctgcat ctgtaggaga cagagtcacc    60
atcacttgcc gggccagtca gagtattagt agccggttgg cctggtatca gcagaaacca  120
```

```
gggaaagccc ctaagctcct gatctataag gcatctagct tagaaactgg ggtcccatca    180
aggttcagcg gcagtggatc tgggacagaa ttcactctca ccatcagcag cctgcagcct    240
gatgattttg caacttacta ttgtcaacag acgaacagtt tccctctcac tttcggcgga    300
gggaccaagg tggagatcaa a                                              321
```

<210> SEQ ID NO 160
<211> LENGTH: 107
<212> TYPE: PRT
<213> ORGANISM: Artificial Sequence
<220> FEATURE:
<223> OTHER INFORMATION: HL161-11H light

<400> SEQUENCE: 160

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Arg
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Thr Asn Ser Phe Pro Leu
                85                  90                  95

Thr Phe Gly Gly Gly Thr Lys Val Glu Ile Lys
            100                 105
```

<210> SEQ ID NO 161
<211> LENGTH: 333
<212> TYPE: DNA
<213> ORGANISM: Artificial Sequence
<220> FEATURE:
<223> OTHER INFORMATION: A11-C07 light

<400> SEQUENCE: 161

```
cagtctgcac ttactcagcc agccagtgtg tctggagtc ctggacagtc gatcaccatt    60
tcctgcacgg gatcaagtag cgatgtgggt ggctataatt atgtgtcctg gtaccagcag   120
cacccaggca aggcccccaa actgatgatt tacgacgtaa caaagcgccc ctcaggggtc   180
tccaatcgct tttctggcag taaaagcgga aacacagcct ccctgactat cagcggcctc   240
caagctgaag acgaggctga ttattattgt gcttcttact ctagcaacac ttttacgtt   300 ttcggaaccg ggacaaaggt gaccgtcttg ggc                                333
```

<210> SEQ ID NO 162
<211> LENGTH: 110
<212> TYPE: PRT
<213> ORGANISM: Artificial Sequence
<220> FEATURE:
<223> OTHER INFORMATION: A11-C07 light

<400> SEQUENCE: 162

```
Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
            20                  25                  30

Asn Tyr Val Ser Trp Tyr Gln Gln His Pro Gly Lys Ala Pro Lys Leu
```

```
                    35                  40                  45
Met Ile Tyr Asp Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Ala Ser Tyr Ser Ser Asn Thr
                85                  90                  95

Phe Tyr Val Phe Gly Thr Gly Thr Lys Val Thr Val Leu Gly
            100                 105                 110

<210> SEQ ID NO 163
<211> LENGTH: 333
<212> TYPE: DNA
<213> ORGANISM: Artificial Sequence
<220> FEATURE:
<223> OTHER INFORMATION: A11-G06 light

<400> SEQUENCE: 163
cagtctgcac ttactcagcc agccagtgtg tctgggagtc ctggacagtc gatcaccatt      60
tcctgcacgg gatcaagtag cgatgtgggt ggctataatt atgtgtcctg gtaccagcag     120
cacccaggca aggccccccaa actgatgatt tacgacgtaa caaagcgccc ctcaggggtc    180
tccaatcgct tttctggcag taaaagcgga acacagcct ccctgactat cagcggcctc      240
caagctgaag acgaggctga ttattattgt ggttcttaca ataacaacac tttttacgtt    300
ttcggaaccg ggacaaaggt gaccgtcttg ggc                                  333

<210> SEQ ID NO 164
<211> LENGTH: 110
<212> TYPE: PRT
<213> ORGANISM: Artificial Sequence
<220> FEATURE:
<223> OTHER INFORMATION: A11-G06 light

<400> SEQUENCE: 164

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Gly Ser Tyr Asn Asn Asn Thr
                85                  90                  95

Phe Tyr Val Phe Gly Thr Gly Thr Lys Val Thr Val Leu Gly
            100                 105                 110

<210> SEQ ID NO 165
<211> LENGTH: 333
<212> TYPE: DNA
<213> ORGANISM: Artificial Sequence
<220> FEATURE:
<223> OTHER INFORMATION: A12-C09 light

<400> SEQUENCE: 165
cagtctgcac ttactcagcc agccagtgtg tctgggagtc ctggacagtc gatcaccatt      60
```

```
tcctgcacgg gatcaagtag cgatgtgggt ggctataatt atgtgtcctg gtaccagcag      120
cacccaggca aggcccccaa actgatgatt tacgacgtaa caaagcgccc ctcaggggtc      180
tccaatcgct tttctggcag taaaagcgga aacacagcct ccctgactat cagcggcctc      240
caagctgaag acgaggctga ttattattgt ggttcttact ctagcaacac ttttttacgtt      300 ttcggaaccg ggacaaaggt gaccgtcttg ggc                                    333
```

```
<210> SEQ ID NO 166
<211> LENGTH: 110
<212> TYPE: PRT
<213> ORGANISM: Artificial Sequence
<220> FEATURE:
<223> OTHER INFORMATION: A12-C09 light

<400> SEQUENCE: 166
```

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Gly Ser Tyr Ser Ser Asn Thr
                85                  90                  95

Phe Tyr Val Phe Gly Thr Gly Thr Lys Val Thr Val Leu Gly
            100                 105                 110

```
<210> SEQ ID NO 167
<211> LENGTH: 333
<212> TYPE: DNA
<213> ORGANISM: Artificial Sequence
<220> FEATURE:
<223> OTHER INFORMATION: A12-D55 light

<400> SEQUENCE: 167
cagtctgcac ttactcagcc agccagtgcg tctgggagtc ctggacagtc gatcaccatt      60
tcctgcacgg gatcaagtag cgatgtgggt ggctataatt atgtgtcctg gtaccagcag      120
cacccaggca aggcccccaa actgatgatt tacgacgtaa caaagcgccc ctcaggggtc      180
tccaatcgct tttctggcag taaaagcgga aacacagcct ccctgactat cagcggcctc      240
caagctgaag acgaggctga ttattattgt ggttcttaca atagcaacac ttttttacgtt      300 ttcggaaccg ggacaaaggt gaccgtcttg ggc                                    333
```

```
<210> SEQ ID NO 168
<211> LENGTH: 110
<212> TYPE: PRT
<213> ORGANISM: Artificial Sequence
<220> FEATURE:
<223> OTHER INFORMATION: A12-D55 light

<400> SEQUENCE: 168
```

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Gly Ser Tyr Asn Asn Ser Thr
                 85                  90                  95

Phe Tyr Val Phe Gly Thr Gly Lys Val Thr Val Leu Gly
                100                 105                 110

<210> SEQ ID NO 169
<211> LENGTH: 333
<212> TYPE: DNA
<213> ORGANISM: Artificial Sequence
<220> FEATURE:
<223> OTHER INFORMATION: A12-E01 light

<400> SEQUENCE: 169
cagtctgcac ttactcagcc agccagtgtg tctggagtc ctggacagtc gatcaccatt      60
tcctgcacgg gatcaagtag cgatgtgggt ggctataatt atgtgtcctg gtaccagcag     120
cacccaggca aggccccaa actgatgatt tacgacgtaa caaagcgccc ctcagggtc      180 tccaatcgct tttctggcag taaaagcgga aacacagcct ccctgactat cagcggcctc     240
caagctgaag acgaggctga ttattattgt tcttcttact ctaacaacac ttttacgtt     300 ttcggaaccg ggacaaaggt gaccgtcttg ggc                                  333

<210> SEQ ID NO 170
<211> LENGTH: 110
<212> TYPE: PRT
<213> ORGANISM: Artificial Sequence
<220> FEATURE:
<223> OTHER INFORMATION: A12-E01 light

<400> SEQUENCE: 170

Gln Ser Ala Leu Thr Gln Pro Ala Ser Val Ser Gly Ser Pro Gly Gln
 1               5                  10                  15

Ser Ile Thr Ile Ser Cys Thr Gly Ser Ser Ser Asp Val Gly Gly Tyr
                 20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Gly Ser Tyr Ser Asn Asn Asn
                 85                  90                  95

Phe Tyr Val Phe Gly Thr Gly Lys Val Thr Val Leu Gly
                100                 105                 110

<210> SEQ ID NO 171
<211> LENGTH: 333
<212> TYPE: DNA
<213> ORGANISM: Artificial Sequence
<220> FEATURE:
<223> OTHER INFORMATION: A12-E04 light

<400> SEQUENCE: 171
cagtctgcac ttactcagcc agccagtgtg tctggagtc ctggacagtc gatcaccatt      60

```
tcctgcacgg gatcaagtag cgatgtgggt ggctataatt atgtgtcctg gtaccagcag      120
cacccaggca aggcccccaa actgatgatt tacgacgtaa caaagcgccc ctcaggggtc      180
tccaatcgct tttctggcag taaaagcgga acacagcct ccctgactat cagcggcctc      240
caagctgaag acgaggctga ttattattgt gcttcttaca ataactccac ttttttacgtt    300 ttcggaaccg ggacaaaggt gaccgtcttg ggc                                   333
```

```
<210> SEQ ID NO 172
<211> LENGTH: 110
<212> TYPE: PRT
<213> ORGANISM: Artificial Sequence
<220> FEATURE:
<223> OTHER INFORMATION: A12-E04 light

<400> SEQUENCE: 172
```

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Gly Ser Tyr Ser Asn Ser Asn
                85                  90                  95

Phe Tyr Val Phe Gly Thr Gly Thr Lys Val Thr Val Leu Gly
            100                 105                 110

```
<210> SEQ ID NO 173
<211> LENGTH: 333
<212> TYPE: DNA
<213> ORGANISM: Artificial Sequence
<220> FEATURE:
<223> OTHER INFORMATION: A12-F02 light

<400> SEQUENCE: 173
```

```
cagtctgcac ttactcagcc agccagtgtg tctgggagtc ctggacagtc gatcaccatt      60
tcctgcacgg gatcaagtag cgatgtgggt ggctataatt atgtgtcctg gtaccagcag     120
cacccaggca aggcccccaa actgatgatt tacgacgtaa caaagcgccc ctcaggggtc     180
tccaatcgct tttctggcag taaaagcgga acacagcct ccctgactat cagcggcctc     240
caagctgaag acgaggctga ttattattgt ggttcttacg atagcaacac ttttttacgtt    300 ttcggaaccg ggacaaaggt gaccgtcttg ggc                                   333
```

```
<210> SEQ ID NO 174
<211> LENGTH: 110
<212> TYPE: PRT
<213> ORGANISM: Artificial Sequence
<220> FEATURE:
<223> OTHER INFORMATION: A12-F02 light

<400> SEQUENCE: 174
```

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Gly Ser Tyr Asp Ser Asn Thr
                 85                  90                  95

Phe Tyr Val Phe Gly Thr Gly Thr Lys Val Thr Val Leu Gly
            100                 105                 110

<210> SEQ ID NO 175
<211> LENGTH: 333
<212> TYPE: DNA
<213> ORGANISM: Artificial Sequence
<220> FEATURE:
<223> OTHER INFORMATION: A12-H04 light

<400> SEQUENCE: 175
cagtctgcac ttactcagcc agccagtgtg tctgggagtc ctggacagtc gatcaccatt      60
tcctgcacgg gatcaagtag cgatgtgggt ggctataatt atgtgtcctg gtaccagcag     120
cacccaggca aggcccccaa actgatgatt tacgacgtaa caaagcgccc ctcaggggtc     180
tccaatcgct tttctggcag taaaagcgga aacacagcct cccctgactat cagcggcctc     240 caggctgaag acgaggctga ttattattgt ggtgcttact ctaacaccaa ttttttacgtt     300 ttcggaaccg ggacaaaggt gaccgtcttg ggc                                  333

<210> SEQ ID NO 176
<211> LENGTH: 110
<212> TYPE: PRT
<213> ORGANISM: Artificial Sequence
<220> FEATURE:
<223> OTHER INFORMATION: A12-H04 light

<400> SEQUENCE: 176

Gln Ser Ala Leu Thr Gln Pro Ala Ser Val Ser Gly Ser Pro Gly Gln
 1               5                  10                  15

Ser Ile Thr Ile Ser Cys Thr Gly Ser Ser Ser Asp Val Gly Gly Tyr
                 20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Gly Ala Tyr Ser Asn Thr Asn
                 85                  90                  95

Phe Tyr Val Phe Gly Thr Gly Thr Lys Val Thr Val Leu Gly
            100                 105                 110

<210> SEQ ID NO 177
<211> LENGTH: 333
<212> TYPE: DNA
<213> ORGANISM: Artificial Sequence
<220> FEATURE:
<223> OTHER INFORMATION: A23-3H04 light

<400> SEQUENCE: 177

```
cagtctgcac ttactcagcc agccagtgtg tctgggagtc ctggacagtc gatcaccatt    60
tcctgcggcg gatcaagtag cgatgtcggt ggctataatt atgtgtcctg gtaccagcag   120
cacccaggca aggcccccaa actgatgatt tacgacgtta acaagcgccc ctcagggggtc  180 tccaatcgct tttctggcag taaaagcgga aacacagcct ccctgactat cagcggcctc   240
caagctgaag acgaggctga ttattattgt ggttcttacg atagcaacac tttttacgtt   300
ttcggaaccg ggacaaaggt gaccgtcttg ggc                                333
```

<210> SEQ ID NO 178
<211> LENGTH: 111
<212> TYPE: PRT
<213> ORGANISM: Artificial Sequence
<220> FEATURE:
<223> OTHER INFORMATION: A23-3H04 light
<400> SEQUENCE: 178

```
Gln Ser Ala Leu Thr Gln Pro Ala Ser Val Ser Gly Ser Pro Gly Gln
1               5                   10                  15

Ser Ile Thr Ile Ser Cys Gly Gly Ser Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Ser Asn
                85                  90                  95

Thr Phe Tyr Val Phe Gly Thr Gly Thr Lys Val Thr Val Leu Gly
            100                 105                 110
```

<210> SEQ ID NO 179
<211> LENGTH: 333
<212> TYPE: DNA
<213> ORGANISM: Artificial Sequence
<220> FEATURE:
<223> OTHER INFORMATION: A21-4C03 light
<400> SEQUENCE: 179

```
cagtctgcac ttactcagcc agccagtgtg tctgggagtc ctggacagtc gatcaccatt    60
tcctgcaccg gatcaagtag cgatatcggt ggctataatt atgtgtcctg gtaccagcag   120
cacccaggca aggcccccaa actgatgatt tacgacgtta gcgatcgccc ctcagggggtc  180 tccaatcgct tttctggcag taaaagcgga aacacagcct ccctgactat cagcggcctc   240
caagctgaag acgaggctga ttattattgt ggttcttact ctagcaacac tttttacgtt   300
ttcggaaccg ggacaaaggt gaccgtcttg ggc                                333
```

<210> SEQ ID NO 180
<211> LENGTH: 111
<212> TYPE: PRT
<213> ORGANISM: Artificial Sequence
<220> FEATURE:
<223> OTHER INFORMATION: A21-4C03 light
<400> SEQUENCE: 180

```
Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Ile Gly Gly Tyr
            20                  25                  30
```

```
                    20                  25                  30

Asn Tyr Val Ser Trp Tyr Gln Gln His Pro Gly Lys Ala Pro Lys Leu
            35                  40                  45

Met Ile Tyr Asp Val Ser Asp Arg Pro Ser Gly Val Ser Asn Arg Phe
    50                  55                  60

Ser Gly Ser Lys Ser Gly Asn Thr Ala Ser Leu Thr Ile Ser Gly Leu
 65                 70                  75                  80

Gln Ala Glu Asp Glu Ala Asp Tyr Tyr Cys Gly Ser Tyr Ser Ser Asn
                85                  90                  95

Thr Phe Tyr Val Phe Gly Thr Gly Thr Lys Val Thr Val Leu Gly
            100                 105                 110
```

<210> SEQ ID NO 181
<211> LENGTH: 333
<212> TYPE: DNA
<213> ORGANISM: Artificial Sequence
<220> FEATURE:
<223> OTHER INFORMATION: A24-1G10 light

<400> SEQUENCE: 181

```
cagtctgcac ttactcagcc agccagtgtg tctgggagtc ctggacagtc gatcaccatt      60
tcctgcggcg atcaagtag caatatcggt ggctataatt atgtgtcctg gtaccagcag     120
cacccaggca aggcccccaa actgatgatt tacgacgtta acaagcgccc ctcaggggtc     180
tccaatcgct tttctggcag taaaagcgga aacacagcct ccctgactat cagcggcctc     240
caagctgaag acgaggctga ttattattgt gcttcttact ctaactccaa ttttttacgtt    300 ttcggaaccg ggacaaaggt gaccgtcttg ggc                                  333
```

<210> SEQ ID NO 182
<211> LENGTH: 111
<212> TYPE: PRT
<213> ORGANISM: Artificial Sequence
<220> FEATURE:
<223> OTHER INFORMATION: A24-1G10 light

<400> SEQUENCE: 182

```
Gln Ser Ala Leu Thr Gln Pro Ala Ser Val Ser Gly Ser Pro Gly Gln
 1               5                  10                  15

Ser Ile Thr Ile Ser Cys Gly Gly Ser Ser Asn Ile Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
 65                 70                  75                  80

Gln Ala Glu Asp Glu Ala Asp Tyr Tyr Cys Ala Ser Tyr Ser Asn Ser
                85                  90                  95

Asn Phe Tyr Val Phe Gly Thr Gly Thr Lys Val Thr Val Leu Gly
            100                 105                 110
```

<210> SEQ ID NO 183
<211> LENGTH: 333
<212> TYPE: DNA
<213> ORGANISM: Artificial Sequence
<220> FEATURE:
<223> OTHER INFORMATION: A24-1F07 light

<400> SEQUENCE: 183

```
cagtctgcac ttactcagcc agccagtgtg tctgggagtc ctggacagtc gatcaccatt    60
tcctgcagcg gatcaagtag caatgtcggt agctataatt atgtgtcctg gtaccagcag   120
cacccaggca aggccccaa actgatgatt tacgacgtta ccaagcgccc ctcaggggtc    180
tccaatcgct tttctggcag taaaagcgga aacacagcct ccctgactat cagcggcctc   240
caagctgaag acgaggctga ttattattgt ggttcttact ctaactccaa ttttttacgtt  300 ttcggaaccg ggacaaaggt gaccgtcttg ggc                                333
```

<210> SEQ ID NO 184
<211> LENGTH: 111
<212> TYPE: PRT
<213> ORGANISM: Artificial Sequence
<220> FEATURE:
<223> OTHER INFORMATION: A24-1F07 light

<400> SEQUENCE: 184

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Asn Val Gly Ser Tyr
                20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Asn Ser
                85                  90                  95

Asn Phe Tyr Val Phe Gly Thr Gly Thr Lys Val Thr Val Leu Gly
            100                 105                 110

<210> SEQ ID NO 185
<211> LENGTH: 333
<212> TYPE: DNA
<213> ORGANISM: Artificial Sequence
<220> FEATURE:
<223> OTHER INFORMATION: A21-4B10 light

<400> SEQUENCE: 185

```
cagtctgcac ttactcagcc agccagtgtg tctgggagtc ctggacagtc gatcaccatt    60
tcctgcagcg gatcaagtag caatatcggt ggctataatt atgtgtcctg gtaccagcag   120
cacccaggca aggccccaa actgatgatt tacgacgtta gcaagcgccc ctcaggggtc    180
tccaatcgct tttctggcag taaaagcgga aacacagcct ccctgactat cagcggcctc   240
caagctgaag acgaggctga ttattattgt ggttcttacg atagcaacac ttttttacgtt  300 ttcggaaccg ggacaaaggt gaccgtcttg ggc                                333
```

<210> SEQ ID NO 186
<211> LENGTH: 111
<212> TYPE: PRT
<213> ORGANISM: Artificial Sequence
<220> FEATURE:
<223> OTHER INFORMATION: A21-4B10 light

<400> SEQUENCE: 186

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Asn Ile Gly Gly Tyr
              20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Ser Asn
                85                  90                  95

Thr Phe Tyr Val Phe Gly Thr Gly Thr Lys Val Thr Val Leu Gly
            100                 105                 110

<210> SEQ ID NO 187
<211> LENGTH: 333
<212> TYPE: DNA
<213> ORGANISM: Artificial Sequence
<220> FEATURE:
<223> OTHER INFORMATION: A21-4G04 light

<400> SEQUENCE: 187
cagtctgcac ttactcagcc agccagtgtg tctgggagtc ctggacagtc gatcaccatt      60
tcctgcagcg gatcaagtag caatatcggt ggctataatt atgtgtcctg gtaccagcag     120
cacccaggca aggcccccaa actgatgatt tacgacgtta acgagcgccc tcaggggtc      180 tccaatcgct tttctggcag taaaagcgga acacagcct ccctgactat cagcggcctc      240
caagctgaag acgaggctga ttattattgt ggttcttact ctaacaacaa ttttttacgtt    300 ttcggaaccg ggacaaaggt gaccgtcttg ggc                                  333

<210> SEQ ID NO 188
<211> LENGTH: 111
<212> TYPE: PRT
<213> ORGANISM: Artificial Sequence
<220> FEATURE:
<223> OTHER INFORMATION: A21-4G04 light

<400> SEQUENCE: 188

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Asn Ile Gly Gly Tyr
              20                  25                  30

Asn Tyr Val Ser Trp Tyr Gln Gln His Pro Gly Lys Ala Pro Lys Leu
            35                  40                  45

Met Ile Tyr Asp Val Asn Glu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Asn Asn
                85                  90                  95

Asn Phe Tyr Val Phe Gly Thr Gly Thr Lys Val Thr Val Leu Gly
            100                 105                 110

<210> SEQ ID NO 189
<211> LENGTH: 333
<212> TYPE: DNA
<213> ORGANISM: Artificial Sequence
<220> FEATURE:
<223> OTHER INFORMATION: A23-3H05 light

<400> SEQUENCE: 189

```
cagtctgcac ttactcagcc agccagtgtg tctgggagtc ctggacagtc gatcaccatt      60
tcctgcggcg atcaagtag caatgtcggt ggctataatt atgtgtcctg gtaccagcag     120
cacccaggca aggcccccaa actgatgatt tacgacgtta gcaatcgccc ctcaggggtc     180
tccaatcgct tttctggcag taaaagcgga aacacagcct ccctgactat cagcggcctc     240
caagctgaag acgaggctga ttattattgt ggttcttact ctaactccaa ttttttacgtt    300
ttcggaaccg ggacaaaggt gaccgtcttg ggc                                  333
```

<210> SEQ ID NO 190
<211> LENGTH: 111
<212> TYPE: PRT
<213> ORGANISM: Artificial Sequence
<220> FEATURE:
<223> OTHER INFORMATION: A23-3H05 light

<400> SEQUENCE: 190

```
Gln Ser Ala Leu Thr Gln Pro Ala Ser Val Ser Gly Ser Pro Gly Gln
1               5                   10                  15

Ser Ile Thr Ile Ser Cys Gly Gly Ser Ser Asn Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Asn Ser
                85                  90                  95

Asn Phe Tyr Val Phe Gly Thr Gly Thr Lys Val Thr Val Leu Gly
            100                 105                 110
```

<210> SEQ ID NO 191
<211> LENGTH: 333
<212> TYPE: DNA
<213> ORGANISM: Artificial Sequence
<220> FEATURE:
<223> OTHER INFORMATION: A21-3A09 light

<400> SEQUENCE: 191

```
cagtctgcac ttactcagcc agccagtgtg tctgggagtc ctggacagtc gatcaccatt      60
tcctgcagcg atcaagtag cgatatcggt ggctataatt atgtgtcctg gtaccagcag     120
cacccaggca aggcccccaa actgatgatt tacgacgtta acaagcgccc ctcaggggtc     180
tccaatcgct tttctggcag taaaagcgga aacacagcct ccctgactat cagcggcctc     240
caagctgaag acgaggctga ttattattgt gcttcttact ctagcaacac ttttttacgtt    300
ttcggaaccg ggacaaaggt gaccgtcttg ggc                                  333
```

<210> SEQ ID NO 192
<211> LENGTH: 111
<212> TYPE: PRT
<213> ORGANISM: Artificial Sequence
<220> FEATURE:
<223> OTHER INFORMATION: A21-3A09 light

<400> SEQUENCE: 192

```
Gln Ser Ala Leu Thr Gln Pro Ala Ser Val Ser Gly Ser Pro Gly Gln
1               5                   10                  15
```

Ser Ile Thr Ile Ser Cys Ser Gly Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ser Ser Asn
                85                  90                  95

Thr Phe Tyr Val Phe Gly Thr Gly Thr Lys Val Thr Val Leu Gly
            100                 105                 110

<210> SEQ ID NO 193
<211> LENGTH: 333
<212> TYPE: DNA
<213> ORGANISM: Artificial Sequence
<220> FEATURE:
<223> OTHER INFORMATION: A21-4B06 light

<400> SEQUENCE: 193
cagtctgcac ttactcagcc agccagtgtg tctgggagtc ctggacagtc gatcaccatt      60
tcctgcagcg gatcaagtag caatatcggt agctataatt atgtgtcctg gtaccagcag     120
cacccaggca aggcccccaa actgatgatt tacgacgtta ccgatcgccc ctcaggggtc     180
tccaatcgct tttctggcag taaaagcgga aacacagcct ccctgactat cagcggcctc     240
caagctgaag acgaggctga ttattattgt ggttcttact ctagcaacac tttttacgtt     300
ttcggaaccg ggacaaaggt gaccgtcttg ggc                                  333

<210> SEQ ID NO 194
<211> LENGTH: 111
<212> TYPE: PRT
<213> ORGANISM: Artificial Sequence
<220> FEATURE:
<223> OTHER INFORMATION: A21-4B06 light

<400> SEQUENCE: 194

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Asn Ile Gly Ser Tyr
            20                  25                  30

Asn Tyr Val Ser Trp Tyr Gln Gln His Pro Gly Lys Ala Pro Lys Leu
        35                  40                  45

Met Ile Tyr Asp Val Thr Asp Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Ser Asn
                85                  90                  95

Thr Phe Tyr Val Phe Gly Thr Gly Thr Lys Val Thr Val Leu Gly
            100                 105                 110

<210> SEQ ID NO 195
<211> LENGTH: 333
<212> TYPE: DNA
<213> ORGANISM: Artificial Sequence
<220> FEATURE:
<223> OTHER INFORMATION: A24-1B05 light

<400> SEQUENCE: 195

```
cagtctgcac ttactcagcc agccagtgtg tctgggagtc ctggacagtc gatcaccatt    60
tcctgcgccg gatcaagtag cgatatcggt ggctataatt atgtgtcctg gtaccagcag   120
cacccaggca aggccccaa actgatgatt tacgacgtta gcaagcgccc ctcaggggtc    180
tccaatcgct tttctggcag taaaagcgga acacagcct ccctgactat cagcggcctc    240
caagctgaag acgaggctga ttattattgt ggttcttacg atagcaacac ttttttacgtt   300
ttcggaaccg ggacaaaggt gaccgtcttg ggc                                333
```

<210> SEQ ID NO 196
<211> LENGTH: 111
<212> TYPE: PRT
<213> ORGANISM: Artificial Sequence
<220> FEATURE:
<223> OTHER INFORMATION: A24-1B05 light

<400> SEQUENCE: 196

```
Gln Ser Ala Leu Thr Gln Pro Ala Ser Val Ser Gly Ser Pro Gly Gln
 1               5                  10                  15
Ser Ile Thr Ile Ser Cys Ala Gly Ser Ser Ser Asp Ile Gly Gly Tyr
             20                  25                  30
Asn Tyr Val Ser Trp Tyr Gln Gln His Pro Gly Lys Ala Pro Lys Leu
         35                  40                  45
Met Ile Tyr Asp Val Ser Lys Arg Pro Ser Gly Val Ser Asn Arg Phe
     50                  55                  60
Ser Gly Ser Lys Ser Gly Asn Thr Ala Ser Leu Thr Ile Ser Gly Leu
 65                  70                  75                  80
Gln Ala Glu Asp Glu Ala Asp Tyr Tyr Cys Gly Ser Tyr Asp Ser Asn
                 85                  90                  95
Thr Phe Tyr Val Phe Gly Thr Gly Thr Lys Val Thr Val Leu Gly
            100                 105                 110
```

<210> SEQ ID NO 197
<211> LENGTH: 333
<212> TYPE: DNA
<213> ORGANISM: Artificial Sequence
<220> FEATURE:
<223> OTHER INFORMATION: A23-3A08 light

<400> SEQUENCE: 197

```
cagtctgcac ttactcagcc agccagtgtg tctgggagtc ctggacagtc gatcaccatt    60
tcctgcgccg gatcaagtag caatatcggt ggctataatt atgtgtcctg gtaccagcag   120
cacccaggca aggccccaa actgatgatt tacgacgtta gcaagcgccc ctcaggggtc    180
tccaatcgct tttctggcag taaaagcgga acacagcct ccctgactat cagcggcctc    240
caagctgaag acgaggctga ttattattgt ggttcttact ctaactccaa ttttttacgtt   300
ttcggaaccg ggacaaaggt gaccgtcttg ggc                                333
```

<210> SEQ ID NO 198
<211> LENGTH: 111
<212> TYPE: PRT
<213> ORGANISM: Artificial Sequence
<220> FEATURE:
<223> OTHER INFORMATION: A23-3A08 light

<400> SEQUENCE: 198

```
Gln Ser Ala Leu Thr Gln Pro Ala Ser Val Ser Gly Ser Pro Gly Gln
```

```
  1               5                  10                 15
Ser Ile Thr Ile Ser Cys Ala Gly Ser Ser Asn Ile Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Asn Ser
                85                  90                  95

Asn Phe Tyr Val Phe Gly Thr Gly Thr Lys Val Thr Val Leu Gly
            100                 105                 110
```

<210> SEQ ID NO 199
<211> LENGTH: 333
<212> TYPE: DNA
<213> ORGANISM: Artificial Sequence
<220> FEATURE:
<223> OTHER INFORMATION: A21-4C08 light

<400> SEQUENCE: 199

```
cagtctgcac ttactcagcc agccagtgtg tctgggagtc ctggacagtc gatcaccatt     60
tcctgcagcg gatcaagtag caatgtcggt agctataatt atgtgtcctg gtaccagcag    120
cacccaggca aggcccccaa actgatgatt tacgacgtta acaatcgccc ctcaggggtc    180
tccaatcgct tttctggcag taaaagcgga aacacagcct ccctgactat cagcggcctc    240
caagctgaag acgaggctga ttattattgt ggttcttact ctagcaacac tttctacgtt    300
ttcggaaccg ggacaaaggt gaccgtcttg ggc                                 333
```

<210> SEQ ID NO 200
<211> LENGTH: 111
<212> TYPE: PRT
<213> ORGANISM: Artificial Sequence
<220> FEATURE:
<223> OTHER INFORMATION: A21-4C08 light

<400> SEQUENCE: 200

```
Gln Ser Ala Leu Thr Gln Pro Ala Ser Val Ser Gly Ser Pro Gly Gln
1               5                   10                  15

Ser Ile Thr Ile Ser Cys Ser Gly Ser Ser Asn Val Gly Ser Tyr
            20                  25                  30

Asn Tyr Val Ser Trp Tyr Gln Gln His Pro Gly Lys Ala Pro Lys Leu
            35                  40                  45

Met Ile Tyr Asp Val Asn Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Ser Asn
                85                  90                  95

Thr Phe Tyr Val Phe Gly Thr Gly Thr Lys Val Thr Val Leu Gly
            100                 105                 110
```

<210> SEQ ID NO 201
<211> LENGTH: 333
<212> TYPE: DNA
<213> ORGANISM: Artificial Sequence
<220> FEATURE:

<223> OTHER INFORMATION: A23-4D09 light

<400> SEQUENCE: 201

```
cagtctgcac ttactcagcc agccagtgtg tctgggagtc ctggacagtc gatcaccatt     60
tcctgcagcg gatcaagtag caatatcggt agctataatt atgtgtcctg gtaccagcag    120
cacccaggca aggcccccaa actgatgatt tacgacgtta ccgatcgccc ctcaggggtc    180
tccaatcgct tttctggcag taaaagcgga aacacagcct ccctgactat cagcggcctc    240
caagctgaag acgaggctga ttattattgt ggttcttact ctagcaacac ttttacgtt     300
ttcggaaccg ggacaaaggt gaccgtcttg ggc                                 333
```

<210> SEQ ID NO 202
<211> LENGTH: 111
<212> TYPE: PRT
<213> ORGANISM: Artificial Sequence
<220> FEATURE:
<223> OTHER INFORMATION: A23-4D09 light

<400> SEQUENCE: 202

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Asn Ile Gly Ser Tyr
                20                  25                  30

Asn Tyr Val Ser Trp Tyr Gln Gln His Pro Gly Lys Ala Pro Lys Leu
            35                  40                  45

Met Ile Tyr Asp Val Thr Asp Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Ser Asn
                85                  90                  95

Thr Phe Tyr Val Phe Gly Thr Gly Thr Lys Val Thr Val Leu Gly
            100                 105                 110

<210> SEQ ID NO 203
<211> LENGTH: 333
<212> TYPE: DNA
<213> ORGANISM: Artificial Sequence
<220> FEATURE:
<223> OTHER INFORMATION: A23-3D03 light

<400> SEQUENCE: 203

```
cagtctgcac ttactcagcc agccagtgtg tctgggagtc ctggacagtc gatcaccatt     60
tcctgcaccg gatcaagtag cgatgtcggt ggctataatt atgtgtcctg gtaccagcag    120
cacccaggca aggcccccaa actgatgatt tacgacgtta ccaatcgccc ctcaggggtc    180
tccaatcgct tttctggcag taaaagcgga aacacagcct ccctgactat cagcggcctc    240
caagctgaag acgaggctga ttattattgt ggttcttacg atagcaacac ttttacgtt     300
ttcggaaccg ggacaaaggt gaccgtcttg ggc                                 333
```

<210> SEQ ID NO 204
<211> LENGTH: 111
<212> TYPE: PRT
<213> ORGANISM: Artificial Sequence
<220> FEATURE:
<223> OTHER INFORMATION: A23-3D03 light

<400> SEQUENCE: 204

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Ser Asn
                85                  90                  95

Thr Phe Tyr Val Phe Gly Thr Gly Thr Lys Val Thr Val Leu Gly
            100                 105                 110

<210> SEQ ID NO 205
<211> LENGTH: 333
<212> TYPE: DNA
<213> ORGANISM: Artificial Sequence
<220> FEATURE:
<223> OTHER INFORMATION: A21-4B03 light

<400> SEQUENCE: 205
cagtctgcac ttactcagcc agccagtgtg tctgggagtc ctggacagtc gatcaccatt     60
tcctgcagcg gatcaagtag caatatcggt agctataatt atgtgtcctg gtaccagcag    120
cacccaggca aggcccccaa actgatgatt tacgacgtta acaagcgccc ctcaggggtc    180
tccaatcgct tttctggcag taaaagcgga aacacagcct ccctgactat cagcggcctc    240
caagctgaag acgaggctga ttattattgt gcttcttact ctagcaacac tttttacgtt    300
ttcggaaccg ggacaaaggt gaccgtcttg ggc                                 333

<210> SEQ ID NO 206
<211> LENGTH: 111
<212> TYPE: PRT
<213> ORGANISM: Artificial Sequence
<220> FEATURE:
<223> OTHER INFORMATION: A21-4B03 light

<400> SEQUENCE: 206

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Asn Ile Gly Ser Tyr
            20                  25                  30

Asn Tyr Val Ser Trp Tyr Gln Gln His Pro Gly Lys Ala Pro Lys Leu
        35                  40                  45

Met Ile Tyr Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ser Ser Asn
                85                  90                  95

Thr Phe Tyr Val Phe Gly Thr Gly Thr Lys Val Thr Val Leu Gly
            100                 105                 110

<210> SEQ ID NO 207
<211> LENGTH: 333
<212> TYPE: DNA
<213> ORGANISM: Artificial Sequence
<220> FEATURE:
<223> OTHER INFORMATION: A21-3D10 light

<400> SEQUENCE: 207

| | | | | |
|---|---|---|---|---|
| cagtctgcac ttactcagcc agccagtgtg tctgggagtc ctggacagtc gatcaccatt | 60 |
| tcctgcggcg aacaagtag caatatcggt ggctataatt atgtgtcctg gtaccagcag | 120 |
| cacccaggca aggcccccaa actgatgatt tacgacgtta ccaatcgccc ctcaggggtc | 180 |
| tccaatcgct tttctggcag taaaagcgga aacacagcct ccctgactat cagcggcctc | 240 |
| caagctgaag acgaggctga ttattattgt ggttcttact ctaacaccaa ttttttacgtt | 300 |
| ttcggaaccg ggacaaaggt gaccgtcttg ggc | 333 |

<210> SEQ ID NO 208
<211> LENGTH: 111
<212> TYPE: PRT
<213> ORGANISM: Artificial Sequence
<220> FEATURE:
<223> OTHER INFORMATION: A21-3D10 light

<400> SEQUENCE: 208

Gln Ser Ala Leu Thr Gln Pro Ala Ser Val Ser Gly Ser Pro Gly Gln
1               5                   10                  15

Ser Ile Thr Ile Ser Cys Gly Gly Thr Ser Ser Asn Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Asn Thr
                85                  90                  95

Asn Phe Tyr Val Phe Gly Thr Gly Thr Lys Val Thr Val Leu Gly
            100                 105                 110

<210> SEQ ID NO 209
<211> LENGTH: 333
<212> TYPE: DNA
<213> ORGANISM: Artificial Sequence
<220> FEATURE:
<223> OTHER INFORMATION: A21-3A10 light

<400> SEQUENCE: 209

| | | | | |
|---|---|---|---|---|
| cagtctgcac ttactcagcc agccagtgtg tctgggagtc ctggacagtc gatcaccatt | 60 |
| tcctgcgccg atcaagtag caatatcggt ggctataatt atgtgtcctg gtaccagcag | 120 |
| cacccaggca aggcccccaa actgatgatt tacgacgtta gcaagcgccc ctcaggggtc | 180 |
| tccaatcgct tttctggcag taaaagcgga aacacagcct ccctgactat cagcggcctc | 240 |
| caagctgaag acgaggctga ttattattgt ggttcttact ctaactccaa ttttttacgtt | 300 |
| ttcggaaccg ggacaaaggt gaccgtcttg ggc | 333 |

<210> SEQ ID NO 210
<211> LENGTH: 111
<212> TYPE: PRT
<213> ORGANISM: Artificial Sequence
<220> FEATURE:
<223> OTHER INFORMATION: A21-3A10 light

<400> SEQUENCE: 210

Gln Ser Ala Leu Thr Gln Pro Ala Val Ser Gly Ser Pro Gly Gln
1               5                   10                  15

Ser Ile Thr Ile Ser Cys Ala Gly Ser Ser Asn Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Gly Ser Tyr Ser Asn Ser
            85                  90                  95

Asn Phe Tyr Val Phe Gly Thr Gly Thr Lys Val Thr Val Leu Gly
            100                 105                 110

<210> SEQ ID NO 211
<211> LENGTH: 333
<212> TYPE: DNA
<213> ORGANISM: Artificial Sequence
<220> FEATURE:
<223> OTHER INFORMATION: A21-4H04 light

<400> SEQUENCE: 211
cagtctgcac ttactcagcc agccagtgtg tctggagtc ctggacagtc gatcaccatt     60
tcctgcagcg gaacaagtag cgatatcggt ggctataatt atgtgtcctg gtaccagcag    120
cacccaggca aggcccccaa actgatgatt tacgacgtta gcaagcgccc ctcaggggtc    180
tccaatcgct tttctggcag taaaagcgga acacagcct ccctgactat cagcggcctc     240
caagctgaag acgaggctga ttattattgt ggttcttact ctaacaacaa ttttacgtt     300 ttcggaaccg ggacaaaggt gaccgtcttg ggc                                 333

<210> SEQ ID NO 212
<211> LENGTH: 111
<212> TYPE: PRT
<213> ORGANISM: Artificial Sequence
<220> FEATURE:
<223> OTHER INFORMATION: A21-4H04 light

<400> SEQUENCE: 212

Gln Ser Ala Leu Thr Gln Pro Ala Val Ser Gly Ser Pro Gly Gln
1               5                   10                  15

Ser Ile Thr Ile Ser Cys Ser Gly Thr Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Gly Ser Tyr Ser Asn Asn
            85                  90                  95

Asn Phe Tyr Val Phe Gly Thr Gly Thr Lys Val Thr Val Leu Gly
            100                 105                 110

<210> SEQ ID NO 213
<211> LENGTH: 333
<212> TYPE: DNA

<213> ORGANISM: Artificial Sequence
<220> FEATURE:
<223> OTHER INFORMATION: A21-4F11 light

<400> SEQUENCE: 213

```
cagtctgcac ttactcagcc agccagtgtg tctgggagtc ctggacagtc gatcaccatt     60
tcctgcggcg gaacaagtag caatatcggt ggctataatt atgtgtcctg gtaccagcag    120
cacccaggca aggcccccaa actgatgatt tacgacgtta acgatcgccc ctcaggggtc    180
tccaatcgct ttctggcag taaaagcgga aacacagcct ccctgactat cagcggcctc    240
caagctgaag acgaggctga ttattattgt gcttcttact ctagcaacac ttttttacgtt    300
ttcggaaccg ggacaaaggt gaccgtcttg ggc                                 333
```

<210> SEQ ID NO 214
<211> LENGTH: 111
<212> TYPE: PRT
<213> ORGANISM: Artificial Sequence
<220> FEATURE:
<223> OTHER INFORMATION: A21-4F11 light

<400> SEQUENCE: 214

```
Gln Ser Ala Leu Thr Gln Pro Ala Ser Val Ser Gly Ser Pro Gly Gln
1               5                   10                  15
Ser Ile Thr Ile Ser Cys Gly Gly Thr Ser Ser Asn Ile Gly Gly Tyr
            20                  25                  30
Asn Tyr Val Ser Trp Tyr Gln Gln His Pro Gly Lys Ala Pro Lys Leu
        35                  40                  45
Met Ile Tyr Asp Val Asn Asp Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ala Ser Tyr Ser Ser Asn
                85                  90                  95
Thr Phe Tyr Val Phe Gly Thr Gly Thr Lys Val Thr Val Leu Gly
            100                 105                 110
```

<210> SEQ ID NO 215
<211> LENGTH: 333
<212> TYPE: DNA
<213> ORGANISM: Artificial Sequence
<220> FEATURE:
<223> OTHER INFORMATION: A23-3G05 light

<400> SEQUENCE: 215

```
cagtctgcac ttactcagcc agccagtgtg tctgggagtc ctggacagtc gatcaccatt     60
tcctgcgccg gatcaagtag caatatcggt agctataatt atgtgtcctg gtaccagcag    120
cacccaggca aggcccccaa actgatgatt tacgacgtta gcaatcgccc ctcaggggtc    180
tccaatcgct ttctggcag taaaagcgga aacacagcct ccctgactat cagcggcctc    240
caagctgaag acgaggctga ttattattgt ggttcttacg atagcaacac ttttttacgtt    300
ttcggaaccg ggacaaaggt gaccgtcttg ggc                                 333
```

<210> SEQ ID NO 216
<211> LENGTH: 111
<212> TYPE: PRT
<213> ORGANISM: Artificial Sequence
<220> FEATURE:
<223> OTHER INFORMATION: A23-3G05 light

<400> SEQUENCE: 216

Gln Ser Ala Leu Thr Gln Pro Ala Ser Val Ser Gly Ser Pro Gly Gln
1               5                   10                  15

Ser Ile Thr Ile Ser Cys Ala Gly Ser Ser Asn Ile Gly Ser Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Ser Asn
                85                  90                  95

Thr Phe Tyr Val Phe Gly Thr Gly Thr Lys Val Thr Val Leu Gly
            100                 105                 110

<210> SEQ ID NO 217
<211> LENGTH: 333
<212> TYPE: DNA
<213> ORGANISM: Artificial Sequence
<220> FEATURE:
<223> OTHER INFORMATION: A23-3A10 light

<400> SEQUENCE: 217
cagtctgcac ttactcagcc agccagtgtg tctgggagtc ctggacagtc gatcaccatt      60
tcctgcgccg gatcaagtag caatatcggt ggctataatt atgtgtcctg gtaccagcag     120
cacccaggca aggcccccaa actgatgatt tacgacgtta gcgatcgccc ctcaggggtc     180
tccaatcgct tttctggcag taaaagcgga aacacagcct ccctgactat cagcggcctc     240
caagctgaag acgaggctga ttattattgt ggttcttacg atagcaacac tttttacgtt     300
ttcggaaccg ggacaaaggt gaccgtcttg ggc                                   333

<210> SEQ ID NO 218
<211> LENGTH: 111
<212> TYPE: PRT
<213> ORGANISM: Artificial Sequence
<220> FEATURE:
<223> OTHER INFORMATION: A23-3A10 light

<400> SEQUENCE: 218

Gln Ser Ala Leu Thr Gln Pro Ala Ser Val Ser Gly Ser Pro Gly Gln
1               5                   10                  15

Ser Ile Thr Ile Ser Cys Ala Gly Ser Ser Asn Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asp Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Ser Asn
                85                  90                  95

Thr Phe Tyr Val Phe Gly Thr Gly Thr Lys Val Thr Val Leu Gly
            100                 105                 110

<210> SEQ ID NO 219
<211> LENGTH: 333

```
<212> TYPE: DNA
<213> ORGANISM: Artificial Sequence
<220> FEATURE:
<223> OTHER INFORMATION: A25-1H04 light

<400> SEQUENCE: 219
cagtctgcac ttactcagcc agccagtgtg tctgggagtc ctggacagtc gatcaccatt      60
tcctgcgccg gatcaagtag cgatatcggt ggctataatt atgtgtcctg gtaccagcag     120
cacccaggca aggcccccaa actgatgatt tacgacgtta gcgagcgccc ctcaggggtc     180
tccaatcgct tttctggcag taaaagcgga aacacagcct ccctgactat cagcggcctc     240
caagctgaag acgaggctga ttattattgt ggttcttacg atagcaacac tttttacgtt     300
ttcggaaccg ggacaaaggt gaccgtcttg ggc                                  333

<210> SEQ ID NO 220
<211> LENGTH: 111
<212> TYPE: PRT
<213> ORGANISM: Artificial Sequence
<220> FEATURE:
<223> OTHER INFORMATION: A25-1H04 light

<400> SEQUENCE: 220
```

Gln Ser Ala Leu Thr Gln Pro Ala Ser Val Ser Gly Ser Pro Gly Gln
 1               5                  10                  15

Ser Ile Thr Ile Ser Cys Ala Gly Ser Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Glu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Ser Asn
                85                  90                  95

Thr Phe Tyr Val Phe Gly Thr Gly Thr Lys Val Thr Val Leu Gly
            100                 105                 110

```
<210> SEQ ID NO 221
<211> LENGTH: 333
<212> TYPE: DNA
<213> ORGANISM: Artificial Sequence
<220> FEATURE:
<223> OTHER INFORMATION: A23-3B06 light

<400> SEQUENCE: 221
cagtctgcac ttactcagcc agccagtgtg tctgggagtc ctggacagtc gatcaccatt      60
tcctgcagcg gatcaagtag cgatgtcggt ggctataatt atgtgtcctg gtaccagcag     120
cacccaggca aggcccccaa actgatgatt tacgacgtta gcgagcgccc ctcaggggtc     180
tccaatcgct tttctggcag taaaagcgga aacacagcct ccctgactat cagcggcctc     240
caagctgaag acgaggctga ttattattgt ggttcttacg atagcaacac tttttacgtt     300
ttcggaaccg ggacaaaggt gaccgtcttg ggc                                  333

<210> SEQ ID NO 222
<211> LENGTH: 111
<212> TYPE: PRT
<213> ORGANISM: Artificial Sequence
<220> FEATURE:
<223> OTHER INFORMATION: A23-3B06 light
```

<400> SEQUENCE: 222

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Glu Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Ser Asn
                85                  90                  95

Thr Phe Tyr Val Phe Gly Thr Gly Thr Lys Val Thr Val Leu Gly
            100                 105                 110

<210> SEQ ID NO 223
<211> LENGTH: 333
<212> TYPE: DNA
<213> ORGANISM: Artificial Sequence
<220> FEATURE:
<223> OTHER INFORMATION: A23-4A09 light

<400> SEQUENCE: 223
cagtctgcac ttactcagcc agccagtgtg tctgggagtc ctggacagtc gatcaccatt     60
tcctgcggcg gatcaagtag caatatcggt ggctataatt atgtgtcctg gtaccagcag    120
cacccaggca aggcccccaa actgatgatt tacgacgtta ccaagcgccc ctcaggggtc    180
tccaatcgct tttctggcag taaaagcgga aacacagcct ccctgactat cagcggcctc    240
caagctgaag acgaggctga ttattattgt gcttcttact ctagcaacac tttttacgtt    300
ttcggaaccg ggacaaaggt gaccgtcttg ggc                                 333

<210> SEQ ID NO 224
<211> LENGTH: 111
<212> TYPE: PRT
<213> ORGANISM: Artificial Sequence
<220> FEATURE:
<223> OTHER INFORMATION: A23-4A09 light

<400> SEQUENCE: 224

Gln Ser Ala Leu Thr Gln Pro Ala Ser Val Ser Gly Ser Pro Gly Gln
1               5                   10                  15

Ser Ile Thr Ile Ser Cys Gly Gly Ser Ser Asn Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ser Ser Asn
                85                  90                  95

Thr Phe Tyr Val Phe Gly Thr Gly Thr Lys Val Thr Val Leu Gly
            100                 105                 110

<210> SEQ ID NO 225

<211> LENGTH: 333
<212> TYPE: DNA
<213> ORGANISM: Artificial Sequence
<220> FEATURE:
<223> OTHER INFORMATION: A25-1D09 light

<400> SEQUENCE: 225

```
cagtctgcac ttactcagcc agccagtgtg tctgggagtc ctggacagtc gatcaccatt      60
tcctgcggcg gaacaagtag cgatgtcggt agctataatt atgtgtcctg gtaccagcag     120
cacccaggca aggcccccaa actgatgatt tacgacgtta acaagcgccc ctcaggggtc     180
tccaatcgct tttctggcag taaaagcgga aacacagcct ccctgactat cagcggcctc     240
caagctgaag acgaggctga ttattattgt ggttcttact ctaactccaa ttttttacgtt     300
ttcggaaccg ggacaaaggt gaccgtcttg ggc                                    333
```

<210> SEQ ID NO 226
<211> LENGTH: 111
<212> TYPE: PRT
<213> ORGANISM: Artificial Sequence
<220> FEATURE:
<223> OTHER INFORMATION: A25-1D09 light

<400> SEQUENCE: 226

Gln Ser Ala Leu Thr Gln Pro Ala Ser Val Ser Gly Ser Pro Gly Gln
1               5                   10                  15
Ser Ile Thr Ile Ser Cys Gly Gly Thr Ser Ser Asp Val Gly Ser Tyr
            20                  25                  30
Asn Tyr Val Ser Trp Tyr Gln Gln His Pro Gly Lys Ala Pro Lys Leu
        35                  40                  45
Met Ile Tyr Asp Val Asn Lys Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Gly Ser Tyr Ser Asn Ser
                85                  90                  95
Asn Phe Tyr Val Phe Gly Thr Gly Thr Lys Val Thr Val Leu Gly
            100                 105                 110

<210> SEQ ID NO 227
<211> LENGTH: 333
<212> TYPE: DNA
<213> ORGANISM: Artificial Sequence
<220> FEATURE:
<223> OTHER INFORMATION: A21-4E10 light

<400> SEQUENCE: 227

```
cagtctgcac ttactcagcc agccagtgtg tctgggagtc ctggacagtc gatcaccatt      60
tcctgcaccg gatcaagtag caatgtcggt ggctataatt atgtgtcctg gtaccagcag     120
cacccaggca aggcccccaa actgatgatt tacgacgtta gcaagcgccc ctcaggggtc     180
tccaatcgct tttctggcag taaaagcgga aacacagcct ccctgactat cagcggcctc     240
caagctgaag acgaggctga ttattattgt ggttcttact ctagcaacac ttttttacgtt     300
ttcggaaccg ggacaaaggt gaccgtcttg ggc                                    333
```

<210> SEQ ID NO 228
<211> LENGTH: 111
<212> TYPE: PRT
<213> ORGANISM: Artificial Sequence
<220> FEATURE:

<223> OTHER INFORMATION: A21-4E10 light

<400> SEQUENCE: 228

```
Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asn Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Ser Asn
                85                  90                  95

Thr Phe Tyr Val Phe Gly Thr Gly Thr Lys Val Thr Val Leu Gly
            100                 105                 110
```

<210> SEQ ID NO 229
<211> LENGTH: 333
<212> TYPE: DNA
<213> ORGANISM: Artificial Sequence
<220> FEATURE:
<223> OTHER INFORMATION: A23-3C04 light

<400> SEQUENCE: 229

```
cagtctgcac ttactcagcc agccagtgtg tctgggagtc ctggacagtc gatcaccatt    60
tcctgcagcg gaacaagtag cgatatcggt ggctataatt atgtgtcctg gtaccagcag   120
cacccaggca aggcccccaa actgatgatt tacgacgtta ccgagccccc ctcagggggtc   180
tccaatcgct tttctggcag taaaagcgga aacacagcct ccctgactat cagcggcctc   240
caagctgaag acgaggctga ttattattgt gcttcttact ctagcaacac ttttttacgtt   300
ttcggaaccg ggacaaaggt gaccgtcttg ggc                                 333
```

<210> SEQ ID NO 230
<211> LENGTH: 111
<212> TYPE: PRT
<213> ORGANISM: Artificial Sequence
<220> FEATURE:
<223> OTHER INFORMATION: A23-3C04 light

<400> SEQUENCE: 230

```
Gln Ser Ala Leu Thr Gln Pro Ala Ser Val Ser Gly Ser Pro Gly Gln
1               5                   10                  15

Ser Ile Thr Ile Ser Cys Ser Gly Thr Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Glu Pro Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ser Ser Asn
                85                  90                  95

Thr Phe Tyr Val Phe Gly Thr Gly Thr Lys Val Thr Val Leu Gly
            100                 105                 110
```

<210> SEQ ID NO 231
<211> LENGTH: 333
<212> TYPE: DNA
<213> ORGANISM: Artificial Sequence
<220> FEATURE:
<223> OTHER INFORMATION: A23-3G06 light

<400> SEQUENCE: 231

```
cagtctgcac ttactcagcc agccagtgtg tctgggagtc ctggacagtc gatcaccatt      60
tcctgcgccg gaacaagtag caatatcggt ggctataatt atgtgtcctg gtaccagcag     120
cacccaggca aggcccccaa actgatgatt tacgacgtta acgatcgccc ctcaggggtc     180
tccaatcgct ttctggcag taaaagcgga aacacagcct ccctgactat cagcggcctc      240
caagctgaag acgaggctga ttattattgt ggttcttacg atagcaacac tttttacgtt     300
ttcggaaccg ggacaaaggt gaccgtcttg ggc                                  333
```

<210> SEQ ID NO 232
<211> LENGTH: 111
<212> TYPE: PRT
<213> ORGANISM: Artificial Sequence
<220> FEATURE:
<223> OTHER INFORMATION: A23-3G06 light

<400> SEQUENCE: 232

```
Gln Ser Ala Leu Thr Gln Pro Ala Ser Val Ser Gly Ser Pro Gly Gln
1               5                   10                  15

Ser Ile Thr Ile Ser Cys Ala Gly Thr Ser Ser Asn Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asp Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Ser Asn
                85                  90                  95

Thr Phe Tyr Val Phe Gly Thr Gly Thr Lys Val Thr Val Leu Gly
            100                 105                 110
```

<210> SEQ ID NO 233
<211> LENGTH: 333
<212> TYPE: DNA
<213> ORGANISM: Artificial Sequence
<220> FEATURE:
<223> OTHER INFORMATION: A24-1E09 light

<400> SEQUENCE: 233

```
cagtctgcac ttactcagcc agccagtgtg tctgggagtc ctggacagtc gatcaccatt      60
tcctgcaccg gatcaagtag caatatcggt ggctataatt atgtgtcctg gtaccagcag     120
cacccaggca aggcccccaa actgatgatt tacgacgtta ccaatcgccc ctcaggggtc     180
tccaatcgct ttctggcag taaaagcgga aacacagcct ccctgactat cagcggcctc      240
caggctgaag acgaggctga ttattattgt ggttcttact ctaactccaa tttttacgtt     300
ttcggaaccg ggacaaaggt gaccgtcttg ggc                                  333
```

<210> SEQ ID NO 234
<211> LENGTH: 111
<212> TYPE: PRT
<213> ORGANISM: Artificial Sequence
<220> FEATURE:
<223> OTHER INFORMATION: A24-1E09 light

<400> SEQUENCE: 234

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Asn Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Asn Ser
                85                  90                  95

Asn Phe Tyr Val Phe Gly Thr Gly Thr Lys Val Thr Val Leu Gly
            100                 105                 110

<210> SEQ ID NO 235
<211> LENGTH: 333
<212> TYPE: DNA
<213> ORGANISM: Artificial Sequence
<220> FEATURE:
<223> OTHER INFORMATION: A23-3F03 light

<400> SEQUENCE: 235
cagtctgcac ttactcagcc agccagtgtg tctggagtc ctggacagtc gatcaccatt      60
tcctgcggcg gatcaagtag caatatcggt agctataatt atgtgtcctg gtaccagcag     120
cacccaggca aggcccccaa actgatgatt tacgacgtaa caaagcgccc ctcagggggtc    180
tccaatcgct tttctggcag taaaagcgga acacagcct ccctgactat cagcggcctc     240
caagctgaag acgaggctga ttattattgt ggttcttacg atagcaacac ttttacgtt      300
ttcggaaccg ggacaaaggt gaccgtcttg ggc                                  333

<210> SEQ ID NO 236
<211> LENGTH: 111
<212> TYPE: PRT
<213> ORGANISM: Artificial Sequence
<220> FEATURE:
<223> OTHER INFORMATION: A23-3F03 light

<400> SEQUENCE: 236

Gln Ser Ala Leu Thr Gln Pro Ala Ser Val Ser Gly Ser Pro Gly Gln
1               5                   10                  15

Ser Ile Thr Ile Ser Cys Gly Gly Ser Ser Asn Ile Gly Ser Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Ser Asn
                85                  90                  95

Thr Phe Tyr Val Phe Gly Thr Gly Thr Lys Val Thr Val Leu Gly
            100                 105                 110

<210> SEQ ID NO 237
<211> LENGTH: 333
<212> TYPE: DNA
<213> ORGANISM: Artificial Sequence
<220> FEATURE:
<223> OTHER INFORMATION: A21-4F07 light

<400> SEQUENCE: 237

```
cagtctgcac ttactcagcc agccagtgtg tctgggagtc ctggacagtc gatcaccatt      60
tcctgcagcg aacaagtag  caatgtcggt ggctataatt atgtgtcctg gtaccagcag     120
cacccaggca aggcccccaa actgatgatt tacgacgtta gcgatcgccc ctcaggggtc     180
tccaatcgct tttctggcag taaaagcgga aacacagcct ccctgactat cagcggcctc     240
caagctgaag acgaggctga ttattattgt ggttcttact ctaactccaa ttttttacgtt    300
ttcggaaccg ggacaaaggt gaccgtcttg ggc                                  333
```

<210> SEQ ID NO 238
<211> LENGTH: 111
<212> TYPE: PRT
<213> ORGANISM: Artificial Sequence
<220> FEATURE:
<223> OTHER INFORMATION: A21-4F07 light

<400> SEQUENCE: 238

```
Gln Ser Ala Leu Thr Gln Pro Ala Ser Val Ser Gly Ser Pro Gly Gln
1               5                   10                  15

Ser Ile Thr Ile Ser Cys Ser Gly Thr Ser Ser Asn Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asp Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Asn Ser
                85                  90                  95

Asn Phe Tyr Val Phe Gly Thr Gly Thr Lys Val Thr Val Leu Gly
            100                 105                 110
```

<210> SEQ ID NO 239
<211> LENGTH: 333
<212> TYPE: DNA
<213> ORGANISM: Artificial Sequence
<220> FEATURE:
<223> OTHER INFORMATION: A24-1A03 light

<400> SEQUENCE: 239

```
cagtctgcac ttactcagcc agccagtgtg tctgggagtc ctggacagtc gatcaccatt      60
tcctgcggcg gatcaagtag caatgtcggt ggctataatt atgtgtcctg gtaccagcag     120
cacccaggca aggcccccaa actgatgatt tacgacgtta gcaagcgccc ctcaggggtc     180
tccaatcgct tttctggcag taaaagcgga aacacagcct ccctgactat cagcggcctc     240
caagctgaag acgaggctga ttattattgt ggttcttact ctaactccaa ttttttacgtt    300
ttcggaaccg ggacaaaggt gaccgtcttg ggc                                  333
```

<210> SEQ ID NO 240
<211> LENGTH: 111
<212> TYPE: PRT

<213> ORGANISM: Artificial Sequence
<220> FEATURE:
<223> OTHER INFORMATION: A24-1A03 light

<400> SEQUENCE: 240

Gln Ser Ala Leu Thr Gln Pro Ala Ser Val Ser Gly Ser Pro Gly Gln
1               5                   10                  15

Ser Ile Thr Ile Ser Cys Gly Gly Ser Ser Asn Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Asn Ser
                85                  90                  95

Asn Phe Tyr Val Phe Gly Thr Gly Thr Lys Val Thr Val Leu Gly
            100                 105                 110

<210> SEQ ID NO 241
<211> LENGTH: 333
<212> TYPE: DNA
<213> ORGANISM: Artificial Sequence
<220> FEATURE:
<223> OTHER INFORMATION: A24-1H11 light

<400> SEQUENCE: 241
cagtctgcac ttactcagcc agccagtgtg tctgggagtc ctggacagtc gatcaccatt    60
tcctgcaccg gatcaagtag cgatgtcggt ggctataatt atgtgtcctg gtaccagcag   120
cacccaggca aggccccaa actgatgatt tacgaagtta acaagcgccc ctcagggtc    180
tccaatcgct tttctggcag taaaagcgga aacacagcct ccctgactat cagcggcctc   240
caagctgaag acgaggctga ttattattgt gcttcttact ctagcaacac ttttttacgtt   300
ttcggaaccg ggacaaaggt gaccgtcttg ggc                                333

<210> SEQ ID NO 242
<211> LENGTH: 111
<212> TYPE: PRT
<213> ORGANISM: Artificial Sequence
<220> FEATURE:
<223> OTHER INFORMATION: A24-1H11 light

<400> SEQUENCE: 242

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Asn Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ser Ser Asn
                85                  90                  95

Thr Phe Tyr Val Phe Gly Thr Gly Thr Lys Val Thr Val Leu Gly
            100                 105                 110

<210> SEQ ID NO 243
<211> LENGTH: 333
<212> TYPE: DNA
<213> ORGANISM: Artificial Sequence
<220> FEATURE:
<223> OTHER INFORMATION: A21-3D09 light

<400> SEQUENCE: 243

```
cagtctgcac ttactcagcc agccagtgtg tctgggagtc ctggacagtc gatcaccatt      60
tcctgcagcg gaacaagtag caatgtcggt ggctataatt atgtgtcctg gtaccagcag     120
cacccaggca aggcccccaa actgatgatt tacgacgtta acaagcgccc ctcaggggtc     180
tccaatcgct tttctggcag taaaagcgga aacacagcct ccctgactat cagcggcctc     240
caagctgaag acgaggctga ttattattgt ggttcttact ctaactccaa ttttttacgtt     300 ttcggaaccg ggacaaaggt gaccgtcttg ggc                                  333
```

<210> SEQ ID NO 244
<211> LENGTH: 111
<212> TYPE: PRT
<213> ORGANISM: Artificial Sequence
<220> FEATURE:
<223> OTHER INFORMATION: A21-3D09 light

<400> SEQUENCE: 244

```
Gln Ser Ala Leu Thr Gln Pro Ala Ser Val Ser Gly Ser Pro Gly Gln
  1               5                  10                  15

Ser Ile Thr Ile Ser Cys Ser Gly Thr Ser Ser Asn Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Asn Lys Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Ser Tyr Ser Asn Ser
                 85                  90                  95

Asn Phe Tyr Val Phe Gly Thr Gly Thr Lys Val Thr Val Leu Gly
            100                 105                 110
```

<210> SEQ ID NO 245
<211> LENGTH: 333
<212> TYPE: DNA
<213> ORGANISM: Artificial Sequence
<220> FEATURE:
<223> OTHER INFORMATION: A24-1D10 light

<400> SEQUENCE: 245

```
cagtctgcac ttactcagcc agccagtgtg tctgggagtc ctggacagtc gatcaccatt      60
tcctgcagcg gatcaagtag cgatatcggt ggctataatt atgtgtcctg gtaccagcag     120
cacccaggca aggcccccaa actgatgatt tacgacgtta ccgatcgccc ctcaggggtc     180
tccaatcgct tttctggcag taaaagcgga aacacagcct ccctgactat cagcggcctc     240
caagctgaag acgaggctga ttattattgt ggttcttact ctaacaacaa ttttttacgtt     300 ttcggaaccg ggacaaaggt gaccgtcttg ggc                                  333
```

<210> SEQ ID NO 246
<211> LENGTH: 111

```
<212> TYPE: PRT
<213> ORGANISM: Artificial Sequence
<220> FEATURE:
<223> OTHER INFORMATION: A24-1D10 light

<400> SEQUENCE: 246

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Asp Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Asn Asn
                85                  90                  95

Asn Phe Tyr Val Phe Gly Thr Gly Thr Lys Val Thr Val Leu Gly
            100                 105                 110

<210> SEQ ID NO 247
<211> LENGTH: 333
<212> TYPE: DNA
<213> ORGANISM: Artificial Sequence
<220> FEATURE:
<223> OTHER INFORMATION: A21-4B04 light

<400> SEQUENCE: 247
cagtctgcac ttactcagcc agccagtgtg tctgggagtc ctggacagtc gatcaccatt    60
tcctgcgccg gaacaagtag caatatcggt ggctataatt atgtgtcctg gtaccagcag   120
cacccaggca aggcccccaa actgatgatt tacgacgtta gcaatcgccc ctcaggggtc   180
tccaatcgct ttctggcag taaaagcgga aacacagcct ccctgactat cagcggcctc   240
caagctgaag acgaggctga ttattattgt gcttcttact ctagcaacac tttttacgtt   300
ttcggaaccg gacaaaggt gaccgtcttg ggc                                 333

<210> SEQ ID NO 248
<211> LENGTH: 111
<212> TYPE: PRT
<213> ORGANISM: Artificial Sequence
<220> FEATURE:
<223> OTHER INFORMATION: A21-4B04 light

<400> SEQUENCE: 248

Gln Ser Ala Leu Thr Gln Pro Ala Ser Val Ser Gly Ser Pro Gly Gln
1               5                   10                  15

Ser Ile Thr Ile Ser Cys Ala Gly Thr Ser Ser Asn Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ser Ser Asn
                85                  90                  95

Thr Phe Tyr Val Phe Gly Thr Gly Thr Lys Val Thr Val Leu Gly
```

<210> SEQ ID NO 249
<211> LENGTH: 333
<212> TYPE: DNA
<213> ORGANISM: Artificial Sequence
<220> FEATURE:
<223> OTHER INFORMATION: A23-4C12 light

<400> SEQUENCE: 249

```
cagtctgcac ttactcagcc agccagtgtg tctgggagtc ctggacagtc gatcaccatt    60
tcctgcagcg gaacaagtag cgatgtcggt ggctataatt atgtgtcctg gtaccagcag   120
cacccaggca aggcccccaa actgatgatt tacgacgtta ccaagcgccc ctcaggggtc   180
tccaatcgct tttctggcag taaaagcgga aacacagcct ccctgactat cagcggcctc   240
caagctgaag acgaggctga ttattattgt ggttcttact ctagcaacac tttttacgtt   300
ttcggaaccg ggacaaaggt gaccgtcttg ggc                                 333
```

<210> SEQ ID NO 250
<211> LENGTH: 111
<212> TYPE: PRT
<213> ORGANISM: Artificial Sequence
<220> FEATURE:
<223> OTHER INFORMATION: A23-4C12 light

<400> SEQUENCE: 250

```
Gln Ser Ala Leu Thr Gln Pro Ala Ser Val Ser Gly Ser Pro Gly Gln
 1               5                  10                  15

Ser Ile Thr Ile Ser Cys Ser Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Ser Asn
                85                  90                  95

Thr Phe Tyr Val Phe Gly Thr Gly Thr Lys Val Thr Val Leu Gly
           100                 105                 110
```

<210> SEQ ID NO 251
<211> LENGTH: 333
<212> TYPE: DNA
<213> ORGANISM: Artificial Sequence
<220> FEATURE:
<223> OTHER INFORMATION: A21-4G06 light

<400> SEQUENCE: 251

```
cagtctgcac ttactcagcc agccagtgtg tctgggagtc ctggacagtc gatcaccatt    60
tcctgcgccg gatcaagtag caatgtcggt ggctataatt atgtgtcctg gtaccaacag   120
cacccaggca aggcccccaa actgatgatt tacgacgtaa caaagcgccc ctcaggggtc   180
tccaatcgct tttctggcag taaaagcgga aacacagcct ccctgactat cagcggcctc   240
caagctgaag acgaggctga ttattattgt ggttcttact ctaactccaa tttttacgtt   300
ttcggaaccg ggacaaaggt gaccgtcttg ggc                                 333
```

<210> SEQ ID NO 252

<211> LENGTH: 111
<212> TYPE: PRT
<213> ORGANISM: Artificial Sequence
<220> FEATURE:
<223> OTHER INFORMATION: A21-4G06 light

<400> SEQUENCE: 252

Gln Ser Ala Leu Thr Gln Pro Ala Ser Val Ser Gly Ser Pro Gly Gln
1               5                   10                  15

Ser Ile Thr Ile Ser Cys Ala Gly Ser Ser Asn Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Asn Ser
                85                  90                  95

Asn Phe Tyr Val Phe Gly Thr Gly Thr Lys Val Thr Val Leu Gly
            100                 105                 110

<210> SEQ ID NO 253
<211> LENGTH: 333
<212> TYPE: DNA
<213> ORGANISM: Artificial Sequence
<220> FEATURE:
<223> OTHER INFORMATION: A23-3E04 light

<400> SEQUENCE: 253
cagtctgcac ttactcagcc agccagtgtg tctgggagtc ctggacagtc gatcaccatt      60
tcctgcaccg atcaagtag cgatgtcggt ggctataatt atgtgtcctg gtaccagcag     120
cacccaggca aggcccccaa actgatgatt tacgacgtta ccgatcgccc ctcgggggtc     180
tccaatcgct tttctggcag taaaagcgga aacacagcct ccctgactat cagcggcctc     240
caagctgaag acgaggctga ttattattgt ggttcttact ctaactccaa ttttttacgtt     300 ttcggaaccg ggacaaaggt gaccgtcttg ggc                                   333

<210> SEQ ID NO 254
<211> LENGTH: 111
<212> TYPE: PRT
<213> ORGANISM: Artificial Sequence
<220> FEATURE:
<223> OTHER INFORMATION: A23-3E04 light

<400> SEQUENCE: 254

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Thr Asp Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Asn Ser
                85                  90                  95

```
Asn Phe Tyr Val Phe Gly Thr Gly Thr Lys Val Thr Val Leu Gly
            100                 105                 110
```

<210> SEQ ID NO 255
<211> LENGTH: 333
<212> TYPE: DNA
<213> ORGANISM: Artificial Sequence
<220> FEATURE:
<223> OTHER INFORMATION: A24-1C09 light

<400> SEQUENCE: 255

```
cagtctgcac ttactcagcc agccagtgtg tctgggagtc ctggacagtc gatcaccatt      60
tcctgcaccg gaacaagtag caatgtcggt agctataatt atgtgtcctg gtaccagcag     120
cacccaggca aggcccccaa actgatgatt tacgacgtta acgatcgccc ctcaggggtc     180
tccaatcgct tttctggcag taaaagcgga aacacagcct ccctgactat cagcggcctc     240
caagctgaag acgaggctga ttattattgt ggttcttacg atagcaacac tttttacgtt     300
ttcggaaccg ggacaaaggt gaccgtcttg ggc                                   333
```

<210> SEQ ID NO 256
<211> LENGTH: 111
<212> TYPE: PRT
<213> ORGANISM: Artificial Sequence
<220> FEATURE:
<223> OTHER INFORMATION: A24-1C09 light

<400> SEQUENCE: 256

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Val Gly Ser Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asp Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Ser Asn
                85                  90                  95

Thr Phe Tyr Val Phe Gly Thr Gly Thr Lys Val Thr Val Leu Gly
            100                 105                 110
```

<210> SEQ ID NO 257
<211> LENGTH: 333
<212> TYPE: DNA
<213> ORGANISM: Artificial Sequence
<220> FEATURE:
<223> OTHER INFORMATION: A24-1C04 light

<400> SEQUENCE: 257

```
cagtctgcac ttactcagcc agccagtgtg tctgggagtc ctggacagtc gatcaccatt      60
tcctgcaccg gaacaagtag caatatcggt ggctataatt atgtgtcctg gtaccagcag     120
cacccaggca aggcccccaa actgatgatt tacgacgtta ccaagcgccc ctcaggggtc     180
tccaatcgct tttctggcag taaaagcgga aacacagcct ccctgactat cagcggcctc     240
caagctgaag acgaggctga ttattattgt ggttcttact ctaactccaa tttttacgtt     300
ttcggaaccg ggacaaaggt gaccgtcttg ggc                                   333
```

-continued

```
<210> SEQ ID NO 258
<211> LENGTH: 111
<212> TYPE: PRT
<213> ORGANISM: Artificial Sequence
<220> FEATURE:
<223> OTHER INFORMATION: A24-1C04 light

<400> SEQUENCE: 258
```

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Asn Ser
                85                  90                  95

Asn Phe Tyr Val Phe Gly Thr Gly Thr Lys Val Thr Val Leu Gly
            100                 105                 110

```
<210> SEQ ID NO 259
<211> LENGTH: 333
<212> TYPE: DNA
<213> ORGANISM: Artificial Sequence
<220> FEATURE:
<223> OTHER INFORMATION: A25-1H10 light

<400> SEQUENCE: 259
```
cagtctgcac ttactcagcc agccagtgtg tctgggagtc ctggacagtc gatcaccatt    60
tcctgcggcg gatcaagtag cgatgtcggt ggctataatt atgtgtcctg gtaccagcag   120
cacccaggca aggcccccaa actgatgatt tacgaagtta gcaatcgccc ctcaggggtc   180
tccaatcgct tttctggcag taaaagcgga aacacagcct ccctgactat cagcggcctc   240
caagctgaag acgaggctga ttattattgt ggttcttact ctaactccaa ttttacgtt    300 ttcggaaccg ggacaaaggt gaccgtcttg ggc                                 333

```
<210> SEQ ID NO 260
<211> LENGTH: 111
<212> TYPE: PRT
<213> ORGANISM: Artificial Sequence
<220> FEATURE:
<223> OTHER INFORMATION: A25-1H10 light

<400> SEQUENCE: 260
```

Gln Ser Ala Leu Thr Gln Pro Ala Ser Val Ser Gly Ser Pro Gly Gln
1               5                   10                  15

Ser Ile Thr Ile Ser Cys Gly Gly Ser Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Asn Ser
                85                  90                  95

Asn Phe Tyr Val Phe Gly Thr Gly Thr Lys Val Thr Val Leu Gly
            100                 105                 110

<210> SEQ ID NO 261
<211> LENGTH: 365
<212> TYPE: DNA
<213> ORGANISM: Artificial Sequence
<220> FEATURE:
<223> OTHER INFORMATION: A21-4D08 light

<400> SEQUENCE: 261
caggcggagg tgggtccggc ggtggcggat cgcagtctgc acttactcag ccagccagtg     60
tgtctgggag tcctggacag tcgatcacca tttcctgcgg cggaacaagt agcgatgtcg    120
gtggctataa ttatgtgtcc tggtaccagc agcacccagg caaggccccc aaactgatga    180
tttacgacgt taacgatcgc ccctcagggg tctccaatcg cttttctggc agtaaaagcg    240
gaaacacagc ctccctgact atcagcggcc tccaagctga agacgaggct gattattatt    300
gtggttctta ctctaacaac aattttttacg ttttcggaac cgggacaaag gtgaccgtct    360
tgggc                                                                 365

<210> SEQ ID NO 262
<211> LENGTH: 111
<212> TYPE: PRT
<213> ORGANISM: Artificial Sequence
<220> FEATURE:
<223> OTHER INFORMATION: A21-4D08 light

<400> SEQUENCE: 262

Gln Ser Ala Leu Thr Gln Pro Ala Ser Val Ser Gly Ser Pro Gly Gln
1               5                   10                  15

Ser Ile Thr Ile Ser Cys Gly Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Asn Asp Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Asn Asn
                85                  90                  95

Asn Phe Tyr Val Phe Gly Thr Gly Thr Lys Val Thr Val Leu Gly
            100                 105                 110

<210> SEQ ID NO 263
<211> LENGTH: 365
<212> TYPE: DNA
<213> ORGANISM: Artificial Sequence
<220> FEATURE:
<223> OTHER INFORMATION: A24-1D08 light

<400> SEQUENCE: 263
caggcggagg tgggtccggc ggtggcggat cgcagtctgc acttactcag ccagccagtg     60
tgtctgggag tcctggacag tcgatcacca tttcctgcgc cggatcaagt agcaatgtcg    120
tgagctataa ttatgtgtcc tggtaccagc agcacccagg caaggccccc aaactgatga    180
tttacgacgt taacaagcgc ccctcagggg tctccaatcg cttttctggc agtaaaagcg    240
gaaacacagc ctccctgact atcagcggcc tccaagctga agacgaggct gattattatt    300
gtggttctta cgatagcaac acttttacg ttttcggaac cgggacaaag gtgaccgtct    360
tgggc    365

<210> SEQ ID NO 264
<211> LENGTH: 111
<212> TYPE: PRT
<213> ORGANISM: Artificial Sequence
<220> FEATURE:
<223> OTHER INFORMATION: A24-1D08 light

<400> SEQUENCE: 264

Gln Ser Ala Leu Thr Gln Pro Ala Ser Val Ser Gly Ser Pro Gly Gln
1               5                   10                  15

Ser Ile Thr Ile Ser Cys Ala Gly Ser Ser Asn Val Val Ser Tyr
            20                  25                  30

Asn Tyr Val Ser Trp Tyr Gln Gln His Pro Gly Lys Ala Pro Lys Leu
        35                  40                  45

Met Ile Tyr Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Gly Ser Tyr Asp Ser Asn
                85                  90                  95

Thr Phe Tyr Val Phe Gly Thr Gly Thr Lys Val Thr Val Leu Gly
            100                 105                 110

<210> SEQ ID NO 265
<211> LENGTH: 333
<212> TYPE: DNA
<213> ORGANISM: Artificial Sequence
<220> FEATURE:
<223> OTHER INFORMATION: A24-1A08 light

<400> SEQUENCE: 265
cagtctgcac ttactcagcc agccagtgtg tctggagtc ctggacagtc gatcaccatt    60
tcctgcaccg gatcaagtag caatatcggt ggctataatt atgtgtcctg gtaccagcag    120
cacccaggca aggccccaa actgatgatt tacgaagtta acaatcgccc ctcagggtc    180 tccaatcgct tttctggcag taaaagcgga acacagcct ccctgactat cagcggcctc    240
caagctgaag acgaggctga ttattattgt gcttcttact ctagcaacac ttttacgtt    300 ttcggaaccg ggacaaaggt gaccgtcttg ggc    333

<210> SEQ ID NO 266
<211> LENGTH: 111
<212> TYPE: PRT
<213> ORGANISM: Artificial Sequence
<220> FEATURE:
<223> OTHER INFORMATION: A24-1A08 light

<400> SEQUENCE: 266

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Asn Ile Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Asn Asn Arg Pro Ser Gly Val Ser Asn Arg Phe
    50                  55                  60

```
Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ser Ser Asn
                85                  90                  95

Thr Phe Tyr Val Phe Gly Thr Gly Thr Lys Val Thr Val Leu Gly
            100                 105                 110

<210> SEQ ID NO 267
<211> LENGTH: 333
<212> TYPE: DNA
<213> ORGANISM: Artificial Sequence
<220> FEATURE:
<223> OTHER INFORMATION: A21-4A07 light

<400> SEQUENCE: 267
cagtctgcac ttactcagcc agccagtgtg tctgggagtc ctggacagtc gatcaccatt      60
tcctgcgccg gatcaagtag caatatcggt ggctataatt atgtgtcctg gtaccagcag     120
cacccaggca aggcccccaa actgatgatt tacgacgtta acgatcgccc tcagggggtc     180
tccaatcgct tttctggcag taaaagcgga acacagcct ccctgactat cagcggcctc      240
caagctgaag acgaggctga ttattattgt ggttcttact ctaactccaa ttttttacgtt    300 ttcggaaccg ggacaaaggt gaccgtcttg ggc                                  333

<210> SEQ ID NO 268
<211> LENGTH: 111
<212> TYPE: PRT
<213> ORGANISM: Artificial Sequence
<220> FEATURE:
<223> OTHER INFORMATION: A21-4A07 light

<400> SEQUENCE: 268

Gln Ser Ala Leu Thr Gln Pro Ala Ser Val Ser Gly Ser Pro Gly Gln
1               5                   10                  15

Ser Ile Thr Ile Ser Cys Ala Gly Ser Ser Ser Asn Ile Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Asn Asp Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ser Asn Ser
                85                  90                  95

Asn Phe Tyr Val Phe Gly Thr Gly Thr Lys Val Thr Val Leu Gly
            100                 105                 110

<210> SEQ ID NO 269
<211> LENGTH: 333
<212> TYPE: DNA
<213> ORGANISM: Artificial Sequence
<220> FEATURE:
<223> OTHER INFORMATION: A24-1B09 light

<400> SEQUENCE: 269
cagtcttcac ttactcagcc agccagtgtg tctgggagtc ctggacagtc gatcaccatt      60
tcctgcaccg gaacaagtag caatatcggt agctataatt atgtgtcctg gtaccagcag     120
cacccaggca aggcccccaa actgatgatt tacgacgtta acaagcgccc tcagggggtc     180
tccaatcgct tttctggcag taaaagcgga acacagcct ccctgactat cagcggcctc      240
```

```
caagctgaag acgaggctga ttattattgt ggttcttacg atagcaacac ttttacgtt    300 ttcggaaccg ggacaaaggt gaccgtcttg ggc                                333
```

<210> SEQ ID NO 270
<211> LENGTH: 111
<212> TYPE: PRT
<213> ORGANISM: Artificial Sequence
<220> FEATURE:
<223> OTHER INFORMATION: A24-1B09 light

<400> SEQUENCE: 270

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Ile Gly Ser Tyr
            20                  25                  30

Asn Tyr Val Ser Trp Tyr Gln Gln His Pro Gly Lys Ala Pro Lys Leu
        35                  40                  45

Met Ile Tyr Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Ser Asn
                85                  90                  95

Thr Phe Tyr Val Phe Gly Thr Gly Thr Lys Val Thr Val Leu Gly
            100                 105                 110
```

<210> SEQ ID NO 271
<211> LENGTH: 333
<212> TYPE: DNA
<213> ORGANISM: Artificial Sequence
<220> FEATURE:
<223> OTHER INFORMATION: A24-1E07 light

<400> SEQUENCE: 271

```
cagtctgcac ttactcagcc agccagtgtg tctgggagtc ctggacagtc gatcaccatt    60
tcctgcgccg gatcaagtag caatgtcggt ggctataatt atgtgtcctg gtaccagcag    120
cacccaggca aggcccccaa actgatgatt tacgaagtta gcaatcgccc ctcagggggtc   180 tccaatcgct tttctggcag taaaagcgga aacacagcct ccctgactat cagcggcctc    240
caagctgaag acgaggctga ttattattgt ggttcttacg atagcaacac ttttacgtt    300 ttcggaaccg ggacaaaggt gaccgtcttg ggc                                333
```

<210> SEQ ID NO 272
<211> LENGTH: 111
<212> TYPE: PRT
<213> ORGANISM: Artificial Sequence
<220> FEATURE:
<223> OTHER INFORMATION: A24-1E07 light

<400> SEQUENCE: 272

```
Gln Ser Ala Leu Thr Gln Pro Ala Ser Val Ser Gly Ser Pro Gly Gln
1               5                   10                  15

Ser Ile Thr Ile Ser Cys Ala Gly Ser Ser Ser Asn Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60
```

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Ser Asn
                85                  90                  95

Thr Phe Tyr Val Phe Gly Thr Gly Thr Lys Val Thr Val Leu Gly
            100                 105                 110

<210> SEQ ID NO 273
<211> LENGTH: 321
<212> TYPE: DNA
<213> ORGANISM: Artificial Sequence
<220> FEATURE:
<223> OTHER INFORMATION: H21-3A07 light

<400> SEQUENCE: 273
gacatccaga tgacccagtc tccttccacc ctgtctgcat ctgtaggaga cagagtcacc      60
atcacttgtc gagctagtca gagtattagt aaccggttgg cttggtatca gcagaaacca    120
gggaaagccc ctaagctcct gatctataag gcatctaact tagaaagtgg ggtcccatca    180
aggttcagcg gcagtggatc tgggacagaa ttcactctca ccatcagcag cctgcagcct    240
gatgattttg caacttacta ttgtcaacag acgaacagtt tccctctcac tttcggcgga    300
gggaccaagg tggagatcaa a                                              321

<210> SEQ ID NO 274
<211> LENGTH: 110
<212> TYPE: PRT
<213> ORGANISM: Artificial Sequence
<220> FEATURE:
<223> OTHER INFORMATION: H21-3A07 light

<400> SEQUENCE: 274

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Arg
            20                  25                  30

Leu Ala Trp Tyr Gln Gln Lys Pro Gly Lys Ala Pro Lys Leu Leu Ile
        35                  40                  45

Tyr Lys Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Thr Asn Ser Phe Pro Leu
                85                  90                  95

Thr Phe Gly Gly Gly Thr Lys Val Glu Ile Lys Arg Thr Val
            100                 105                 110

<210> SEQ ID NO 275
<211> LENGTH: 321
<212> TYPE: DNA
<213> ORGANISM: Artificial Sequence
<220> FEATURE:
<223> OTHER INFORMATION: H21-4D11 light

<400> SEQUENCE: 275
gacatccaga tgacccagtc tccttccacc ctgtctgcat ctgtaggaga cagagtcacc      60
atcacttgtc aagctagtca gggtattagt aaccggttgg cttggtatca gcagaaacca    120
gggaaagccc ctaagctcct gatctataag gcatctaact tacaaagtag ggtcccatca    180

```
aggttcagcg gcagtggatc tgggacagaa ttcactctca ccatcagcag cctgcagcct    240
gatgattttg caacttacta ttgtcaacag acgaacagtt tccctctcac tttcggcgga    300
gggaccaagg tggagatcaa a                                              321
```

<210> SEQ ID NO 276
<211> LENGTH: 110
<212> TYPE: PRT
<213> ORGANISM: Artificial Sequence
<220> FEATURE:
<223> OTHER INFORMATION: H21-4D11 light

<400> SEQUENCE: 276

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Gly Ile Ser Asn Arg
            20                  25                  30

Leu Ala Trp Tyr Gln Gln Lys Pro Gly Lys Ala Pro Lys Leu Leu Ile
        35                  40                  45

Tyr Lys Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Thr Asn Ser Phe Pro Leu
                85                  90                  95

Thr Phe Gly Gly Gly Thr Lys Val Glu Ile Lys Arg Thr Val
            100                 105                 110
```

<210> SEQ ID NO 277
<211> LENGTH: 321
<212> TYPE: DNA
<213> ORGANISM: Artificial Sequence
<220> FEATURE:
<223> OTHER INFORMATION: H21-3C11 light

<400> SEQUENCE: 277

```
gacatccaga tgacccagtc tccttccacc ctgtctgcat ctgtaggaga cagagtcacc    60
atcacttgtc gagctagtca gagtattagt aaccggttgg cttggtatca gcagaaacca    120
gggaaagccc ctaagctcct gatctataag gcatctagct acaaagtggg gtcccatca    180 aggttcagcg gcagtggatc tgggacagaa ttcactctca ccatcagcag cctgcagcct    240
gatgattttg caacttacta ttgtcaacag acgaacagtt tccctctcac tttcggcgga    300
gggaccaagg tggagatcaa a                                              321
```

<210> SEQ ID NO 278
<211> LENGTH: 110
<212> TYPE: PRT
<213> ORGANISM: Artificial Sequence
<220> FEATURE:
<223> OTHER INFORMATION: H21-3C11 light

<400> SEQUENCE: 278

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Arg
            20                  25                  30

Leu Ala Trp Tyr Gln Gln Lys Pro Gly Lys Ala Pro Lys Leu Leu Ile
        35                  40                  45

Tyr Lys Ala Ser Ser Leu Gln Ser Gly Val Pro Ser Arg Phe Ser Gly
```

```
                    50                  55                  60
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Thr Asn Ser Phe Pro Leu
                 85                  90                  95

Thr Phe Gly Gly Gly Thr Lys Val Glu Ile Lys Arg Thr Val
            100                 105                 110

<210> SEQ ID NO 279
<211> LENGTH: 321
<212> TYPE: DNA
<213> ORGANISM: Artificial Sequence
<220> FEATURE:
<223> OTHER INFORMATION: H21-3A09 light

<400> SEQUENCE: 279
gacatccaga tgacccagtc tccttccacc ctgtctgcat ctgtaggaga cagagtcacc      60
atcacttgtc gagctagtca gagtattagt aaccggttgg cttggtatca gcagaaacca     120
gggaaagccc ctaagctcct gatctataag gcatctaact acaaagtggg gtcccatca     180 aggttcagcg gcagtggatc tgggaaagaa ttcactctca ccatcagcag cctgcagcct     240
gatgattttg caacttacta ttgtcaacag acgaacagtt tccctctcac tttcggcgga     300
gggaccaagg tggagatcaa a                                                321

<210> SEQ ID NO 280
<211> LENGTH: 110
<212> TYPE: PRT
<213> ORGANISM: Artificial Sequence
<220> FEATURE:
<223> OTHER INFORMATION: H21-3A09 light

<400> SEQUENCE: 280

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Asn Arg
                 20                  25                  30

Leu Ala Trp Tyr Gln Gln Lys Pro Gly Lys Ala Pro Lys Leu Leu Ile
             35                  40                  45

Tyr Lys Ala Ser Asn Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Thr Asn Ser Phe Pro Leu
                 85                  90                  95

Thr Phe Gly Gly Gly Thr Lys Val Glu Ile Lys Arg Thr Val
            100                 105                 110

<210> SEQ ID NO 281
<211> LENGTH: 321
<212> TYPE: DNA
<213> ORGANISM: Artificial Sequence
<220> FEATURE:
<223> OTHER INFORMATION: H21-4H04 light

<400> SEQUENCE: 281
gacatccaga tgacccagtc tccttccacc ctgtctgcat ctgtaggaga cagagtcacc      60
atcacttgtc aagctagtca gagtattagt agccggttgg cttggtatca gcagaaacca    120
gggaaagccc ctaagctcct gatctataag gcatctagct acaaagtggg gtcccatca    180
```
aggttcagcg gcggtggatc tgggacagaa ttcactctca ccatcagcag cctgcagcct    240
gatgattttg caacttacta ttgtcaacag acgaacagtt ccctctcac tttcggcgga    300 gggaccaagg tggagatcaa a    321

<210> SEQ ID NO 282
<211> LENGTH: 110
<212> TYPE: PRT
<213> ORGANISM: Artificial Sequence
<220> FEATURE:
<223> OTHER INFORMATION: H21-4H04 light

<400> SEQUENCE: 282

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Ser Ser Arg
            20                  25                  30

Leu Ala Trp Tyr Gln Gln Lys Pro Gly Lys Ala Pro Lys Leu Leu Ile
        35                  40                  45

Tyr Lys Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Thr Asn Ser Phe Pro Leu
                85                  90                  95

Thr Phe Gly Gly Gly Thr Lys Val Glu Ile Lys Arg Thr Val
            100                 105                 110

<210> SEQ ID NO 283
<211> LENGTH: 321
<212> TYPE: DNA
<213> ORGANISM: Artificial Sequence
<220> FEATURE:
<223> OTHER INFORMATION: H23-3D08 light

<400> SEQUENCE: 283
gacatccaga tgacccagtc tccttccacc ctgtctgcat ctgtaggaga cagagtcacc    60
atcacttgtc aagctagtca gggtattagt aaccggttgg cttggtatca gcagaaacca    120
gggaaagccc ctaagctcct gatctataag gcatctaact tagaaactgg ggtcccatca    180
aggttcagcg gcagtggatc tgggacagaa ttcactctca ccatcagcag cctgcagcct    240
gatgattttg caacttacta ttgtcaacag acgaacagtt ccctctcac tttcggcgga    300 gggaccaagg tggagatcaa a    321

<210> SEQ ID NO 284
<211> LENGTH: 110
<212> TYPE: PRT
<213> ORGANISM: Artificial Sequence
<220> FEATURE:
<223> OTHER INFORMATION: H23-3D08 light

<400> SEQUENCE: 284

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Gly Ile Ser Asn Arg
            20                  25                  30

Leu Ala Trp Tyr Gln Gln Lys Pro Gly Lys Ala Pro Lys Leu Leu Ile
        35                  40                  45

```
Tyr Lys Ala Ser Asn Leu Glu Thr Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Thr Asn Ser Phe Pro Leu
                 85                  90                  95

Thr Phe Gly Gly Gly Thr Lys Val Glu Ile Lys Arg Thr Val
            100                 105                 110

<210> SEQ ID NO 285
<211> LENGTH: 321
<212> TYPE: DNA
<213> ORGANISM: Artificial Sequence
<220> FEATURE:
<223> OTHER INFORMATION: H21-4D09 light

<400> SEQUENCE: 285
gacatccaga tgacccagtc tccttccacc ctgtctgcat ctgtaggaga cagagtcacc     60
atcacttgtc aagctagtca gggtattcgt aaccggttgg cttggtatca gcagaaacca    120
gggaaagccc ctaagctcct gatctataag gcatctaact acaaagtggg gtcccatca    180 aggttcagcg gcagtggatc tgggacagaa ttcactctca ccatcagcag cctgcagcct    240
gatgattttg caacttacta ttgtcaacag acgaacagtt ccctctcac tttcggcgga    300 gggaccaagg tggagatcaa a                                              321

<210> SEQ ID NO 286
<211> LENGTH: 110
<212> TYPE: PRT
<213> ORGANISM: Artificial Sequence
<220> FEATURE:
<223> OTHER INFORMATION: H21-4D09 light

<400> SEQUENCE: 286

Asp Ile Gln Met Thr Gln Ser Pro Ser Thr Leu Ser Ala Ser Val Gly
  1               5                  10                  15

Asp Arg Val Thr Ile Thr Cys Gln Ala Ser Gln Gly Ile Arg Asn Arg
                 20                  25                  30

Leu Ala Trp Tyr Gln Gln Lys Pro Gly Lys Ala Pro Lys Leu Leu Ile
             35                  40                  45

Tyr Lys Ala Ser Asn Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Thr Asn Ser Phe Pro Leu
                 85                  90                  95

Thr Phe Gly Gly Gly Thr Lys Val Glu Ile Lys Arg Thr Val
            100                 105                 110

<210> SEQ ID NO 287
<211> LENGTH: 321
<212> TYPE: DNA
<213> ORGANISM: Artificial Sequence
<220> FEATURE:
<223> OTHER INFORMATION: H24-1D11 light

<400> SEQUENCE: 287
gacatccaga tgacccagtc tccttccacc ctgtctgcat ctgtaggaga cagagtcacc     60
atcacttgcc gggccagtca gagtattagt agccggttgg cctggtatca gcagaaacca    120
```

```
gggaaagccc ctaagctcct gatctataag gcatctagct tagaaactgg ggtcccatca    180
aggttcagcg gcagtggatc tgggacagaa ttcactctca ccatcagcag cctgcagcct    240
gatgattttg caacttacta ttgtcaacag acgaacagtt tccctctcac tttcggcgga    300
gggaccaagg tggagatcaa a                                              321
```

```
<210> SEQ ID NO 288
<211> LENGTH: 110
<212> TYPE: PRT
<213> ORGANISM: Artificial Sequence
<220> FEATURE:
<223> OTHER INFORMATION: H24-1D11 light

<400> SEQUENCE: 288
```

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Arg
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Thr Asn Ser Phe Pro Leu
                85                  90                  95

Thr Phe Gly Gly Gly Thr Lys Val Glu Ile Lys Arg Thr Val
            100                 105                 110
```

```
<210> SEQ ID NO 289
<211> LENGTH: 445
<212> TYPE: PRT
<213> ORGANISM: Artificial Sequence
<220> FEATURE:
<223> OTHER INFORMATION: Germline 1Ag Heavy chain

<400> SEQUENCE: 289
```

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Glu Tyr
            20                  25                  30

Gly Met His Trp Val Arg Gln Ala Pro Gly Lys Gly Leu Glu Trp Val
        35                  40                  45

Ser Gly Val Ser Trp Asn Ser Gly Ser Ile Ala Tyr Ala Asp Ser Val
50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Ser Met Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160
```

```
Leu Thr Ser Gly Val His Thr Phe Pro Ala Val Leu Gln Ser Ser Gly
            165                 170                 175
Leu Tyr Ser Leu Ser Ser Val Val Thr Val Pro Ser Ser Ser Leu Gly
        180                 185                 190
Thr Gln Thr Tyr Ile Cys Asn Val Asn His Lys Pro Ser Asn Thr Lys
    195                 200                 205
Val Asp Lys Lys Val Glu Pro Lys Ser Cys Asp Lys Thr His Thr Cys
210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 290
<211> LENGTH: 218
<212> TYPE: PRT
<213> ORGANISM: Artificial Sequence
<220> FEATURE:
<223> OTHER INFORMATION: Germline 1Ag Light chain

<400> SEQUENCE: 290

Gln Ser Ala Leu Thr Gln Pro Ala Ser Val Ser Gly Ser Pro Gly Gln
1               5                   10                  15
Ser Ile Thr Ile Ser Cys Thr Gly Ser Ser Asp Val Gly Gly Tyr
            20                  25                  30
Asn Tyr Val Ser Trp Tyr Gln Gln His Pro Gly Lys Ala Pro Lys Leu
        35                  40                  45
Met Ile Tyr Asp Val Thr Lys Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
```

```
Gln Ala Glu Asp Glu Ala Asp Tyr Tyr Cys Ser Ser Tyr Ser Ser Ser
                85                  90                  95

Thr Phe Tyr Val Phe Gly Thr Gly Thr Lys Val Thr Val Leu Gly Arg
            100                 105                 110

Ser Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 291
<211> LENGTH: 449
<212> TYPE: PRT
<213> ORGANISM: Artificial Sequence
<220> FEATURE:
<223> OTHER INFORMATION: Germline 11Hg Heavy chain

<400> SEQUENCE: 291

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Gly Arg Asp Ala Phe Asp Val Trp Gly Gln Gly
            100                 105                 110

Thr Met Ile Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
        245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
        325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 292
<211> LENGTH: 214
<212> TYPE: PRT
<213> ORGANISM: Artificial Sequence
<220> FEATURE:
<223> OTHER INFORMATION: Germline 11Hg Light chain

<400> SEQUENCE: 292

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Arg
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Thr Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Thr Asn Ser Phe Pro Leu
            85                  90                  95

Thr Phe Gly Gly Gly Thr Lys Val Glu Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala 130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 293
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 293

Glu Tyr Gly Met His
1               5

<210> SEQ ID NO 294
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 294

Thr Tyr Gly Met Asn
1               5

<210> SEQ ID NO 295
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 295

Ala Tyr Gly Met His
1               5

<210> SEQ ID NO 296
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 296

Ser Tyr Gly Met His
1               5

<210> SEQ ID NO 297
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 297

Ala Tyr Gly Met Asn
1               5

<210> SEQ ID NO 298
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 298

Asn Tyr Gly Met Asn
1               5

<210> SEQ ID NO 299
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 299

Lys Tyr Gly Met Asn
1               5

<210> SEQ ID NO 300
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 300

Thr Tyr Gly Met His
1               5

<210> SEQ ID NO 301
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 301

Asn Tyr Gly Met His
1               5

<210> SEQ ID NO 302
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 302

Lys Tyr Gly Met His
1               5

<210> SEQ ID NO 303
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 303

Gly Tyr Gly Met His

```
1               5

<210> SEQ ID NO 304
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 304

Arg Tyr Gly Met His
1               5

<210> SEQ ID NO 305
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 305

Asn Tyr Tyr Met Asn
1               5

<210> SEQ ID NO 306
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 306

Asn Tyr Ala Met Asn
1               5

<210> SEQ ID NO 307
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 307

Asn Tyr Ala Met His
1               5

<210> SEQ ID NO 308
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 308

Asn Tyr Asp Ile His
1               5

<210> SEQ ID NO 309
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 309

Ser Tyr Ala Ile His
1               5
```

```
<210> SEQ ID NO 310
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 310

Asp Tyr Asp Met His
1               5

<210> SEQ ID NO 311
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 311

Asn Tyr Tyr Ile Asn
1               5

<210> SEQ ID NO 312
<211> LENGTH: 5
<212> TYPE: PRT
<213> ORGANISM: Artificial Sequence
<220> FEATURE:
<223> OTHER INFORMATION: Heavy chain CDR1

<400> SEQUENCE: 312

Ser Tyr Ala Met His
1               5

<210> SEQ ID NO 313
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 313

Gly Val Ser Trp Asn Ser Gly Ser Ile Ala Tyr Ala Asp Ser Val Arg
1               5                   10                  15

Gly

<210> SEQ ID NO 314
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 314

Gly Ile Ser Tyr Asn Gly Gly Thr Thr Ala Tyr Ala Asp Ser Val Arg
1               5                   10                  15

Gly

<210> SEQ ID NO 315
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 315
```

```
Gly Ile Ser Tyr Asn Ser Gly Thr Lys Ala Tyr Ala Asp Ser Val Lys
1               5                   10                  15

Gly
```

<210> SEQ ID NO 316
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 316

```
Gly Val Ser Tyr Asn Ser Gly Thr Thr Ala Tyr Ala Asp Ser Val Arg
1               5                   10                  15

Gly
```

<210> SEQ ID NO 317
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 317

```
Gly Ile Ser Tyr Asn Ser Gly Asn Lys Ala Tyr Ala Asp Ser Val Arg
1               5                   10                  15

Gly
```

<210> SEQ ID NO 318
<211> LENGTH: 17
<212> TYPE: PRT
<213> ORGANISM: Artificial Sequence
<220> FEATURE:
<223> OTHER INFORMATION: Heavy chain CFR2

<400> SEQUENCE: 318

```
Gly Ile Ser Tyr Asn Gly Gly Asn Thr Ala Tyr Ala Asp Ser Val Arg
1               5                   10                  15

Gly
```

<210> SEQ ID NO 319
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 319

```
Gly Ile Ser Tyr Asn Ser Gly Thr Ile Ala Tyr Ala Asp Ser Val Lys
1               5                   10                  15

Gly
```

<210> SEQ ID NO 320
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 320

```
Gly Ile Ser Tyr Asn Gly Gly Ser Lys Ala Tyr Ala Asp Ser Val Arg
1               5                   10                  15
```

Gly

<210> SEQ ID NO 321
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 321

Gly Ile Ser Tyr Asn Ser Gly Asn Thr Ala Tyr Ala Asp Ser Val Arg
1               5                   10                  15

Gly

<210> SEQ ID NO 322
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 322

Gly Ile Ser Tyr Asn Ser Gly Thr Thr Ala Tyr Ala Asp Ser Val Lys
1               5                   10                  15

Gly

<210> SEQ ID NO 323
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 323

Gly Ile Ser Tyr Asn Ala Gly Asn Lys Ala Tyr Ala Asp Ser Val Arg
1               5                   10                  15

Gly

<210> SEQ ID NO 324
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 324

Gly Val Ser Tyr Asp Ala Gly Asn Thr Ala Tyr Ala Asp Ser Val Arg
1               5                   10                  15

Gly

<210> SEQ ID NO 325
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 325

Gly Ile Ser Tyr Asn Ala Gly Ser Thr Ala Tyr Ala Asp Ser Val Arg
1               5                   10                  15

Gly

<210> SEQ ID NO 326

```
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 326

Gly Ile Ser Tyr Asp Ala Gly Thr Thr Ala Tyr Ala Asp Ser Val Lys
1               5                   10                  15

Gly

<210> SEQ ID NO 327
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 327

Gly Ile Ser Tyr Asn Ser Gly Asn Lys Ala Tyr Ala Asp Ser Val Lys
1               5                   10                  15

Gly

<210> SEQ ID NO 328
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 328

Gly Ile Ser Tyr Asn Gly Gly Thr Lys Ala Tyr Ala Asp Ser Val Arg
1               5                   10                  15

Gly

<210> SEQ ID NO 329
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 329

Gly Ile Ser Tyr Asn Ser Gly Thr Ile Ala Tyr Ala Asp Ser Val Arg
1               5                   10                  15

Gly

<210> SEQ ID NO 330
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 330

Gly Ile Ser Tyr Asn Ala Gly Ser Lys Ala Tyr Ala Asp Ser Val Lys
1               5                   10                  15

Gly

<210> SEQ ID NO 331
<211> LENGTH: 17
<212> TYPE: PRT
<213> ORGANISM: Artificial Sequence
<220> FEATURE:
```

<223> OTHER INFORMATION: Heavy chain CDR2

<400> SEQUENCE: 331

Gly Ile Ser Tyr Asn Ser Gly Ser Lys Ala Tyr Ala Asp Ser Val Lys
1               5                   10                  15

Gly

<210> SEQ ID NO 332
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 332

Gly Ile Ser Tyr Asp Ser Gly Asn Lys Ala Tyr Ala Asp Ser Val Lys
1               5                   10                  15

Gly

<210> SEQ ID NO 333
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 333

Gly Ile Ser Tyr Asn Gly Gly Thr Ile Ala Tyr Ala Asp Ser Val Lys
1               5                   10                  15

Gly

<210> SEQ ID NO 334
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 334

Gly Val Ser Tyr Asn Ala Gly Asn Lys Ala Tyr Ala Asp Ser Val Arg
1               5                   10                  15

Gly

<210> SEQ ID NO 335
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 335

Gly Ile Ser Tyr Asp Ser Gly Thr Thr Ala Tyr Ala Asp Ser Val Lys
1               5                   10                  15

Gly

<210> SEQ ID NO 336
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 336

```
Gly Ile Ser Tyr Asn Ser Gly Asn Ile Ala Tyr Ala Asp Ser Val Arg
1               5                   10                  15

Gly

<210> SEQ ID NO 337
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 337

Gly Val Ser Tyr Asn Ala Gly Thr Thr Ala Tyr Ala Asp Ser Val Arg
1               5                   10                  15

Gly

<210> SEQ ID NO 338
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 338

Gly Ile Ser Tyr Asn Ser Gly Asn Ile Ala Tyr Ala Asp Ser Val Lys
1               5                   10                  15

Gly

<210> SEQ ID NO 339
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 339

Gly Ile Ser Tyr Asn Ala Gly Asn Lys Ala Tyr Ala Asp Ser Val Lys
1               5                   10                  15

Gly

<210> SEQ ID NO 340
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 340

Gly Ile Ser Tyr Asn Ala Gly Asn Thr Ala Tyr Ala Asp Ser Val Lys
1               5                   10                  15

Gly

<210> SEQ ID NO 341
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 341

Gly Ile Ser Tyr Asn Ser Gly Thr Thr Ala Tyr Ala Asp Ser Val Arg
1               5                   10                  15

Gly
```

<210> SEQ ID NO 342
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 342

Gly Ile Ser Tyr Asp Ala Gly Asn Ile Ala Tyr Ala Asp Ser Val Arg
1               5                   10                  15

Gly

<210> SEQ ID NO 343
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 343

Gly Val Ser Tyr Asn Ser Gly Asn Lys Ala Tyr Ala Asp Ser Val Arg
1               5                   10                  15

Gly

<210> SEQ ID NO 344
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 344

Gly Ile Ser Tyr Asn Ala Gly Thr Lys Ala Tyr Ala Asp Ser Val Arg
1               5                   10                  15

Gly

<210> SEQ ID NO 345
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 345

Gly Ile Ser Tyr Asn Ala Gly Thr Thr Ala Tyr Ala Asp Ser Val Lys
1               5                   10                  15

Gly

<210> SEQ ID NO 346
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 346

Gly Ile Ser Tyr Asn Gly Gly Asn Lys Ala Tyr Ala Asp Ser Val Arg
1               5                   10                  15

Gly

<210> SEQ ID NO 347
<211> LENGTH: 17

```
<212> TYPE: PRT
<213> ORGANISM: Artificial Sequence
<220> FEATURE:
<223> OTHER INFORMATION: Heavy chain CDR2

<400> SEQUENCE: 347

Gly Ile Ser Tyr Asn Ser Gly Ser Thr Ala Tyr Ala Asp Ser Val Arg
1               5                   10                  15

Gly

<210> SEQ ID NO 348
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 348

Gly Val Ser Tyr Asn Ser Gly Asn Lys Ala Tyr Ala Asp Ser Val Lys
1               5                   10                  15

Gly

<210> SEQ ID NO 349
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 349

Gly Ile Ser Tyr Asn Ser Gly Asn Thr Gly Tyr Ala Asp Ser Val Arg
1               5                   10                  15

Gly

<210> SEQ ID NO 350
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 350

Gly Ile Ser Tyr Asp Ala Gly Asn Thr Ala Tyr Ala Asp Ser Val Arg
1               5                   10                  15

Gly

<210> SEQ ID NO 351
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 351

Gly Val Ser Tyr Asn Ser Gly Ser Lys Ala Tyr Ala Asp Ser Val Lys
1               5                   10                  15

Gly

<210> SEQ ID NO 352
<211> LENGTH: 17
<212> TYPE: PRT
<213> ORGANISM: Artificial Sequence
<220> FEATURE:
<223> OTHER INFORMATION: Heavy chain CDR2
```

```
<400> SEQUENCE: 352

Gly Val Ser Tyr Asp Gly Gly Thr Thr Ala Tyr Ala Asp Ser Val Arg
1               5                   10                  15

Gly

<210> SEQ ID NO 353
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 353

Gly Ile Ser Tyr Asp Ala Gly Ser Thr Ala Tyr Ala Asp Ser Val Arg
1               5                   10                  15

Gly

<210> SEQ ID NO 354
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 354

Thr Val Ser Tyr Asp Ser Gly Asn Lys Tyr Tyr Ala Asp Ser Val Lys
1               5                   10                  15

Gly

<210> SEQ ID NO 355
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 355

Ile Ile Ser Tyr Asp Ser Ser Ser Lys Tyr Tyr Ala Asp Ser Val Lys
1               5                   10                  15

Gly

<210> SEQ ID NO 356
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 356

Val Val Ser Tyr Asp Gly Gly Asn Ile Tyr Tyr Ala Asp Ser Val Lys
1               5                   10                  15

Gly

<210> SEQ ID NO 357
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 357

Val Val Ser Tyr Asp Gly Ser Asn Thr Tyr Tyr Ala Asp Ser Val Lys
```

-continued

```
1               5                   10                  15

Gly

<210> SEQ ID NO 358
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 358

Val Val Ser Tyr Asp Gly Gly Ser Lys Tyr Tyr Ala Asp Ser Val Lys
1               5                   10                  15

Gly

<210> SEQ ID NO 359
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 359

Val Ile Ser Tyr Asp Gly Gly Ser Lys Tyr Tyr Ala Asp Ser Val Lys
1               5                   10                  15

Gly

<210> SEQ ID NO 360
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 360

Ser Val Ser Tyr Asp Gly Gly Ser Ile Tyr Tyr Ala Asp Ser Val Lys
1               5                   10                  15

Gly

<210> SEQ ID NO 361
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 361

Val Ile Ser Tyr Asp Gly Ser Asn Lys Tyr Tyr Ala Asp Ser Val Lys
1               5                   10                  15

Gly

<210> SEQ ID NO 362
<211> LENGTH: 6
<212> TYPE: PRT
<213> ORGANISM: Artificial Sequence
<220> FEATURE:
<223> OTHER INFORMATION: Heavy chain CDR3

<400> SEQUENCE: 362

Gly Arg Tyr Ser Asp Val
1               5

<210> SEQ ID NO 363
```

```
<211> LENGTH: 6
<212> TYPE: PRT
<213> ORGANISM: Artificial Sequence
<220> FEATURE:
<223> OTHER INFORMATION: Heavy chain CDR3

<400> SEQUENCE: 363

Gly Arg Met Leu Asp Val
1               5

<210> SEQ ID NO 364
<211> LENGTH: 6
<212> TYPE: PRT
<213> ORGANISM: Artificial Sequence
<220> FEATURE:
<223> OTHER INFORMATION: Heavy chain CDR3

<400> SEQUENCE: 364

Gly Arg Thr Met Asp Val
1               5

<210> SEQ ID NO 365
<211> LENGTH: 6
<212> TYPE: PRT
<213> ORGANISM: Artificial Sequence
<220> FEATURE:
<223> OTHER INFORMATION: Heavy chain CDR3

<400> SEQUENCE: 365

Gly Arg Ser Leu Asp Val
1               5

<210> SEQ ID NO 366
<211> LENGTH: 6
<212> TYPE: PRT
<213> ORGANISM: Artificial Sequence
<220> FEATURE:
<223> OTHER INFORMATION: Heavy chain CDR3

<400> SEQUENCE: 366

Gly Arg Leu Leu Asp Val
1               5

<210> SEQ ID NO 367
<211> LENGTH: 6
<212> TYPE: PRT
<213> ORGANISM: Artificial Sequence
<220> FEATURE:
<223> OTHER INFORMATION: Heavy chain CDR3

<400> SEQUENCE: 367

Gly Arg Leu Phe Asp Val
1               5

<210> SEQ ID NO 368
<211> LENGTH: 6
<212> TYPE: PRT
<213> ORGANISM: Artificial Sequence
<220> FEATURE:
<223> OTHER INFORMATION: Heavy chain CDR3

<400> SEQUENCE: 368

Gly Arg Tyr Leu Asp Val
1               5

<210> SEQ ID NO 369
<211> LENGTH: 9
```

-continued

```
<212> TYPE: PRT
<213> ORGANISM: Artificial Sequence
<220> FEATURE:
<223> OTHER INFORMATION: Heavy chain CDR3

<400> SEQUENCE: 369

Gly Ser Arg Arg Asp Ala Phe Asp Val
1               5

<210> SEQ ID NO 370
<211> LENGTH: 10
<212> TYPE: PRT
<213> ORGANISM: Artificial Sequence
<220> FEATURE:
<223> OTHER INFORMATION: Heavy chain CDR3

<400> SEQUENCE: 370

Gly Ser Gly Lys Arg Asp Ala Phe Asp Val
1               5                   10

<210> SEQ ID NO 371
<211> LENGTH: 10
<212> TYPE: PRT
<213> ORGANISM: Artificial Sequence
<220> FEATURE:
<223> OTHER INFORMATION: Heavy chain CDR3

<400> SEQUENCE: 371

Gly Ser Gly Arg Arg Asp Ala Phe Asp Val
1               5                   10

<210> SEQ ID NO 372
<211> LENGTH: 10
<212> TYPE: PRT
<213> ORGANISM: Artificial Sequence
<220> FEATURE:
<223> OTHER INFORMATION: Heavy chain CDR3

<400> SEQUENCE: 372

Gly Ser Gly Gln Arg Asp Ala Phe Asp Val
1               5                   10

<210> SEQ ID NO 373
<211> LENGTH: 10
<212> TYPE: PRT
<213> ORGANISM: Artificial Sequence
<220> FEATURE:
<223> OTHER INFORMATION: Heavy chain CDR3

<400> SEQUENCE: 373

Gly Ser Gly Gly Arg Asp Ala Phe Asp Val
1               5                   10

<210> SEQ ID NO 374
<211> LENGTH: 14
<212> TYPE: PRT
<213> ORGANISM: Artificial Sequence
<220> FEATURE:
<223> OTHER INFORMATION: Light chain CDR1

<400> SEQUENCE: 374

Thr Gly Ser Ser Ser Asp Val Gly Gly Tyr Asn Tyr Val Ser
1               5                   10

<210> SEQ ID NO 375
<211> LENGTH: 14
<212> TYPE: PRT
```

```
<213> ORGANISM: Artificial Sequence
<220> FEATURE:
<223> OTHER INFORMATION: Light chain CDR1

<400> SEQUENCE: 375

Gly Gly Ser Ser Ser Asp Val Gly Gly Tyr Asn Tyr Val Ser
1               5                   10

<210> SEQ ID NO 376
<211> LENGTH: 14
<212> TYPE: PRT
<213> ORGANISM: Artificial Sequence
<220> FEATURE:
<223> OTHER INFORMATION: Light chain CDR1

<400> SEQUENCE: 376

Gly Gly Ser Ser Ser Asn Ile Gly Gly Tyr Asn Tyr Val Ser
1               5                   10

<210> SEQ ID NO 377
<211> LENGTH: 14
<212> TYPE: PRT
<213> ORGANISM: Artificial Sequence
<220> FEATURE:
<223> OTHER INFORMATION: Light chain CDR1

<400> SEQUENCE: 377

Ser Gly Ser Ser Ser Asn Val Gly Ser Tyr Asn Tyr Val Ser
1               5                   10

<210> SEQ ID NO 378
<211> LENGTH: 14
<212> TYPE: PRT
<213> ORGANISM: Artificial Sequence
<220> FEATURE:
<223> OTHER INFORMATION: Light chain CDR1

<400> SEQUENCE: 378

Ser Gly Ser Ser Ser Asn Ile Gly Gly Tyr Asn Tyr Val Ser
1               5                   10

<210> SEQ ID NO 379
<211> LENGTH: 14
<212> TYPE: PRT
<213> ORGANISM: Artificial Sequence
<220> FEATURE:
<223> OTHER INFORMATION: Light chain CDR1

<400> SEQUENCE: 379

Gly Gly Ser Ser Ser Asn Val Gly Gly Tyr Asn Tyr Val Ser
1               5                   10

<210> SEQ ID NO 380
<211> LENGTH: 14
<212> TYPE: PRT
<213> ORGANISM: Artificial Sequence
<220> FEATURE:
<223> OTHER INFORMATION: Light chain CDR1

<400> SEQUENCE: 380

Ser Gly Ser Ser Ser Asp Ile Gly Gly Tyr Asn Tyr Val Ser
1               5                   10

<210> SEQ ID NO 381
<211> LENGTH: 14
<212> TYPE: PRT
<213> ORGANISM: Artificial Sequence
```

<220> FEATURE:
<223> OTHER INFORMATION: Light chain CDR1

<400> SEQUENCE: 381

Ser Gly Ser Ser Ser Asn Ile Gly Ser Tyr Asn Tyr Val Ser
1               5                   10

<210> SEQ ID NO 382
<211> LENGTH: 14
<212> TYPE: PRT
<213> ORGANISM: Artificial Sequence
<220> FEATURE:
<223> OTHER INFORMATION: Light chain CDR1

<400> SEQUENCE: 382

Ala Gly Ser Ser Ser Asp Ile Gly Gly Tyr Asn Tyr Val Ser
1               5                   10

<210> SEQ ID NO 383
<211> LENGTH: 14
<212> TYPE: PRT
<213> ORGANISM: Artificial Sequence
<220> FEATURE:
<223> OTHER INFORMATION: Light chain CDR1

<400> SEQUENCE: 383

Ala Gly Ser Ser Ser Asn Ile Gly Gly Tyr Asn Tyr Val Ser
1               5                   10

<210> SEQ ID NO 384
<211> LENGTH: 14
<212> TYPE: PRT
<213> ORGANISM: Artificial Sequence
<220> FEATURE:
<223> OTHER INFORMATION: Light chain CDR1

<400> SEQUENCE: 384

Gly Gly Thr Ser Ser Asn Ile Gly Gly Tyr Asn Tyr Val Ser
1               5                   10

<210> SEQ ID NO 385
<211> LENGTH: 14
<212> TYPE: PRT
<213> ORGANISM: Artificial Sequence
<220> FEATURE:
<223> OTHER INFORMATION: Light chain CDR1

<400> SEQUENCE: 385

Ala Gly Ser Ser Ser Asn Ile Gly Ser Tyr Asn Tyr Val Ser
1               5                   10

<210> SEQ ID NO 386
<211> LENGTH: 14
<212> TYPE: PRT
<213> ORGANISM: Artificial Sequence
<220> FEATURE:
<223> OTHER INFORMATION: Light chain CDR1

<400> SEQUENCE: 386

Ser Gly Thr Ser Ser Asp Ile Gly Gly Tyr Asn Tyr Val Ser
1               5                   10

<210> SEQ ID NO 387
<211> LENGTH: 14
<212> TYPE: PRT
<213> ORGANISM: Artificial Sequence
<220> FEATURE:

<223> OTHER INFORMATION: Light chain CDR1

<400> SEQUENCE: 387

Ser Gly Ser Ser Ser Asp Val Gly Gly Tyr Asn Tyr Val Ser
1               5                   10

<210> SEQ ID NO 388
<211> LENGTH: 14
<212> TYPE: PRT
<213> ORGANISM: Artificial Sequence
<220> FEATURE:
<223> OTHER INFORMATION: Light chain CDR1

<400> SEQUENCE: 388

Gly Gly Thr Ser Ser Asp Val Gly Ser Tyr Asn Tyr Val Ser
1               5                   10

<210> SEQ ID NO 389
<211> LENGTH: 14
<212> TYPE: PRT
<213> ORGANISM: Artificial Sequence
<220> FEATURE:
<223> OTHER INFORMATION: Light chain CDR1

<400> SEQUENCE: 389

Thr Gly Ser Ser Ser Asn Val Gly Gly Tyr Asn Tyr Val Ser
1               5                   10

<210> SEQ ID NO 390
<211> LENGTH: 14
<212> TYPE: PRT
<213> ORGANISM: Artificial Sequence
<220> FEATURE:
<223> OTHER INFORMATION: Light chain CDR1

<400> SEQUENCE: 390

Ala Gly Thr Ser Ser Asn Ile Gly Gly Tyr Asn Tyr Val Ser
1               5                   10

<210> SEQ ID NO 391
<211> LENGTH: 14
<212> TYPE: PRT
<213> ORGANISM: Artificial Sequence
<220> FEATURE:
<223> OTHER INFORMATION: Light chain CDR1

<400> SEQUENCE: 391

Thr Gly Ser Ser Ser Asn Ile Gly Gly Tyr Asn Tyr Val Ser
1               5                   10

<210> SEQ ID NO 392
<211> LENGTH: 14
<212> TYPE: PRT
<213> ORGANISM: Artificial Sequence
<220> FEATURE:
<223> OTHER INFORMATION: Light chain CDR1

<400> SEQUENCE: 392

Gly Gly Ser Ser Ser Asn Ile Gly Ser Tyr Asn Tyr Val Ser
1               5                   10

<210> SEQ ID NO 393
<211> LENGTH: 14
<212> TYPE: PRT
<213> ORGANISM: Artificial Sequence
<220> FEATURE:
<223> OTHER INFORMATION: Light chain CDR1

<400> SEQUENCE: 393

Ser Gly Thr Ser Ser Asn Val Gly Gly Tyr Asn Tyr Val Ser
1               5                   10

<210> SEQ ID NO 394
<211> LENGTH: 14
<212> TYPE: PRT
<213> ORGANISM: Artificial Sequence
<220> FEATURE:
<223> OTHER INFORMATION: Light chain CDR1

<400> SEQUENCE: 394

Ser Gly Thr Ser Ser Asp Val Gly Gly Tyr Asn Tyr Val Ser
1               5                   10

<210> SEQ ID NO 395
<211> LENGTH: 14
<212> TYPE: PRT
<213> ORGANISM: Artificial Sequence
<220> FEATURE:
<223> OTHER INFORMATION: Light chain CDR1

<400> SEQUENCE: 395

Ala Gly Ser Ser Ser Asn Val Gly Gly Tyr Asn Tyr Val Ser
1               5                   10

<210> SEQ ID NO 396
<211> LENGTH: 14
<212> TYPE: PRT
<213> ORGANISM: Artificial Sequence
<220> FEATURE:
<223> OTHER INFORMATION: Light chain CDR1

<400> SEQUENCE: 396

Thr Gly Thr Ser Ser Asn Val Gly Ser Tyr Asn Tyr Val Ser
1               5                   10

<210> SEQ ID NO 397
<211> LENGTH: 14
<212> TYPE: PRT
<213> ORGANISM: Artificial Sequence
<220> FEATURE:
<223> OTHER INFORMATION: Light chain CDR1

<400> SEQUENCE: 397

Thr Gly Thr Ser Ser Asn Ile Gly Gly Tyr Asn Tyr Val Ser
1               5                   10

<210> SEQ ID NO 398
<211> LENGTH: 14
<212> TYPE: PRT
<213> ORGANISM: Artificial Sequence
<220> FEATURE:
<223> OTHER INFORMATION: Light chain CDR1

<400> SEQUENCE: 398

Gly Gly Thr Ser Ser Asp Val Gly Gly Tyr Asn Tyr Val Ser
1               5                   10

<210> SEQ ID NO 399
<211> LENGTH: 14
<212> TYPE: PRT
<213> ORGANISM: Artificial Sequence
<220> FEATURE:
<223> OTHER INFORMATION: Light chain CDR1

<400> SEQUENCE: 399

Ala Gly Ser Ser Ser Asn Val Val Ser Tyr Asn Tyr Val Ser
1               5                   10

<210> SEQ ID NO 400
<211> LENGTH: 14
<212> TYPE: PRT
<213> ORGANISM: Artificial Sequence
<220> FEATURE:
<223> OTHER INFORMATION: Light chain CDR1

<400> SEQUENCE: 400

Thr Gly Thr Ser Ser Asn Ile Gly Ser Tyr Asn Tyr Val Ser
1               5                   10

<210> SEQ ID NO 401
<211> LENGTH: 11
<212> TYPE: PRT
<213> ORGANISM: Artificial Sequence
<220> FEATURE:
<223> OTHER INFORMATION: Light chain CDR1

<400> SEQUENCE: 401

Arg Ala Ser Gln Ser Ile Ser Asn Arg Leu Ala
1               5                   10

<210> SEQ ID NO 402
<211> LENGTH: 11
<212> TYPE: PRT
<213> ORGANISM: Artificial Sequence
<220> FEATURE:
<223> OTHER INFORMATION: Light chain CDR1

<400> SEQUENCE: 402

Gln Ala Ser Gln Gly Ile Ser Asn Arg Leu Ala
1               5                   10

<210> SEQ ID NO 403
<211> LENGTH: 11
<212> TYPE: PRT
<213> ORGANISM: Artificial Sequence
<220> FEATURE:
<223> OTHER INFORMATION: Light chain CDR1

<400> SEQUENCE: 403

Gln Ala Ser Gln Ser Ile Ser Ser Arg Leu Ala
1               5                   10

<210> SEQ ID NO 404
<211> LENGTH: 11
<212> TYPE: PRT
<213> ORGANISM: Artificial Sequence
<220> FEATURE:
<223> OTHER INFORMATION: Light chain CDR1

<400> SEQUENCE: 404

Gln Ala Ser Gln Gly Ile Arg Asn Arg Leu Ala
1               5                   10

<210> SEQ ID NO 405
<211> LENGTH: 11
<212> TYPE: PRT
<213> ORGANISM: Artificial Sequence
<220> FEATURE:
<223> OTHER INFORMATION: Light chain CDR1

<400> SEQUENCE: 405

Arg Ala Ser Gln Ser Ile Ser Ser Arg Leu Ala
1               5                   10

<210> SEQ ID NO 406
<211> LENGTH: 7
<212> TYPE: PRT
<213> ORGANISM: Artificial Sequence
<220> FEATURE:
<223> OTHER INFORMATION: Light chain CDR2

<400> SEQUENCE: 406

Asp Val Thr Lys Arg Pro Ser
1               5

<210> SEQ ID NO 407
<211> LENGTH: 7
<212> TYPE: PRT
<213> ORGANISM: Artificial Sequence
<220> FEATURE:
<223> OTHER INFORMATION: Light chain CDR2

<400> SEQUENCE: 407

Asp Val Asn Lys Arg Pro Ser
1               5

<210> SEQ ID NO 408
<211> LENGTH: 7
<212> TYPE: PRT
<213> ORGANISM: Artificial Sequence
<220> FEATURE:
<223> OTHER INFORMATION: Light chain CDR2

<400> SEQUENCE: 408

Asp Val Ser Lys Arg Pro Ser
1               5

<210> SEQ ID NO 409
<211> LENGTH: 7
<212> TYPE: PRT
<213> ORGANISM: Artificial Sequence
<220> FEATURE:
<223> OTHER INFORMATION: Light chain CDR2

<400> SEQUENCE: 409

Asp Val Asn Glu Arg Pro Ser
1               5

<210> SEQ ID NO 410
<211> LENGTH: 7
<212> TYPE: PRT
<213> ORGANISM: Artificial Sequence
<220> FEATURE:
<223> OTHER INFORMATION: Light chain CDR2

<400> SEQUENCE: 410

Asp Val Ser Asn Arg Pro Ser
1               5

<210> SEQ ID NO 411
<211> LENGTH: 7
<212> TYPE: PRT
<213> ORGANISM: Artificial Sequence
<220> FEATURE:
<223> OTHER INFORMATION: Light chain CDR2

<400> SEQUENCE: 411

Asp Val Thr Asp Arg Pro Ser
1               5

<210> SEQ ID NO 412
<211> LENGTH: 7
<212> TYPE: PRT
<213> ORGANISM: Artificial Sequence
<220> FEATURE:
<223> OTHER INFORMATION: Light chain CDR2

<400> SEQUENCE: 412

Asp Val Asn Asn Arg Pro Ser
1               5

<210> SEQ ID NO 413
<211> LENGTH: 7
<212> TYPE: PRT
<213> ORGANISM: Artificial Sequence
<220> FEATURE:
<223> OTHER INFORMATION: Light chain CDR2

<400> SEQUENCE: 413

Asp Val Thr Asn Arg Pro Ser
1               5

<210> SEQ ID NO 414
<211> LENGTH: 7
<212> TYPE: PRT
<213> ORGANISM: Artificial Sequence
<220> FEATURE:
<223> OTHER INFORMATION: Light chain CDR2

<400> SEQUENCE: 414

Asp Val Asn Asp Arg Pro Ser
1               5

<210> SEQ ID NO 415
<211> LENGTH: 7
<212> TYPE: PRT
<213> ORGANISM: Artificial Sequence
<220> FEATURE:
<223> OTHER INFORMATION: Light chain CDR2

<400> SEQUENCE: 415

Asp Val Ser Asp Arg Pro Ser
1               5

<210> SEQ ID NO 416
<211> LENGTH: 7
<212> TYPE: PRT
<213> ORGANISM: Artificial Sequence
<220> FEATURE:
<223> OTHER INFORMATION: Light chain CDR2

<400> SEQUENCE: 416

Asp Val Ser Glu Arg Pro Ser
1               5

<210> SEQ ID NO 417
<211> LENGTH: 7
<212> TYPE: PRT
<213> ORGANISM: Artificial Sequence
<220> FEATURE:
<223> OTHER INFORMATION: Light chain CDR2

<400> SEQUENCE: 417

Asp Val Thr Glu Pro Pro Ser

```
1               5

<210> SEQ ID NO 418
<211> LENGTH: 7
<212> TYPE: PRT
<213> ORGANISM: Artificial Sequence
<220> FEATURE:
<223> OTHER INFORMATION: Light chain CDR2

<400> SEQUENCE: 418

Glu Val Asn Lys Arg Pro Ser
1               5

<210> SEQ ID NO 419
<211> LENGTH: 7
<212> TYPE: PRT
<213> ORGANISM: Artificial Sequence
<220> FEATURE:
<223> OTHER INFORMATION: Light chain CDR2

<400> SEQUENCE: 419

Glu Val Ser Asn Arg Pro Ser
1               5

<210> SEQ ID NO 420
<211> LENGTH: 7
<212> TYPE: PRT
<213> ORGANISM: Artificial Sequence
<220> FEATURE:
<223> OTHER INFORMATION: light chain CDR2

<400> SEQUENCE: 420

Glu Val Asn Asn Arg Pro Ser
1               5

<210> SEQ ID NO 421
<211> LENGTH: 7
<212> TYPE: PRT
<213> ORGANISM: Artificial Sequence
<220> FEATURE:
<223> OTHER INFORMATION: Light chain CDR2

<400> SEQUENCE: 421

Lys Ala Ser Asn Leu Glu Ser
1               5

<210> SEQ ID NO 422
<211> LENGTH: 7
<212> TYPE: PRT
<213> ORGANISM: Artificial Sequence
<220> FEATURE:
<223> OTHER INFORMATION: Light chain CDR2

<400> SEQUENCE: 422

Lys Ala Ser Asn Leu Gln Ser
1               5

<210> SEQ ID NO 423
<211> LENGTH: 7
<212> TYPE: PRT
<213> ORGANISM: Artificial Sequence
<220> FEATURE:
<223> OTHER INFORMATION: Light chain CDR2

<400> SEQUENCE: 423

Lys Ala Ser Ser Leu Gln Ser
1               5
```

```
<210> SEQ ID NO 424
<211> LENGTH: 7
<212> TYPE: PRT
<213> ORGANISM: Artificial Sequence
<220> FEATURE:
<223> OTHER INFORMATION: Light chain CDR2

<400> SEQUENCE: 424

Lys Ala Ser Asn Leu Glu Thr
1               5

<210> SEQ ID NO 425
<211> LENGTH: 7
<212> TYPE: PRT
<213> ORGANISM: Artificial Sequence
<220> FEATURE:
<223> OTHER INFORMATION: Light chain CDR2

<400> SEQUENCE: 425

Lys Ala Ser Ser Leu Glu Thr
1               5

<210> SEQ ID NO 426
<211> LENGTH: 10
<212> TYPE: PRT
<213> ORGANISM: Artificial Sequence
<220> FEATURE:
<223> OTHER INFORMATION: Light chain CDR3

<400> SEQUENCE: 426

Ala Ser Tyr Ser Ser Asn Thr Phe Tyr Val
1               5                   10

<210> SEQ ID NO 427
<211> LENGTH: 10
<212> TYPE: PRT
<213> ORGANISM: Artificial Sequence
<220> FEATURE:
<223> OTHER INFORMATION: Light chain CDR3

<400> SEQUENCE: 427

Gly Ser Tyr Asn Asn Asn Thr Phe Tyr Val
1               5                   10

<210> SEQ ID NO 428
<211> LENGTH: 10
<212> TYPE: PRT
<213> ORGANISM: Artificial Sequence
<220> FEATURE:
<223> OTHER INFORMATION: Light chain CDR3

<400> SEQUENCE: 428

Gly Ser Tyr Ser Ser Asn Thr Phe Tyr Val
1               5                   10

<210> SEQ ID NO 429
<211> LENGTH: 10
<212> TYPE: PRT
<213> ORGANISM: Artificial Sequence
<220> FEATURE:
<223> OTHER INFORMATION: Light chain CDR3

<400> SEQUENCE: 429

Gly Ser Tyr Ser Asn Asn Asn Phe Tyr Val
1               5                   10
```

<210> SEQ ID NO 430
<211> LENGTH: 10
<212> TYPE: PRT
<213> ORGANISM: Artificial Sequence
<220> FEATURE:
<223> OTHER INFORMATION: Light chain CDR3

<400> SEQUENCE: 430

Gly Ser Tyr Ser Asn Ser Asn Phe Tyr Val
1               5                   10

<210> SEQ ID NO 431
<211> LENGTH: 10
<212> TYPE: PRT
<213> ORGANISM: Artificial Sequence
<220> FEATURE:
<223> OTHER INFORMATION: Light chain CDR3

<400> SEQUENCE: 431

Gly Ser Tyr Asp Ser Asn Thr Phe Tyr Val
1               5                   10

<210> SEQ ID NO 432
<211> LENGTH: 10
<212> TYPE: PRT
<213> ORGANISM: Artificial Sequence
<220> FEATURE:
<223> OTHER INFORMATION: Light chain CDR3

<400> SEQUENCE: 432

Gly Ala Tyr Ser Asn Thr Asn Phe Tyr Val
1               5                   10

<210> SEQ ID NO 433
<211> LENGTH: 10
<212> TYPE: PRT
<213> ORGANISM: Artificial Sequence
<220> FEATURE:
<223> OTHER INFORMATION: Light chain CDR3

<400> SEQUENCE: 433

Ala Ser Tyr Ser Asn Ser Asn Phe Tyr Val
1               5                   10

<210> SEQ ID NO 434
<211> LENGTH: 10
<212> TYPE: PRT
<213> ORGANISM: Artificial Sequence
<220> FEATURE:
<223> OTHER INFORMATION: Light chain CDR3

<400> SEQUENCE: 434

Gly Ser Tyr Ser Asn Thr Asn Phe Tyr Val
1               5                   10

<210> SEQ ID NO 435
<211> LENGTH: 9
<212> TYPE: PRT
<213> ORGANISM: Artificial Sequence
<220> FEATURE:
<223> OTHER INFORMATION: Light chain CDR3

<400> SEQUENCE: 435

Gln Gln Thr Asn Ser Phe Pro Leu Thr
1               5

FCRN-SPECIFIC HUMAN ANTIBODY AND COMPOSITION FOR TREATMENT OF AUTOIMMUNE DISEASES

TECHNICAL FIELD

The present invention relates to a human antibody specific for FcRn (stands for neonatal Fc receptor, also called FcRP, FcRB or Brambell receptor) that is a receptor with a high affinity for IgG, a production method thereof, a composition for treating autoimmune disease, which comprises the antibody, and a method of treating and diagnosing autoimmune disease using the same. The FcRn-specific antibody according to the present invention can bind to FcRn non-competitively with IgG or the like to reduce serum pathogenic auto-antibody levels, and thus can be used for the treatment of autoimmune diseases.

BACKGROUND ART

Antibodies are immunological proteins that bind to a specific antigen. In most animals, including humans and mice, antibodies are constructed from paired heavy and light polypeptide chains. Each chain is made up of two distinct regions, referred to as the variable and constant regions. The light and heavy chain variable regions show significant sequence diversity between antibodies, and are responsible for binding the target antigen. The constant regions show less sequence diversity, and are responsible for binding a number of natural proteins to elicit important biochemical events. In humans there are five different classes of antibodies including IgA (which includes subclasses IgA1 and IgA2), IgD, IgE, IgG (which includes subclasses IgG1, IgG2, IgG3, and IgG4), and IgM. The distinguishing feature between these antibody classes is their constant regions.

IgG antibodies are most abundantly present in serum, protect the body from the invasion of pathogens, hasten the recruitment of immune system components, and mediate inflammatory responses in tissues. IgG antibodies are tetrameric proteins composed of two heavy chains and two light chains. The IgG heavy chain is composed of four immunoglobulin domains linked from N- to C-terminus in the order VH-CH1-CH2-CH3, referring to the heavy chain variable domain (VH), heavy chain constant domain 1 (CH1), heavy chain constant domain 2 (CH2), and heavy chain constant domain 3 (CH3), respectively.

The IgG light chain is composed of two immunoglobulin domains linked from N- to C-terminus in the order of VL-CL, referring to the light chain variable domain (VL) and the light chain constant domain (CL), respectively.

Under normal conditions, the half-life of most IgG excluding IgG3 isotype in serum is about 22-23 days in humans, which is a prolonged period relative to the serum half-life of other plasma proteins. With respect to this prolonged serum half-life of IgG, IgG that entered cells by endocytosis can strongly bind to neonatal Fc receptor (FcRn, a kind of Fc gamma receptor) in endosomes at a pH of 6.0 to avoid the degradative lysosomal pathway. When the IgG-FcRn complex cycles to the plasma membrane, IgG dissociates rapidly from FcRn in the bloodstream at slightly basic pH (~7.4). By this receptor-mediated recycling mechanism, FcRn effectively rescues the IgG from degradation in lysosomes, thereby prolonging the half-life of IgG (Roopenian et al. J. Immunol. 170:3528, 2003).

FcRn was identified in the neonatal rat gut, where it functions to mediate the absorption of IgG antibody from the mother's milk and facilitates its transport to the circulatory system. FcRn has also been isolated from human placenta, where it mediates absorption and transport of maternal IgG to the fetal circulation. In adults, FcRn is expressed in a number of tissues, including epithelial tissues of the lung, intestine, kidney, as well as nasal, vaginal, and biliary tree surfaces.

FcRn is a non-covalent heterodimer that typically resides in the endosomes of endothelial and epithelial cells. FcRn is a membrane bound receptor having three heavy chain alpha domains ($\alpha 1$, $\alpha 2$ and $\alpha 3$) and a single soluble light chain $\beta 2$-microglobulin ($\beta 2m$) domain. Structurally, it belongs to a family of major histocompatibility complex class 1 molecules that have $\beta 2m$ as a common light chain. The FcRn chain has a molecular weight of about 46 kD and is composed of an ectodomain containing the $\alpha 1$, $\alpha 2$, and $\alpha 3$ heavy chain domains and a $\beta 2m$ light chain domain and having a single sugar chain, a single-pass transmembrane, and a relatively short cytoplasmic tail (Burmeister et al. Nature 372:366, 1994.).

In order to study the contributions of FcRn to IgG homeostasis, mice have been engineered so that at least part of the genes encoding $\beta 2m$ and FcRn heavy chains have been "knocked out" so that these proteins are not expressed. In these mice, the serum half-life and concentrations of IgG were dramatically reduced (Junghans et al, Proc. Natl. Acad. Sci. 93:5512, 1996), suggesting a FcRn-dependent mechanism for IgG homeostasis. It has also been suggested that anti-human FcRn antibodies may be generated in these FcRn knockout mice and that these antibodies may prevent the binding of IgG to FcRn. However, such antibodies have not been generated or tested (WO 02/43658 A).

The inhibition of IgG binding to FcRn negatively alters IgG serum half-life by preventing IgG recycling, so that autoimmune diseases caused by auto-antibodies can be treated. This possibility was shown in a mouse model of autoimmune cutaneous bullous diseases (Li et al. J. Clin. Invest. 115:3440, 2005). Accordingly, agents that block or antagonize the binding of IgG to FcRn may be used in a method for treating or preventing autoimmune and inflammatory diseases, which are mediated by IgG.

Autoimmune diseases and alloimmune diseases are mediated by pathogenic antibodies, and typical examples thereof include immune neutropenia, Guillain-Barré syndrome, epilepsy, autoimmune encephalitis, Isaac's syndrome, nevus syndrome, pemphigus vulgaris, Pemphigus foliaceus, Bullous pemphigoid, epidermolysis bullosa acquisita, pemphigoid gestationis, mucous membrane pemphigoid, antiphospholipid syndrome, autoimmune anemia, autoimmune Grave's disease, Goodpasture's syndrome, myasthenia gravis, multiple sclerosis, rheumatoid arthritis, lupus, and idiopathic thrombocytopenic purpura (hereinafter referred to as ITP). ITP is a disease caused by the destruction of peripheral platelets due to the generation of auto-antibodies that bind to a specific platelet membrane glycoprotein. Anti-platelet antibodies opsonize platelets and result in rapid platelet destruction by reticular cells (e.g., macrophages).

In general, attempts to treat ITP include suppressing the immune system, and consequently causing an increase in platelet levels. ITP affects women more frequently than men, and more common in children than adults. The incidence is 1 out of 10,000 people. Chronic ITP is one of the major blood disorders in both adults and children. It is a source of significant hospitalization and treatment cost at specialized hematological departments in the US and around the world. Each year there are approximately 20,000 new cases in the US, and the cost for ITP care and special therapy is extremely high. Most children with ITP have a very low platelet count that causes sudden bleeding, with typical symptoms including bruises, small red dots on the skin, nosebleeds and bleeding gums. Although children can sometimes recover with no treatment, many doctors recommend careful observation and mitigation of bleeding and treatment with intravenous infusions of gamma globulin.

Methods of treating autoimmune diseases by intravenous administration of IgG (IVIG) in large amounts have been widely used (Arnson autoimmunity 42:553 (2009)). IVIG effects are explained by various mechanisms, but are also explained by a mechanism that increases the clearance of pathogenic antibodies by competition with endogenous IgG for FcRn. Intravenous administration of human immunoglobulin (IVIG) in large amounts has been shown to increase platelet counts in children afflicted with immune ITP, and IVIG has shown to be beneficial as a treatment for several other autoimmune conditions. Many studies have investigated the mechanisms by which IVIG achieves effects in the treatment of autoimmune diseases. With regard to ITP, early investigations led to the conclusion that IVIG effects are mainly due to blockade of the Fc receptors responsible for phagocytosis of antibody-opsonized platelets. Subsequent studies showed that Fc-depleted IVIG preparations provided increases in platelet counts in some patients with ITP, and recently it was reported that IVIG effects are due to stimulation of FcγRIIb expression on macrophage cells, leading to inhibition of platelet phagocytosis.

However, such IVIG treatments have substantial side effects and are very costly to administer. Further, other therapies used for the treatment of autoimmune/alloimmune conditions other than IVIG include polyclonal anti-D immunoglobulin, corticosteroids, immuno-suppressants (including chemotherapeutics), cytokines, plasmapheresis, extracorporeal antibody adsorption (e.g., using Prosorba columns), surgical interventions such as splenectomy, and others. However, like IVIG, these therapies are also complicated by incomplete efficacy and high cost. Also, very high doses of IVIG are required to produce substantial increases in the clearance of pathogenic antibody due to the putative mechanism of IVIG inhibition of FcRn binding with pathogenic antibody (i.e., competitive inhibition) and due to the fact that IgG shows very low affinity for FcRn at physiologic pH (i.e., pH 7.2-7.4), and the typical clinical dose of IVIG is about 2 g/kg.

The use of an inhibitor that competitively inhibits the binding of IgG to FcRn to treat autoimmune diseases is a promising therapeutic method. However, owing to the high affinity of endogenous IgG for FcRn and to the high concentrations of endogenous IgG in blood, it is likely that competitive inhibition of FcRn would require very high doses, and thus have the same limitations similar to those of the current IVIG treatment.

Accordingly, there is an urgent need for the development of a human antibody that has a high affinity for FcRn, and thus can remove pathogenic antibody even at low doses and reduce immunogenicity.

DISCLOSURE OF INVENTION

Technical Problem

The present inventors have made extensive efforts to solve the above-described problems and to develop a human antibody that has a high affinity for FcRn, and thus can remove pathogenic antibody even at low doses and reduce immunogenicity. As a result, the present inventors have produced and selected a human antibody, which binds specifically to the FcRn chain in a pH-independent manner, from a human antibody cDNA library. In addition, the present inventors have found that the antibody can be used to prevent or treat autoimmune disease, thereby completing the present invention.

Therefore, it is an object of the present invention to provide a therapeutic agent capable of efficiently and radically treating autoimmune diseases, including ITP, an antibody having the ability to bind specifically to FcRn, and a method for producing the antibody.

The FcRn-specific antibody according to the present invention can bind specifically to FcRn in a pH-independent manner to non-competitively inhibit the binding of the antibody Fc to FcRn to thereby reduce in vivo auto-antibody that is the cause of autoimmune diseases, thereby treating autoimmune diseases.

Another object of the present invention is to provide a pharmaceutical composition for treating autoimmune diseases, including ITP, immune neutropenia, Guillain-Barré syndrome, epilepsy, autoimmune encephalitis, Isaac's syndrome, nevus syndrome, pemphigus vulgaris, Pemphigus foliaceus, Bullous pemphigoid, epidermolysis bullosa acquisita, pemphigoid gestationis, mucous membrane pemphigoid, antiphospholipid syndrome, autoimmune anemia, autoimmune Grave's disease, Goodpasture's syndrome, myasthenia gravis, multiple sclerosis, rheumatoid arthritis, and lupus, the composition containing the FcRn-specific antibody.

Still another object of the present invention is to provide methods for preventing or treating and diagnosing autoimmune diseases, including ITP, immune neutropenia, Guillain-Barré syndrome, epilepsy, autoimmune encephalitis, Isaac's syndrome, nevus syndrome, pemphigus vulgaris, Pemphigus foliaceus, Bullous pemphigoid, epidermolysis bullosa acquisita, pemphigoid gestationis, mucous membrane pemphigoid, antiphospholipid syndrome, autoimmune anemia, autoimmune Grave's disease, Goodpasture's syndrome, myasthenia gravis, multiple sclerosis, rheumatoid arthritis, and lupus, the method comprising using the FcRn-specific antibody.

Technical Solution

To achieve the above objects, the present inventors have developed a complete human antibody, which can bind specifically to FcRn with high affinity in a pH-independent manner and is composed of a human-derived sequence, and thus causes little or no immune response when being administered in vivo. The present inventors have also developed an antibody having a higher affinity by affinity maturation of this complete human antibody.

The antibody according to the present invention is a polyclonal or monoclonal antibody having binding specificity to FcRn. Preferably, it is in the form of monoclonal antibody, particularly human monoclonal antibody, for human FcRn, and acts as a non-competitive inhibitor of IgG in binding to FcRn. The binding of the antibody of the present invention to FcRn results in the inhibition of pathogenic antibody to FcRn, which promotes the clearance (i.e., removal) of pathogenic antibody from the body of the subject to reduce the half-life of the pathogenic antibody.

As used herein, the term "pathogenic antibody" means antibodies that cause pathological conditions or diseases. Examples of such antibodies include, but are not limited to, anti-platelet antibodies, anti-acetylcholine antibodies, antinucleic acid antibodies, anti-phospholipid antibodies, anti-collagen antibodies, anti-ganglioside antibodies, anti-desmoglein antibodies, etc.

The antibody according to the present invention has an advantage in that it makes it possible to non-competitively inhibit the binding of pathogenic antibody to FcRn at physiological pH (i.e., pH 7.0-7.4). US 2002/0138863A and the like describe that an antibody should bind to FcRn at the same site critical for the binding of IgG to Fc so that the binding of IgG to FcRn is inhibited. FcRn binds to its ligand (i.e., IgG) and does not substantially show affinity for IgG at physiological pH rather than acidic pH. Thus, the anti-FcRn antibody that binds specifically to FcRn at physiological pH acts as a non-competitive inhibitor of the binding of IgG to FcRn, and in this case, the binding of the anti-FcRn antibody to FcRn is not influenced by the presence of IgG. Thus, the inventive antibody that binds to FcRn non-competitively with IgG in a pH-independent manner has an advantage over conventional competitive inhibitors (i.e., antibodies that bind to FcRn competitively with IgG) in that it can treat diseases even at significantly low concentrations by the FcRn-mediated signaling of IgG. In addition, in the procedure of intracellular migration in a state bound to FcRn, the anti-FcRn antibody according to the present invention maintains its binding to FcRn with an affinity higher than IgG in blood, and thus can inhibit the binding of IgG to FcRn even in endosomes that are acidic pH environments in which IgG can bind to FcRn, thereby promoting the clearance of IgG.

In summary, unlike the antibodies disclosed in prior art documents, the antibody according to the present invention has an affinity for FcRn even in a physiological pH environment (i.e., pH 7.0-7.4) in which IgG does not bind to FcRn. At a pH of 6.0, the antibody of the present invention has a higher affinity for FcRn compared to serum IgG, suggesting that it acts as a non-competitive inhibitor.

In the present invention, a complete human antibody that binds to FcRn with high affinity and specificity was obtained from a single-chain Fv (scFv) phage library using phage display technology. Phage library preparation and phage display may be performed as described in U.S. Pat. Nos. 7,063,943B, 6,172,197B, and the like. From the library constructed by inducing random mutations in the selected variable region of the complete human antibody, a complete human antibody having increased specificity and affinity was obtained by performing affinity maturation for selecting a human antibody having higher affinity and specificity for FcRn using phage display technology. Affinity maturation may be performed according to the methods described in U.S. Pat. Nos. 5,977,322, 5,994,511, 6,218,149, and the like.

The inventive antibody that is obtained by the above-described method has any one of the heavy-chain variable regions of FcRn-specific antibody, which comprise CDR1, CDR2 and CDR3 contained in any one amino acid sequence selected from the group consisting of even numbers between SEQ ID NOS: 2 to 144 (e.g., 2, 4, 66, 128, etc.), or in an amino acid sequence set forth in SEQ ID NO: 289 or 291, or a heavy-chain variable region having a sequence homology thereto of at least 90%, preferably at least 95%, and/or any one of the light-chain variable regions of FcRn-specific antibody, which comprise CDR1, CDR2 and CDR3 contained in any one amino acid sequence selected from the group consisting of even numbers between SEQ ID NOS: 146 to 288 (e.g., 148, 196, 244, 266, etc.), or in an amino acid sequence set forth in SEQ ID NO: 290 or 292, or a light-chain variable region having a sequence homology thereto of at least 90%, preferably at least 95%.

Particularly, the antibody according to the present invention has a heavy-chain variable region and a light-chain variable region selected from among the following heavy-chain and light-chain variable regions (1) to (74):

(1) a heavy-chain variable region, which comprises CDR1, CDR2 and CDR3 contained in an amino acid sequence of SEQ ID NO: 2, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 146, or a light-chain variable region having a sequence homology thereto of at least 90%, preferably at least 95%;

(2) a heavy-chain variable region, which comprises CDR1, CDR2 and CDR3 contained in an amino acid sequence of SEQ ID NO: 4, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 148, or a light-chain variable region having a sequence homology thereto of at least 90%, preferably at least 95%;

(3) a heavy-chain variable region, which comprises CDR1, CDR2 and CDR3 contained in an amino acid sequence of SEQ ID NO: 6, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 150, or a light-chain variable region having a sequence homology thereto of at least 90%, preferably at least 95%;

(4) a heavy-chain variable region, which comprises CDR1, CDR2 and CDR3 contained in an amino acid sequence of SEQ ID NO: 8, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 152, or a light-chain variable region having a sequence homology thereto of at least 90%, preferably at least 95%;

(5) a heavy-chain variable region, which comprises CDR1, CDR2 and CDR3 contained in an amino acid sequence of SEQ ID NO: 10, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 154, or a light-chain variable region having a sequence homology thereto of at least 90%, preferably at least 95%;

(6) a heavy-chain variable region, which comprises CDR1, CDR2 and CDR3 contained in an amino acid sequence of SEQ ID NO: 12, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 156, or a light-chain variable region having a sequence homology thereto of at least 90%, preferably at least 95%;

(7) a heavy-chain variable region, which comprises CDR1, CDR2 and CDR3 contained in an amino acid sequence of SEQ ID NO: 14, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 158, or a light-chain variable region having a sequence homology thereto of at least 90%, preferably at least 95%;

(8) a heavy-chain variable region, which comprises CDR1, CDR2 and CDR3 contained in an amino acid sequence of SEQ ID NO: 16, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 160, or a light-chain variable region having a sequence homology thereto of at least 90%, preferably at least 95%;

(9) a heavy-chain variable region, which comprises CDR1, CDR2 and CDR3 contained in an amino acid sequence of SEQ ID NO: 18, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 162, or a light-chain variable region having a sequence homology thereto of at least 90%, preferably at least 95%;

(10) a heavy-chain variable region, which comprises CDR1, CDR2 and CDR3 contained in an amino acid sequence of SEQ ID NO: 20, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 164, or a light-chain variable region having a sequence homology thereto of at least 90%, preferably at least 95%;

(11) a heavy-chain variable region, which comprises CDR1, CDR2 and CDR3 contained in an amino acid sequence of SEQ ID NO: 22, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 166, or a light-chain variable region having a sequence homology thereto of at least 90%, preferably at least 95%;

(12) a heavy-chain variable region, which comprises CDR1, CDR2 and CDR3 contained in an amino acid sequence of SEQ ID NO: 24, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 168, or a light-chain variable region having a sequence homology thereto of at least 90%, preferably at least 95%;

(13) a heavy-chain variable region, which comprises CDR1, CDR2 and CDR3 contained in an amino acid sequence of SEQ ID NO: 26, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 170, or a light-chain variable region having a sequence homology thereto of at least 90%, preferably at least 95%;

(14) a heavy-chain variable region, which comprises CDR1, CDR2 and CDR3 contained in an amino acid sequence of SEQ ID NO: 28, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 172, or a light-chain variable region having a sequence homology thereto of at least 90%, preferably at least 95%;

(15) a heavy-chain variable region, which comprises CDR1, CDR2 and CDR3 contained in an amino acid sequence of SEQ ID NO: 30, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 174, or a light-chain variable region having a sequence homology thereto of at least 90%, preferably at least 95%;

(16) a heavy-chain variable region, which comprises CDR1, CDR2 and CDR3 contained in an amino acid sequence of SEQ ID NO: 32, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 176, or a light-chain variable region having a sequence homology thereto of at least 90%, preferably at least 95%;

(17) a heavy-chain variable region, which comprises CDR1, CDR2 and CDR3 contained in an amino acid sequence of SEQ ID NO: 34, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 178, or a light-chain variable region having a sequence homology thereto of at least 90%, preferably at least 95%;

(18) a heavy-chain variable region, which comprises CDR1, CDR2 and CDR3 contained in an amino acid sequence of SEQ ID NO: 36, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 180, or a light-chain variable region having a sequence homology thereto of at least 90%, preferably at least 95%;

(19) a heavy-chain variable region, which comprises CDR1, CDR2 and CDR3 contained in an amino acid sequence of SEQ ID NO: 38, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 182, or a light-chain variable region having a sequence homology thereto of at least 90%, preferably at least 95%;

(20) a heavy-chain variable region, which comprises CDR1, CDR2 and CDR3 contained in an amino acid sequence of SEQ ID NO: 40, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 184, or a light-chain variable region having a sequence homology thereto of at least 90%, preferably at least 95%;

(21) a heavy-chain variable region, which comprises CDR1, CDR2 and CDR3 contained in an amino acid sequence of SEQ ID NO: 42, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 186, or a light-chain variable region having a sequence homology thereto of at least 90%, preferably at least 95%;

(22) a heavy-chain variable region, which comprises CDR1, CDR2 and CDR3 contained in an amino acid sequence of SEQ ID NO: 44, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 188, or a light-chain variable region having a sequence homology thereto of at least 90%, preferably at least 95%;

(23) a heavy-chain variable region, which comprises CDR1, CDR2 and CDR3 contained in an amino acid sequence of SEQ ID NO: 46, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 190, or a light-chain variable region having a sequence homology thereto of at least 90%, preferably at least 95%;

(24) a heavy-chain variable region, which comprises CDR1, CDR2 and CDR3 contained in an amino acid sequence of SEQ ID NO: 48, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 192, or a light-chain variable region having a sequence homology thereto of at least 90%, preferably at least 95%;

(25) a heavy-chain variable region, which comprises CDR1, CDR2 and CDR3 contained in an amino acid sequence of SEQ ID NO: 50, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 194, or a light-chain variable region having a sequence homology thereto of at least 90%, preferably at least 95%;

(26) a heavy-chain variable region, which comprises CDR1, CDR2 and CDR3 contained in an amino acid sequence of SEQ ID NO: 52, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 196, or a light-chain variable region having a sequence homology thereto of at least 90%, preferably at least 95%;

(27) a heavy-chain variable region, which comprises CDR1, CDR2 and CDR3 contained in an amino acid sequence of SEQ ID NO: 54, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 198, or a light-chain variable region having a sequence homology thereto of at least 90%, preferably at least 95%;

(28) a heavy-chain variable region, which comprises CDR1, CDR2 and CDR3 contained in an amino acid sequence of SEQ ID NO: 56, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 200, or a light-chain variable region having a sequence homology thereto of at least 90%, preferably at least 95%;

(29) a heavy-chain variable region, which comprises CDR1, CDR2 and CDR3 contained in an amino acid sequence of SEQ ID NO: 58, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 202, or a light-chain variable region having a sequence homology thereto of at least 90%, preferably at least 95%;

(30) a heavy-chain variable region, which comprises CDR1, CDR2 and CDR3 contained in an amino acid sequence of SEQ ID NO: 60, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 204, or a light-chain variable region having a sequence homology thereto of at least 90%, preferably at least 95%;

(31) a heavy-chain variable region, which comprises CDR1, CDR2 and CDR3 contained in an amino acid sequence of SEQ ID NO: 62, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 206, or a light-chain variable region having a sequence homology thereto of at least 90%, preferably at least 95%;

(32) a heavy-chain variable region, which comprises CDR1, CDR2 and CDR3 contained in an amino acid sequence of SEQ ID NO: 64, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 208, or a light-chain variable region having a sequence homology thereto of at least 90%, preferably at least 95%;

(33) a heavy-chain variable region, which comprises CDR1, CDR2 and CDR3 contained in an amino acid sequence of SEQ ID NO: 66, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 210, or a light-chain variable region having a sequence homology thereto of at least 90%, preferably at least 95%;

(34) a heavy-chain variable region, which comprises CDR1, CDR2 and CDR3 contained in an amino acid sequence of SEQ ID NO: 68, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 212, or a light-chain variable region having a sequence homology thereto of at least 90%, preferably at least 95%;

(35) a heavy-chain variable region, which comprises CDR1, CDR2 and CDR3 contained in an amino acid sequence of SEQ ID NO: 70, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 214, or a light-chain variable region having a sequence homology thereto of at least 90%, preferably at least 95%;

(36) a heavy-chain variable region, which comprises CDR1, CDR2 and CDR3 contained in an amino acid sequence of SEQ ID NO: 72, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 216, or a light-chain variable region having a sequence homology thereto of at least 90%, preferably at least 95%;

(37) a heavy-chain variable region, which comprises CDR1, CDR2 and CDR3 contained in an amino acid sequence of SEQ ID NO: 74, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 218, or a light-chain variable region having a sequence homology thereto of at least 90%, preferably at least 95%;

(38) a heavy-chain variable region, which comprises CDR1, CDR2 and CDR3 contained in an amino acid sequence of SEQ ID NO: 76, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 220, or a light-chain variable region having a sequence homology thereto of at least 90%, preferably at least 95%;

(39) a heavy-chain variable region, which comprises CDR1, CDR2 and CDR3 contained in an amino acid sequence of SEQ ID NO: 78, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 222, or a light-chain variable region having a sequence homology thereto of at least 90%, preferably at least 95%;

(40) a heavy-chain variable region, which comprises CDR1, CDR2 and CDR3 contained in an amino acid sequence of SEQ ID NO: 80, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 224, or a light-chain variable region having a sequence homology thereto of at least 90%, preferably at least 95%;

(41) a heavy-chain variable region, which comprises CDR1, CDR2 and CDR3 contained in an amino acid sequence of SEQ ID NO: 82, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 226, or a light-chain variable region having a sequence homology thereto of at least 90%, preferably at least 95%;

(42) a heavy-chain variable region, which comprises CDR1, CDR2 and CDR3 contained in an amino acid sequence of SEQ ID NO: 84, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 228, or a light-chain variable region having a sequence homology thereto of at least 90%, preferably at least 95%;

(43) a heavy-chain variable region, which comprises CDR1, CDR2 and CDR3 contained in an amino acid sequence of SEQ ID NO: 86, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 230, or a light-chain variable region having a sequence homology thereto of at least 90%, preferably at least 95%;

(44) a heavy-chain variable region, which comprises CDR1, CDR2 and CDR3 contained in an amino acid sequence of SEQ ID NO: 88, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 232, or a light-chain variable region having a sequence homology thereto of at least 90%, preferably at least 95%;

(45) a heavy-chain variable region, which comprises CDR1, CDR2 and CDR3 contained in an amino acid sequence of SEQ ID NO: 90, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 234, or a light-chain variable region having a sequence homology thereto of at least 90%, preferably at least 95%;

(46) a heavy-chain variable region, which comprises CDR1, CDR2 and CDR3 contained in an amino acid sequence of SEQ ID NO: 92, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 236, or a light-chain variable region having a sequence homology thereto of at least 90%, preferably at least 95%;

(47) a heavy-chain variable region, which comprises CDR1, CDR2 and CDR3 contained in an amino acid sequence of SEQ ID NO: 94, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 238, or a light-chain variable region having a sequence homology thereto of at least 90%, preferably at least 95%;

(48) a heavy-chain variable region, which comprises CDR1, CDR2 and CDR3 contained in an amino acid sequence of SEQ ID NO: 96, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 240, or a light-chain variable region having a sequence homology thereto of at least 90%, preferably at least 95%;

(49) a heavy-chain variable region, which comprises CDR1, CDR2 and CDR3 contained in an amino acid sequence of SEQ ID NO: 98, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 242, or a light-chain variable region having a sequence homology thereto of at least 90%, preferably at least 95%;

(50) a heavy-chain variable region, which comprises CDR1, CDR2 and CDR3 contained in an amino acid sequence of SEQ ID NO: 100, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 244, or a light-chain variable region having a sequence homology thereto of at least 90%, preferably at least 95%;

(51) a heavy-chain variable region, which comprises CDR1, CDR2 and CDR3 contained in an amino acid sequence of SEQ ID NO: 102, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 246, or a light-chain variable region having a sequence homology thereto of at least 90%, preferably at least 95%;

(52) a heavy-chain variable region, which comprises CDR1, CDR2 and CDR3 contained in an amino acid sequence of SEQ ID NO: 104, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 248, or a light-chain variable region having a sequence homology thereto of at least 90%, preferably at least 95%;

(53) a heavy-chain variable region, which comprises CDR1, CDR2 and CDR3 contained in an amino acid sequence of SEQ ID NO: 106, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 250, or a light-chain variable region having a sequence homology thereto of at least 90%, preferably at least 95%;

(54) a heavy-chain variable region, which comprises CDR1, CDR2 and CDR3 contained in an amino acid sequence of SEQ ID NO: 108, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 252, or a light-chain variable region having a sequence homology thereto of at least 90%, preferably at least 95%;

(55) a heavy-chain variable region, which comprises CDR1, CDR2 and CDR3 contained in an amino acid sequence of SEQ ID NO: 110, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 254, or a light-chain variable region having a sequence homology thereto of at least 90%, preferably at least 95%;

(56) a heavy-chain variable region, which comprises CDR1, CDR2 and CDR3 contained in an amino acid sequence of SEQ ID NO: 112, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 256, or a light-chain variable region having a sequence homology thereto of at least 90%, preferably at least 95%;

(57) a heavy-chain variable region, which comprises CDR1, CDR2 and CDR3 contained in an amino acid sequence of SEQ ID NO: 114, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 258, or a light-chain variable region having a sequence homology thereto of at least 90%, preferably at least 95%;

(58) a heavy-chain variable region, which comprises CDR1, CDR2 and CDR3 contained in an amino acid sequence of SEQ ID NO: 116, or a heavy-chain variable region having a sequence homology thereto of at least 90%, preferably at least 95%, and a light-chain variable region, which comprises CDR1, CDR2 and CDR3 contained in an amino acid sequence of SEQ ID NO: 260, or a light-chain variable region having a sequence homology thereto of at least 90%, preferably at least 95%;

(59) a heavy-chain variable region, which comprises CDR1, CDR2 and CDR3 contained in an amino acid sequence of SEQ ID NO: 118 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 262 or a light-chain variable region having a sequence homology thereto of at least 90%, preferably at least 95%;

(60) a heavy-chain variable region, which comprises CDR1, CDR2 and CDR3 contained in an amino acid sequence of SEQ ID NO: 120 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 264 or a light-chain variable region having a sequence homology thereto of at least 90%, preferably at least 95%;

(61) a heavy-chain variable region, which comprises CDR1, CDR2 and CDR3 contained in an amino acid sequence of SEQ ID NO: 122 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 266 or a light-chain variable region having a sequence homology thereto of at least 90%, preferably at least 95%;

(62) a heavy-chain variable region, which comprises CDR1, CDR2 and CDR3 contained in an amino acid sequence of SEQ ID NO: 124 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 268 or a light-chain variable region having a sequence homology thereto of at least 90%, preferably at least 95%;

(63) a heavy-chain variable region, which comprises CDR1, CDR2 and CDR3 contained in an amino acid sequence of SEQ ID NO: 126 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 270 or a light-chain variable region having a sequence homology thereto of at least 90%, preferably at least 95%;

(64) a heavy-chain variable region, which comprises CDR1, CDR2 and CDR3 contained in an amino acid sequence of SEQ ID NO: 128 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 272 or a light-chain variable region having a sequence homology thereto of at least 90%, preferably at least 95%;

(65) a heavy-chain variable region, which comprises CDR1, CDR2 and CDR3 contained in an amino acid sequence of SEQ ID NO: 130 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 274 or a light-chain variable region having a sequence homology thereto of at least 90%, preferably at least 95%;

(66) a heavy-chain variable region, which comprises CDR1, CDR2 and CDR3 contained in an amino acid sequence of SEQ ID NO: 132 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 276 or a light-chain variable region having a sequence homology thereto of at least 90%, preferably at least 95%;

(67) a heavy-chain variable region, which comprises CDR1, CDR2 and CDR3 contained in an amino acid sequence of SEQ ID NO: 134 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 278 or a light-chain variable region having a sequence homology thereto of at least 90%, preferably at least 95%;

(68) a heavy-chain variable region, which comprises CDR1, CDR2 and CDR3 contained in an amino acid sequence of SEQ ID NO: 136 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 280 or a light-chain variable region having a sequence homology thereto of at least 90%, preferably at least 95%;

(69) a heavy-chain variable region, which comprises CDR1, CDR2 and CDR3 contained in an amino acid sequence of SEQ ID NO: 138 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 282 or a light-chain variable region having a sequence homology thereto of at least 90%, preferably at least 95%;

(70) a heavy-chain variable region, which comprises CDR1, CDR2 and CDR3 contained in an amino acid sequence of SEQ ID NO: 140 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 284 or a light-chain variable region having a sequence homology thereto of at least 90%, preferably at least 95%;

(71) a heavy-chain variable region, which comprises CDR1, CDR2 and CDR3 contained in an amino acid sequence of SEQ ID NO: 142 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 286 or a light-chain variable region having a sequence homology thereto of at least 90%, preferably at least 95%;

(72) a heavy-chain variable region, which comprises CDR1, CDR2 and CDR3 contained in an amino acid sequence of SEQ ID NO: 144 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 288 or a light-chain variable region having a sequence homology thereto of at least 90%, preferably at least 95%;

(73) a heavy-chain variable region, which comprises CDR1, CDR2 and CDR3 contained in an amino acid sequence of SEQ ID NO: 289 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 290 or a light-chain variable region having a sequence homology thereto of at least 90%, preferably at least 95%; and

(74) a heavy-chain variable region, which comprises CDR1, CDR2 and CDR3 contained in an amino acid sequence of SEQ ID NO: 291 or a heavy-chain variable region having a sequence homology thereto of at least 90%, preferably at least 95%, and a light-chain variable region, which comprises CDR1, CDR2 and CDR3 contained in an amino acid sequence of SEQ ID NO: 292 or a light-chain variable region having a sequence homology thereto of at least 90%, preferably at least 95%.

More preferably, the antibody according to the present invention has a heavy-chain variable region and a light-chain variable region selected from among the following heavy-chain and light-chain variable regions (1) to (74):

(1) a heavy-chain variable region having an amino acid sequence of SEQ ID NO: 2, or a heavy-chain variable region having a sequence homology thereto of at least 90%, preferably at least 95%, and a light-chain variable region having an amino acid sequence of SEQ ID NO: 146, or a light-chain variable region having a sequence homology thereto of at least 90%, preferably at least 95%;

(2) a heavy-chain variable region having an amino acid sequence of SEQ ID NO: 4, or a heavy-chain variable region having a sequence homology thereto of at least 90%, preferably at least 95%, and a light-chain variable region having an amino acid sequence of SEQ ID NO: 148, or a light-chain variable region having a sequence homology thereto of at least 90%, preferably at least 95%;

(3) a heavy-chain variable region having an amino acid sequence of SEQ ID NO: 6, or a heavy-chain variable region having a sequence homology thereto of at least 90%, preferably at least 95%, and a light-chain variable region having an amino acid sequence of SEQ ID NO: 150, or a light-chain variable region having a sequence homology thereto of at least 90%, preferably at least 95%;

(4) a heavy-chain variable region having an amino acid sequence of SEQ ID NO: 8, or a heavy-chain variable region having a sequence homology thereto of at least 90%, preferably at least 95%, and a light-chain variable region having an amino acid sequence of SEQ ID NO: 152, or a light-chain variable region having a sequence homology thereto of at least 90%, preferably at least 95%;

(5) a heavy-chain variable region having an amino acid sequence of SEQ ID NO: 10, or a heavy-chain variable region having a sequence homology thereto of at least 90%, preferably at least 95%, and a light-chain variable region having an amino acid sequence of SEQ ID NO: 154, or a light-chain variable region having a sequence homology thereto of at least 90%, preferably at least 95%;

(6) a heavy-chain variable region having an amino acid sequence of SEQ ID NO: 12, or a heavy-chain variable region having a sequence homology thereto of at least 90%, preferably at least 95%, and a light-chain variable region having an amino acid sequence of SEQ ID NO: 156, or a light-chain variable region having a sequence homology thereto of at least 90%, preferably at least 95%;

(7) a heavy-chain variable region having an amino acid sequence of SEQ ID NO: 14, or a heavy-chain variable region having a sequence homology thereto of at least 90%, preferably at least 95%, and a light-chain variable region having an amino acid sequence of SEQ ID NO: 158, or a light-chain variable region having a sequence homology thereto of at least 90%, preferably at least 95%;

(8) a heavy-chain variable region having an amino acid sequence of SEQ ID NO: 16, or a heavy-chain variable region having a sequence homology thereto of at least 90%, preferably at least 95%, and a light-chain variable region having an amino acid sequence of SEQ ID NO: 160, or a light-chain variable region having a sequence homology thereto of at least 90%, preferably at least 95%;

(9) a heavy-chain variable region having an amino acid sequence of SEQ ID NO: 18, or a heavy-chain variable region having a sequence homology thereto of at least 90%, preferably at least 95%, and a light-chain variable region having an amino acid sequence of SEQ ID NO: 162, or a light-chain variable region having a sequence homology thereto of at least 90%, preferably at least 95%;

(10) a heavy-chain variable region having an amino acid sequence of SEQ ID NO: 20, or a heavy-chain variable region having a sequence homology thereto of at least 90%, preferably at least 95%, and a light-chain variable region having an amino acid sequence of SEQ ID NO: 164, or a light-chain variable region having a sequence homology thereto of at least 90%, preferably at least 95%;

(11) a heavy-chain variable region having an amino acid sequence of SEQ ID NO: 22, or a heavy-chain variable region having a sequence homology thereto of at least 90%, preferably at least 95%, and a light-chain variable region having an amino acid sequence of SEQ ID NO: 166, or a light-chain variable region having a sequence homology thereto of at least 90%, preferably at least 95%;

(12) a heavy-chain variable region having an amino acid sequence of SEQ ID NO: 24, or a heavy-chain variable region having a sequence homology thereto of at least 90%, preferably at least 95%, and a light-chain variable region having an amino acid sequence of SEQ ID NO: 168, or a light-chain variable region having a sequence homology thereto of at least 90%, preferably at least 95%;

(13) a heavy-chain variable region having an amino acid sequence of SEQ ID NO: 26, or a heavy-chain variable region having a sequence homology thereto of at least 90%, preferably at least 95%, and a light-chain variable region having an amino acid sequence of SEQ ID NO: 170, or a light-chain variable region having a sequence homology thereto of at least 90%, preferably at least 95%;

(14) a heavy-chain variable region having an amino acid sequence of SEQ ID NO: 28, or a heavy-chain variable region having a sequence homology thereto of at least 90%, preferably at least 95%, and a light-chain variable region having an amino acid sequence of SEQ ID NO: 172, or a light-chain variable region having a sequence homology thereto of at least 90%, preferably at least 95%;

(15) a heavy-chain variable region having an amino acid sequence of SEQ ID NO: 30, or a heavy-chain variable region having a sequence homology thereto of at least 90%, preferably at least 95%, and a light-chain variable region having an amino acid sequence of SEQ ID NO: 174, or a light-chain variable region having a sequence homology thereto of at least 90%, preferably at least 95%;

(16) a heavy-chain variable region having an amino acid sequence of SEQ ID NO: 32, or a heavy-chain variable region having a sequence homology thereto of at least 90%, preferably at least 95%, and a light-chain variable region having an amino acid sequence of SEQ ID NO: 176, or a light-chain variable region having a sequence homology thereto of at least 90%, preferably at least 95%;

(17) a heavy-chain variable region having an amino acid sequence of SEQ ID NO: 34, or a heavy-chain variable region having a sequence homology thereto of at least 90%, preferably at least 95%, and a light-chain variable region having an amino acid sequence of SEQ ID NO: 178, or a light-chain variable region having a sequence homology thereto of at least 90%, preferably at least 95%;

(18) a heavy-chain variable region having an amino acid sequence of SEQ ID NO: 36, or a heavy-chain variable region having a sequence homology thereto of at least 90%, preferably at least 95%, and a light-chain variable region having an amino acid sequence of SEQ ID NO: 180, or a light-chain variable region having a sequence homology thereto of at least 90%, preferably at least 95%;

(19) a heavy-chain variable region having an amino acid sequence of SEQ ID NO: 38, or a heavy-chain variable region having a sequence homology thereto of at least 90%, preferably at least 95%, and a light-chain variable region having an amino acid sequence of SEQ ID NO: 182, or a light-chain variable region having a sequence homology thereto of at least 90%, preferably at least 95%;

(20) a heavy-chain variable region having an amino acid sequence of SEQ ID NO: 40, or a heavy-chain variable region having a sequence homology thereto of at least 90%, preferably at least 95%, and a light-chain variable region having an amino acid sequence of SEQ ID NO: 184, or a light-chain variable region having a sequence homology thereto of at least 90%, preferably at least 95%;

(21) a heavy-chain variable region having an amino acid sequence of SEQ ID NO: 42, or a heavy-chain variable region having a sequence homology thereto of at least 90%, preferably at least 95%, and a light-chain variable region having an amino acid sequence of SEQ ID NO: 186, or a light-chain variable region having a sequence homology thereto of at least 90%, preferably at least 95%;

(22) a heavy-chain variable region having an amino acid sequence of SEQ ID NO: 44, or a heavy-chain variable region having a sequence homology thereto of at least 90%, preferably at least 95%, and a light-chain variable region having an amino acid sequence of SEQ ID NO: 188, or a light-chain variable region having a sequence homology thereto of at least 90%, preferably at least 95%;

(23) a heavy-chain variable region having an amino acid sequence of SEQ ID NO: 46, or a heavy-chain variable region having a sequence homology thereto of at least 90%, preferably at least 95%, and a light-chain variable region having an amino acid sequence of SEQ ID NO: 190, or a light-chain variable region having a sequence homology thereto of at least 90%, preferably at least 95%;

(24) a heavy-chain variable region having an amino acid sequence of SEQ ID NO: 48, or a heavy-chain variable region having a sequence homology thereto of at least 90%, preferably at least 95%, and a light-chain variable region having an amino acid sequence of SEQ ID NO: 192, or a light-chain variable region having a sequence homology thereto of at least 90%, preferably at least 95%;

(25) a heavy-chain variable region having an amino acid sequence of SEQ ID NO: 50, or a heavy-chain variable region having a sequence homology thereto of at least 90%, preferably at least 95%, and a light-chain variable region having an amino acid sequence of SEQ ID NO: 194, or a light-chain variable region having a sequence homology thereto of at least 90%, preferably at least 95%;

(26) a heavy-chain variable region having an amino acid sequence of SEQ ID NO: 52, or a heavy-chain variable region having a sequence homology thereto of at least 90%, preferably at least 95%, and a light-chain variable region having an amino acid sequence of SEQ ID NO: 196, or a light-chain variable region having a sequence homology thereto of at least 90%, preferably at least 95%;

(27) a heavy-chain variable region having an amino acid sequence of SEQ ID NO: 54, or a heavy-chain variable region having a sequence homology thereto of at least 90%, preferably at least 95%, and a light-chain variable region having an amino acid sequence of SEQ ID NO: 198, or a light-chain variable region having a sequence homology thereto of at least 90%, preferably at least 95%;

(28) a heavy-chain variable region having an amino acid sequence of SEQ ID NO: 56, or a heavy-chain variable region having a sequence homology thereto of at least 90%, preferably at least 95%, and a light-chain variable region having an amino acid sequence of SEQ ID NO: 200, or a light-chain variable region having a sequence homology thereto of at least 90%, preferably at least 95%;

(29) a heavy-chain variable region having an amino acid sequence of SEQ ID NO: 58, or a heavy-chain variable region having a sequence homology thereto of at least 90%, preferably at least 95%, and a light-chain variable region having an amino acid sequence of SEQ ID NO: 202, or a light-chain variable region having a sequence homology thereto of at least 90%, preferably at least 95%;

(30) a heavy-chain variable region having an amino acid sequence of SEQ ID NO: 60, or a heavy-chain variable region having a sequence homology thereto of at least 90%, preferably at least 95%, and a light-chain variable region having an amino acid sequence of SEQ ID NO: 204, or a light-chain variable region having a sequence homology thereto of at least 90%, preferably at least 95%;

(31) a heavy-chain variable region having an amino acid sequence of SEQ ID NO: 62, or a heavy-chain variable region having a sequence homology thereto of at least 90%, preferably at least 95%, and a light-chain variable region having an amino acid sequence of SEQ ID NO: 206, or a light-chain variable region having a sequence homology thereto of at least 90%, preferably at least 95%;

(32) a heavy-chain variable region having an amino acid sequence of SEQ ID NO: 64, or a heavy-chain variable region having a sequence homology thereto of at least 90%, preferably at least 95%, and a light-chain variable region having an amino acid sequence of SEQ ID NO: 208, or a light-chain variable region having a sequence homology thereto of at least 90%, preferably at least 95%;

(33) a heavy-chain variable region having an amino acid sequence of SEQ ID NO: 66, or a heavy-chain variable region having a sequence homology thereto of at least 90%, preferably at least 95%, and a light-chain variable region having an amino acid sequence of SEQ ID NO: 210, or a light-chain variable region having a sequence homology thereto of at least 90%, preferably at least 95%;

(34) a heavy-chain variable region having an amino acid sequence of SEQ ID NO: 68, or a heavy-chain variable region having a sequence homology thereto of at least 90%, preferably at least 95%, and a light-chain variable region having an amino acid sequence of SEQ ID NO: 212, or a light-chain variable region having a sequence homology thereto of at least 90%, preferably at least 95%;

(35) a heavy-chain variable region having an amino acid sequence of SEQ ID NO: 70, or a heavy-chain variable region having a sequence homology thereto of at least 90%, preferably at least 95%, and a light-chain variable region having an amino acid sequence of SEQ ID NO: 214, or a light-chain variable region having a sequence homology thereto of at least 90%, preferably at least 95%;

(36) a heavy-chain variable region having an amino acid sequence of SEQ ID NO: 72, or a heavy-chain variable region having a sequence homology thereto of at least 90%, preferably at least 95%, and a light-chain variable region having an amino acid sequence of SEQ ID NO: 216, or a light-chain variable region having a sequence homology thereto of at least 90%, preferably at least 95%;

(37) a heavy-chain variable region having an amino acid sequence of SEQ ID NO: 74, or a heavy-chain variable region having a sequence homology thereto of at least 90%, preferably at least 95%, and a light-chain variable region having an amino acid sequence of SEQ ID NO: 218, or a light-chain variable region having a sequence homology thereto of at least 90%, preferably at least 95%;

(38) a heavy-chain variable region having an amino acid sequence of SEQ ID NO: 76, or a heavy-chain variable region having a sequence homology thereto of at least 90%, preferably at least 95%, and a light-chain variable region having an amino acid sequence of SEQ ID NO: 220, or a light-chain variable region having a sequence homology thereto of at least 90%, preferably at least 95%;

(39) a heavy-chain variable region having an amino acid sequence of SEQ ID NO: 78, or a heavy-chain variable region having a sequence homology thereto of at least 90%, preferably at least 95%, and a light-chain variable region having an amino acid sequence of SEQ ID NO: 222, or a light-chain variable region having a sequence homology thereto of at least 90%, preferably at least 95%;

(40) a heavy-chain variable region having an amino acid sequence of SEQ ID NO: 80, or a heavy-chain variable region having a sequence homology thereto of at least 90%, preferably at least 95%, and a light-chain variable region having an amino acid sequence of SEQ ID NO: 224, or a light-chain variable region having a sequence homology thereto of at least 90%, preferably at least 95%;

(41) a heavy-chain variable region having an amino acid sequence of SEQ ID NO: 82, or a heavy-chain variable region having a sequence homology thereto of at least 90%, preferably at least 95%, and a light-chain variable region having an amino acid sequence of SEQ ID NO: 226, or a light-chain variable region having a sequence homology thereto of at least 90%, preferably at least 95%;

(42) a heavy-chain variable region having an amino acid sequence of SEQ ID NO: 84, or a heavy-chain variable region having a sequence homology thereto of at least 90%, preferably at least 95%, and a light-chain variable region having an amino acid sequence of SEQ ID NO: 228, or a light-chain variable region having a sequence homology thereto of at least 90%, preferably at least 95%;

(43) a heavy-chain variable region having an amino acid sequence of SEQ ID NO: 86, or a heavy-chain variable region having a sequence homology thereto of at least 90%, preferably at least 95%, and a light-chain variable region having an amino acid sequence of SEQ ID NO: 230, or a light-chain variable region having a sequence homology thereto of at least 90%, preferably at least 95%;

(44) a heavy-chain variable region having an amino acid sequence of SEQ ID NO: 88, or a heavy-chain variable region having a sequence homology thereto of at least 90%, preferably at least 95%, and a light-chain variable region having an amino acid sequence of SEQ ID NO: 232, or a light-chain variable region having a sequence homology thereto of at least 90%, preferably at least 95%;

(45) a heavy-chain variable region having an amino acid sequence of SEQ ID NO: 90, or a heavy-chain variable region having a sequence homology thereto of at least 90%, preferably at least 95%, and a light-chain variable region having an amino acid sequence of SEQ ID NO: 234, or a light-chain variable region having a sequence homology thereto of at least 90%, preferably at least 95%;

(46) a heavy-chain variable region having an amino acid sequence of SEQ ID NO: 92, or a heavy-chain variable region having a sequence homology thereto of at least 90%, preferably at least 95%, and a light-chain variable region having an amino acid sequence of SEQ ID NO: 236, or a light-chain variable region having a sequence homology thereto of at least 90%, preferably at least 95%;

(47) a heavy-chain variable region having an amino acid sequence of SEQ ID NO: 94, or a heavy-chain variable region having a sequence homology thereto of at least 90%, preferably at least 95%, and a light-chain variable region having an amino acid sequence of SEQ ID NO: 238, or a light-chain variable region having a sequence homology thereto of at least 90%, preferably at least 95%;

(48) a heavy-chain variable region having an amino acid sequence of SEQ ID NO: 96, or a heavy-chain variable region having a sequence homology thereto of at least 90%, preferably at least 95%, and a light-chain variable region having an amino acid sequence of SEQ ID NO: 240, or a light-chain variable region having a sequence homology thereto of at least 90%, preferably at least 95%;

(49) a heavy-chain variable region having an amino acid sequence of SEQ ID NO: 98, or a heavy-chain variable region having a sequence homology thereto of at least 90%, preferably at least 95%, and a light-chain variable region having an amino acid sequence of SEQ ID NO: 242, or a light-chain variable region having a sequence homology thereto of at least 90%, preferably at least 95%;

(50) a heavy-chain variable region having an amino acid sequence of SEQ ID NO: 100, or a heavy-chain variable region having a sequence homology thereto of at least 90%, preferably at least 95%, and a light-chain variable region having an amino acid sequence of SEQ ID NO: 244, or a light-chain variable region having a sequence homology thereto of at least 90%, preferably at least 95%;

(51) a heavy-chain variable region having an amino acid sequence of SEQ ID NO: 102, or a heavy-chain variable region having a sequence homology thereto of at least 90%, preferably at least 95%, and a light-chain variable region having an amino acid sequence of SEQ ID NO: 246, or a light-chain variable region having a sequence homology thereto of at least 90%, preferably at least 95%;

(52) a heavy-chain variable region having an amino acid sequence of SEQ ID NO: 104, or a heavy-chain variable region having a sequence homology thereto of at least 90%, preferably at least 95%, and a light-chain variable region having an amino acid sequence of SEQ ID NO: 248, or a light-chain variable region having a sequence homology thereto of at least 90%, preferably at least 95%;

(53) a heavy-chain variable region having an amino acid sequence of SEQ ID NO: 106, or a heavy-chain variable region having a sequence homology thereto of at least 90%, preferably at least 95%, and a light-chain variable region having an amino acid sequence of SEQ ID NO: 250, or a light-chain variable region having a sequence homology thereto of at least 90%, preferably at least 95%;

(54) a heavy-chain variable region having an amino acid sequence of SEQ ID NO: 108, or a heavy-chain variable region having a sequence homology thereto of at least 90%, preferably at least 95%, and a light-chain variable region having an amino acid sequence of SEQ ID NO: 252, or a light-chain variable region having a sequence homology thereto of at least 90%, preferably at least 95%;

(55) a heavy-chain variable region having an amino acid sequence of SEQ ID NO: 110, or a heavy-chain variable region having a sequence homology thereto of at least 90%, preferably at least 95%, and a light-chain variable region having an amino acid sequence of SEQ ID NO: 254, or a light-chain variable region having a sequence homology thereto of at least 90%, preferably at least 95%;

(56) a heavy-chain variable region having an amino acid sequence of SEQ ID NO: 112, or a heavy-chain variable region having a sequence homology thereto of at least 90%, preferably at least 95%, and a light-chain variable region having an amino acid sequence of SEQ ID NO: 256, or a light-chain variable region having a sequence homology thereto of at least 90%, preferably at least 95%;

(57) a heavy-chain variable region having an amino acid sequence of SEQ ID NO: 114, or a heavy-chain variable region having a sequence homology thereto of at least 90%, preferably at least 95%, and a light-chain variable region having an amino acid sequence of SEQ ID NO: 258, or a light-chain variable region having a sequence homology thereto of at least 90%, preferably at least 95%;

(58) a heavy-chain variable region having an amino acid sequence of SEQ ID NO: 116, or a heavy-chain variable region having a sequence homology thereto of at least 90%, preferably at least 95%, and a light-chain variable region having an amino acid sequence of SEQ ID NO: 260, or a light-chain variable region having a sequence homology thereto of at least 90%, preferably at least 95%;

(59) a heavy-chain variable region having an amino acid sequence of SEQ ID NO: 118 or a heavy-chain variable region having a sequence homology thereto of at least 90%, preferably at least 95%, and a light-chain variable region having an amino acid sequence of SEQ ID NO: 262 or a light-chain variable region having a sequence homology thereto of at least 90%, preferably at least 95%;

(60) a heavy-chain variable region having an amino acid sequence of SEQ ID NO: 120 or a heavy-chain variable region having a sequence homology thereto of at least 90%, preferably at least 95%, and a light-chain variable region having an amino acid sequence of SEQ ID NO: 264 or a light-chain variable region having a sequence homology thereto of at least 90%, preferably at least 95%;

(61) a heavy-chain variable region having an amino acid sequence of SEQ ID NO: 122 or a heavy-chain variable region having a sequence homology thereto of at least 90%, preferably at least 95%, and a light-chain variable region having an amino acid sequence of SEQ ID NO: 266 or a light-chain variable region having a sequence homology thereto of at least 90%, preferably at least 95%;

(62) a heavy-chain variable region having an amino acid sequence of SEQ ID NO: 124 or a heavy-chain variable region having a sequence homology thereto of at least 90%, preferably at least 95%, and a light-chain variable region having an amino acid sequence of SEQ ID NO: 268 or a light-chain variable region having a sequence homology thereto of at least 90%, preferably at least 95%;

(63) a heavy-chain variable region having an amino acid sequence of SEQ ID NO: 126 or a heavy-chain variable region having a sequence homology thereto of at least 90%, preferably at least 95%, and a light-chain variable region having an amino acid sequence of SEQ ID NO: 270 or a light-chain variable region having a sequence homology thereto of at least 90%, preferably at least 95%;

(64) a heavy-chain variable region having an amino acid sequence of SEQ ID NO: 128 or a heavy-chain variable region having a sequence homology thereto of at least 90%, preferably at least 95%, and a light-chain variable region having an amino acid sequence of SEQ ID NO: 272 or a light-chain variable region having a sequence homology thereto of at least 90%, preferably at least 95%;

(65) a heavy-chain variable region having an amino acid sequence of SEQ ID NO: 130 or a heavy-chain variable region having a sequence homology thereto of at least 90%, preferably at least 95%, and a light-chain variable region having an amino acid sequence of SEQ ID NO: 274 or a light-chain variable region having a sequence homology thereto of at least 90%, preferably at least 95%;

(66) a heavy-chain variable region having an amino acid sequence of SEQ ID NO: 132 or a heavy-chain variable region having a sequence homology thereto of at least 90%, preferably at least 95%, and a light-chain variable region having an amino acid sequence of SEQ ID NO: 276 or a light-chain variable region having a sequence homology thereto of at least 90%, preferably at least 95%;

(67) a heavy-chain variable region having an amino acid sequence of SEQ ID NO: 134 or a heavy-chain variable region having a sequence homology thereto of at least 90%, preferably at least 95%, and a light-chain variable region having an amino acid sequence of SEQ ID NO: 278 or a light-chain variable region having a sequence homology thereto of at least 90%, preferably at least 95%;

(68) a heavy-chain variable region having an amino acid sequence of SEQ ID NO: 136 or a heavy-chain variable region having a sequence homology thereto of at least 90%, preferably at least 95%, and a light-chain variable region having an amino acid sequence of SEQ ID NO: 280 or a light-chain variable region having a sequence homology thereto of at least 90%, preferably at least 95%;

(69) a heavy-chain variable region having an amino acid sequence of SEQ ID NO: 138 or a heavy-chain variable region having a sequence homology thereto of at least 90%, preferably at least 95%, and a light-chain variable region having an amino acid sequence of SEQ ID NO: 282 or a light-chain variable region having a sequence homology thereto of at least 90%, preferably at least 95%;

(70) a heavy-chain variable region having an amino acid sequence of SEQ ID NO: 140 or a heavy-chain variable region having a sequence homology thereto of at least 90%, preferably at least 95%, and a light-chain variable region having an amino acid sequence of SEQ ID NO: 284 or a light-chain variable region having a sequence homology thereto of at least 90%, preferably at least 95%;

(71) a heavy-chain variable region having an amino acid sequence of SEQ ID NO: 142 or a heavy-chain variable region having a sequence homology thereto of at least 90%, preferably at least 95%, and a light-chain variable region having an amino acid sequence of SEQ ID NO: 286 or a light-chain variable region having a sequence homology thereto of at least 90%, preferably at least 95%;

(72) a heavy-chain variable region having an amino acid sequence of SEQ ID NO: 144 or a heavy-chain variable region having a sequence homology thereto of at least 90%, preferably at least 95%, and a light-chain variable region having an amino acid sequence of SEQ ID NO: 288 or a light-chain variable region having a sequence homology thereto of at least 90%, preferably at least 95%;

(73) a heavy-chain variable region having an amino acid sequence of SEQ ID NO: 289 or a heavy-chain variable region having a sequence homology thereto of at least 90%, preferably at least 95%, and a light-chain variable region having an amino acid sequence of SEQ ID NO: 290 or a light-chain variable region having a sequence homology thereto of at least 90%, preferably at least 95%; and

(74) a heavy-chain variable region having an amino acid sequence of SEQ ID NO: 291 or a heavy-chain variable region having a sequence homology thereto of at least 90%, preferably at least 95%, and a light-chain variable region having an amino acid sequence of SEQ ID NO: 292 or a light-chain variable region having a sequence homology thereto of at least 90%, preferably at least 95%.

The antibodies according to the present invention also include fragments of the antibody. Fragments of the antibody according to the present invention include, but are not limited to, single-chain antibodies, diabodies, triabodies, tetrabodies, Fab fragments, F(ab')$_2$ fragments, Fd, scFv, domain antibodies, dual-specific antibodies, minibodies, scap, IgD antibodies, IgE antibodies, IgM antibodies, IgG1 antibodies, IgG2 antibodies, IgG3 antibodies, IgG4 antibodies, derivatives in antibody constant regions, and synthetic antibodies based on protein scaffolds, which have the ability to bind to FcRn. It will be obvious to those skilled in the art that any fragment of the antibody according to the present invention will show the same properties as those of the antibody of the present invention, as long as its ability to bind to FcRn is maintained.

In addition, antibodies having a mutation in the variable region are included in the scope of the present invention, as long as they retain the properties of the antibody of the present invention. Examples of such antibodies include antibodies having a conservative substitution of an amino acid residue in the variable region. As used herein, the term "conservative substitution" refers to substitution with another amino acid residue having properties similar to those of the original amino acid residue. For example, lysine, arginine and histidine have similar properties in that they have a basic side-chain, and aspartic acid and glutamic acid have similar properties in that they have an acidic side chain. In addition, glycine, aspargin, glutamine, serine, threonine, tyrosine, cysteine and tryptophan have similar properties in that they have an uncharged polar side-chain, and alanine, valine, leucine, threonine, isoleucine, proline, phenylalanine and methionine have similar properties in that they have a non-polar side-chain. Also, tyrosine, phenylalanine, tryptophan and histidine have similar properties in that they have an aromatic side-chain. Thus, it will be obvious to those skilled in the art that, even when substitution of amino acid residues in groups showing similar properties as described above occurs; it will show no particular change in the properties. Accordingly, antibodies having a mutation caused by conservative substitution in the variable region are included in the scope of the present invention, as long as they retain the properties of the antibody of the present invention.

In addition, the antibody according to the present invention or its fragment may be used as a conjugate with another substance. Substances that may be used as conjugates with the antibody according to the present invention or its fragment include therapeutic agents that is generally used for the treatment of autoimmune diseases, substances capable of inhibiting the activity of FcRn, and a moiety that is physically associated with the antibody to improve its stabilization and/or retention in circulation, for example, in blood, serum, lymph, or other tissues. For example, the FcRn-binding antibody can be associated with a polymer, e.g., a non-antigenic polymer such as polyalkylene oxide or polyethylene oxide. Suitable polymers will vary substantially by weight. Polymers having molecular number average weights ranging from about 200 to about 35,000 (or about 1,000 to about 15,000, and 2,000 to about 12,500) can be used. For example, the FcRn-binding antibody can be conjugated to water soluble polymers, e.g., hydrophilic polyvinyl polymers, e.g. polyvinylalcohol and polyvinylpyrrolidone. A non-limiting list of such polymers includes, but is not limited to, polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

The present invention also provides a pharmaceutical composition comprising the antibody of the present invention or a fragment thereof. The pharmaceutical composition may comprise a pharmaceutically acceptable carrier, excipient, and the like, which are well known in the art. The pharmaceutically acceptable carrier that may be used in the present invention should be compatible with the active ingredient such as the antibody according to the present invention and may be physiological saline, sterile water, Ringer's solution, buffered saline, dextrose solution, maltodextrin solution, glycerol, ethanol, or a mixture of two or more thereof. In addition, the pharmaceutical composition of the present invention may, if necessary, comprise other conventional additives, including antioxidants, buffers, and bacteriostatic agents. Further, the pharmaceutical composition of the present invention may be formulated as injectable forms such as aqueous solutions, suspensions or emulsions with the aid of diluents, dispersants, surfactants, binders and lubricants. In addition, the pharmaceutical composition of the present invention may be provided by formulating into a various form such as powder, tablet, capsule, liquid, inject, ointment, syrup etc, and single-dosage or multi-dosage container such as sealed ample or vial.

The pharmaceutical composition of the present invention may be applied to all autoimmune diseases that are mediated by IgG and FcRn, and typical examples of such autoimmune diseases include, but are not limited to, immune neutropenia, Guillain-Barré syndrome, epilepsy, autoimmune encephalitis, Isaac's syndrome, nevus syndrome, pemphigus vulgaris, Pemphigus foliaceus, Bullous pemphigoid, epidermolysis bullosa acquisita, pemphigoid gestationis, mucous membrane pemphigoid, antiphospholipid syndrome, autoimmune anemia, autoimmune Grave's disease, Goodpasture's syndrome, myasthenia gravis, multiple sclerosis, rheumatoid arthritis, lupus, and idiopathic thrombocytopenic purpura (ITP).

The present invention also provides a method for ameliorating an autoimmune or alloimmune condition, the method comprising administering the antibody of the present invention or a fragment of the antibody to a subject in need of treatment. The present invention also provides a specific anti-FcRn therapy.

The inventive method for ameliorating an autoimmune or alloimmune condition or the inventive anti-FcRn therapy can be achieved by administering the pharmaceutical composition of the present invention to a subject. The pharmaceutical composition of the present invention can be administered orally or parenterally. The pharmaceutical composition according to the present invention can be administered by various routes, including, but not limited to, oral, intravenous, intramuscular, intra-arterial, intramedullary, intradural, intracardial, transdermal, subcutaneous, intraperitoneal, gastrointestinal, sublingual, and local routes. The dose of the composition of the present invention may vary depending on various factors, such as a patient's body weight, age, sex, health condition and diet, the time and method of administration, excretion rate, and severity of a disease, and may be easily determined by a person of ordinary skill in the art. Generally, 1-200 mg/kg, and preferably, 1-40 mg/kg of the composition may be administered to patients afflicted with autoimmune or alloimmune conditions, and these regimens are preferably designed to reduce the serum endogenous IgG concentration to less than 75% of pretreatment values. Intermittent and/or chronic (continuous) dosing strategies may be applied in view of the conditions of patients.

The present invention also provides a diagnostic composition comprising the antibody of the present invention or a fragment thereof, and a diagnostic method that uses the diagnostic composition. In other words, the antibody of the present invention or a fragment thereof, which binds to FcRn, have in vitro and in vivo diagnostic utilities.

In one aspect, the present invention provides a method for detecting the presence of FcRn in vitro and in vivo.

The in vitro detection method may, for example, comprise the steps of: (1) bringing a sample into contact with the FcRn-binding antibody; (2) detecting the formation of a complex between the FcRn-binding antibody and the sample; and/or (3) bringing a reference sample (e.g., a control sample) into contact with the antibody; and (4) determining the degree of formation of the complex between the antibody and the sample by comparison with that in the reference sample. A change (e.g., a statistically significant change) in the formation of the complex in the sample or the subject as compared to that in the control sample or subject may mean the presence of FcRn in the sample.

The in vivo detection method may comprise the steps of: (1) administering the FcRn-binding antibody to a subject; and (2) detecting the formation of a complex between the FcRn-binding antibody and the subject. The detecting may include determining location or time of formation of the complex. The FcRn-binding antibody can be directly or indirectly labeled with a detectable substance to facilitate detection of the bound or unbound antibody. Suitable detectable substances include various enzymes, prosthetic groups, fluorescent materials, luminescent materials, and radioactive materials. The formation of a complex between the FcRn-binding antibody and FcRn can be detected by measuring or visualizing the antibody bound or not bound to FcRn. A conventional detection assay, for example, enzyme-linked immunosorbent assay (ELISA), radioimmunoassay (RIA) or tissue immunohistochemistry may be used. In addition to labeling of the FcRn-binding antibody, the presence of FcRn can be assayed in a sample by competition immunoassay using a standard labeled with a detectable substance and an unlabeled FcRn-binding antibody. In one example of this assay, the biological sample, the labeled standard and the FcRn-binding antibody are combined and the amount of labeled standard unbound to FcRn is determined. The amount of FcRn in the biological sample is inversely proportional to the amount of labeled standard unbound to FcRn.

For use for therapeutic purposes, the antibody of the present invention or a fragment thereof can be labeled with a fluorophore and a chromophore. Because antibodies and other proteins absorb light having wavelengths up to about 310 nm, the fluorescent moieties should be selected to have substantial absorption at wavelengths above 310 nm and preferably above 400 nm. The antibody of the present invention or a fragment thereof can be labeled with a variety of suitable fluorescers and chromophores. One group of fluorescers is xanthene dyes, which include fluoresceins and rhodamines. Another group of fluorescent compounds are naphthylamines. Once labeled with a fluorophore or chromophore, the antibody can be used to detect the presence or localization of the FcRn in a sample, e.g., using fluorescent microscopy (such as confocal or deconvolution microscopy).

Detection of the presence or localization of FcRn using the antibody of the present invention or a fragment thereof can be performed by various methods as described below.

Histological Analysis:

The antibody of the present invention or a fragment thereof can be synthesized with a label (such as a purification or epitope tag), or can be detectably labeled, e.g., by conjugating a label or label-binding group. The antibody is then contacted to a histological preparation, e.g., a fixed section of tissue that is on a microscope slide. After incubation for binding, the preparation is washed to remove unbound antibody. The preparation is then analyzed, e.g., using microscopy, to identify if the antibody bound to the preparation. Of course, the antibody can be unlabeled at the time of binding. After binding and washing, the antibody is labeled in order to render it detectable.

Protein Arrays:

The antibody of the present invention or a fragment thereof can be immobilized on a protein array. The protein array can be used as a diagnostic tool, e.g., to screen medical samples (such as isolated cells, blood, sera, biopsies, and the like). Of course, the protein array can also include other ligands, e.g., that bind to FcRn or to other target molecules. Polypeptides for the array can be spotted at high speed using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

FACS (Fluorescence Activated Cell Sorting):

The antibody of the present invention or a fragment thereof can be used to label cells, e.g., cells in a sample (e.g., a patient sample). The antibody is also attached to a fluorescent compound. The cells can then be sorted using fluorescence activated cell sorter (e.g., using a sorter available from Becton Dickinson). As cells pass through the sorter, a laser beam excites the fluorescent compound while a detector counts cells that pass through and determines whether a fluorescent compound is attached to the cell by detecting fluorescence. The amount of label bound to each cell can be quantified and analyzed to characterize the sample.

In the present invention, the presence of FcRn or FcRn-expressing tissue in vivo can be performed by an in vivo Imaging method. The method includes (i) administering to a subject (e.g., a patient having an autoimmune disorder) an anti-FcRn antibody, conjugated to a detectable marker; and (ii) exposing the subject to a means for detecting said detectable marker to the FcRn-expressing tissues or cells. For example, the subject is imaged, e.g., by NMR or other tomographic means. Examples of labels useful for diagnostic imaging include radiolabels, fluorescent labels, positron emitting isotopes, chemiluminescers, and enzymatic markers. A radiolabeled antibody can also be used for in vitro diagnostic tests. The specific activity of a isotopically-labeled antibody depends upon the half life, the isotopic purity of the radioactive label, and how the label is incorporated into the antibody.

The present invention also provides a kit comprising an antibody that binds to FcRn and instructions for diagnostic use, e.g., the use of the FcRn-binding antibody or antigen-binding fragment thereof, to detect FcRn, in vitro, e.g., in a sample, e.g., a biopsy or cells from a patient having an autoimmune disorder, or in vivo, e.g., by imaging a subject. The kit can further contain at least one additional reagent, such as a label or additional diagnostic agent. For in vivo use, the antibody can be formulated as a pharmaceutical composition.

The present invention also provides polynucleotide sequences that encode the variable regions of the antibody of the present invention or a fragment thereof.

Specifically, a polynucleotide sequence that encodes the heavy-chain variable region of the antibody of the present invention or a fragment thereof is a sequence that encodes either any one of the heavy-chain variable regions of FcRn-specific antibody, which comprise CDR1, CDR2 and CDR3 contained in any one amino acid sequence selected from the group consisting of even numbers between SEQ ID NOS: 2 to 144 (e.g., 2, 4, 66, 128, etc.) or in an amino acid sequence set forth in SEQ ID NO: 289 or 291, or a heavy-chain variable region having a sequence homology thereto of at least 90%, preferably at least 95%.

A polynucleotide sequence that encodes the light-chain variable region of the antibody of the present invention or a fragment thereof is a sequence that encodes either any one of the light-chain variable regions of FcRn-specific antibody, which comprise CDR1, CDR2 and CDR3 contained in any one amino acid sequence selected from the group consisting of even numbers between SEQ ID NOS: 146 to 288 (e.g., 148, 196, 244, 266, etc.) or in an amino acid sequence set forth in SEQ ID NO: 290 or 292, or a heavy-chain variable region having a sequence homology thereto of at least 90%, preferably at least 95%.

Preferably, the polynucleotide sequence that encodes the heavy-chain variable region of the antibody of the present invention or a fragment thereof has either any one sequence selected from the group consisting of uneven numbers between SEQ ID NOS: 1 to 143 (e.g., 1, 3, 87, 121, etc.), or a sequence homology thereto of at least 90%, preferably at least 95%, and the polynucleotide sequence that encodes the light-chain variable region has either any one sequence selected from the group consisting of uneven numbers between SEQ ID NOS: 145 to 287 (e.g., 147, 193, 267, 283, etc.), or a sequence homology thereto of at least 90%, preferably at least 95%.

More preferably, the polynucleotide sequences that encode the heavy-chain or light-chain variable regions of the antibody of the present invention or a fragment thereof may be selected from the following sequences:

(1) a sequence of SEQ ID NO: 1 or a sequence having a sequence homology thereto of at least 90%, preferably 95%, and a sequence of SEQ ID NO: 145 or a sequence having a sequence homology thereto of at least 90%, preferably 95%;

(2) a sequence of SEQ ID NO: 3 or a sequence having a sequence homology thereto of at least 90%, preferably 95%, and a sequence of SEQ ID NO: 147 or a sequence having a sequence homology thereto of at least 90%, preferably 95%;

(3) a sequence of SEQ ID NO: 5 or a sequence having a sequence homology thereto of at least 90%, preferably 95%, and a sequence of SEQ ID NO: 149 or a sequence having a sequence homology thereto of at least 90%, preferably 95%;

(4) a sequence of SEQ ID NO: 7 or a sequence having a sequence homology thereto of at least 90%, preferably 95%, and a sequence of SEQ ID NO: 151 or a sequence having a sequence homology thereto of at least 90%, preferably 95%;

(5) a sequence of SEQ ID NO: 9 or a sequence having a sequence homology thereto of at least 90%, preferably 95%, and a sequence of SEQ ID NO: 153 or a sequence having a sequence homology thereto of at least 90%, preferably 95%;

(6) a sequence of SEQ ID NO: 11 or a sequence having a sequence homology thereto of at least 90%, preferably 95%, and a sequence of SEQ ID NO: 155 or a sequence having a sequence homology thereto of at least 90%, preferably 95%;

(7) a sequence of SEQ ID NO: 13 or a sequence having a sequence homology thereto of at least 90%, preferably 95%, and a sequence of SEQ ID NO: 157 or a sequence having a sequence homology thereto of at least 90%, preferably 95%;

(8) a sequence of SEQ ID NO: 15 or a sequence having a sequence homology thereto of at least 90%, preferably 95%, and a sequence of SEQ ID NO: 159 or a sequence having a sequence homology thereto of at least 90%, preferably 95%;

(9) a sequence of SEQ ID NO: 17 or a sequence having a sequence homology thereto of at least 90%, preferably 95%, and a sequence of SEQ ID NO: 161 or a sequence having a sequence homology thereto of at least 90%, preferably 95%;

(10) a sequence of SEQ ID NO: 19 or a sequence having a sequence homology thereto of at least 90%, preferably 95%, and a sequence of SEQ ID NO: 163 or a sequence having a sequence homology thereto of at least 90%, preferably 95%;

(11) a sequence of SEQ ID NO: 21 or a sequence having a sequence homology thereto of at least 90%, preferably 95%, and a sequence of SEQ ID NO: 165 or a sequence having a sequence homology thereto of at least 90%, preferably 95%;

(12) a sequence of SEQ ID NO: 23 or a sequence having a sequence homology thereto of at least 90%, preferably 95%, and a sequence of SEQ ID NO: 167 or a sequence having a sequence homology thereto of at least 90%, preferably 95%;

(13) a sequence of SEQ ID NO: 25 or a sequence having a sequence homology thereto of at least 90%, preferably 95%, and a sequence of SEQ ID NO: 169 or a sequence having a sequence homology thereto of at least 90%, preferably 95%;

(14) a sequence of SEQ ID NO: 27 or a sequence having a sequence homology thereto of at least 90%, preferably 95%, and a sequence of SEQ ID NO: 171 or a sequence having a sequence homology thereto of at least 90%, preferably 95%;

(15) a sequence of SEQ ID NO: 29 or a sequence having a sequence homology thereto of at least 90%, preferably 95%, and a sequence of SEQ ID NO: 173 or a sequence having a sequence homology thereto of at least 90%, preferably 95%;

(16) a sequence of SEQ ID NO: 31 or a sequence having a sequence homology thereto of at least 90%, preferably 95%, and a sequence of SEQ ID NO: 175 or a sequence having a sequence homology thereto of at least 90%, preferably 95%;

(17) a sequence of SEQ ID NO: 33 or a sequence having a sequence homology thereto of at least 90%, preferably 95%, and a sequence of SEQ ID NO: 177 or a sequence having a sequence homology thereto of at least 90%, preferably 95%;

(18) a sequence of SEQ ID NO: 35 or a sequence having a sequence homology thereto of at least 90%, preferably 95%, and a sequence of SEQ ID NO: 179 or a sequence having a sequence homology thereto of at least 90%, preferably 95%;

(19) a sequence of SEQ ID NO: 37 or a sequence having a sequence homology thereto of at least 90%, preferably 95%, and a sequence of SEQ ID NO: 181 or a sequence having a sequence homology thereto of at least 90%, preferably 95%;

(20) a sequence of SEQ ID NO: 39 or a sequence having a sequence homology thereto of at least 90%, preferably 95%, and a sequence of SEQ ID NO: 183 or a sequence having a sequence homology thereto of at least 90%, preferably 95%;

(21) a sequence of SEQ ID NO: 41 or a sequence having a sequence homology thereto of at least 90%, preferably 95%, and a sequence of SEQ ID NO: 185 or a sequence having a sequence homology thereto of at least 90%, preferably 95%;

(22) a sequence of SEQ ID NO: 43 or a sequence having a sequence homology thereto of at least 90%, preferably 95%, and a sequence of SEQ ID NO: 187 or a sequence having a sequence homology thereto of at least 90%, preferably 95%;

(23) a sequence of SEQ ID NO: 45 or a sequence having a sequence homology thereto of at least 90%, preferably 95%, and a sequence of SEQ ID NO: 189 or a sequence having a sequence homology thereto of at least 90%, preferably 95%;

(24) a sequence of SEQ ID NO: 47 or a sequence having a sequence homology thereto of at least 90%, preferably 95%, and a sequence of SEQ ID NO: 191 or a sequence having a sequence homology thereto of at least 90%, preferably 95%;

(25) a sequence of SEQ ID NO: 49 or a sequence having a sequence homology thereto of at least 90%, preferably 95%, and a sequence of SEQ ID NO: 193 or a sequence having a sequence homology thereto of at least 90%, preferably 95%;

(26) a sequence of SEQ ID NO: 51 or a sequence having a sequence homology thereto of at least 90%, preferably 95%, and a sequence of SEQ ID NO: 195 or a sequence having a sequence homology thereto of at least 90%, preferably 95%;

(27) a sequence of SEQ ID NO: 53 or a sequence having a sequence homology thereto of at least 90%, preferably 95%, and a sequence of SEQ ID NO: 197 or a sequence having a sequence homology thereto of at least 90%, preferably 95%;

(28) a sequence of SEQ ID NO: 55 or a sequence having a sequence homology thereto of at least 90%, preferably 95%, and a sequence of SEQ ID NO: 199 or a sequence having a sequence homology thereto of at least 90%, preferably 95%;

(29) a sequence of SEQ ID NO: 57 or a sequence having a sequence homology thereto of at least 90%, preferably 95%, and a sequence of SEQ ID NO: 201 or a sequence having a sequence homology thereto of at least 90%, preferably 95%;

(30) a sequence of SEQ ID NO: 59 or a sequence having a sequence homology thereto of at least 90%, preferably 95%, and a sequence of SEQ ID NO: 203 or a sequence having a sequence homology thereto of at least 90%, preferably 95%;

(31) a sequence of SEQ ID NO: 61 or a sequence having a sequence homology thereto of at least 90%, preferably 95%, and a sequence of SEQ ID NO: 205 or a sequence having a sequence homology thereto of at least 90%, preferably 95%;

(32) a sequence of SEQ ID NO: 63 or a sequence having a sequence homology thereto of at least 90%, preferably 95%, and a sequence of SEQ ID NO: 207 or a sequence having a sequence homology thereto of at least 90%, preferably 95%;

(33) a sequence of SEQ ID NO: 65 or a sequence having a sequence homology thereto of at least 90%, preferably 95%, and a sequence of SEQ ID NO: 209 or a sequence having a sequence homology thereto of at least 90%, preferably 95%;

(34) a sequence of SEQ ID NO: 67 or a sequence having a sequence homology thereto of at least 90%, preferably 95%, and a sequence of SEQ ID NO: 211 or a sequence having a sequence homology thereto of at least 90%, preferably 95%;

(35) a sequence of SEQ ID NO: 69 or a sequence having a sequence homology thereto of at least 90%, preferably 95%, and a sequence of SEQ ID NO: 213 or a sequence having a sequence homology thereto of at least 90%, preferably 95%;

(36) a sequence of SEQ ID NO: 71 or a sequence having a sequence homology thereto of at least 90%, preferably 95%, and a sequence of SEQ ID NO: 215 or a sequence having a sequence homology thereto of at least 90%, preferably 95%;

(37) a sequence of SEQ ID NO: 73 or a sequence having a sequence homology thereto of at least 90%, preferably 95%, and a sequence of SEQ ID NO: 217 or a sequence having a sequence homology thereto of at least 90%, preferably 95%;

(38) a sequence of SEQ ID NO: 75 or a sequence having a sequence homology thereto of at least 90%, preferably 95%, and a sequence of SEQ ID NO: 219 or a sequence having a sequence homology thereto of at least 90%, preferably 95%;

(39) a sequence of SEQ ID NO: 77 or a sequence having a sequence homology thereto of at least 90%, preferably 95%, and a sequence of SEQ ID NO: 221 or a sequence having a sequence homology thereto of at least 90%, preferably 95%;

(40) a sequence of SEQ ID NO: 79 or a sequence having a sequence homology thereto of at least 90%, preferably 95%, and a sequence of SEQ ID NO: 223 or a sequence having a sequence homology thereto of at least 90%, preferably 95%;

(41) a sequence of SEQ ID NO: 81 or a sequence having a sequence homology thereto of at least 90%, preferably 95%, and a sequence of SEQ ID NO: 225 or a sequence having a sequence homology thereto of at least 90%, preferably 95%;

(42) a sequence of SEQ ID NO: 83 or a sequence having a sequence homology thereto of at least 90%, preferably 95%, and a sequence of SEQ ID NO: 227 or a sequence having a sequence homology thereto of at least 90%, preferably 95%;

(43) a sequence of SEQ ID NO: 85 or a sequence having a sequence homology thereto of at least 90%, preferably 95%, and a sequence of SEQ ID NO: 229 or a sequence having a sequence homology thereto of at least 90%, preferably 95%;

(44) a sequence of SEQ ID NO: 87 or a sequence having a sequence homology thereto of at least 90%, preferably 95%, and a sequence of SEQ ID NO: 231 or a sequence having a sequence homology thereto of at least 90%, preferably 95%;

(45) a sequence of SEQ ID NO: 89 or a sequence having a sequence homology thereto of at least 90%, preferably 95%, and a sequence of SEQ ID NO: 233 or a sequence having a sequence homology thereto of at least 90%, preferably 95%;

(46) a sequence of SEQ ID NO: 91 or a sequence having a sequence homology thereto of at least 90%, preferably 95%, and a sequence of SEQ ID NO: 235 or a sequence having a sequence homology thereto of at least 90%, preferably 95%;

(47) a sequence of SEQ ID NO: 93 or a sequence having a sequence homology thereto of at least 90%, preferably 95%, and a sequence of SEQ ID NO: 237 or a sequence having a sequence homology thereto of at least 90%, preferably 95%;

(48) a sequence of SEQ ID NO: 95 or a sequence having a sequence homology thereto of at least 90%, preferably 95%, and a sequence of SEQ ID NO: 239 or a sequence having a sequence homology thereto of at least 90%, preferably 95%;

(49) a sequence of SEQ ID NO: 97 or a sequence having a sequence homology thereto of at least 90%, preferably 95%, and a sequence of SEQ ID NO: 241 or a sequence having a sequence homology thereto of at least 90%, preferably 95%;

(50) a sequence of SEQ ID NO: 99 or a sequence having a sequence homology thereto of at least 90%, preferably 95%, and a sequence of SEQ ID NO: 243 or a sequence having a sequence homology thereto of at least 90%, preferably 95%;

(51) a sequence of SEQ ID NO: 101 or a sequence having a sequence homology thereto of at least 90%, preferably 95%, and a sequence of SEQ ID NO: 245 or a sequence having a sequence homology thereto of at least 90%, preferably 95%;

(52) a sequence of SEQ ID NO: 103 or a sequence having a sequence homology thereto of at least 90%, preferably 95%, and a sequence of SEQ ID NO: 247 or a sequence having a sequence homology thereto of at least 90%, preferably 95%;

(53) a sequence of SEQ ID NO: 105 or a sequence having a sequence homology thereto of at least 90%, preferably 95%, and a sequence of SEQ ID NO: 249 or a sequence having a sequence homology thereto of at least 90%, preferably 95%;

(54) a sequence of SEQ ID NO: 107 or a sequence having a sequence homology thereto of at least 90%, preferably 95%, and a sequence of SEQ ID NO: 251 or a sequence having a sequence homology thereto of at least 90%, preferably 95%;

(55) a sequence of SEQ ID NO: 109 or a sequence having a sequence homology thereto of at least 90%, preferably 95%, and a sequence of SEQ ID NO: 253 or a sequence having a sequence homology thereto of at least 90%, preferably 95%;

(56) a sequence of SEQ ID NO: 111 or a sequence having a sequence homology thereto of at least 90%, preferably 95%, and a sequence of SEQ ID NO: 255 or a sequence having a sequence homology thereto of at least 90%, preferably 95%;

(57) a sequence of SEQ ID NO: 113 or a sequence having a sequence homology thereto of at least 90%, preferably 95%, and a sequence of SEQ ID NO: 257 or a sequence having a sequence homology thereto of at least 90%, preferably 95%;

(58) a sequence of SEQ ID NO: 115 or a sequence having a sequence homology thereto of at least 90%, preferably 95%, and a sequence of SEQ ID NO: 259 or a sequence having a sequence homology thereto of at least 90%, preferably 95%;

(59) a sequence of SEQ ID NO: 117 or a sequence having a sequence homology thereto of at least 90%, preferably 95%, and a sequence of SEQ ID NO: 261 or a sequence having a sequence homology thereto of at least 90%, preferably 95%;

(60) a sequence of SEQ ID NO: 119 or a sequence having a sequence homology thereto of at least 90%, preferably 95%, and a sequence of SEQ ID NO: 263 or a sequence having a sequence homology thereto of at least 90%, preferably 95%;

(61) a sequence of SEQ ID NO: 121 or a sequence having a sequence homology thereto of at least 90%, preferably 95%, and a sequence of SEQ ID NO: 265 or a sequence having a sequence homology thereto of at least 90%, preferably 95%;

(62) a sequence of SEQ ID NO: 123 or a sequence having a sequence homology thereto of at least 90%, preferably 95%, and a sequence of SEQ ID NO: 267 or a sequence having a sequence homology thereto of at least 90%, preferably 95%;

(63) a sequence of SEQ ID NO: 125 or a sequence having a sequence homology thereto of at least 90%, preferably 95%, and a sequence of SEQ ID NO: 269 or a sequence having a sequence homology thereto of at least 90%, preferably 95%;

(64) a sequence of SEQ ID NO: 127 or a sequence having a sequence homology thereto of at least 90%, preferably 95%, and a sequence of SEQ ID NO: 271 or a sequence having a sequence homology thereto of at least 90%, preferably 95%;

(65) a sequence of SEQ ID NO: 129 or a sequence having a sequence homology thereto of at least 90%, preferably 95%, and a sequence of SEQ ID NO: 273 or a sequence having a sequence homology thereto of at least 90%, preferably 95%;

(66) a sequence of SEQ ID NO: 131 or a sequence having a sequence homology thereto of at least 90%, preferably 95%, and a sequence of SEQ ID NO: 275 or a sequence having a sequence homology thereto of at least 90%, preferably 95%;

(67) a sequence of SEQ ID NO: 133 or a sequence having a sequence homology thereto of at least 90%, preferably 95%, and a sequence of SEQ ID NO: 277 or a sequence having a sequence homology thereto of at least 90%, preferably 95%;

(68) a sequence of SEQ ID NO: 135 or a sequence having a sequence homology thereto of at least 90%, preferably 95%, and a sequence of SEQ ID NO: 279 or a sequence having a sequence homology thereto of at least 90%, preferably 95%;

(69) a sequence of SEQ ID NO: 137 or a sequence having a sequence homology thereto of at least 90%, preferably 95%, and a sequence of SEQ ID NO: 281 or a sequence having a sequence homology thereto of at least 90%, preferably 95%;

(70) a sequence of SEQ ID NO: 139 or a sequence having a sequence homology thereto of at least 90%, preferably 95%, and a sequence of SEQ ID NO: 283 or a sequence having a sequence homology thereto of at least 90%, preferably 95%;

(71) a sequence of SEQ ID NO: 141 or a sequence having a sequence homology thereto of at least 90%, preferably 95%, and a sequence of SEQ ID NO: 285 or a sequence having a sequence homology thereto of at least 90%, preferably 95%; and

(72) a sequence of SEQ ID NO: 143 or a sequence having a sequence homology thereto of at least 90%, preferably 95%, and a sequence of SEQ ID NO: 287 or a sequence having a sequence homology thereto of at least 90%, preferably 95%.

The present invention also provides a recombinant vector comprising the above-described nucleotide sequence, a host cell comprising the recombinant vector, and a method of producing the inventive antibody, which binds specifically to FcRn, using the above recombinant vector or host cell. Particularly, the antibody of the present invention is preferably produced by expression and purification using a gene recombination method. Specifically, the variable regions that encode the inventive antibody that binds specifically to FcRn are preferably produced by being expressed in separate host cells or simultaneously in a single host cell.

As used herein, the term "recombinant vector" refers to an expression vector capable of expressing the protein of interest in a suitable host cell and means a DNA construct including essential regulatory elements operably linked to express a nucleic acid insert. As used herein, the term "operably linked" means that a nucleic acid expression control sequence is functionally linked to a nucleic acid sequence encoding the protein of interest so as to execute general functions. Operable linkage with the recombinant vector can be performed using a gene recombination technique well known in the art, and site-specific DNA cleavage and ligation can be easily performed using enzymes generally known in the art.

A suitable expression vector that may be used in the present invention may comprise expression regulatory elements such as a promoter, an operator, an initiation codon, a stop codon, a polyadenylation signal, and an enhancer, as well as a signal sequence for membrane targeting or secretion. The initiation and stop codons are generally considered as part of a nucleotide sequence encoding the immunogenic target protein, and are necessary to be functional in an individual to whom a genetic construct has been administered, and must be in frame with the coding sequence. Promoters may generally be constitutive or inducible. Prokaryotic promoters include, but are not limited to, lac, tac, T3 and T7 promoters. Eukaryotic promoters include, but are not limited to, simian virus 40 (SV40) promoter, mouse mammary tumor virus (MMTV) promoter, human immunodeficiency virus (HIV) promoter such as the HIV Long Terminal Repeat (LTR) promoter, moloney virus promoter, cytomegalovirus (CMV) promoter, epstein barr virus (EBV) promoter, rous sarcoma virus (RSV) promoter, as well as promoters from human genes such as human β-actin, human hemoglobin, human muscle creatine and human metallothionein. The expression vector may include a selectable marker that allows selection of host cells containing the vector. Genes coding for products that confer selectable phenotypes, such as resistance to drugs, nutrient requirement, resistance to cytotoxic agents or expression of surface proteins, are used as general selectable markers. Since only cells expressing a selectable marker survive in the environment treated with a selective agent, transformed cells can be selected. Also, a replicable expression vector may include a replication origin, a specific nucleic acid sequence that initiates replication. Recombinant expression vectors that may be used in the present invention include various vectors such as plasmids, viruses and cosmids. The kind of recombinant vector is not specifically limited, as long as it functions to express a desired gene and produce a desired protein in various host cells such as prokaryotic and eukaryotic cells. However, it is preferred to use a vector that can produce a large amount of a foreign protein similar to a natural protein while having strong expression ability with a promoter showing strong activity.

In the present invention, a variety of expression host/vector combinations may be used to express the antibody or an antibody fragment of the present invention. For example, expression vectors suitable for the eukaryotic host include, but are not limited to, SV40, bovine papillomavirus, adenovirus, adeno-associated virus, cytomegalovirus, and retrovirus. Expression vectors that may be used for bacterial hosts include bacterial plasmids such as pET, pRSET, pBluescript, pGEX2T, pUC, col E1, pCR1, pBR322, pMB9 and derivatives thereof, a plasmid such as RP4 having a wider host range, phage DNA represented as various phage lambda derivatives such as gt10, gt11 and NM989, and other DNA phages such as M13 and filamentous single-stranded DNA phage. Expression vectors useful in yeast cells include 2 μm plasmid and derivatives thereof. A vector useful in insect cells is pVL941.

The recombinant vector is introduced into a host cell to form a transformant. Host cells suitable for use in the present invention include prokaryotic cells such as E. coli, Bacillus subtilis, Streptomyces sp., Pseudomonas sp., Proteus mirabilis and Staphylococcus sp., fungi such as Aspergillus sp., yeasts such as Pichia pastoris, Saccharomyces cerevisiae, Schizosaccharomyces sp., and Neurospora crassa, and eukaryotic cells such as lower eukaryotic cells, and higher other eukaryotic cells such as insect cells.

Host cells that may be used in the present invention are preferably derived from plants and mammals, and examples thereof include, but are not limited to, monkey kidney cells (COST), NSO cells, SP2/0, Chinese hamster ovary (CHO) cells, W138, baby hamster kidney (BHK) cells, MDCK, myeloma cells, HuT 78 cells and HEK293 cells. Preferably, CHO cells are used.

In the present invention, transfection or transformation into a host cell includes any method by which nucleic acids can be introduced into organisms, cells, tissues or organs, and, as known in the art, may be performed using a suitable standard technique selected according to the kind of host cell. These methods include, but are not limited to, electroporation, protoplast fusion, calcium phosphate ($CaPO_4$) precipitation, calcium chloride ($CaCl_2$) precipitation, agitation with silicon carbide fiber, and agrobacterium-, PEG-, dextran sulfate-, lipofectamine- and desiccation/inhibition-mediated transformation.

The FcRn-specific antibody according to the present invention can be produced in large amounts by culturing the transformant comprising the recombinant vector in nutrient medium, and the medium and culture conditions that are used in the present invention can be suitable selected depending on the kind of host cell. During culture, conditions, including temperature, the pH of medium, and culture time, can be controlled so as to be suitable for the growth of cells and the mass production of protein. The antibody or antibody fragment produced by the recombination method as described can be collected from the medium or cell lysate and can be isolated and purified by conventional biochemical isolation techniques (Sambrook et al., Molecular Cloning: A laboratory Manual, 2nd Ed., Cold Spring Harbor Laboratory Press (1989); Deuscher, M., Guide to Protein Purification Methods Enzymology, Vol. 182. Academic Press. Inc., San Diego, Calif. (1990)). These techniques include, but are not limited to, electrophoresis, centrifugation, gel filtration, precipitation, dialysis, chromatography (ion exchange chromatography, affinity chromatography, immunosorbent chromatography, size exclusion chromatography, etc.), isoelectric point focusing, and various modifications and combinations thereof. Preferably, the antibody or the antibody fragment is isolated and purified using protein A.

Advantageous Effects

The inventive human antibody specific for FcRn that is a receptor having a high affinity for IgG has high affinity and specificity, causes little or no immunogenicity-related problems, and binds to FcRn non-competitively with IgG or the like to reduce serum auto-antibody levels. By virtue of such properties, the antibody is useful for the treatment and diagnosis of autoimmune diseases.

EXAMPLES

Figure 1:
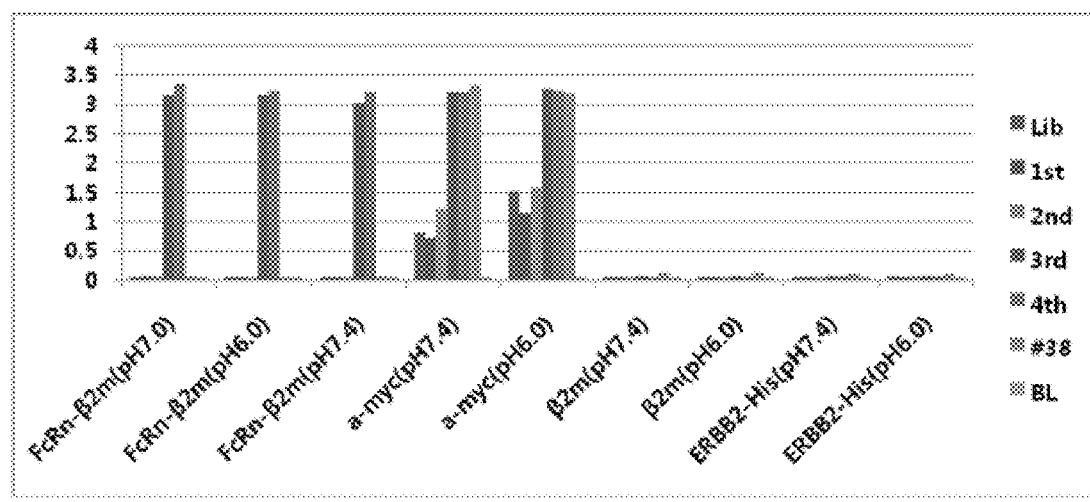
FIG. 1 shows the results of selecting antibody variable domains that bind only to the αFcRn of human FcRn protein without binding to β2m. The results in FIG. 1 were obtained by treating αFcRn (heavy chain)-, β2m- and α-Myc-coated 96-well plates with phages constructed from a human antibody cDNA library and panning phages, which bind to αFcRn (heavy chain) at a pH of 6.0 and a pH of 7.4 without binding to β2m, by ELISA.

Hereinafter, the present invention will be described in further detail with reference to examples. It will be obvious to a person having ordinary skill in the art that these examples are illustrative purposes only and are not to be construed to limit the scope of the present invention.

Part I: Development of FcRn-Specific Human Antibody

Example 1: Construction of Soluble FcRn Expression Vector

FcRn is a non-covalently associated heterodimeric protein composed of a transmembrane anchored-α heavy chain (αFcRn) and a β, chain (β2m), in which are linked by non-covalent bond. Thus, to construct a soluble FcRn expression vector, the two genes were constructed in a single expression vector using the multisite gateway system. The αFcRn and β2m genes having the signal sequences of human growth hormone were amplified by PCR using the primers, shown in Table 1 below and comprised of the restriction enzyme sequences of αFcRn 5-end NheI/3-end XhoI and β2m 5-end NheI/3-end XbaI in addition to the genes, respectively. The amplification products were cloned into a pcDNA3.1(+) vector.

Specifically, a clone (αFcRn: hMU008093/β2m: hMU005156) was purchased from the Korea Research Institute of Bioscience and Biotechnology, and plasmid DNA was extracted from the clone. 2 µl of 200 ng template, 2 µl of 10 pmole N-primer, 2 µl of 10 pmole C-primer, 25 µl of 2× Solgent mixture and 19 µl of distilled water were mixed with each other to make 50 µl of a reaction solution.

The PCR reaction was performed under the following conditions: initial denaturation at 95° C. for 2 min, and then 25 cycles of denaturation at 95° C. at 20 sec, primer annealing at 60° C. for 40 sec and elongation at 72° C. for 1 min, followed by final enzymatic reaction at 72° C. for 5 min. The amplification of the hGH signaling sequence was performed using the same composition as above, and after completion of each PCR reaction, DNA was extracted from the PCR band on agarose gel and used as a template for the next PCR reaction. The hGH leader αFcRn gene amplification product was treated with NheI and XhoI enzymes at 37° C. for at least 4 hours, and the hGH leader β2m gene amplification product was treated with NheI and XbaI enzymes at 37° C. for at least 4 hours, and the pcDNA3.1(+) vector was treated with NheI/XhoI and NheI/XbaI enzymes at 37° C. for at least 4 hours, followed by electrophoresis.

Each of the DNA fragments was electrophoresed on agarose gel to confirm its size and recovered using an agarose gel extraction kit. The DNA fragment and the vector fragment were mixed with each other at a ratio of 1:5 to form a total of 10 µl of a mixture, and 10 µl of NEB ligase buffer and 1 j of ligase were added thereto, followed by incubation at room temperature for 2 hours. 5 µl of the ligation mixture was added to DH5α competent cells and transformed into the cells by heat shock at 42° C. for 1 minute, and the cells were stationary cultured in ampicillin-containing LB solid medium to obtain colonies. The colonies were cultured in ampicillin-containing LB liquid medium at 37° C. for 24 hours, and plasmid DNA was isolated therefrom and sequenced. The results of the sequencing indicated that each of natural leader αFcRn, hGH leader αFcRn, natural leader β2m and hGH leader β2m genes was cloned into pcDNA3.1 (+).

PCR was performed using the two plasmid DNAs cloned into the pcDNA3.1(+) vector as a template together with PCR primers having an attB site inserted into the 5' and 3' ends, using a Jump-In™ fast gateway cloning kit according to the manufacturer's instructions, thereby constructing an expression vector comprising the hGH leader αFcRn/β2m cloned into the pJTI™ FastDEST vector. The genes in the constructed expression vector were sequenced.

TABLE 1

Primer sequences used in construction of vector

| | | | Forward-primer | Reverse-primer |
|---|---|---|---|---|
| Common Leader primer sequence | 1st | | 5'-CTCTGCCTGCCCTGGCTTCAAGAGGGC AGTGCC-3' | |
| | 2nd | | 5'-TGGCTTTTGGCCTGCTCTGCCTGCCCT GGCTTCAAG-3' | |
| | 3rd | | 5'-GGACGTCCCTGCTCCTGGCTTTTGGCC TGCTCTGCC-3' | |
| | 4th | | 5'-ACCATGGCTACAGGCTCCCGGACGTCC CTGCTCCTGGCT-3' | |
| Human FcRn | Soluble FcRn | αFcRn | 5'-TTC AAG AGG GCA GTG CCG CAG AAA GCC ACC TCT CCC TC-3' | 5'-GCT CGA GTC AGG CGG TGG CTG GAA TC-3' |
| | | β2M | 5'-TTC AAG AGG GCA GTG CCA TCC AGC GTA CTC CAA AGA TT-3' | 5'-GTC TAG ATT ACA TGT CTC GAT CCC ACT T-3' |
| | Full length FcRn | αFcRn | 5'-GGC TAG CAT GGG GGT CCC GCG-3' | 5'-GCT CGA GTC AGG CGG TGG CTG GAA TC-3' |
| | | β2M | 5'-GGC TAG CAT GTC TCG CTC CGT GGC C-3' | 5'-GTC TAG ATT ACA TGT CTC GAT CCC ACT T-3' |

TABLE 1-continued

Primer sequences used in construction of vector

| | | | Forward-primer | Reverse-primer |
|---|---|---|---|---|
| Mouse FcRn | Full length FcRn | αFcRn | 5'-GGG TAC CAT GGG GAT GCC ACT GCC-3' | 5'-GCT CGA GTC AGG AAG TGG CTG GAA A-3' |
| | | β2M | 5'-GGG TAC CAT GGC TCG CTC GGT GAC-3' | 5'-GCT CGA GTC ACA TGT CTC GAT CCC A-3' |
| Rat FcRn | Full length FcRn | αFcRn | 5'-GGG TAC CAT GGG GAT GTC CCA GCC-3' | 5'-GCT CGA GTC AGG AAG TGG CCG GAA A-3' |
| | | β2M | 5'-GGG TAC CAT GGC TCG CTC GGT GAC-3' | 5'-GCT CGA GTT ACA TGT CTC GGT CCC AG-3' |
| Monkey FcRn | Full length FcRn | αFcRn | 5'-GGG ATC CAT GAG GGT CCC GCG G-3' | 5'-GCT CGA GTC AGG CAG TGG CTG GG-3' |
| | | β2M | 5'-GGG TAC CAT GTC TCC CTC AGT GGC-3' | 5'-GCT CGA GTT ACA TGT CTC GAT CCC A-3' |
| Common primer | pJTI™ FA STDEST vector | αFcRn | 5'-GGG GAC AAG TTT GTA CAA AAA AGC AGG CTC CGT TGA CAT TGA TTA TTG ACT AGT T-3' | 5'-GGG GAC AAC TTT GTG TAT ACA AAG TTG T CCA TAG AGC CCA CCG CAT CCC CAG-3' |
| | | β2M | 5'-GGG GAC AAC TTT GTA TAC AAA AGT TGC CGT TGA CAT TGA TTA TTG ACT AGT T-3' | 5'-GGG GAC CAC TTT GTA CAA GAA AGC TGG GTA CCA TAG AGC CCA CCG CAT CCC CAG-3' |

Example 2: Construction of Cell Line Expressing Soluble FcRn

Because plasmid DNA to be used for transfection should have high concentration and purity, QIAGEN plasmid purification was performed. The bacterial clone of the sequenced hGH leader FcRn pJTI™ FastDEST vector was inoculated into a 100-ml LB flask containing ampicillin. The bacterial cells were recovered by centrifugation at 3600 rpm for 15 minutes. After removal of the medium, the pellet was completely dissolved in 10 ml of P1 solution by vortexing, and then 10 ml of P2 solution was added thereto. The mixture was gently inverted five times and incubated at room temperature for 5 minutes. Then, 10 ml of P3 solution was added to the mixture, which was then inverted five times and incubated on ice for 30 minutes. After completion of incubation, the solution was centrifuged at 4° C. and 15,000 rpm for 30 minutes. The supernatant was transferred into a 50-ml fresh centrifuge tube and additionally centrifuged for 5 minutes. The supernatant was loaded into a column equilibrated with 10 ml of QBT solution. When loading of the solution by gravity was completed, the column was washed twice with 30 ml of QC solution. A 50-ml centrifuge tube was placed below the column, and then elution with 15 ml of QF solution was performed. 10.5 ml of isopropanol was added to the eluate and centrifuged at 4° C. and 15,000 rpm for 30 minutes. After the DNA pellet was visually observed, the supernatant was carefully removed, and 5 ml of 70% ethanol was added to the pellet. Then, the solution was centrifuged for 15 minutes, and the supernatant was removed so that the pellet was not detached, after which the pellet was dissolved in 150 μl of LAR water. After the pellet was completely dissolved, the solution was filtered through a 0.22 μm filter. The DNA concentration was analyzed by a Nanodrop spectrophotometer, and the DNA measured to have a purity corresponding to an A260 value of 0.1-1.0 was used for transfection.

24 hours before transfection, $6-7 \times 10^3$ cells/ml were inoculated. After 24 hours, the cell viability and number were measured. To remove a cell clump, the cells were transferred into a 50 ml tube and vortexed at 20° C. for 30 seconds. Then, the cells were transferred to 28 ml of medium in a fresh flask at a concentration of $3 \times 10^7$ viable cells.

20 μg of each of an FcRn DEST vector having the hGH leader sequence and a phiC31 integrase vector was diluted in ml of OptiMEM® medium. Then, 80 μg of 293 fectin was diluted in 1 ml of OptiMEM® medium and allowed to stand at room temperature for 5 minutes. When fectin is allowed to stand for 5 minutes or longer, the activity of fectin will decrease, and for this reason, fectin was not allowed to stand for a long period of time. Next, 1 ml of the diluted vector was mixed with 1 ml of the diluted fectin, and the mixture was allowed to stand at room temperature for 30 minutes so that a complex of DNA and fectin could be formed. Next, the mixture was added to the flask containing $3 \times 10^7$ viable cells. The flask was mounted in an orbital shaker in an 8% $CO_2$ incubator at 37° C., and then shaken at 125 rpm. After 24 hours of transfection, the medium was replaced with fresh 293 medium, and the cells were cultured.

The expression level of FcRn could be increased by selectively killing non-integrated cells using a process for selecting cells comprising the FcRn expression vector permanently integrated into the chromosome. After 48 hours of transfection, hygromycin B was added to the cells, and selection of cells was started. Medium replacement and antibiotic treatment were performed once at 3-day intervals during culture, and the cell viability and number were measured as a function of time, thereby constructing an expression cell line.

The expression of FcRn in the constructed stable cell line was analyzed by Western blotting using primary antibodies against αFcRn and β2m. Quantitative analysis was performed using commercially available human β2-microglobulin as a standard, and the results were analyzed by imaging.

During culture of the FcRn stable cell line, the medium was sampled and centrifuged at 15,000 rpm for 10 minutes. 20 μl of the supernatant was collected, and 4 μl of 5× reducing sample loading dye was added thereto and allowed to stand at 95° C. for 5 minutes. 12 μl of the resulting sample was loaded onto 12% NuPAGE Bis-Tris gel. The human β2-microglobulin standard was loaded in amounts of 5 ng and 10 ng. The PAGE gel was run at 250 volt for 35 minutes and transferred to a PVDF membrane at 30 volt for 90 minutes. Blocking was performed with 10% skim milk for 1 hour. Primary antibody against each of αFcRn and β2m was diluted at 1:1,000 in TBST solution and incubated at room temperature for 1 hour, and secondary antibody was diluted at 1:5,000 in TBST solution and incubated at room temperature for 30 minutes. Next, the membrane was washed with TBST solution for 30 minutes more. ECL solutions A and B were mixed with each other at a ratio of 1:1, applied to the membrane, and then allowed to react for 1 minute. Color was developed with manual increment at 10-sec intervals, and the results were imaged.

Example 3: Expression and Purification of Soluble FcRn

FcRn expressed in the constructed stable cell line is secreted from the medium. An experiment was performed to determine the time when soluble FcRn is collected from the culture of the stable cell line. 30-ml flasks containing $30 \times 10^4$ cells/ml and $60 \times 10^4$ cells/ml were prepared, and samples were collected for 7 days from the day of inoculation of cells. The samples were analyzed by WB (Western blotting), and the day at which the expression of soluble FcRn reached the highest after inoculation was determined as the time for collecting the sample medium. After inoculation and culture of the cells, the medium was centrifuged at 4° C. and 3,600 rpm for 10 minutes. Only the supernatant medium was collected in such a manner that the cell pellet was not detached, and then the supernatant was filtered through a 0.22 μm filter. To purify 800-1,000 ml of the collected sample, a buffer change and concentration process by UF (ultra filtration) was performed. In order to remove NaOH from the filter, about 2 L of distilled water was allowed to flow through the filter, and the filter was sufficiently washed with distilled water, and then 200 ml or more of a buffer comprising 20 mM Bis-Tris and 150 mM NaCl (pH 6.0) was allowed to flow through the filter. The degree of removal of NaOH from the filter could be determined by measuring and comparing the pH of the buffer added to the feed reservoir and the pH of the permeate. When the pH of the permeate reached pH 6.0, the sample was injected into the feed reservoir and concentrated to 200 ml. To change the buffer of the medium sample into a buffer comprising 20 mM Bis-Tris and 150 mM NaCl (pH 6.0), about 2 L (corresponding to about 10 times or more) was filtered. The pressure sensor used was connected to the feed/inlet P1 and operated in a manual mode. The trans-membrane pressure (TMP) was between 0.15 and 0.20 and did not exceed 0.5. After completion of buffer change, 200 ml of the sample medium was concentrated to 50 ml. The concentrated sample was centrifuged at 4° C., 3,600 rpm for 15 minutes, and the supernatant was collected.

About 50 ml of the sample prepared by UF was purified by affinity chromatography using IgG Sepharose 6 Fast Flow. IgG Sepharose 6 Fast Flow was packed into an XK16 column and used in a column volume of 8 ml, and affinity chromatography was performed at a linear velocity of 150 cm/hr (5 ml/min). After 50 ml of the concentrated sample was injected at a flow rate of 2 ml/min, the column was washed with about 5 CV or more of washing buffer (20 mM Bis-Tris, 150 mM NaCl pH 5.8) until the baseline was restored. Next, elusion buffer (50 mM Tris-Cl, pH8.0) was allowed to flow through the column at a flow rate of 4 ml/min, and the eluate was collected as 2-ml fractions. Protein concentrations were measured by the Bradford quantification method, and purity analysis was performed by Coomassie staining after electrophoresis.

Example 4: Selection of Polyphages and Monophages by Phage Display Method

Using the isolated and purified shFcRn (soluble human FcRn) as an antigen, polyphages that bind to the FcRn a chain at a pH between 6.0 and 7.4 in a pH-independent manner without binding to β2m were selected from a human antibody cDNA library (see FIG. 1), and among them, 8 monophages were used in the analysis of hit gene.

Specifically, a library having a diversity of $2.7 \times 10^{10}$ was cultured at 30° C. for 16 hours, concentrated in PEG (polyethyleneglycol), and then added to PBS buffer. Three-round panning was performed using shFcRn as an antigen, and in round 3, it was shown that the colony titer of the phages against the antigen was amplified by about 10-100 times. A group of monoclonal phage antibodies was prepared from a group of polyclonal phage antibodies resulting from round 3. The ability of each of the antibodies to bind to the antigen was analyzed, and monoclonal phage antibodies were obtained by fingerprinting and sequencing. The cells obtained from the library cells by the three-round panning were transfected with a helper phage and cultured, and poly ScFv-phages present in the supernatant were analyzed by ELSIA using an immuno-plate reader. As a result, it was found that the poly ScFv-phages had an enhanced ability to bind to the antigen (see FIG. 1).

To sequence each of the monophage clones confirmed by fingerprinting with BstN1, DNA was isolated from the monoclonal cells and sequenced. The $V_H$ and $V_L$ CDR regions of the selected antibodies were analyzed, and the similarity between these antibodies and a germ line antibody group was examined using the Ig BLAST program of NCBI (http://www.ncbi.nlm.nih.gov/igblast/). As a result, 8 kinds of shFcRn-specific phage antibodies could be selected. The variable region sequences of the 8 selected antibodies and the nucleotide sequences that encode the variable region sequences are shown in Tables 2 and 3 below. In addition, the CDR sequences in each of the variable regions are shown in Table 4 below.

TABLE 2

Amino acid sequences of heavy-chain and light-chain variable regions of selected antibodies

| | Sequences of heavy-chain variable regions | | Sequences of light-chain variable regions | |
|---|---|---|---|---|
| Antibody name | SEQ ID NO: | Amino acid sequences | SEQ ID NO: | Amino acid sequences |
| HL161-1A | 2 | QVQLVQSGGG LVQPGRSLRL | 146 | NFMLTQPASV SGSPGQTITI |

TABLE 2-continued

Amino acid sequences of heavy-chain and light-chain variable regions of selected antibodies

| | Sequences of heavy-chain variable regions | | Sequences of light-chain variable regions | |
|---|---|---|---|---|
| Antibody name | SEQ ID NO: | Amino acid sequences | SEQ ID NO: | Amino acid sequences |
| | | SCAASGFSFG EYGMHWVRQA PGKGLEWVSG VSWNSGSIAY ADSVRGRFTI SRDNSKNSLY LQMNSLRAED TAVYYCARGR SMDVWGQGTT VTVSS | | SCTGSSSDVG GYNYVSWYQQ HPGKAPQLII YDVTKRPSGV SNRFSGSKSG NSASLTISGL QAEDEADYYC SSYSSSTFYV FGTGTKVTVL |
| HL161-2A | 4 | QMQLVQSGAE VKKPGSSVKV SCKASGGTFN NYAVSWVRQA PGQGLEWMGR IIPILGIANY AQTFQGRVTI TADKSTTTAY MELSSLRSED TAVYYCARDR YGMDVWGQGT TVTVSS | 148 | QLVLTQPPST SETPGQRVTI SCSGSSSNIG SNYVYWYQQL PGTAPKLLIY RNNQRPSGVP DRFSGSKSGT SASLAISGLR SEDEADYYCA SWDDSLSGVV FGGGTKLTVL |
| HL161-2D | 6 | QVQLVESGGG LVQPGRSLRL SCTASGFTFG DYAMSWVRQA PGKGLEWVGF IRSKAYGGTT EYAASVKGRF TISRDDSKSI AYLQMNSLRA EDTAVYYCAR EGLFLPLGGF DLWGLGTMVT VSS | 150 | NFMLTQPHSV SESPGKTVTI SCTRSSGSIA ANYVHWYQQR PGSPPTTVIY NDNQRPSGVP DRFSGSIDRS SNSASLTISG LKTEDEADYY CQSYDSTTYA FGGGTKLTVL |
| HL161-6C | 8 | QVQLVESGAE VKKPGASVKV SCKASGYTFT SYYMHWVRQA PGQGLEWMGI INPSGGSTSY AQKFQGRVTM TRDTSTSTVY MELSSLRSED TAVYYCARGG GAFDIWGQGT MVTVSS | 152 | DIQMTQSPSS VSASVGDRVT ITCRASQGIS NWVAWYQQKP GKAPKLLIYA ASSLQSGVPS RFSGSGSGTD FTLTISSLQP EDFAIYYCQQ GHSFPYTFGQ GTKVEIK |
| HL161-9F | 10 | QVQLVESGGG LVQSGRSLRL SCTASGFTFG DYAMSWVRQA PGKGLEWVGF IRSKAYGGTT EYAASVKGRF TISRDDSKSI AYLQMNSLRA EDTAVYYCAR EGLFLPLGGF DLWGLGTMVT VSS | 154 | NFMLTQPHSV SESPGKTVTI SCTRSSGSIA ANYVHWYQQR PGSPPTTVIY NDNQRPSGVP DRFSGSIDRS SNSASLTISG LKTEDEADYY CQSYDSTTYA FGGGTKLTVL |
| HL161 10E | 12 | QVQLVESGGG LVQPGGSLRL SCAASGFRFS NFAMTWVRQA PGKGLEWVST LSGSGGSIHH ADSVKGRFTI | 156 | SYELTQPLSV SMSPGQTARI TCSGDALSKQ YASWYQLKPG QAPVVMYKD TERPSGIPDR FSGSSSGTTV |

TABLE 2-continued

Amino acid sequences of heavy-chain and light-chain variable regions of selected antibodies

| Antibody name | Sequences of heavy-chain variable regions | | Sequences of light-chain variable regions | |
|---|---|---|---|---|
| | SEQ ID NO: | Amino acid sequences | SEQ ID NO: | Amino acid sequences |
| | | SRDNSKNTLY LQMNSLRAED TAVYYCAKGP LRGQPAYLDP WGQGTLVTVS S | | TLTISGVQAE DEADYYCQSI TDKSGTDVIF GGGTKLTVL |
| HL161-11G | 14 | QMQLVESGGG VVQPGRSLRL SCVGSGFNFN SYGIHWVRQA PGKGLEWVGG IFYDGSQVKY ADSVKGRVSI SRDNSKNTAY LQMNSLRAED TAVYYCARRN LLDYWGQGTV VTVSS | 158 | NFMLTQPASV SGSPGQSITI SCTGSSSDVG GYNYVSWYQQ HPGKAPQLII YDVTKRPSGV SNRFSGSKSG NSASLTISGL QAEDEADYYC SSYSSSTFYV FGTGTKVTVL |
| HL161-11H | 16 | QMQLVESGGG LVQPGRSLRL SCAASGFTFS SYAMHWVRQA PGKGLEWVAV ISYDGSNKYY ADSVKGRFTI SRDNSKNTLY LQMNSLRSED TAVYYCSRGS GGRDAFDVWG QGTMITVSS | 160 | DIQMTQSPST LSASVGDRVT ITCRASQSIS SRLAWYQQKP GKAPKLLIYK ASSLETGVPS RFSGSGSGTE FTLTISSLQP DDFATYYCQQ TNSFPLTFGG GTKVEIK |

TABLE 3

Polynucleotide sequences of heavy-chain and light-chain variable regions of selected antibodies

| Antibody name | Sequences of heavy-chain variable regions | | Sequences of light-chain variable regions | |
|---|---|---|---|---|
| | SEQ ID NO: | Polynucleotide sequences | SEQ ID NO: | Polynucleotide sequences |
| HL161-1A | 1 | CAGGTGCAGC TGGTGCAGTC TGGGGGAGGC TTGGTACAGC CTGGCAGGTC CCTGAGACTC TCCTGTGCAG CCTCTGGTTT CAGTTTTGGT GAATATGGCA TGCACTGGGT CCGGCAAGCT CCAGGGAAGG GCCTGGAGTG GGTCTCAGGT GTTAGTTGGA ACAGTGGTAG CATTGCCTAT GCGGACTCTG TGAGGGGCCG ATTCACCATC TCCAGAGACA ACAGCAAAAA CTCCCTGTAT CTGCAAATGA ACAGTCTGAG | 145 | AATTTTATGC TGACTCAGCC CGCCTCCGTG TCTGGGTCTC CTGGACAGAC GATCACCATC TCCTGCACTG GAAGCAGCAG CGACGTTGGT GGTTATAACT ATGTCTCCTG GTACCAACAG CACCCAGGCA AAGCCCCCCA ACTCATCATT TATGATGTCA CTAAGCGGCC CTCAGGGGTT TCTAATCGCT TCTCCGGCTC CAAGTCTGGC AACTCGGCCT CCCTGACCAT CTCTGGACTC CAGGCTGAGG ACGAGGCTGA |

TABLE 3-continued

Polynucleotide sequences of heavy-chain and
light-chain variable regions of selected antibodies

| Antibody name | Sequences of heavy-chain variable regions | | Sequences of light-chain variable regions | |
|---|---|---|---|---|
| | SEQ ID NO: | Polynucleotide sequences | SEQ ID NO: | Polynucleotide sequences |
| | | AGCCGAGGAC ACGGCCGTGT ATTACTGTGC GAGAGGTAGA AGTATGGACG TCTGGGGCCAA GGGACCACG GTCACCGTCT CCTCA | | TTATTACTGC AGCTCATACA GCAGCAGCAC TTTTTACGTC TTCGGAACTG GGACCAAGGT CACCGTCCTA |
| HL161-2A | 3 | CAGATGCAGC TGGTGCAGTC TGGGGCTGAG GTGAAGAAGC CTGGGTCCTC GGTGAAGGTC TCCTGCAAGG CTTCTGGAGG CACCTTCAAC AACTATGCTG TCAGCTGGGT GCGACAGGCC CCTGGACAAG GGCTTGAGTG GATGGGAAGG ATCATCCCTA TCCTTGGTAT AGCAAACTAC GCACAGACAT TCCAGGGCAG AGTCACGATT ACCGCGGACA AATCCACGAC CACAGCCTAC ATGGAGCTGA GCAGCCTGAG ATCTGAGGAC ACGGCCGTGT ATTACTGTGC AAGAGATCGT TACGGTATGG ACGTCTGGGG CCAAGGGACC ACGGTCACCG TCTCCTCA | 147 | CAGCTCGTGC TGACTCAGCC ACCCTCAACG TCTGAGACCC CCGGGCAGAG GTCACCATC TCTTGTTCTG GAAGCAGCTC CAACATCGGA AGTAATTATG TATACTGGTA CCAGCAACTC CCAGGAACGG CCCCCAAACT CCTCATCTAT AGGAATAATC AGCGGCCCTC AGGGGTCCCT GACCGATTCT CTGGCTCCAA GTCTGGCACT TCAGCCTCCC TGGCCATCAG TGGGCTCCGG TCCGAGGATG AGGCTGATTA TTACTGTGCA TCATGGGATG ACAGCCTGAG TGGTGTGGTT TTCGGCGGAG GGACCAAGCT GACCGTCCTA |
| HL161-2D | 5 | CAGGTGCAGC TGGTGGAGTC TGGGGGAGGC TTGGTACAGC CAGGGCGGTC CCTGAGACTC TCCTGTACAG CTTCTGGATT CACCTTTGGT GATTATGCTA TGAGCTGGGT CCGCCAGGCT CCAGGGAAGG GGCTGGAGTG GGTAGGTTTC ATTAGAAGCA AAGCTTATGG TGGGACAACA GAATACGCCG CGTCTGTGAA AGGCAGATTC ACCATCTCAA GAGATGATTC CAAAAGCATC GCCTATCTGC AAATGAACAG TCTGAGAGCC | 149 | AATTTTATGC TGACTCAGCC CCACTCTGTG TCGGAGTCTC CGGGGAAGAC GGTCACCATC TCCTGCACCC GCAGCAGTGG CAGCATTGCC GCCAACTATG TGCACTGGTA CCAACAGCGC CCGGGCAGTC CCCCCACCAC TGTCATCTAT AACGATAACC AAAGACCCTC TGGAGTCCCT GATCGGTTCT CTGGGTCCAT CGACAGGTCC TCCAACTCTG CCTCCCTCAC CATCTCTGGA CTGAAGACTG AGGACGAGGC TGACTACTAC |

TABLE 3-continued

Polynucleotide sequences of heavy-chain and
light-chain variable regions of selected antibodies

| Antibody name | Sequences of heavy-chain variable regions | | Sequences of light-chain variable regions | |
|---|---|---|---|---|
| | SEQ ID NO: | Polynucleotide sequences | SEQ ID NO: | Polynucleotide sequences |
| | | GAGGACACGG CCGTGTATTA CTGTGCGAGA GAGGGGCTGT TCCTGCCCCT GGGAGGTTTT GATTTATGGG GCCTAGGGAC AATGGTCACC GTCTCCTCA | | TGTCAGTCCT ACGATAGTAC CACTTATGCA TTCGGCGGAG GGACCAAGCT GACCGTCCTA |
| HL161-6C | 7 | CAGGTGCAGC TGGTGGAGTC TGGGGCTGAG GTGAAGAAGC CTGGGGCCTC AGTGAAGGTT TCCTGCAAGG CATCTGGATA CACCTTCACC AGCTACTATA TGCACTGGGT GCGACAGGCC CCTGGACAAG GGCTTGAGTG GATGGGAATA ATCAACCCTA GTGGTGGTAG CACAAGCTAC GCACAGAAGT TCCAGGGCAG AGTCACCATG ACCAGGGACA CGTCCACGAG CACAGTCTAC ATGGAGCTGA GCAGCCTGAG ATCTGAGGAC ACGGCCGTGT ATTACTGTGC AAGAGGGGGG GGGGCTTTTG ATATCTGGGG CCAAGGGACA ATGGTCACCG TCTCCTCA | 151 | GACATCCAGA TGACCCAGTC TCCATCTTCC GTGTCTGCAT CTGTAGGAGA CAGAGTCACC ATCACTTGTC GGGCGAGTCA GGGTATCAGC AACTGGGTAG CCTGGTATCA GCAGAAACCA GGCAAAGCCC CTAAGCTCCT GATCTATGCT GCATCCAGTT TGCAAAGTGG GGTCCCATCA AGGTTCAGCG GCAGTGGATC TGGGACAGAC TTCACTCTCA CCATCAGCAG CCTGCAGCCT GAAGATTTTG CAATTTACTA TTGTCAACAG GGTCACAGTT TCCCGTACAC TTTTGGCCAA GGGACCAAGG TGGAAATCAA A |
| HL161-9F | 9 | CAGGTGCAGC TGGTGGAGTC TGGGGGAGGC TTGGTACAGT CAGGGCGGTC CCTGAGACTC TCCTGTACAG CTTCTGGATT CACCTTTGGT GATTATGCTA TGAGCTGGGT CCGCCAGGCT CCAGGGAAGG GGCTGGAGTG GGTAGGTTTC ATTAGAAGCA AAGCTTATGG TGGGACAACA GAATACGCCG CGTCTGTGAA AGGCAGATTC ACCATCTCAA GAGATGATTC CAAAAGCATC GCCTATCTGC | 153 | AATTTTATGC TGACTCAGCC CCACTCTGTG TCGGAGTCTC CGGGGAAGAC GGTCACCATC TCCTGCACCC GCAGCAGTGG CAGCATTGCC GCCAACTATG TGCACTGGTA CCAACAGCGC CCGGGCAGTC CCCCCACCAC TGTCATCTAT AACGATAACC AAAGACCCTC TGGAGTCCCT GATCGGTTCT CTGGGTCCAT CGACAGGTCC TCCAACTCTG CCTCCCTCAC CATCTCTGGA CTGAAGACTG |

TABLE 3-continued

Polynucleotide sequences of heavy-chain and
light-chain variable regions of selected antibodies

| Antibody name | Sequences of heavy-chain variable regions | | Sequences of light-chain variable regions | |
|---|---|---|---|---|
| | SEQ ID NO: | Polynucleotide sequences | SEQ ID NO: | Polynucleotide sequences |
| | | AAATGAACAG TCTGAGAGCC GAGGACACGG CCGTGTATTA CTGTGCGAGA GAGGGGCTGT TCCTGCCCCT GGGAGGTTTT GATTTATGGG GCCTAGGGAC AATGGTCACC GTCTCCTCA | | AGGACGAGGC TGACTACTAC TGTCAGTCCT ACGATAGTAC CACTTATGCA TTCGGCGGAG GGACCAAGCT GACCGTCCTA |
| HL161 10E | 11 | CAGGTGCAGC TGGTGGAGTC TGGGGGAGGC TTAGTACAGC CTGGGGGGTC CCTGAGACTC TCCTGTGCAG CCTCTGGCTT CAGATTCAGC AACTTTGCCA TGACCTGGGT CCGCCAGGCT CCAGGGAAGG GGCTGGAGTG GGTCTCAACT CTTAGTGGTA GTGGTGGTAG TATACACCAC GCAGACTCCG TGAAGGGCCG ATTCACCATC TCCAGAGACA ATTCCAAGAA CACGCTGTAT CTGCAAATGA ACAGTCTGAG AGCCGAGGAC ACGGCCGTGT ATTACTGTGC GAAAGGGCCC TTGAGGGGAC AGCCGGCCTA CCTTGACCCC TGGGGCCAGG GAACCCTGGT CACCGTCTCC TCA | 155 | TCCTATGAGC TGACACAGCC ACTCTCGGTG TCAATGTCCC CAGGACAAAC GGCCAGGATC ACCTGTTCTG GAGATGCTTT GTCAAAGCAA TATGCTTCTT GGTACCAGCT GAAGCCAGGC CAGGCCCCTG TGGTGGTGAT GTATAAAGAC ACTGAGAGGC CCTCAGGGAT CCCTGACCGA TTCTCTGGCT CCAGCTCCGG GACAACAGTC ACGTTGACCA TCAGTGGAGT CCAGGCAGAA GACGAGGCTG ATTATTACTG TCAATCAATA ACAGACAAGA GTGGTACTGA TGTGATCTTC GGCGGAGGGA CCAAGCTGAC CGTCCTA |
| HL161-11G | 13 | CAGATGCAGC TGGTGGAGTC GGGGGGAGGC GTGGTCCAGC CTGGGAGGTC TCTGAGACTC TCCTGTGTAG GGTCTGGATT CAACTTCAAC AGTTATGGCA TACACTGGGT CCGCCAGGCT CCAGGCAAGG GGCTGGAGTG GGTGGGAGGA ATATTTTATG ATGGAAGTCA AGTAAAGTAT GCAGACTCCG TGAAGGGCCG AGTCTCCATC | 157 | AATTTTATGC TGACTCAGCC CGCCTCCGTG TCTGGGTCCC CTGGACAGTC GATCACCATC TCCTGCACTG GAAGCAGCAG CGACGTTGGT GGTTATAACT ATGTCTCCTG GTACCAACAG CACCCAGGCA AAGCCCCCCA ACTCATCATT TATGATGTCA CTAAGCGGCC CTCAGGGGTT TCTAATCGAT TCTCCGGCTC CAAGTCTGGC |

TABLE 3-continued

Polynucleotide sequences of heavy-chain and
light-chain variable regions of selected antibodies

| Antibody name | Sequences of heavy-chain variable regions | | Sequences of light-chain variable regions | |
|---|---|---|---|---|
| | SEQ ID NO: | Polynucleotide sequences | SEQ ID NO: | Polynucleotide sequences |
| | | TATGCCATGA ATTCCAAGAA CACAGCGTAT CTGCAAATGA ACAGTCTGAG AGCCGAGGAC ACGGCCGTGT ATTACTGTGC GCGACGAAAC CTCCTGGACT ACTGGGGCCA GGGAACGGTG GTCACCGTCT CCTCA | | AACTCGGCCT CCCTGACCAT CTCTGGACTC CAGGCTGAGG ACGAGGCTGA TTATTACTGC AGCTCATACA GCAGCAGCAC TTTTTACGTC TTCGGAACTG GGACCAAGGT CACCGTCCTA |
| HL161-11H | 15 | CAGATGCAGC TGGTAGAGTC TGGGGGAGGT TTGGTACAGC CGGGCAGGTC CCTGAGACTC TCCTGTGCAG CCTCTGGATT CACCTTCAGT AGCTATGCTA TGCACTGGGT CCGCCAGGCT CCAGGCAAGG GGCTGGAGTG GGTGGCAGTT ATATCATATG ATGGAAGCAA TAAATACTAC GCAGACTCCG TGAAGGGCCG ATTCACCATC TCCAGAGACA ATTCCAAGAA CACGCTGTAT CTGCAAATGA ACAGCCTGAG ATCTGAGGAC ACGGCCGTGT ATTACTGTGC GAGAGGTAGT GGTGGTCGTG ACGCTTTTGA TGTCTGGGGC CAAGGAACAA TGATCACCGT CTCCTCA | 159 | GACATCCAGA TGACCCAGTC TCCTTCCACC CTGTCTGCAT CTGTAGGAGA CAGAGTCACC ATCACTTGCC GGGCCAGTCA GAGTATTAGT AGCCGGTTGG CCTGGTATCA GCAGAAACCA GGGAAAGCCC CTAAGCTCCT GATCTATAAG GCATCTAGCT TAGAAACTGG GGTCCCATCA AGGTTCAGCG GCAGTGGATC TGGGACAGAA TTCACTCTCA CCATCAGCAG CCTGCAGCCT GATGATTTTG CAACTTACTA TTGTCAACAG ACGAACAGTT TCCCTCTCAC TTTCGGCGGA GGGACCAAGG TGGAGATCAA A |

TABLE 4

CDR sequences of heavy-chain and light-chain
variable regions of selected antibodies

| Antibody name | CDR sequences of heavy-chain variable regions | | | | CDR sequences of light-chain variable regions | | | |
|---|---|---|---|---|---|---|---|---|
| | SEQ ID NO: | CDR1 | CDR2 | CDR3 | SEQ ID NO: | CDR1 | CDR2 | CDR3 |
| HL161-1A | 2 | EYGMH | GVSWNSGS IAYADSVRG | GRSMDV | 146 | GPLRGQPAYL DP | DVTKRPS | SSYSSST FYV |
| HL161-2A | 4 | NYAVS | RIIPILGI ANYAQTFQG | DRYGMDV | 148 | SGSSSNIGSN YVY | RNNQRPS | ASWDDSL SGVV |

TABLE 4-continued

CDR sequences of heavy-chain and light-chain
variable regions of selected antibodies

| Antibody name | CDR sequences of heavy-chain variable regions | | | CDR sequences of light-chain variable regions | | | |
|---|---|---|---|---|---|---|---|
| | SEQ ID NO: | CDR1 | CDR2 | CDR3 | SEQ ID NO: | CDR1 | CDR2 | CDR3 |
| HL161-2D | 6 | DYAMS | FIRSKAYGGTTEYAASVKG | EGLFLPLGGFDL | 150 | TRSSGSIAANYVH | NDNQRPS | QSYDSTTYAFGGGTKLTVLG |
| HL161-6C | 8 | SYYMH | IINPSGGSTSYAQKFQG | GGGAFDI | 152 | RASQGISNWVA | AASSLQS | QQGHSFPYT |
| HL161-9F | 10 | DYAMS | FIRSKAYGGTTEYAASVKG | EGLFLPLGGFDL | 154 | TRSSGSIAANYVH | NDNQRPS | QSYDSTTYA |
| HL161 10E | 12 | NFAMT | TLSGSGGSIHHADSVKG | GPLRGQPAYLDP | 156 | TRSSGSIAANYVH | DNQRPS | QSYDSTTYA |
| HL161-11G | 14 | SYGIH | GIFYDGSQVKYADSVKG | RNLLDY | 158 | TGSSSDVGGYNYVS | DVTKRPS | SSYSSSTFYV |
| HL161-11H | 16 | SYAMH | VISYDGSNKYYADSVKG | GSGGRDAFDV | 160 | RASQSISSRLA | KASSLET | QQTNSFPLT |

Example 5: Construction and Production of Human Antibodies

Each of the heavy-chain and light-chain variable regions from the selected monoclonal scFv phages was amplified by PCR, and then cloned into a pNATAB vector for human antibody expression. The pNATAB vector for heavy-chain expression had Fc gene already constructed therein, and the pNATAB vector for light-chain expression had a light-chain constant region already constructed therein, and thus the Fc gene and the light-chain constant region were ligated with the cloned variable region gene and expressed in the form of whole human IgG. A human antibody was obtained by transiently transfecting 293E cells with two kinds of plasmids, which express the heavy chain region and the light chain region, and purifying an antibody secreted into the medium using a protein A column.

Specifically, before a day of transfection, $5 \times 10^6$ 293E cells were seeded into a 100-mm culture dish. When the cells reached a confluence of 90%, transfection was performed. 5 g of each of heavy-chain and light-chain plasmid DNAs was prepared and added to 500 µl of serum-free DMEM medium. 20 µg of polyethylenimine (polyscience, cat#. 23966) as a transfection reagent was added to the plasmid DNA-containing medium and well mixed with a pipette, followed by incubation at room temperature for 15 minutes. Next, a DNA/transfection reagent mixture was added to the medium in which 293E cells have grown. The next day, the medium was replaced with fresh serum-free medium, and then the medium was harvested while the medium was replaced at 2-day intervals. The antibody-containing medium was concentrated using a Pellicon 3 filter (Millipore, cat#. P3C030C01), and then the human antibody was purified using a Hi-Trap protein A FF column (GE healthcare, cat#. 17-5079-01) in an AKTA purifier system. The antibody eluted with 100 mM glycine-HCl (pH3.3) buffer was dialyzed with PBS and quantified by measuring the absorbance at a wavelength of 280 nm.

Example 6: Measurement of Binding Ability of Antibody by SPR

Measurement of the binding ability of antibody by SPR was performed by immobilizing shFcRn as a ligand onto a Proteon GLC chip (Bio-Rad) and measuring affinity.

To determine the $K_D$ of anti-FcRn 161 antibody that bind to FcRn, SPR analysis was performed using Proteon XPR36 (Bio-Rad). The analysis of ligand and analyte was performed using a Proteon GLC chip, and the interaction was analyzed at a pH of 6.0 and a pH of 7.4. Immobilization of the ligand was activated by injecting a 1:1 mixture of 1×EDAC (EDC) and 1× Surfo-NHS for 5 minutes. shFcRn was diluted in 10 mM sodium acetate (pH 4.5) at a concentration of 25 µg/ml and added to the ligand at a flow rate of 30 µl/min for 5 minutes. Deactivation was performed with ethanolamine HCl at a flow rate of 30 µl/min for 5 minutes, and it could be seen that shFcRn was immobilized at a level of about 1200-1500 RU. The analyte antibody was allowed to flow on the immobilized chip at a flow rate of 30 µl/min. The analyte antibody was diluted in 0.05% Tween 20/PBS (pH 6.0 or pH 7.4) at concentrations of 100 nM, 50 nM, 20 nM, 10 nM, 5 nM and 2.5 nM before injection. The association time of the analyte antibody was 240 seconds, and the dissociation time was 600 seconds. Regeneration of the chip was performed by injecting 10 mM glycine (pH 2.5) at a flow rate of 100 µl/min for 18 seconds. Based on sensorgrams resulting from six concentrations of the analyte, kinetics analysis was performed using Proteon XPR36 software. The kinetic parameters of the antibody, obtained by the SPR analysis, are shown in Table 5 below.

TABLE 5

Results of SPR analysis by FcRn immobilization

| | shFcRn immobilization | | | | | |
|---|---|---|---|---|---|---|
| Antibody | SPR (pH 6.0) | | | SPR (pH 7.4) | | |
| name | $k_{on}$ (M$^{-1}$s$^{-1}$) | $k_{off}$ (s$^{-1}$) | $K_D$ (M) | $k_{on}$ (M$^{-1}$s$^{-1}$) | $k_{off}$ (s$^{-1}$) | $K_D$ (M) |
| HL161-1A | $4.0 \times 10^6$ | $3.2 \times 10^{-3}$ | $8.0 \times 10^{-10}$ | $1.1 \times 10^6$ | $9.3 \times 10^{-3}$ | $8.5 \times 10^{-9}$ |
| HL161-2A | $6.9 \times 10^5$ | $1.1 \times 10^{-3}$ | $1.6 \times 10^{-9}$ | $4.2 \times 10^5$ | $6.7 \times 10^{-4}$ | $1.6 \times 10^{-9}$ |
| HL161-2D | $6.9 \times 10^5$ | $6.8 \times 10^{-4}$ | $9.8 \times 10^{-10}$ | $3.8 \times 10^5$ | $1.7 \times 10^{-3}$ | $4.5 \times 10^{-9}$ |
| HL161-6C | $1.0 \times 10^6$ | $1.9 \times 10^{-3}$ | $1.9 \times 10^{-9}$ | $4.7 \times 10^5$ | $3.1 \times 10^{-3}$ | $6.6 \times 10^{-9}$ |
| HL161-9F | $7.5 \times 10^5$ | $7.0 \times 10^{-4}$ | $9.3 \times 10^{-10}$ | $4.5 \times 10^5$ | $1.6 \times 10^{-3}$ | $3.6 \times 10^{-9}$ |
| HL161-10E | $1.2 \times 10^6$ | $4.6 \times 10^{-3}$ | $3.8 \times 10^{-9}$ | $3.1 \times 10^5$ | $8.2 \times 10^{-3}$ | $2.6 \times 10^{-8}$ |
| HL161-11G | $1.2 \times 10^6$ | $1.9 \times 10^{-4}$ | $1.6 \times 10^{-10}$ | $5.2 \times 10^5$ | $1.2 \times 10^{-4}$ | $2.3 \times 10^{-10}$ |
| HL161-11H | $9.7 \times 10^5$ | $3.4 \times 10^{-4}$ | $3.5 \times 10^{-10}$ | $5.0 \times 10^5$ | $4.5 \times 10^{-4}$ | $9.0 \times 10^{-10}$ |
| hIgG$_1$ | $3.2 \times 10^5$ | $4.6 \times 10^{-4}$ | $1.4 \times 10^{-9}$ | No binding | No binding | No binding |

Example 7: Construction of Full-Length FcRn Expression Vector

In order to examine whether the eight antibodies bind to hFcRn on the human cell surface and inhibit the interaction between hFcRn and IgG Fc and to examine the cross-reactivity of the antibodies with FcRn of each of humans, monkeys, mice and rats, an expression vector for constructing a cell line of each species that overexpresses FcRn on the cell surface was constructed.

1) Human FcRn

A clone (αFcRn: hMU008093/β2m: hMU005156) was purchased from the Korea Research Institute of Bioscience and Biotechnology, and plasmid DNA was extracted from the clone. 2 μl of 200 ng template, 2 μl of 10 pmole N-primer, 2 μl of 10 pmole C-primer, 25 μl of 2× Solgent mixture and 19 μl of distilled water were mixed with each other to make 50 μl of a reaction solution. The primer sequences used in the experiment are shown in Table 1. The PCR reaction was performed under the following conditions: initial denaturation at 95° C. for 2 min, and then 25 cycles of denaturation at 95° C. at 20 sec, primer annealing at 60° C. for sec and elongation at 72° C. for 1 min, followed by final enzymatic reaction at 72° C. for 5 min. The αFcRn gene amplification product was treated with NheI and XhoI enzymes at 37° C. for at least 4 hours, and the β2m gene amplification product was treated with NheI and XbaI enzymes at 37° C. for at least 4 hours, and the pcDNA3.1(+) vector was treated with each of NheI/XhoI and NheI/XbaI enzymes at 37° C. for at least hours, followed by electrophoresis. Each of the DNA fragments was electrophoresed on agarose gel to confirm its size and recovered using an agarose gel extraction kit. The DNA fragment and the vector fragment were mixed with each other at a ratio of 1:5 to form a total of 10 ul of a mixture, and 10 μl of NEB ligase buffer and 1 μl of ligase were added thereto, followed by incubation at room temperature for 2 hours. 5 μl of the ligation mixture was added to DH5α competent cells and transformed into the cells by heat shock at 42° C. for 1 minute, and the cells were stationary cultured in ampicillin-containing LB solid medium to obtain colonies. The colonies were cultured in ampicillin-containing LB liquid medium at 37° C. for 24 hours, and plasmid DNA was isolated therefrom and sequenced. The results of the DNA sequencing indicated that each of the αFcRn and β2m genes was cloned into pcDNA3.1(+).

PCR was performed using the two plasmid DNAs cloned into the pcDNA3.1(+) vector as a template together with PCR primers having an attB site inserted into the 5' and 3' ends, using a Jump-In™ fast gateway cloning kit according to the manufacturer's instructions, thereby constructing an expression vector comprising the hGH leader αFcRn/β2m cloned into the pJTI™ FastDEST vector. The genes in the constructed expression vector were sequenced.

2) Construction of Mouse, Rat and Monkey Full-Length FcRn Expression Vectors

Mouse, rat and monkey cDNA libraries used in this Example were purchased from BioChain. Mouse cDNA (C1334149), rat cDNA (C1434149) and monkey cDNA (C1534150-cy) were used as templates. 1 μl of template, 2 μl of 10 pmole N-primer shown in Table 1, 2 μl of 10 pmole C-primer shown in Table 1, 25 μl of 2× Solgent mixture and 20 μl of distilled water were mixed with each other to make 50 μl of a reaction solution. The nucleotide sequences of the primers used in the experiment are shown in Table 1. PCR reaction was performed under the following conditions: initial denaturation at 95° C. for 2 min, and then 25 cycles of denaturation at 95° C. for 20 sec, primer annealing at 56° C. for 40 sec and extension at 72° C. for 1 min, followed by final enzymatic reaction at 72° C. for 5 min. The αFcRn and β2m gene amplification products were treated with Kpn and Xho enzymes at 37° C. for at least 4 hours, and the pcDNA3.1(+) vector was treated with Kpn/Xho enzymes, followed by electrophoresis. Each of the DNA fragments was electrophoresed on agarose gel to confirm its size and recovered using an agarose gel extraction kit. The DNA fragment and the vector fragment were mixed with each other at a ratio of 1:5 to form a total of 10 ul of a mixture, and 10 μl of NEB ligase buffer and 1 μl of ligase were added thereto, followed by incubation at room temperature for 2 hours. 5 μl of the ligation mixture was added to DH5α competent cells and transformed into the cells by heat shock at 42° C. for 1 minute, and the cells were stationary cultured in ampicillin-containing LB solid medium to obtain colonies. The colonies were cultured in ampicillin-containing LB liquid medium at 37° C. for 24 hours, and plasmid DNA was isolated therefrom and sequenced. The results of the DNA sequencing indicated that each of the αFcRn and β2m genes was cloned into pcDNA3.1(+). PCR was performed using the two plasmid DNAs cloned into the pcDNA3.1(+) vector as a template together with PCR primers having an attB site inserted into the 5' and 3' ends, using a Jump-In™ fast gateway cloning kit according to the manufacturer's instructions. In this way, expression vectors having the hGH leader and the αFcRn/β2m genes of different species in pJTI™ FastDEST vector were constructed. The genes in the constructed expression vectors were sequenced.

Example 8: Construction of Cell Lines Expressing Full-Length FcRn

Because plasmid DNA to be used for transfection should have high concentration and purity, QIAGEN plasmid purification was performed. The bacterial clone of the sequenced hGH leader FcRn pJTI™ FastDEST vector was inoculated into a 100-ml LB flask containing ampicillin. The bacterial cells were recovered by centrifugation at 3600 rpm for 15 minutes. After removal of the medium, the pellet was completely dissolved in 10 ml of P1 solution by vortexing, and then 10 ml of P2 solution was added thereto. The mixture was gently inverted five times and incubated at room temperature for 5 minutes. Then, 10 ml of P3 solution was added to the mixture, which was then inverted five times and incubated on ice for 30 minutes. After completion of incubation, the solution was centrifuged at 4° C. and 15,000 rpm for 30 minutes. The supernatant was transferred into a 50-ml fresh centrifuge tube and additionally centrifuged for minutes. The supernatant was loaded into a column equilibrated with 10 ml of QBT solution. When loading of the solution by gravity was completed, the column was washed twice with 30 ml of QC solution. A 50-ml centrifuge tube was placed below the column, and then elution with 15 ml of QF solution was performed. 10.5 ml of isopropanol was added to the eluate and centrifuged at 4° C. and 15,000 rpm for 30 minutes. After the DNA pellet was visually observed, the supernatant was carefully removed, and 5 ml of 70% ethanol was added to the pellet. Then, the solution was centrifuged for 15 minutes, and the supernatant was removed in such a manner that the pellet was not detached, after which the pellet was dissolved in 150 μl of LAR water. After the pellet was completely dissolved, the solution was filtered through a 0.22 μm filter. The DNA concentration was analyzed by a Nanodrop spectrophotometer, and the DNA measured to have a purity corresponding to an A260 value of 0.1-1.0 was used for transfection.

Cell lines, which express human FcRn, rat FcRn and monkey FcRn, respectively, were constructed in the following manner. The HEK293 cell line for human FcRn, the 3T3L1 cell line for mouse FcRn, Rat-2 fibroblasts for rat FcRn, and the COS-7 cell line for monkey FcRn were used. 24 hours before transfection, each of the cell lines was seeded into T75 flask and grown to a confluence of 80%. After 24 hours, the medium was replaced with fresh medium.

5 μg of each of a FcRn DEST vector and a phiC31 Integrase vector was diluted in 500 μl of OptiMEM medium. Then, 20 μl of Lipofectamine 2000 was diluted in 500 μl of OptiMEM medium, and allowed to stand at room temperature for 5 minutes. Next, the two dilutions were mixed with each other and allowed to stand at room temperature for 30 minutes so that a complex of DNA and Lipofectamine could be formed. Next, the mixture was added to a flask containing cells. The cells were cultured in a 5% $CO_2$ incubator at 37° C. for 6 hours, and then the medium was replaced with refresh 10% FBS/DMEM medium, and the cells were further cultured.

To select cells comprising the FcRn expression vector permanently integrated into the chromosome, the following process was performed. Through this process, the expression level of FcRn could be increased by selectively killing non-integrated cells. After 48 hours of transfection, hygromycin B was added to the cells to perform selection. Medium replacement and antibiotic treatment were performed at 3-day intervals during cell culture, and the formed colonies were detached at various time points and cultured. From the selected cell groups, stable monoclonal cell lines were selected by clonal selection.

Confirmation of the selected stable cell lines was performed by FACS analysis. Alexa488-labeled hIgG1 was bound to the human FcRn-expressing stable cell line at a pH of 6.0 to measure a shift in population. Likewise, Alexa488-labeled Cynomolgus monkey IgG1 was bound to the monkey FcRn-expressing stable cell line at a pH of 6.0 to measure a shift in population. In the case of the mouse FcRn-expressing stable cell line, mouse IgG1 was bound to the cell line at a pH of 6.0 for 1 hour, the level of bound mouse IgG1 was measured by FACS using FITC-labeled anti-mouse IgG1, thereby measuring a shift in population. In the case of the rat FcRn-expressing stable cell line, anti-rat FcRn mouse antibody was bound to the cell line at a pH of 7.4 for 1 hour, and then the level of bound rat IgG was measured by FACS using FITC-labeled anti-rat IgG antibody, thereby measuring a shift in population.

Example 9: Analysis of Binding of Antibody to FcRn by FACS

Figure 2:
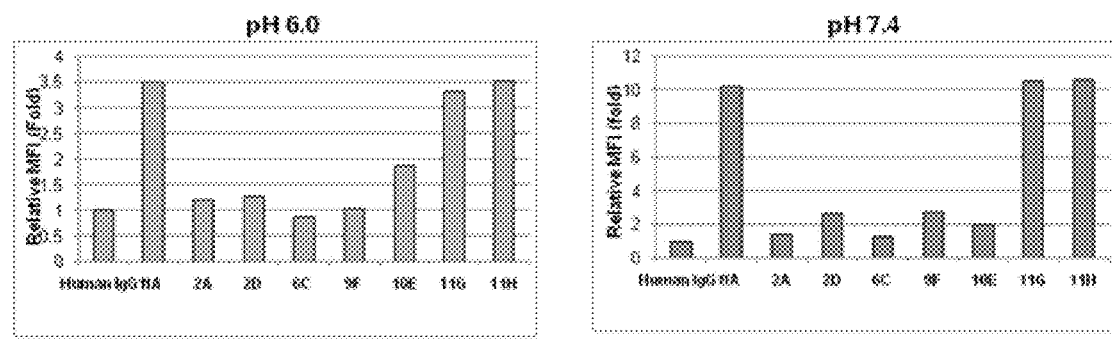
FIG. 2 shows the ability of HIT antibodies to bind to human FcRn (hFcRn) on the cell surface. The results in FIG. 2 were obtained by treating human FcRn-overexpressing HEK293 cells with 8 different antibodies that bind to human FcRn on the cell surface and confirming antibodies that bind to the cell surface FcRn at a pH of 6.0 and a pH of 7.4. The binding of the antibody to FcRn was measured by treating cells with the antibody at each pH, and then analyzing the cells by fluorescent activated cell sorter (FACS) using Alexa488-labeled anti-human goat antibody, and measurement results for the ability of the HIT antibodies to bind to the cell surface were expressed as values relative to the MFI of human IgG1 (hIgG1).

In stable HEK293 cells expressing human FcRn, the degrees of binding of antibody to FcRn at various pHs were analyzed using a FACS system. Specifically, 100,000 stable HEK293 cells were washed with PBS and centrifuged in a table top microcentrifuge at 4500 rpm for 5 minutes to obtain pellets. 1 μg of antibody was added to 100 μl of pH 6.0 or pH 7.4 PBS/10 mM EDTA. The cell pellets were resuspended in 100 μl of the antibody solution and incubated on ice for 60 minutes. The cells were washed once with 150 μl of buffer having pH difference, and then pellets were obtained therefrom. Alexa488-labeled anti-human antibody goat antibody (1 mg/ml) was diluted at 1:20 in buffer having pH difference, and the pellets were resuspended in 100 μl of the buffer, and then cultured on ice for 60 minutes. The cells were washed once with 150 μl of buffer having pH difference, and pellets were obtained therefrom and resuspended in buffer having pH difference. The suspension was transferred into a tube for FACS analysis. These cells were analyzed by FACS using BD FACSDiva™ v6.1.3 software (BD Bioscience). The results of the analysis were expressed as Mean Fluorescence Intensity (MFI) (see FIG. 2). It was shown that, among the eight selected antibodies, HL161-1A, HL161-11G and HL161-11H did strongly bind to hFcRn on the cell surface compared to the comparative substance IgG1.

Example 10: Analysis of Blocking Function of Antibody by FACS

HEK293 cells expressing hFcRn on the surface were treated with the eight antibodies confirmed to have the ability to bind to hFcRn on the cell surface, and whether the binding of Alexa-Fluo-488-labeled hIgG1 decreased was analyzed to examine the blocking function of the antibodies.

The analysis process was performed in the following manner.

1) Labeling of Human IgG1 with Alexa-Fluor-488

Human IgG1 (Calbiochem, cat#.400120) was labeled by a Alexa Fluor 488 labeling kit (Molecular Probed/Invitrogen, Carlsbad, Calif.) according to the manufacturer's protocol. Specifically, 50 μl of 1 M sodium bicarbonate (pH 9.0) was added to 500 μl of 2 mg/ml solution of IgG in PBS. This protein solution was added to Alexa-Fluor-488 succinimidyl ester (dry powder) and incubated with stirring at room temperature for 1 hour. The protein was purified by size-exclusion chromatography using the kit component column (Bio-Rad BioGel P-30 Fine size exclusion purification resin). The sample was loaded onto the column and eluted with PBS. The first colored band contained the labeled protein. The degree of labeling was determined by measuring the absorbance of the eluted IgG at A280 (absorbance at 280 nm) and A494 (absorbance at 494 nm). The protein molar concentration was determined using the following formula:

$(M)=[A280-(A494\times0.11)\times \text{dilution factor}]/203{,}000.$

In addition, the formula used to derive the moles of dye per mole of protein was as follows:

$(M)=A494\times \text{dilution factor}/71{,}000\times \text{protein concentration}.$ Typically, 4-5 moles of Alexa-Fluor 488 were incorporated per mole of IgG.

2) Cell Competition Assay Using FcRn-Expressing Cells

In stable HEK293 cells expressing human FcRn, the blocking of the antibody against FcRn was analyzed by FACS. The antibody was diluted in binding buffer (PBS pH 6.0, 10 mM EDTA) at concentrations of 2,000 nM, 400 nM and 80 nM to make 50 μl of dilutions, which were dispensed into tubes. To each of the tubes, 10 μl of 1 uM Alexa488-labeled hIgG1 (pH 6.0) was added. Stable HEK293 cells were diluted in binding buffer at a concentration of 2,500,000 cells/ml, and 40 μl of the cell dilution was added to each of the labeled antibody-containing tubes. Thus, a final volume of 100 μl contained 100,000 cells, 100 nM labeled antibody and 1000 nM, 500 nM or 250 nM competitor antibody. The cells were washed once with 150 μl of buffer (pH 6.0), and pellets were obtained therefrom and resuspended in 150 μl of buffer having pH difference. The suspension was transferred into a tube for FACS analysis. The cells were analyzed by FACS using BD FACSDiva™ v6.1.3 software (BD Bioscience). The results of the analysis were expressed as mean fluorescence intensity (MFI).

The MFI of the test group was processed after subtracting the MFI (background signal) measured in cells alone. The ratio of the MFI of the competitor-containing tube relative to the MFI (taken as 100%) of the control tube (Alexa Fluor 488 alone and without competitor) was calculated.

Figure 3:
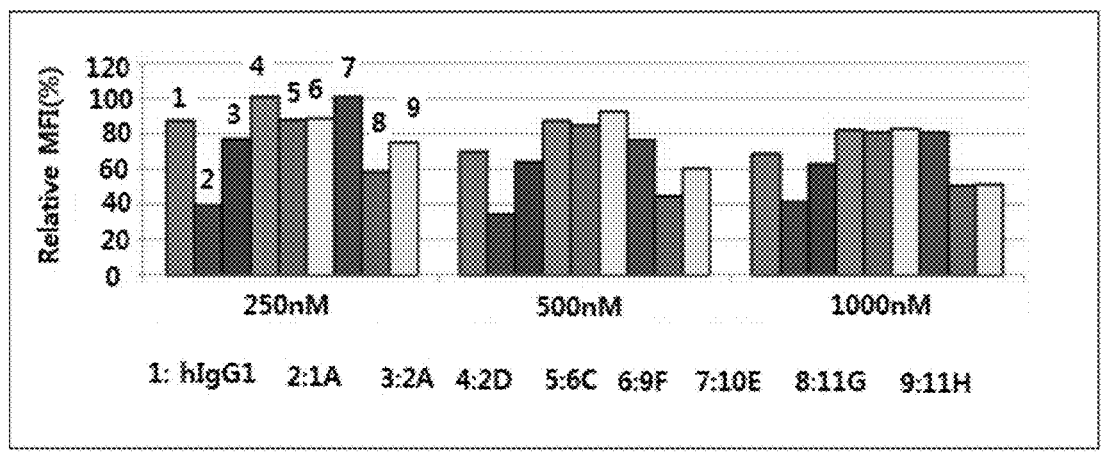
FIG. 3 shows the results of observing whether HIT antibodies that bind to human FcRn on the cell surface can inhibit the binding of human IgG to human FcRn, at the cellular level. Human FcRn-overexpressing HEK293 cells were treated with 8 HIT antibodies confirmed to bind to the cells and 250 nM, 500 nM and 1000 nM of human IgG1, and the ability of the antibodies to inhibit the binding of human IgG to human FcRn was measured based on a decrease in the binding of Alexa488-labeled human IgG1 to the cell surface.

If MFI was lower than the MFI of the human IgG1 competitor-containing tube, it was determined that the binding of the competitor antibody was high. The results in FIG. 3 indicated that HL161-1A, HL161-11G and HL161-11H have blocking functions.

Example 11: Analysis of Cross-Reactivity by FACS

In order to examine whether the three human antibodies having blocking functions bind to FcRn of other species to block the binding of IgG to FcRn of each species, cross-reactivity between species was analyzed in the following manner.

1) Analysis of Cross-Reactivity with Mouse FcRn

Figure 4:
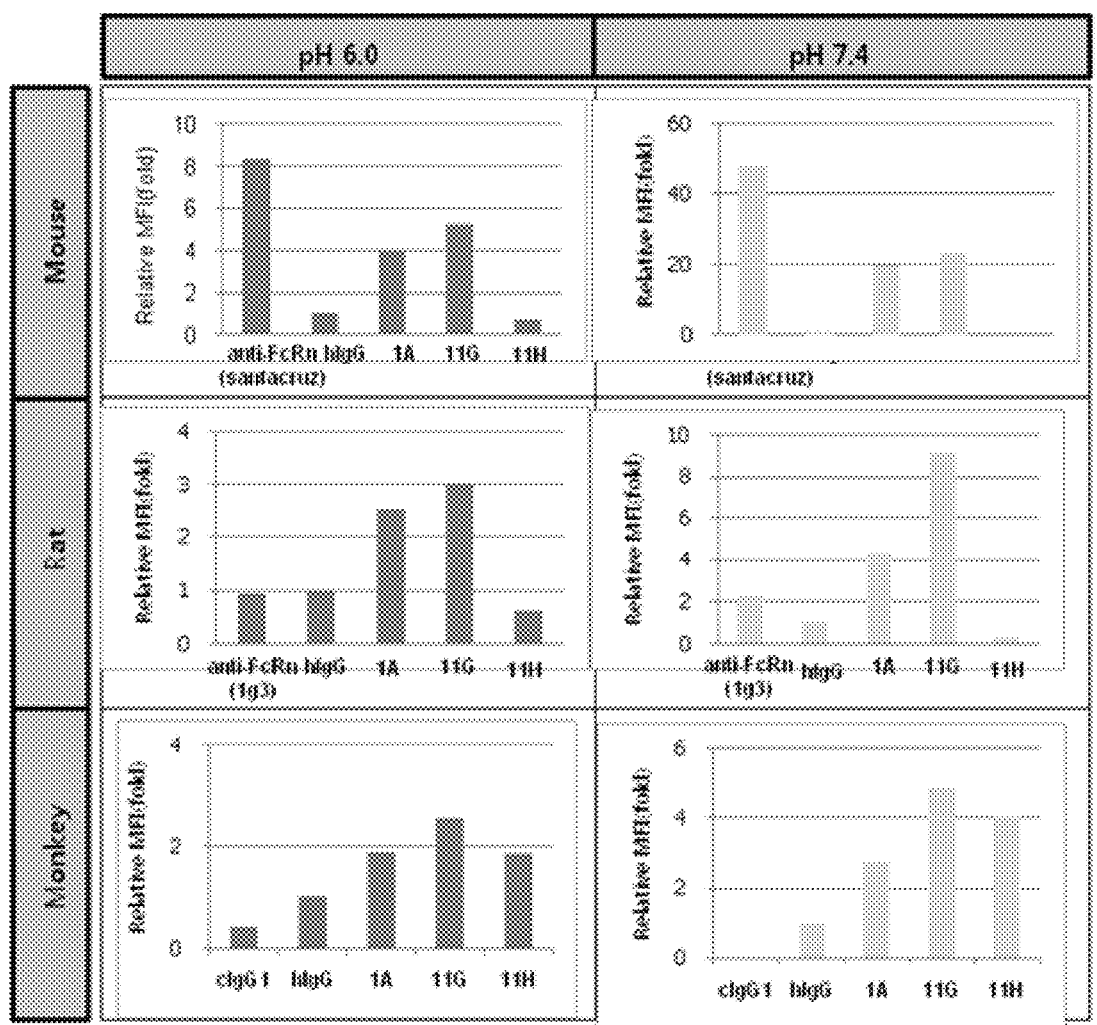
FIG. 4 shows the results of examining whether antibodies that bind to human FcRn also bind to FcRn of other species, by cross-reactivity with mice, rats and monkeys. The results in FIG. 4 were obtained by treating NIH3T3L1, Rat-2 and Cos 7 cells, which overexpress mouse FcRn, rat FcRn and monkey FcRn, with various IgG antibodies, treating the cells with FITC-labeled anti-mouse, anti-rat and anti-human goat antibodies that recognize the antibodies, and analyzing the fluorescence intensity of each antibody bound to the cell surface by FACS. The fluorescence intensities were expressed as the ratios of the MFI values of three HIT antibodies, anti-mouse and anti-rat FcRn antibodies and cynomolgus IgG antibody relative to the MFI of human IgG1.

3T3-L1 cells stably expressing mouse FcRn were cultured in 10% FCS DMEM medium, and then detached from the culture plate by trypsin treatment. The cells were washed three times with cold binding buffer (PBS, pH 6.0 10 mM EDTA), and then diluted in binding buffer at a concentration of $10^5$ cells/ml. 100 μl of the cell dilution was dispensed into each 1.5-ml tube in such a manner that each tube contained $10^4$ cells, and 1 μl of HL161 antibody (1 mg/ml) was added to the dispensed cells. Next, the cells were incubated on ice. As control antibodies, 1 μl of each of rabbit antibody (Santacruz, sc-66893) and human IgG (Abcam, cat#. 409120), which bind to mouse FcRn, was used. The cells were recovered by centrifugation at 4° C. and 4000 rpm for 5 minutes, after which the cells were washed once with binding buffer and resuspended in 100 μl of binding buffer. As FITC-conjugated secondary antibody, 1 μl of anti-human IgG goat antibody (Invitrogen, Cat*. A11013) was added to the cells. In the case of the experiment using anti-mouse FcRn rabbit antibody, the anti-rabbit antibody was incubated with the cells on ice for 1 hour, and then the cells were recovered by centrifugation at 4° C. and 700 g for 5 minutes, washed once with binding buffer, resuspended in 400 ul of binding buffer and analyzed by FACS to examine the cross-reactivity of the HL161 antibodies with mouse FcRn (see FIG. 4). An experiment at a pH of 7.4 was performed using binding buffer at a pH of 7.4 in the same manner as the experiment using binding buffer at a pH of 6.0. The degree of the binding of each antibody to mouse FcRn was presented as relative MFI based on human IgG. At both a pH of 6.0 and a pH of 7.4, the HL161-1A and h1161-11G antibodies did bind to mouse FcRn, but HL161-11H did not bind to mouse FcRn (see FIG. 4).

2) Analysis of Cross-Reactivity with Rat FcRn

Rat-2 (KCTC #AC28203), rat fibroblasts stably expressing rat FcRn, were cultured in 10% FBS DMEM medium, and then detached from the culture plate by trypsin treatment. The cells were washed three times with cold binding buffer (PBS pH 6.0, 10 mM EDTA), and then diluted in binding buffer at a concentration of $10^5$ cells/ml. 100 μl of the cell dilution was dispensed into each 1.5-ml tube in such a manner that each tube contained $10^4$ cells, and 1 μl of HL161 antibody (1 mg/ml) was added to the dispensed cells. Next, the cells were incubated on ice. As control antibodies, 1 μl of each of mouse 1G3 antibody and human IgG antibody (Abcam, cat#. 409120), which bind to rat FcRn, was used. The 1G3 antibody was produced and purified from mouse hybridoma cells (ATCC CRL2434). The cells were recovered by centrifugation at 4° C. and 4000 rpm for 5 minutes, after which the cells were washed once with binding buffer and resuspended in 100 μl of binding buffer. As FITC-conjugated secondary antibody, 1 μl of anti-human IgG goat antibody (Invitrogen, cat#. A11013) was added to the cells. In the case of the experiment using anti-rat FcRn mouse antibody, the anti-mouse IgG goat antibody (Invitrogen, cat#. A11001) was incubated with the cells on ice for 1 hour, and then the cells were recovered by centrifugation at 4° C. and 4000 rpm for 5 minutes, washed once with binding buffer, resuspended in 400 μl of binding buffer and analyzed by FACS to examine the cross-reactivity of the HL161 antibodies with rat FcRn (see FIG. 4). An experiment at a pH of 7.4 was performed using binding buffer at a pH of 7.4 in the same manner as the experiment using binding buffer at a pH of 6.0. The degree of the binding of each antibody to rat FcRn was presented as relative MFI based on human IgG. At both a pH of 6.0 and a pH of 7.4, the HL161-1A and h1161-11G antibodies did bind to rat FcRn, but HL161-11H did not bind to rat FcRn (see FIG. 4).

3) Analysis of Cross-Reactivity with Monkey FcRn

Cos-7 cells stably expressing monkey FcRn were cultured in 10% FBS DMEM medium, and then detached from the culture plate by trypsin treatment. The cells were washed three times with cold binding buffer (PBS pH 6.0, 10 mM EDTA), and then diluted in binding buffer at a concentration of $10^5$ cells/ml. 100 μl of the cell dilution was dispensed into each 1.5-ml tube in such a manner that each tube contained 10⁴ cells, and 1 μl of each HL161 antibody (1 mg/ml) was added to the dispensed cells. Next, the cells were incubated on ice. As control antibodies, 1 μl of each of Cynomolgus monkey IgG (Equitech-Bio Inc, cat#. SLCM66 0100) and human IgG (Abcam, cat#. 409120) was used. The cells were recovered by centrifugation at 4° C. and 700 g for 5 minutes, after which the cells were washed once with binding buffer and resuspended in 100 μl of binding buffer. As FITC-conjugated secondary antibody, 1 μl of anti-human IgG goat antibody (Invitrogen, cat#. A11013) was added to the cells, which were then incubated with on ice for 1 hour. Next, the cells were recovered by centrifugation at 4° C. and 700 g for 5 minutes, washed once with binding buffer, resuspended in 400 J of binding buffer, and then analyzed by FACS to examine the cross-reactivity of the HL161 antibodies with monkey FcRn (see FIG. 4). An experiment at a pH of 7.4 was performed using binding buffer at a pH of 7.4 in the same manner as the experiment using binding buffer at a pH of 6.0. The degree of the binding of each antibody to monkey FcRn was presented as relative MFI based on human IgG. At both a pH of 6.0 and a pH of 7.4, the HL161-1A, h1161-11G and HL161-11H antibodies did bind to monkey FcRn (see FIG. 4).

Example 12: Test for Effect of Human Antibody in mFcRn−/−hFCRN Transgenic 276 Mice Among the three human antibodies determined by FACS analysis to bind to hFcRn to block the binding of hIgG1, two antibodies were selected. Tg276 (hFcRn+/+, h2m+/+, mFcRn−/−, m2m−/−) mice (Jackson Laboratory) expressing hFcRn were injected with human IgG, and then HL161_1A or HL161_11H and human IgG were administered to the mice to examine whether the antibody influences the catabolism of human IgG. Each of two HL161 candidates (HL161_1A and HL161_11H) and human IgG (Greencross, IVglobulinS) was diluted at a concentration of 1 mg/mL, and each dilution was dispensed and stored for 4-day administration. As a vehicle, PBS (phosphate buffered saline; pH 7.4) was used. hFcRn Tg276 mice were acclimated for about 7 days and allowed access to water and feed ad libitum and housed at a temperature of 23±2° C.) and a humidity of (55±5%) with a 12-hr light/12-hr dark cycle. The mice were grouped into three test groups, each consisting of three mice, and a vehicle group consisting of one mouse. In order to use human IgG as a tracer, biotin-conjugated hIgG was prepared using a kit (Pierce, Cat No. 21327) according to the manufacturer's protocol. The prepared biotin-IgG was injected intraperitoneally into the mice at a dose of 5 mg/kg. At 24, 48, 72 and 96 hours after injection of biotin-IgG, the antibody was injected intraperitoneally into the mice at a dose of 10 mg/kg. The mice were gently anesthetized with Forane (Isoflurane, JW pharmaceutical), and then blood was collected from the Retro-orbital plexus using a heparinized micro-hematocrit capillary tube (Fisher) at 6, 12, 24, 48, 72, 96, 120 and 168 hours after injection of biotin-IgG. At 24, 48, 72 and 96 hours after blood collection, the antibody was administered after blood collection. 0.1 mL of the whole blood was received in an Eppendorf tube, and then immediately, plasma was separated by centrifugation and stored in a deep freezer (Thermo) at −70° C. until use in analysis.

The level of biotin-hIgG1 in the collected blood was analyzed by an ELISA assay in the following manner. 100 μl of neutravidin (Pierce, 31000) was seeded into each well of a 96-well plate (Costar, Cat. No: 2592) at a concentration of 1.0 g/ml, and then immobilized at 4° C. for 16 hours. The plate was washed three times with buffer A (0.05% Tween-20, 10 mM PBS, pH 7.4), and then incubated in 1% BSA-containing PBS (pH 7.4) at room temperature for 2 hours. After washing the plate three times with buffer A, a neutravidin plate was prepared at a concentration of 1 μg/ml using 0.5% BSA-containing PBS (pH 7.4). The blood sample was 500-1000-fold serially diluted with buffer B (100 mM MES, 150 mM NaCl, 0.5% BSA IgG-free, 0.05% Tween-20, pH 6.0), and 150 μl of each of the dilutions was injected into each well. The injected sample was allowed to react at room temperature for 1 hour. The plate was washed three times with buffer A, and then 200 j of 1 nM HRP-conjugated anti-human IgG goat antibody was injected into each well and allowed to react at 37° C. for 2 hours. The plate was washed three times with ice-cold buffer B, and then 100 μl of 3,3,5,5-tetramethylbenzidine (RnD, Cat. No: DY999) as a substrate was injected into each well and allowed to react at room temperature for 15 minutes. 50 μl of 1.0M sulfuric acid solution (Samjeon, Cat. No: 52129) was injected into each well to stop the reaction, and then the absorbance at 450 nm was measured.

Figure 5:
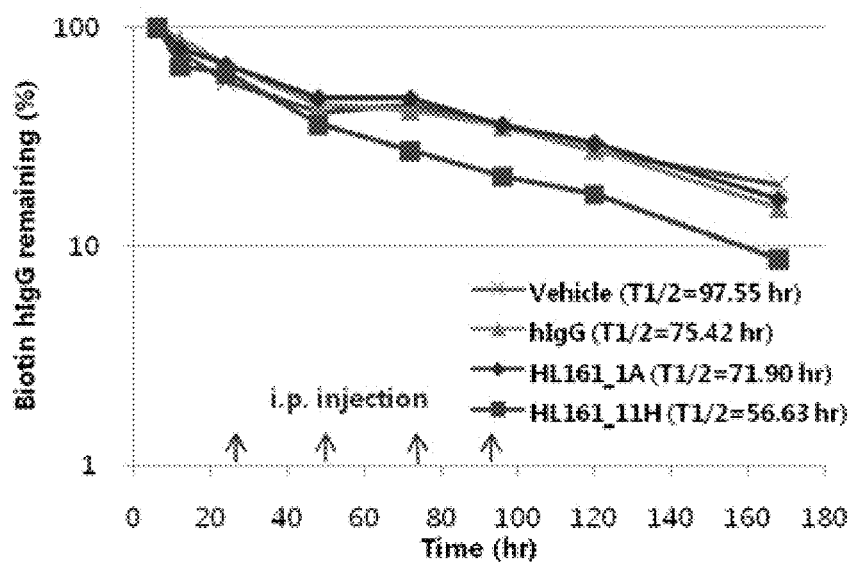
FIG. 5 shows the results of examining the effects of the HIT antibodies HL161_1A and HL161_11H, selected from the human FcRn-expressing transgenic mice Tg276 (hFcRn+/+, hβ2m+/+, mFcRn−/−, mβ2m−/−) on the catabolism of hIgG1. The results in FIG. 5 were obtained by intraperitoneally injecting 5 mg/kg of biotinylated human IgG1 into Tg276 mice, and after 24, 48, 72 and 96 hours, intraperitoneally injecting 10 mg/kg of human IgG1, HL161_1A, HL161_11H or PBS into the mice. Sampling was performed at 6, 12, 24, 48, 72, 96, 120 and 168 hours after injection of biotin-IgG and analyzed by ELISA to determine the level of the remaining biotin-IgG. The results were expressed as the ratio of the level of biotin-IgG remaining at each time point relative to 100% for the level of biotin-IgG remaining at 6 hours.

The concentration of biotin-IgG at 6 hours (approximate $T_{max}$ of biotin-IgG in mice, before the catabolism of biotin-IgG occurred) was set at 100%, and the ratios (%) of biotin-IgG concentrations at other time points relative to the concentration at 6 hours. The results are shown in FIG. 5.

The half-life of the vehicle group was 97.55 hours, and the half-life of the hIgG group used to examine the IVIG effect was 75 hours. The half-lives of the two HL161 candidates HL161-1A and HL161-11H were 72 hours and 57 hours, respectively. The half-life of HL161-1A was shorter than that of the vehicle group by at least 25 hours, but was similar to that of the hIgG group. The half-life of HL161-11H was shorter than that of the vehicle group by at least 40 hours and shorter than that of the hIgG group by about 20 hours or more. These results indicate that the pH-independent, Fc-competitive antibody specific for hFcRn has the effect of increasing the catabolism of endogenous antibody.

Part II: Optimization of FcRn-Specific Antibody by Affinity Maturation

Example 13: Optimization of Candidate Antibody by Affinity Maturation 13-1: Primary Affinity Maturation In order to perform primary affinity maturation, HL161-1A and HL161-11H determined to have the best effect in Examples 1 to 12 using the isolated and purified shFcRn (soluble human FcRn) as an antigen were used as antibodies for affinity maturation. In addition, primary affinity maturation was performed based on 1Ag and 11Hg obtained by modifying the amino acid sequences of HL161-1A and HL161-11H into amino acid sequences that are frequently found in human germ lines. 1Ag and 11Hg have the variable region sequences and CDR sequences shown in Tables 6 and 7 below.

TABLE 6

Variable region sequences of 1Ag and 11Hg

| Clone name | Heavy-chain variable regions SEQ ID NO: | Amino acid sequences | Light-chain variable regions SEQ ID NO: | Amino acid sequences |
|---|---|---|---|---|
| 1Ag | 289 | EVQLVESGGGLVQPGRSLRLSCAASGFTFDEYGMHWVRQAPGKGLEWVSGVSWNSGSIAYADSVRGRFTISRDNAKNSLYLQMNSLRAEDTALYYCARGRYSDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDILMISRIPEVICVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 290 | QSALTQPASVSGSPGQSITISCTGSSSDVGGYNYVSWYQQHPGKAPKLMIYDVTKRPSGVSNRFSGSKSGNTASLTISGLQAEDEADYYCSSYSSSTFYVFGTGTKVTVLGRSVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 11Hg | 291 | QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCARGSGGRDAFDVWGQGTMITVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDILMISRIPEVICVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 292 | DIQMTQSPSTLSASVGDRVTITCRASQSISSRLAWYQQKPGKAPKLLIYKASSLETGVPSRFSGSGSGTEFTLTISSLQPDDFATYYCQQTNSFPLTFGGGTKVEIKRSVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 7

CDR sequences of 1Ag and 11Hg

| Clone name | Heavy-chain variable regions SEQ ID NO: | CDR1 | CDR2 | CDR3 | Light-chain variable regions SEQ ID NO: | CDR1 | CDR2 | CDR3 |
|---|---|---|---|---|---|---|---|---|
| 1Ag | 289 | EYGMH | GVSWNSGSIAYADSVRG | GRSMDV | 290 | TGSSSDVGGYNYVS | DVTKRPS | SSYSSSTFYV |
| 11Hg | 291 | SYAMH | VISYDGSNKYYADSVKG | GSGGRDAFDV | 292 | RASQSISSRLA | KASSLET | QQTNSFPLT |

For affinity maturation, antibodies that bind in a pH-independent manner in the pH range from 6.0 to 7.4 were selected from the scFv format library and sequenced, and then 25 specific antibodies were isolated and purified. Next, the affinities of the antibodies were measured by SPR, and antibodies determined to have enhanced affinity and specificity were selected as templates for use in secondary affinity maturation. A detailed method for affinity maturation is as follows.

(1) Construction of Library

Figure 6:
FIG. 6 is a schematic view of a pComb3X vector cloned with a gene encoding a scFv-type fragment of HL161-1A or HL161-11H to achieve affinity maturation.

The CDR-H3 of each of 1Ag and 11Hg was subjected to saturated randomization at one position in order to minimize the activity of binding to antigen or a change in surface protein in the randomization process. Some residues that are frequently found were not modified or were randomized in a limited manner. The CDR-L3 was subjected to randomization so that it could contain amino acids that were frequently found at positions as a result of analysis of human germ line antibody genes. Oligonucleotides for randomized sites were synthesized, and randomized scFv genes were obtained by PCR. The scFv genes were ligated into pComb3X vectors using a Sfi-I restriction enzyme, and then transformed into an *E. coli* ER2537, thereby constructing a library having a diversity of 8.0×10⁶ for 1Ag and a diversity of 5.0×10⁶ for 11Hg (see FIG. 6).

(2) Panning

In a panning strategy, in order to select clones that strongly bind to antigen at a pH of 6.0 (low KD) and are not easily detached at a pH of 7.4 (low $K_{off}$), biotinylated hFcRn (100 ng) was used as antigen, and hFcRn-expressing HEK293 cells (60-mm, 80% confluence) were used. When HEK293-hFcRn cells were used, the cells were fixed with 3.7% formaldehyde, followed by panning. In the case of 1Ag, fixed soluble cells were used, and in the case of 11Hg, fixed adhesion cells were used. For enhancement of $K_{off}$, the washing time was increased and shFcRn was added. When protein was used, shFcRn was added for 24 hours except for 1$^{st}$ round, followed by washing, and when cells were used, washing was performed 15 times (about 2 hours). When output titer increased as panning progressed, it was considered to be enriched.

(3) ELISA and Dot-Blot Screening

For ELISA and dot-blot screening, each colony was cultured with 0.15 mL of SB medium and induced overnight with mM IPTG, and then a periplasmic extract was obtained therefrom using 0.1 mL of TES. ELISA was performed using TMB reagent after binding periplasmic extract by direct coating with 30 ng, 10 ng and 5 ng of hFcRn and binding anti-HA-HRP. For dot-blot screening, the periplasmic extract was diluted at 1:3 to 1:5 in PBS, and 1 mL of the dilution was dotted onto a nitrocellulose membrane, after which anti-HA-HRP was bound to the membrane which was then analyzed using AbSignal (Abclon, Korea). For numerical comparison with ELISA, a periplasmic extract of parental scFv was serially diluted at 1:2 and used as a standard. For selection of high-affinity binders, based on the dot-blot and ELISA values of parental scFv, clones having lower expression levels and ELISA values higher than parental scFv were selected. In the case of 1Ag, ELISA and dot-blot screening were performed on 855 Strategy-1 4$^{th}$ output colonies, 1425 Strategy-2 3$^{rd}$ output colonies, and 855 Strategy-2 5$^{th}$ output colonies. In order to select binders having high affinity at pH 7.4 and pH 6.0, scFv levels were compared by ELISA for three concentrations of shFcRn. As a result, 40 colonies were selected from Strategy-1 4$^{th}$ outputs, 41 colonies were selected from Strategy-2 3$^{rd}$ outputs, and 40 colonies were selected from Strategy-2 5$^{th}$ outputs.

(4) Nucleotide Sequencing 121 colonies selected from the library based on 1Ag were sequenced, thereby selecting 74 unique sequence clones. Among these sequence clones, 30 clones having no putative glycosylation site were selected.

88 colonies selected from the library based on 11Hg were sequenced, thereby selecting 37 unique clones. Among these clones, 25 clones having no putative glycosylation site were selected.

(5) Purification of 1Ag and 11Hg-Derived Candidate Antibodies Having Improved Affinity In order to perform ELISA, cELISA and the measurement of SPR $K_{off}$, scFv was purified. Specifically, cells were incubated in 20-50 mL of SB and then induced overnight with 1 mM IPTG, after which these cells were extracted with 1:5-1:8 volumes of TES buffer to obtain a periplasmic extract. Purification of scFv was performed by affinity chromatography using Ni-NTA. For measurement of $K_{off}$, 17 clones derived from 1Ag and 8 clones derived from 11Hg were purified.

(6) Measurement of Binding Affinity by ELISA and SPR

ELISA was performed at a pH of 6.0 and a pH of 7.4, and all buffers and samples were used at a pH of 6.0 and a pH of 7.4. shFcRn was diluted in PBS (pH 6.0 or pH 7.4) at a concentration of 2 g/mL, and 100 μl of the dilution was added to each well of a 96-well plate and coated at room temperature for 2 hours (or O/N coated at 4° C.). The plate was washed three times with washing buffer (pH 6.0 or pH 7.4), and then solution was removed from each well by suction. Next, 200 μl of blocking buffer (pH 6.0 or pH 7.4) was added to each well which was then blocked at room temperature for 2 hours. After completion of blocking, the plate was washed three times with washing buffer, and 100 μl of scFv solution at 100 ng/mL for the 1Ag-derived variant or at 150 ng/mL for the 11Hg-derived variant was added to each well of the 96-well plate and incubated for 2 hours. Then, the plate was washed three times with washing buffer. To detect antibody bound to shFcRn, anti-HA-HRP antibody (anti-HA-HRP antibody) (1:2,000, pH 6.0 or pH 7.4) was added to each well and incubated at room temperature for 2 hours. Each well was washed three times with washing buffer (pH 6.0 or pH 7.4), and then 100 μl of TMB solution was added to each well and incubated at room temperature for 10 minutes. After 10 minutes, 50 μl of stop solution ($H_2SO_4$ solution) was added to each well to stop the reaction, and then the absorbance at 450 nm was measured.

The $K_{off}$ rate of scFv was measured using the Biorad-XPR36 system according to the manual. shFcRn was immobilized on a GLC chip, and scFv was added thereto at one concentration to obtain a sensorgram.

TABLE 8

Results of ELISA and SPR analysis of 1Ag CDR-3 random mutations

| | scFv | | | |
|---|---|---|---|---|
| | ELISA (OD450) | | SPR Koff values | |
| Clone name | (pH 6.0) | (pH 7.4) | (pH 6.0) | (pH 7.4) |
| B04 | 0.22 | 0.08 | 3.41E−04 | 3.10E−04 |
| 1Ag (parent) | 0.35 | 0.38 | 2.22E−04 | 2.12E−04 |
| A11-A01 | 1.31 | 0.86 | 1.49E−04 | 2.13E−03 |
| A11-C07 | 3.50 | 2.40 | 3.93E−04 | 2.48E−03 |
| A11-G06 | 1.48 | 0.99 | 2.25E−04 | 4.96E−04 |
| A11-A02 | 0.93 | 0.80 | 1.69E−04 | 8.50E−04 |
| A12-A03 | 0.60 | 0.86 | 3.43E−04 | 4.81E−04 |
| A12-A05 | 0.87 | 0.56 | 6.57E−05 | 3.07E−04 |
| A12-B02 | 1.06 | 0.74 | 1.29E−04 | 3.07E−04 |
| A12-B03 | 1.03 | 0.86 | 1.58E−04 | 6.07E−04 |
| A12-B04 | ND | ND | 2.73E−04 | 3.46E−03 |
| A12-C01 | 0.59 | 0.46 | 2.93E−04 | 3.52E−04 |
| A12-C04 | 0.95 | 0.71 | 2.88E−04 | 3.62E−04 |
| A12-C09 | 1.63 | 1.30 | 1.77E−04 | 9.09E−04 |
| A12-D02 | 0.64 | 0.60 | 1.61E−04 | 4.70E−04 |
| A12-D04 | 0.42 | 0.44 | 8.51E−05 | 8.79E−04 |
| A12-D05 | 1.21 | 1.16 | 1.31E−04 | 9.64E−04 |
| A12-E01 | 1.71 | 1.05 | 5.99E−05 | 1.15E−03 |
| A12-E04 | 1.59 | 1.29 | 1.32E−04 | 1.37E−03 |
| A12-E05 | 2.06 | 1.80 | 2.16E−04 | 2.22E−03 |
| A12-F02 | 2.17 | 2.40 | 3.05E−04 | 2.25E−04 |
| A12-F05 | 0.43 | 0.42 | 1.29E−04 | 4.92E−04 |
| A12-F08 | 1.08 | 0.74 | 1.08E−04 | 9.31E−04 |
| A12-G05 | 0.68 | 0.50 | 7.01E−05 | 3.72E−04 |
| A12-G07 | 0.74 | 0.71 | 1.05E−04 | 5.89E−04 |
| A12-G08 | 0.74 | 0.64 | 1.33E−04 | 4.01E−04 |
| A12-H01 | 0.49 | 0.40 | 3.38E−04 | 3.31E−04 |

TABLE 8-continued

Results of ELISA and SPR analysis of 1Ag CDR-3 random mutations

| | scFv | | | |
|---|---|---|---|---|
| | ELISA (OD450) | | SPR Koff values | |
| Clone name | (pH 6.0) | (pH 7.4) | (pH 6.0) | (pH 7.4) |
| A12-H04 | 2.26 | 1.57 | 2.20E-04 | 2.35E-03 |
| A12-H06 | 1.13 | 0.99 | 2.76E-04 | 5.72E-04 |
| A12-H08 | 0.93 | 0.84 | 2.44E-04 | 4.79E-04 |
| A12-H09 | 1.26 | 1.30 | 3.88E-04 | 2.54E-04 |
| A12-H51 | 0.59 | 0.68 | 2.72E-05 | 1.12E-03 |

TABLE 9

Results of affinity maturation by 11Hg CDR-3 random mutations

| | scFv | | | |
|---|---|---|---|---|
| | ELISA (OD450) | | SPR $K_{off}$ values | |
| Clone Name | (pH 6.0) | (pH 7.4) | (pH 6.0) | (pH 7.4) |
| B04 | 0.32 | 0.15 | 3.41E-04 | 3.10E-04 |
| 11Hg (parent) | 0.24 | 0.42 | 4.34E-04 | 4.33E-04 |
| H11-A02 | 0.29 | 0.36 | 2.29E-04 | 4.18E-04 |
| H11-A03 | 0.38 | 0.68 | 2.44E-04 | 4.17E-04 |
| H11-A05 | 0.27 | 0.27 | 3.45E-04 | 3.38E-04 |
| H11-A07 | 0.22 | 0.70 | 2.17E-04 | 5.52E-04 |
| H11-B03 | 0.28 | 0.39 | 4.30E-04 | 7.81E-04 |
| H11-B04 | 0.16 | 0.09 | 5.43E-04 | 5.46E-04 |
| H11-B07 | 0.21 | 0.45 | 6.99E-04 | 6.04E-04 |
| H11-B08 | 0.19 | 0.12 | 1.15E-03 | 6.57E-04 |
| H11-D07 | 0.33 | 0.47 | 1.60E-04 | 1.15E-03 |
| H11-D08 | 0.20 | 0.62 | 3.81E-04 | 5.97E-04 |
| H11-E03 | 0.17 | 0.07 | 3.65E-04 | 5.13E-04 |
| H11-E05 | 0.23 | 0.20 | 5.46E-04 | 7.02E-04 |
| H11-E08 | 0.20 | 0.80 | 2.59E-04 | 5.15E-04 |
| H11-F04 | 0.18 | 0.21 | 9.02E-04 | 5.93E-04 |
| H11-H05 | 0.15 | 0.04 | 3.01E-04 | 4.52E-04 |
| H11-H06 | 0.15 | 0.09 | 5.25E-04 | 5.45E-04 |
| H12-A01 | 0.26 | 0.36 | 4.57E-04 | 4.23E-04 |
| H12-A09 | 0.21 | 0.54 | 1.50E-04 | 6.34E-04 |
| H12-A11 | 0.22 | 0.24 | 3.72E-04 | 5.54E-04 |
| H12-A12 | 0.14 | 0.11 | 2.62E-04 | 5.27E-04 |
| H12-B01 | 0.22 | 0.12 | 3.24E-04 | 4.46E-04 |
| H12-B09 | 0.26 | 0.49 | 2.96E-04 | 3.81E-04 |
| H12-B11 | 0.15 | 0.58 | 3.63E-04 | 4.54E-04 |
| H12-C09 | 0.16 | 0.16 | 2.83E-04 | 4.35E-04 |
| H12-C10 | ND | ND | ND | 3.31E-03 |
| H12-D12 | 0.17 | 0.12 | 5.90E-04 | 6.79E-04 |
| H12-E12 | ND | ND | 2.57E-04 | 3.72E-04 |
| H12-F09 | 0.40 | 0.58 | 1.40E-03 | 4.18E-04 |
| H12-F10 | ND | ND | 2.39E-04 | 4.48E-04 |

As shown in Tables 8 and 9 above, among the randomly mutated CDR-3 clones, eight clones (A11-007, A11-G06, A12-009, A12-D55, A12-E01, A12-E04, A12-F02 and A12-H04) were determined to have increased affinity compared to the templates, as a result of the ELISA and SPR tests. Thus, these eight clones were selected as templates for use in secondary affinity maturation. In addition, 11Hg-derived clones showed no increase in affinity compared to the templates, and any of these clones was not selected as a template for use in secondary affinity maturation.

Example 13-2: Secondary Affinity Maturation

From the scFv format library for secondary affinity maturation of the 1Ag template antibodies and 11Hg selected in Example 13-1 using the isolated and purified shFcRn (soluble human FcRn) as antigen, antibodies that bind to the antigen in a pH-independent manner in the pH range from 6.0 to 7.4 were selected and sequenced. Then, antigen-specific antibodies were isolated and purified, and the binding affinities of the purified antibodies were measured by SPR, thereby selecting 56 optimized complete human antibodies. A detailed method for affinity maturation is as follows.

(1) Construction of Library

In the case of 1Ag, a sub-library was constructed by randomizing the CDR-1 and CDR-2 of eight clones (A11-007, A11-G06, A12-009, A12-D55, A12-E01, A12-E04, A12-F02, and A12-H04) having improved affinity as a result of randomization of CDR-3. In the case of 11Hg, a sub-library was constructed by randomizing three positions of CDR-H3 and CDR-1/2 while maintaining CDR-L3 at the template sequence.

Amino acids appearing at positions of each of CDR-1 and CDR-2 of the human antibody as a result of sequencing were analyzed, and based on the results of the analysis, CDR-1 and CDR-2 were randomized so as to have a diversity similar to the original diversity. Oligonucleotides for the randomized sites were synthesized, and randomized scFv genes were obtained by PCR and ligated into pComb3X vectors using the restriction enzyme Sfi-I. Next, the vectors were transformed into an *E. coli* ER2537 strain, thereby obtaining $1.0 \times 10^7$ transformants. 83 colonies were sequenced, and as a result, it was found that 29 colonies had the normal scFv sequences and that the diversities of the resulting sub-library were $3.5 \times 10^6$ for 1Ag and $1.3 \times 10^7$ for 11Hg.

(2) Panning

In a panning strategy, in order to select clones that strongly bind to antigen at a pH of 6.0 (low KD) and are not easily detached at a pH of 7.4 (low $K_{off}$), biotinylated hFcRn (biotin-hFcRn) and hFcRn-expressing HEK293 cells (293-hFcRn) were used. When HEK293-hFcRn cells were used, these cells were converted to single cells using trypsin-EDTA and fixed with 3.7% formaldehyde, followed by panning.

(2-a) Panning of 1Ag Sub-Library

Panning was performed according to the method shown in Table 10 below. In Strategy-1 and Strategy-3, only biotin-shFcRn (100 ng) was used, and in Strategy-4 and Strategy-5, biotin-hFcRn was used in rounds 1 and 2, 293-hFcRn cells ($1.0 \times 10^6$ cells) were used in rounds 3 and 4. In Strategy-3, Strategy-4 and Strategy-5, soluble parental IgG was used as a competitor in binding. Binding was performed using $1.0 \times 10^{12}$ phages at a pH of 6.0 at room temperature for 2 hours after quantification using a phage titration kit. To increase the $K_{off}$ rate, the washing time was increased and shFcRn was added. After binding, the cells were washed 10 times with PBS-T to remove unbound phages and cultured with rotation in shFcRn-containing PBS-T at 37° C. for 20 hours. Next, the cells were washed 10 times with PBS-T and treated with 100 mM TEA (triethylamine) to elute phages. The phages obtained from the sub-library were quantified and analyzed by ELISA, and as a result, it was concluded that the ELISA signal was not lower than that of the template. Thus, parental IgG was used as a competitor in binding from round 1.

TABLE 10

Panning strategy of 1Ag sub-library

| Strategy | Step | Factor | 1st Round | 2nd Round | 3rd Round | 4th Round |
|---|---|---|---|---|---|---|
| Strategy-1 | Binding | Antigen | Biotin-hFcRn | Biotin-hFcRn | Biotin-hFcRn | Biotin-hFcRn |
| | | Competitor | — | — | — | — |
| | | pH | 6.0 | 6.0 | 6.0 | 6.0 |
| | Wash | Competitor | shFcRn | shFcRn | shFcRn | shFcRn |
| | | pH | 7.4 | 7.4 | 7.4 | 7.4 |
| Strategy-3 | Binding | Antigen | Biotin-hFcRn | Biotin-hFcRn | Biotin-hFcRn | Biotin-hFcRn |
| | | Competitor | IgG | IgG | IgG | IgG |
| | | pH | 6.0 | 6.0 | 6.0 | 6.0 |
| | Wash | Competitor | shFcRn | shFcRn | shFcRn | shFcRn |
| | | pH | 7.4 | 7.4 | 7.4 | 7.4 |
| Strategy-4 | Binding | Antigen | Biotin-hFcRn | Biotin-hFcRn | 293-hFcRn | 293-hFcRn |
| | | Competitor | IgG | IgG | IgG | IgG |
| | | pH | 6.0 | 6.0 | 6.0 | 6.0 |
| | Wash | Competitor | shFcRn | shFcRn | shFcRn | shFcRn |
| | | pH | 7.4 | 7.4 | 7.4 | 7.4 |
| Strategy-5 | Binding | Antigen | Biotin-hFcRn | Biotin-hFcRn | 293-hFcRn | 293-hFcRn |
| | | Competitor | IgG | IgG | — | — |
| | | pH | 6.0 | 6.0 | 6.0 | 6.0 |
| | Wash | Competitor | shFcRn | shFcRn | shFcRn | shFcRn |
| | | pH | 7.4 | 7.4 | 7.4 | 7.4 |

The obtained output phages were quantified using a phage titration kit, and then ELISA was performed using the same amount of phages. Among output colonies from round 4 of Strategy-1, Strategy-3 and Strategy-4, 95 colonies were randomly selected, and the activities thereof were analyzed by ELISA, and as a result, it was found that 90% of the colonies in all the strategies had binding activity.

(2-b) Panning of 11Hg Sub-Library

Panning was performed according to the method shown in Table 11 below. In Strategy-1 and Strategy-3, only biotin-shFcRn (100 ng) was used, and in Strategy-4 and Strategy-5, biotin-hFcRn was used in rounds 1 and 2, 293-hFcRn cells ($1.0 \times 10^6$ cells) were used in rounds 3 and 4. In Strategy-3, Strategy-4 and Strategy-5, soluble parental IgG was used as a competitor in binding. Binding was performed using $1.0 \times 10^{12}$ phages at a pH of 6.0 at room temperature for 2 hours after quantification using a phage titration kit. To increase the $K_{off}$ rate, the washing time was increased and shFcRn was added. After binding, the cells were washed 10 times with PBS-T to remove unbound phages and cultured with rotation in shFcRn-containing PBS-T at 37° C. for 20 hours. Next, the cells were washed 10 times with PBS-T and treated with 100 mM TEA (triethylamine) to elute phages. The phages obtained from the sub-library were quantified and analyzed by ELISA, and as a result, it was shown that the ELISA signal was not low. Thus, parental IgG was not used as a competitor in round 1 of Strategy-3, Strategy-4 and Strategy-5 and was used from round 2.

TABLE 11

Panning strategy of 11Hg sub-library

| Strategy | Step | Factor | 1st Round | 2nd Round | 3rd Round | 4th Round |
|---|---|---|---|---|---|---|
| Strategy-1 | Binding | Antigen | Biotin-hFcRn | Biotin-hFcRn | Biotin-hFcRn | Biotin-hFcRn |
| | | Competitor | — | — | — | — |
| | | pH | 6.0 | 6.0 | 6.0 | 6.0 |
| | Wash | Competitor | shFcRn | shFcRn | shFcRn | shFcRn |
| | | pH | 7.4 | 7.4 | 7.4 | 7.4 |
| Strategy-3 | Binding | Antigen | Biotin-hFcRn | Biotin-hFcRn | Biotin-hFcRn | Biotin-hFcRn |
| | | Competitor | — | IgG | IgG | IgG |
| | | pH | 6.0 | 6.0 | 6.0 | 6.0 |
| | Wash | Competitor | shFcRn | shFcRn | shFcRn | shFcRn |
| | | pH | 7.4 | 7.4 | 7.4 | 7.4 |
| Strategy-4 | Binding | Antigen | Biotin-hFcRn | Biotin-hFcRn | 293-hFcRn | 293-hFcRn |
| | | Competitor | — | IgG | IgG | IgG |
| | | pH | 6.0 | 6.0 | 6.0 | 6.0 |
| | Wash | Competitor | shFcRn | shFcRn | shFcRn | shFcRn |
| | | pH | 7.4 | 7.4 | 7.4 | 7.4 |

TABLE 11-continued

Panning strategy of 11Hg sub-library

| Strategy | Step | Factor | 1st Round | 2nd Round | 3rd Round | 4th Round |
|---|---|---|---|---|---|---|
| Strategy-5 | Binding | Antigen | Biotin-hFcRn | Biotin-hFcRn | 293-hFcRn | 293-hFcRn |
| | | Competitor | — | IgG | — | — |
| | | pH | 6.0 | 6.0 | 6.0 | 6.0 |
| | Wash | Competitor | shFcRn | shFcRn | shFcRn | shFcRn |
| | | pH | 7.4 | 7.4 | 7.4 | 7.4 |

The obtained output phages were quantified using a phage titration kit, and then ELISA was performed using the same amount of phages. In strategy-1 and strategy-3 performed using biotin-hFcRn as antigen, the ELISA-positive ratio was shown to be about 80%, and thus colonies resulting from panning were subjected to ELISA screening.

(3) ELISA Screening scFv in the periplasmic extract was quantified by an ELISA method that recognizes HA, and ELISA was performed using the same amount of scFv. Next, clones having an absorbance value higher than that of the template scFv were selected.

(3-a) Screening of 1Ag Clones 280 colonies from each of Strategy-1 and Strategy-3 were cultured in 0.15 mL of SB medium and induced with 1 mM IPTG, after which the cells were treated with 0.1 mL of TES to obtain a periplasmic extract. scFv in the periplasmic extract was quantified by ELISA, and scFv was diluted in PBS-T (pH 7.4 or pH 6.0) to final concentrations of 1000 ng/mL and 3000 ng/mL, and shFcRn was coated at a concentration of 1 μg/mL. In this way, ELISA was performed.

As a result of ELISA, colonies having an absorbance higher than that of the template scFv at a pH of 7.4 and a pH of 6.0 were selected. The clones having an absorbance higher than that of the template at a pH of 6.0 mostly showed an absorbance higher than that of the template at a pH of 7.4. Based on the ELISA values for a total of 456 colonies, 200 higher-ranked colonies having an ELISA signal higher than that of the template at a pH of 7.4 were sequenced, and as a result, 77 unique clones were selected. The 77 selected clones had the same H-CDR3 sequence (A11-007), and L-CDR3 from the template clones had various sequences.

(3-b) Screening of 11Hg-Derived Clones

Screening of 11Hg-derived clones was performed in the same manner as described above with respect to ELISA screening of 1Ag-derived clones. As a result of ELISA screening, the number of colonies having an absorbance higher than that of the template scFv at a pH of 7.4 was 64/456 (14.0%), and the number of colonies having an absorbance higher than that of the template scFv at a pH of 6.0 was 32 (7.0%). Based on the ELISA values for a total of 456 colonies, the colonies were ranked based on folds of the ELISA signal compared to the template at a pH of 7.4, and 50 higher-ranked colonies were sequenced. As a result, 10 unique sequence clones were selected.

(4) Purification of Improved 1Ag- and 11Hg-Derived Candidate Antibodies (4-a) Purification of 1Ag-Derived Clones Among 77 unique clones, scFv for 48 clones excluding 29 clones having a putative N-glycosylation site (derived from the template) was purified from periplasmic extracts. Specifically, cells were cultured in 100-400 mL of SB medium and then induced overnight with 1 mM IPTG, after the cells treated with treated with a 1:5 volume of TES buffer to obtain periplasmic extracts. scFv was purified from the periplasmic extracts using Ni-NTA resin, and then concentrated with PBS, and the buffer was replaced. The scFv was quantified by the Bradford assay, and 1 g of the scFv was separated by SDS-PAGE and stained with Coomassie blue, thereby determining the concentration and purity of the scFv.

(4-b) Purification of 11Hg-Derived Clones scFvs for 7 clones among 10 unique clones and for 1Ag, 11Hg and H11-B04 were purified from periplasmic extracts in the same manner as described above with respect to purification of 1Ag.

(5) Measurement of Binding Affinity by ELISA and SPR

Binding affinity was measured according to the above-described Example, and the results of the measurement are shown in Tables 12 and 13.

TABLE 12

Results of affinity maturation by 1Ag CDR-1 and CDR-2 mutations

| | Partially purified scFv | | | |
|---|---|---|---|---|
| | ELISA (fold) | | $K_{off}$ values (fold) | |
| | | | pH 6.0 Two state | pH 7.4 Two state |
| Clone name | pH 6.0 | pH 7.4 | kd1 | kd1 |
| B04 | 1.7 | 1.5 | 10.7 | 33.7 |
| 1Ag | 1.0 | 1.0 | 1.0 | 1.0 |
| A23-3H04 | 25.4 | 25.8 | 27.3 | 11.6 |
| A21-4C03 | 21.8 | 18.8 | 41.6 | 14.6 |
| A24-1G10 | 18.0 | 26.2 | 37.7 | 16.7 |
| A24-1F07 | 17.5 | 24.7 | 29.2 | 16.5 |
| A21-4B10 | 17.4 | 25.9 | 36.3 | 19.9 |
| A21-4G04 | 17.1 | 24.0 | 11.2 | 5.7 |
| A23-3H05 | 15.0 | 20.1 | 20.9 | 10.0 |
| A21-3A09 | 14.2 | 25.2 | 18.8 | 10.8 |
| A21-4B06 | 13.7 | 17.4 | 7.2 | 3.8 |
| A24-1B05 | 12.8 | 20.8 | 26.2 | 11.6 |
| A23-3A08 | 11.1 | 24.0 | 32.6 | 18.3 |
| A21-4C08 | 10.5 | 19.6 | 12.1 | 6.9 |
| A23-4D09 | 10.4 | 15.5 | 24.1 | 10.5 |
| A23-3D03 | 10.1 | 19.8 | 21.3 | 9.3 |
| A21-4B03 | 9.1 | 16.1 | 11.2 | 6.7 |
| A21-3D10 | 8.5 | 18.3 | 19.5 | 13.1 |
| A21-3A10 | 7.9 | 25.6 | 23.3 | 14.5 |
| A21-4H04 | 7.2 | 23.8 | 11.8 | 8.1 |
| A21-4F11 | 5.7 | 19.6 | 13.1 | 5.9 |
| A23-3G05 | 5.5 | 25.0 | 53.2 | 22.7 |
| A23-3A10 | 5.0 | 15.9 | 9.3 | 5.4 |
| A25-1H04 | 5.0 | 20.4 | 47.0 | 2.6 |
| A23-3B06 | 4.8 | 22.8 | 41.8 | 10.5 |
| A23-4A09 | 4.7 | 17.1 | 28.4 | 7.2 |
| A25-1D09 | 4.5 | 26.6 | 42.1 | 43.0 |
| A21-4E10 | 4.0 | 24.3 | 21.9 | 12.0 |
| A23-3C04 | 3.8 | 20.3 | 24.8 | 7.7 |
| A23-3G06 | 3.1 | 6.0 | 12.9 | 4.6 |

TABLE 12-continued

Results of affinity maturation by 1Ag CDR-1 and CDR-2 mutations

| | Partially purified scFv | | | |
|---|---|---|---|---|
| | ELISA (fold) | | $K_{off}$ values (fold) | |
| | | | pH 6.0 Two state | pH 7.4 Two state |
| Clone name | pH 6.0 | pH 7.4 | kd1 | kd1 |
| A24-1E09 | 3.1 | 14.8 | 11.2 | 5.9 |
| A23-3F03 | 3.1 | 20.7 | 17.9 | 11.2 |
| A21-4F07 | 2.9 | 16.2 | 8.7 | 4.1 |
| A24-1A03 | 2.8 | 11.5 | 5.9 | 3.8 |
| A24-1H11 | 2.7 | 21.7 | 19.5 | 10.5 |
| A21-3D09 | 2.5 | 16.9 | 11.8 | 7.2 |
| A24-1D10 | 2.3 | 18.6 | 32.6 | 8.9 |
| A21-4B04 | 2.3 | 9.3 | 24.5 | 8.0 |
| A23-4C12 | 2.2 | 23.8 | 16.7 | 9.5 |
| A21-4G06 | 2.1 | 17.3 | 9.4 | 5.4 |
| A23-3E04 | 2.0 | 12.9 | 10.4 | 5.4 |
| A24-1C09 | 2.0 | 13.1 | 5.1 | 2.8 |
| A24-1C04 | 2.0 | 8.9 | 3.4 | 2.9 |
| A25-1H10 | 1.9 | 15.1 | 11.9 | 6.5 |
| A21-4D08 | 1.6 | 5.5 | 9.0 | 4.8 |
| A24-1D08 | 1.4 | 9.4 | 5.9 | 5.0 |
| A24-1A08 | 1.4 | 4.1 | 5.1 | 2.3 |
| A21-4A07 | 1.3 | 9.1 | 7.0 | 3.9 |
| A24-1B09 | 1.2 | 9.6 | 5.8 | 3.7 |
| A24-1E07 | 1.2 | 3.3 | 4.8 | 2.2 |

TABLE 13

Results of affinity maturation by 11Hg CDR-1 and CDR-2 mutations

| | Partially purified scFv | | | |
|---|---|---|---|---|
| | ELISA (fold) | | $K_{off}$ values (fold) | |
| | | | pH 6.0 Two state | pH 7.4 Two state |
| Clone name | pH 6.0 | pH 7.4 | kd1 | kd1 |
| H11-B04 | 1.3 | 1.6 | 1.372 | 9.611 |
| 11Hg | 1.0 | 1.0 | 1.000 | 1.000 |
| H21-3A07 | 1.0 | 4.2 | 1.075 | 1.499 |
| H21-4D11 | 0.7 | 3.6 | 0.001 | 0.000 |
| H21-3C11 | 1.9 | 10.9 | 1.363 | 1.468 |
| H21-3A09 | 0.7 | 0.2 | 0.174 | 0.002 |
| H21-4H04 | 0.9 | 5.7 | 0.893 | 1.233 |
| H23-3D08 | 3.7 | 7.0 | 2.891 | 1.893 |
| H21-4D09 | ND | ND | NA | NA |
| H24-1D11 | 1.0 | 1.0 | NA | NA |

The amino acid sequences of the variable regions of the antibodies, selected by the above-described primary and secondary affinity maturations and having increased affinity and specificity for FcRn, and nucleotide sequences encoding the amino acid sequences, are shown in Tables 14 and 15 below. In addition, the CDR sequences of the variable regions are shown in Tables 16 and 17 below.

TABLE 14

Amino acid sequences of heavy-chain and light-chain variable regions of selected antibodies

| Antibody name | SEQ ID NO: | Heavy-chain variable regions Amino acid sequences | SEQ ID NO: | Light-chain variable regions Amino acid Sequences |
|---|---|---|---|---|
| A11-007 | 18 | EVQLVESGGGLVQPGRSLRLSCAASGFTFDEYGMHWVRQAPGKGLEWVSGVSWNSGSIAYADSVRGRFTISRDNAKNSLYLQMNSLRAEDTALYYCAKGRYSDVWGQGTTVTVSS | 162 | QSALTQPASVSGSPGQSITISCTGSSSDVGGYNYVSWYQQHPGKAPKLMIYDVTKRPSGVSNRFSGSKSGNTASLTISGLQAEDEADYYASYSSNTFYVFGTGTKVTVLG |
| A11-G06 | 20 | EVQLVESGGGLVQPGRSLRLSCAASGFTFDEYGMHWVRQAPGKGLEWVSGVSWNSGSIAYADSVRGRFTISRDNAKNSLYLQMNSLRAEDTALYYCAKGRLMDVWGQGTTVTVSS | 164 | QSALTQPASVSGSPGQSITISCTGSSSDVGGYNYVSWYQQHPGKAPKLMIYDVTKRPSGVSNRFSGSKSGNTASLTISGLQAEDEADYYGSYNNNTFYVFGTGTKVTVLG |
| A12-C09 | 22 | EVQLVESGGGLVQPGRSLRLSCAASGFTFDEYGMHWVRQAPGKGLEWVSGVSWNSGSIAYADSVRGRFTISRDNAKNSLYLQMNSLRAEDTALYYCAKGRTMDVWGQGTTVTVSS | 166 | QSALTQPASVSGSPGQSITISCTGSSSDVGGYNYVSWYQQHPGKAPKLMIYDVTKRPSGVSNRFSGSKSGNTASLTISGLQAEDEADYYGSYSSNTFYVFGTGTKVTVLG |
| A12-E05 | 24 | EVQLVESGGGLVQPGRSLRLSCAASGFTFDEYGMHWVRQAPGKGLEWVSGVSWNSGSIAYADSVRGRFTISRDNAKNSLYLQMNSLRAEDTALYYCAKGRILDVWGQGTTVTVSS | 168 | QSALTQPASVSGSPGQSITISCTGSSSDVGGYNYVSWYQQHPGKAPKLMIYDVTKRPSGVSNRFSGSKSGNTASLTISGLQAEDEADYYGSYNNSTFYVFGTGTKVTVLG |

TABLE 14-continued

Amino acid sequences of heavy-chain and light-chain variable regions of selected antibodies

| Antibody name | Heavy-chain variable regions SEQ ID NO: | Amino acid sequences | Light-chain variable regions SEQ ID NO: | Amino acid Sequences |
|---|---|---|---|---|
| A12-E01 | 26 | EVQLVESGGGLVQPGRSLRLSCAASGFTFDEYGMHWVRQAPGKGLEWVSGVSWNSGSIAYADSVRGRFTISRDNAKNSLYLQMNSLRAEDTALYYCAKSRSMDVWGQGTTVTVSS | 170 | QSALTQPASVSGSPGQSITISCTGSSSDVGGYNYVSWYQQHPGKAPKLMIYDVTKRPSGVSNRFSGSKSGNTASLTISGLQAEDEADYYGSYSNNNFYVFGTGTKVTVLG |
| A12-E04 | 28 | EVQLVESGGGLVQPGRSLRLSCAASGFTFDEYGMHWVRQAPGKGLEWVSGVSWNSGSIAYADSVRGRFTISRDNAKNSLYLQMNSLRAEDTALYYCAKGRLFDVWGQGTTVTVSS | 172 | QSALTQPASVSGSPGQSITISCTGSSSDVGGYNYVSWYQQHPGKAPKLMIYDVTKRPSGVSNRFSGSKSGNTASLTISGLQAEDEADYYGSYSNSNFYVFGTGTKVTVLG |
| A12-F02 | 30 | EVQLVESGGGLVQPGRSLRLSCAASGFTFDEYGMHWVRQAPGKGLEWVSGVSWNSGSIAYADSVRGRFTISRDNAKNSLYLQMNSLRAEDTALYYCAKGRYLDVWGQGTTVTVSS | 174 | QSALTQPASVSGSPGQSITISCTGSSSDVGGYNYVSWYQQHPGKAPKLMIYDVTKRPSGVSNRFSGSKSGNTASLTISGLQAEDEADYYGSYDSNTFYVFGTGTKVTVLG |
| A12-H04 | 32 | EVQLVESGGGLVQPGRSLRLSCAASGFTFDEYGMHWVRQAPGKGLEWVSGVSWNSGSIAYADSVRGRFTISRDNAKNSLYLQMNSLRAEDTALYYCAKGRLLDVWGQGTTVTVSS | 176 | QSALTQPASVSGSPGQSITISCTGSSSDVGGYNYVSWYQQHPGKAPKLMIYDVTKRPSGVSNRFSGSKSGNTASLTISGLQAEDEADYYGAYSNTNFYVFGTGTKVTVLG |
| A23-3H04 | 34 | EVQLVESGGGLVQPGRSLRLSCAASGFTFDTYGMNWVRQAPGKGLEWVSGISYNSGTTAYADSVRGRFTISRDNAKNSLYLQMNSLRAEDTALYYCARGRYSDVWGQGTTVTVSS | 178 | QSALTQPASVSGSPGQSITISCGGSSSDVGGYNYVSWYQQHPGKAPKLMIYDVNKRPSGVSNRFSGSKSGNTASLTISGLQAEDEADYYCGSYDSNTFYVFGTGTKVTVLG |
| A21-4C03 | 36 | EVQLVESGGGLVQPGRSLRLSCAASGFTFDAYGMNWVRQAPGKGLEWVSGISYNSGTIAYADSVKGRFTISRDNAKNSLYLQMNSLRAEDTALYYCARGRYSDVWGQGTTVTVSS | 180 | QSALTQPASVSGSPGQSITISCTGSSSDIGGYNYVSWYQQHPGKAPKLMIYDVSDRPSGVSNRFSGSKSGNTASLTISGLQAEDEADYYCGSYSSNTFYVFGTGTKVTVLG |
| A24-1G10 | 38 | EVQLVESGGGLVQPGRSLRLSCAASGFTFDAYGMHWVRQAPGKGLEWVSGISYNSGTKAYADSVKGRFTISRDNAKNSLYLQMNSLRAEDTALYYCARGRYSDVWGQGTTVTVSS | 182 | QSALTQPASVSGSPGQSITISCGGSSSNIGGYNYVSWYQQHPGKAPKLMIYDVNKRPSGVSNRFSGSKSGNTASLTISGLQAEDEADYYCASYSNSNFYVFGTGTKVTVLG |
| A24-1F07 | 40 | EVQLVESGGGLVQPGRSLRLSCAASGFTFDAYGMHWVRQAPGKGLEWVSGVSYNSGTTAYADSVRGRFTISRDNAKNSLYLQMNSLRAEDTALYYCARGRYSDVWGQGTTVTVSS | 184 | QSALTQPASVSGSPGQSITISCSGSSSNVGSYNYVSWYQQHPGKAPKLMIYDVTKRPSGVSNRFSGSKSGNTASLTISGLQAEDEADYYCGSYSNSNFYVFGTGTKVTVLG |
| A21-4B10 | 42 | EVQLVESGGGLVQPGRSLRLSCAASGFTFDEYGMHWVRQAPGKGLEWVSGISYNSGNKAYADSVRGRFTISRDNAKNSLYLQMNSLRAEDTALYYCARGRYSDVWGQGTTVTVSS | 186 | QSALTQPASVSGSPGQSITISCSGSSSNIGGYNYVSWYQQHPGKAPKLMIYDVSKRPSGVSNRFSGSKSGNTASLTISGLQAEDEADYYCGSYDSNTFYVFGTGTKVTVLG |

TABLE 14-continued

Amino acid sequences of heavy-chain and light-chain variable regions of selected antibodies

| Antibody name | Heavy-chain variable regions SEQ ID NO: | Amino acid sequences | Light-chain variable regions SEQ ID NO: | Amino acid Sequences |
|---|---|---|---|---|
| A21-4G04 | 44 | EVQLVESGGGLVQPGRSLRLSCAASGFTFDSYGMHWVRQAPGKGLEWVSGISYNGGNTAYADSVRGRFTISRDNAKNSLYLQMNSLRAEDTALYYCARGRYSDVWGQGTTVTVSS | 188 | QSALTQPASVSGSPGQSITISCSGSSSNIGGYNYVSWYQQHPGKAPKLMIYDVNERPSGVSNRFSGSKSGNTASLTISGLQAEDEADYYCGSYSNNNFYVFGTGTKVTVLG |
| A23-3H05 | 46 | EVQLVESGGGLVQPGRSLRLSCAASGFTFDAYGMNWVRQAPGKGLEWVSGISYNSGTIAYADSVKGRFTISRDNAKNSLYLQMNSLRAEDTALYYCARGRYSDVWGQGTTVTVSS | 190 | QSALTQPASVSGSPGQSITISCGGSSSNVGGYNYVSWYQQHPGKAPKLMIYDVSNRPSGVSNRFSGSKSGNTASLTISGLQAEDEADYYCGSYSNSNFYVFGTGTKVTVLG |
| A21-3A09 | 48 | EVQLVESGGGLVQPGRSLRLSCAASGFTFDNYGMNWVRQAPGKGLEWVSGISYNSGTKAYADSVKGRFTISRDNAKNSLYLQMNSLRAEDTALYYCARGRYSDVWGQGTTVTVSS | 192 | QSALTQPASVSGSPGQSITISCSGSSSDIGGYNYVSWYQQHPGKAPKLMIYDVNKRPSGVSNRFSGSKSGNTASLTISGLQAEDEADYYCASYSSNTFYVFGTGTKVTVLG |
| A21-4B06 | 50 | EVQLVESGGGLVQPGRSLRLSCAASGFTFDSYGMHWVRQAPGKGLEWVSGISYNGGSKAYADSVRGRFTISRDNAKNSLYLQMNSLRAEDTALYYCARGRYSDVWGQGTTVTVSS | 194 | QSALTQPASVSGSPGQSITISCSGSSSNIGSYNYVSWYQQHPGKAPKLMIYDVTDRPSGVSNRFSGSKSGNTASLTISGLQAEDEADYYCGSYSSNTFYVFGTGTKVTVLG |
| A24-1B05 | 52 | EVQLVESGGGLVQPGRSLRLSCAASGFTFDKYGMNWVRQAPGKGLEWVSGISYNSGNTAYADSVRGRFTISRDNAKNSLYLQMNSLRAEDTALYYCARGRYSDVWGQGTTVTVSS | 196 | QSALTQPASVSGSPGQSITISCAGSSSDIGGYNYVSWYQQHPGKAPKLMIYDVSKRPSGVSNRFSGSKSGNTASLTISGLQAEDEADYYCGSYDSNTFYVFGTGTKVTVLG |
| A23-3A08 | 54 | EVQLVESGGGLVQPGRSLRLSCAASGFTFDAYGMHWVRQAPGKGLEWVSGISYNSGTTAYADSVKGRFTISRDNAKNSLYLQMNSLRAEDTALYYCARGRYSDVWGQGTTVTVSS | 198 | QSALTQPASVSGSPGQSITISCAGSSSNIGGYNYVSWYQQHPGKAPKLMIYDVSKRPSGVSNRFSGSKSGNTASLTISGLQAEDEADYYCGSYSNSNFYVFGTGTKVTVLG |
| A21-4C08 | 56 | EVQLVESGGGLVQPGRSLRLSCAASGFTFDTYGMHWVRQAPGKGLEWVSGISYNAGNKAYADSVRGRFTISRDNAKNSLYLQMNSLRAEDTALYYCARGRYSDVWGQGTTVTVSS | 200 | QSALTQPASVSGSPGQSITISCSGSSSNVGSYNYVSWYQQHPGKAPKLMIYDVNNRPSGVSNRFSGSKSGNTASLTISGLQAEDEADYYCGSYSSNTFYVFGTGTKVTVLG |
| A23-4D09 | 58 | EVQLVESGGGLVQPGRSLRLSCAASGFTFDAYGMHWVRQAPGKGLEWVSGVSYDAGNTAYADSVRGRFTISRDNAKNSLYLQMNSLRAEDTALYYCARGRYSDVWGQGTTVTVSS | 202 | QSALTQPASVSGSPGQSITISCSGSSSNIGSYNYVSWYQQHPGKAPKLMIYDVTDRPSGVSNRFSGSKSGNTASLTISGLQAEDEADYYCGSYSSNTFYVFGTGTKVTVLG |

TABLE 14-continued

Amino acid sequences of heavy-chain and light-chain variable regions of selected antibodies

| Antibody name | Heavy-chain variable regions SEQ ID NO: | Amino acid sequences | Light-chain variable regions SEQ ID NO: | Amino acid Sequences |
|---|---|---|---|---|
| A23-3D03 | 60 | EVQLVESGGGLVQPGRSLRLSCAASGFTFDAYGMNWVRQAPGKGLEWVSGISYNAGSTAYADSVRGRFTISRDNAKNSLYLQMNSLRAEDTALYYCARGRYSDVWGQGTTVTVSS | 204 | QSALTQPASVSGSPGQSITISCTGSSSDVGGYNYVSWYQQHPGKAPKLMIYDVTNRPSGVSNRFSGSKSGNTASLTISGLQAEDEADYYCGSYDSNTFYVFGTGTKVTVLG |
| A21-1B03 | 62 | EVQLVESGGGLVQPGRSLRLSCAASGFTFDAYGMNWVRQAPGKGLEWVSGISYNAGNKAYADSVRGRFTISRDNAKNSLYLQMNSLRAEDTALYYCARGRYSDVWGQGTTVTVSS | 206 | QSALTQPASVSGSPGQSITISCSGSSSNIGSYNYVSWYQQHPGKAPKLMIYDVNKRPSGVSNRFSGSKSGNTASLTISGLQAEDEADYYCASYSSNTFYVFGTGTKVTVLG |
| A21-3D10 | 64 | EVQLVESGGGLVQPGRSLRLSCAASGFTFDNYGMHWVRQAPGKGLEWVSGISYDAGTTAYADSVKGRFTISRDNAKNSLYLQMNSLRAEDTALYYCARGRYSDVWGQGTTVTVSS | 208 | QSALTQPASVSGSPGQSITISCGGTSSNIGSYNYVSWYQQHPGKAPKLMIYDVTNRPSGVSNRFSGSKSGNTASLTISGLQAEDEADYYCGSYSNTNFYVFGTGTKVTVLG |
| A21-3A10 | 66 | EVQLVESGGGLVQPGRSLRLSCAASGFTFDAYGMHWVRQAPGKGLEWVSGISYNAGNKAYADSVRGRFTISRDNAKNSLYLQMNSLRAEDTALYYCARGRYSDVWGQGTTVTVSS | 210 | QSALTQPASVSGSPGQSITISCAGSSSNIGGYNYVSWYQQHPGKAPKLMIYDVSKRPSGVSNRFSGSKSGNTASLTISGLQAEDEADYYCGSYSNSNFYVFGTGTKVTVLG |
| A21-4H04 | 68 | EVQLVESGGGLVQPGRSLRLSCAASGFTFDSYGMHWVRQAPGKGLEWVSGISYNSGNKAYADSVKGRFTISRDNAKNSLYLQMNSLRAEDTALYYCARGRYSDVWGQGTTVTVSS | 212 | QSALTQPASVSGSPGQSITISCSGTSSDIGGYNYVSWYQQHPGKAPKLMIYDVSKRPSGVSNRFSGSKSGNTASLTISGLQAEDEADYYCGSYSNNNFYVFGTGTKVTVLG |
| A21-4F11 | 70 | EVQLVESGGGLVQPGRSLRLSCAASGFTFDAYGMNWVRQAPGKGLEWVSGISYNGGTKAYADSVRGRFTISRDNAKNSLYLQMNSLRAEDTALYYCARGRYSDVWGQGTTVTVSS | 214 | QSALTQPASVSGSPGQSITISCGGTSSNIGGYNYVSWYQQHPGKAPKLMIYDVNDRPSGVSNRFSGSKSGNTASLTISGLQAEDEADYYCASYSSNTFYVFGTGTKVTVLG |
| A23-3G05 | 72 | EVQLVESGGGLVQPGRSLRLSCAASGFTFDTYGMHWVRQAPGKGLEWVSGISYNSGTIAYADSVRGRFTISRDNAKNSLYLQMNSLRAEDTALYYCARGRYSDVWGQGTTVTVSS | 216 | QSALTQPASVSGSPGQSITISCAGSSSNIGSYNYVSWYQQHPGKAPKLMIYDVSNRPSGVSNRFSGSKSGNTASLTISGLQAEDEADYYCGSYDSNTFYVFGTGTKVTVLG |
| A23-3A10 | 74 | EVQLVESGGGLVQPGRSLRLSCAASGFTFDKYGMHWVRQAPGKGLEWVSGISYNAGSKAYADSVKGRFTISRDNAKNSLYLQMNSLRAEDTALYYCARGRYSDVWGQGTTVTVSS | 218 | QSALTQPASVSGSPGQSITISCAGSSSNIGGYNYVSWYQQHPGKAPKLMIYDVSDRPSGVSNRFSGSKSGNTASLTISGLQAEDEADYYCGSYDSNTFYVFGTGTKVTVLG |
| A25-1H04 | 76 | EVQLVESGGGLVQPGRSLRLSCAASGFTFDAYGMNWVRQAPGKGLEWVSGISYNSGNTAYADSVRGRFTISRDNAKNSLYLQMNSLRAEDTALYYCARGRYSDVWGQGTTVTVSS | 220 | QSALTQPASVSGSPGQSITISCAGSSSDIGGYNYVSWYQQHPGKAPKLMIYDVSERPSGVSNRFSGSKSGNTASLTISGLQAEDEADYYCGSYDSNTFYVFGTGTKVTVLG |

TABLE 14-continued

Amino acid sequences of heavy-chain and light-chain variable regions of selected antibodies

| Antibody name | Heavy-chain variable regions | | Light-chain variable regions | |
|---|---|---|---|---|
| | SEQ ID NO: | Amino acid sequences | SEQ ID NO: | Amino acid Sequences |
| A23-3B06 | 78 | EVQLVESGGGLVQPGRSLRLSCAASGFTFDAYGMHWVRQAPGKGLEWVSGISYNSGSKAYADSVKGRFTISRDNAKNSLYLQMNSLRAEDTALYYCARGRYSDVWGQGTTVTVSS | 222 | QSALTQPASVSGSPGQSITISCSGSSSDVGGYNYVSWYQQHPGKAPKLMIYDVSERPSGVSNRFSGSKSGNTASLTISGLQAEDEADYYCGSYDSNTFYVFGTGTKVTVLG |
| A23-4A09 | 80 | EVQLVESGGGLVQPGRSLRLSCAASGFTFDNYGMNWVRQAPGKGLEWVSGISYDSGNKAYADSVKGRFTISRDNAKNSLYLQMNSLRAEDTALYYCARGRYSDVWGQGTTVTVSS | 224 | QSALTQPASVSGSPGQSITISCGGSSSNIGGYNYVSWYQQHPGKAPKLMIYDVTKRPSGVSNRFSGSKSGNTASLTISGLQAEDEADYYCASYSSNTFYVFGTGTKVTVLG |
| A25-1D09 | 82 | EVQLVESGGGLVQPGRSLRLSCAASGFTFDAYGMHWVRQAPGKGLEWVSGISYNGGTIAYADSVKGRFTISRDNAKNSLYLQMNSLRAEDTALYYCARGRYSDVWGQGTTVTVSS | 226 | QSALTQPASVSGSPGQSITISCGGTSSDVGSYNYVSWYQQHPGKAPKLMIYDVNKRPSGVSNRFSGSKSGNTASLTISGLQAEDEADYYCGSYSNSNFYVFGTGTKVTVLG |
| A21-4E10 | 84 | EVQLVESGGGLVQPGRSLRLSCAASGFTFDAYGMNWVRQAPGKGLEWVSGVSYNAGNKAYADSVRGRFTISRDNAKNSLYLQMNSLRAEDTALYYCARGRYSDVWGQGTTVTVSS | 228 | QSALTQPASVSGSPGQSITISCTGSSSNVGGYNYVSWYQQHPGKAPKLMIYDVSKRPSGVSNRFSGSKSGNTASLTISGLQAEDEADYYCGSYSSNTFYVFGTGTKVTVLG |
| A23-3C04 | 86 | EVQLVESGGGLVQPGRSLRLSCAASGFTFDTYGMHWVRQAPGKGLEWVSGISYDSGTTAYADSVKGRFTISRDNAKNSLYLQMNSLRAEDTALYYCARGRYSDVWGQGTTVTVSS | 230 | QSALTQPASVSGSPGQSITISCSGTSSDIGGYNYVSWYQQHPGKAPKLMIYDVTEPPSGVSNRFSGSKSGNTASLTISGLQAEDEADYYCASYSSNTFYVFGTGTKVTVLG |
| A23-3G06 | 88 | EVQLVESGGGLVQPGRSLRLSCAASGFTFDAYGMNWVRQAPGKGLEWVSGISYNSGNIAYADSVRGRFTISRDNAKNSLYLQMNSLRAEDTALYYCARGRYSDVWGQGTTVTVSS | 232 | QSALTQPASVSGSPGQSITISCAGTSSNIGGYNYVSWYQQHPGKAPKLMIYDVNDRPSGVSNRFSGSKSGNTASLTISGLQAEDEADYYCGSYDSNTFYVFGTGTKVTVLG |
| A24-1E09 | 90 | EVQLVESGGGLVQPGRSLRLSCAASGFTFDKYGMHWVRQAPGKGLEWVSGVSYNAGTTAYADSVRGRFTISRDNAKNSLYLQMNSLRAEDTALYYCARGRYSDVWGQGTTVTVSS | 234 | QSALTQPASVSGSPGQSITISCTGSSSNIGGYNYVSWYQQHPGKAPKLMIYDVTNRPSGVSNRFSGSKSGNTASLTISGLQAEDEADYYCGSYSNSNFYVFGTGTKVTVLG |
| A23-3F03 | 92 | EVQLVESGGGLVQPGRSLRLSCAASGFTFDTYGMHWVRQAPGKGLEWVSGISYNSGNIAYADSVKGRFTISRDNAKNSLYLQMNSLRAEDTALYYCARGRYSDVWGQGTTVTVSS | 236 | QSALTQPASVSGSPGQSITISCGGSSSNIGSYNYVSWYQQHPGKAPKLMIYDVTKRPSGVSNRFSGSKSGNTASLTISGLQAEDEADYYCGSYDSNTFYVFGTGTKVTVLG |
| A21-4F07 | 94 | EVQLVESGGGLVQPGRSLRLSCAASGFTFDAYGMNWVRQAPGKGLEWVSGISYNAGNKAYADSVKGRFTISRDNAKNSLYLQMNSLRAEDTALYYCARGRYSDVWGQGTTVTVSS | 238 | QSALTQPASVSGSPGQSITISCSGTSSNVGGYNYVSWYQQHPGKAPKLMIYDVSDRPSGVSNRFSGSKSGNTASLTISGLQAEDEADYYCGSYSNSNFYVFGTGTKVTVLG |

TABLE 14-continued

Amino acid sequences of heavy-chain and light-chain variable regions of selected antibodies

| Antibody name | Heavy-chain variable regions SEQ ID NO: | Amino acid sequences | Light-chain variable regions SEQ ID NO: | Amino acid Sequences |
|---|---|---|---|---|
| A24-1A03 | 96 | EVQLVESGGGLVQPGRSLRLSCAASGFTFDAYGMNWVRQAPGKGLEWVSGISYNAGNTAYADSVKGRFTISRDNAKNSLYLQMNSLRAEDTALYYCARGRYSDVWGQGTTVTVSS | 240 | QSALTQPASVSGSPGQSITISCGGSSSNVGGYNYVSWYQQHPGKAPKLMIYDVSKRPSGVSNRFSGSKSGNTASLTISGLQAEDEADYYCGSYSNSNFYVFGTGTKVTVLG |
| A24-1H11 | 98 | EVQLVESGGGLVQPGRSLRLSCAASGFTFDAYGMHWVRQAPGKGLEWVSGISYNSGTTAYADSVRGRFTISRDNAKNSLYLQMNSLRAEDTALYYCARGRYSDVWGQGTTVTVSS | 242 | QSALTQPASVSGSPGQSITISCTGSSSDVGGYNYVSWYQQHPGKAPKLMIYEVNKRPSGVSNRFSGSKSGNTASLTISGLQAEDEADYYCASYSSNTFYVFGTGTKVTVLG |
| A21-3D09 | 100 | EVQLVESGGGLVQPGRSLRLSCAASGFTFDNYGMNWVRQAPGKGLEWVSGISYNSGTKAYADSVKGRFTISRDNAKNSLYLQMNSLRAEDTALYYCARGRYSDVWGQGTTVTVSS | 244 | QSALTQPASVSGSPGQSITISCSGTSSNVGGYNYVSWYQQHPGKAPKLMIYDVNKRPSGVSNRFSGSKSGNTASLTISGLQAEDEADYYCGSYSNSNFYVFGTGTKVTVLG |
| A24-1D10 | 102 | EVQLVESGGGLVQPGRSLRLSCAASGFTFDNYGMHWVRQAPGKGLEWVSGISYNSGNKAYADSVKGRFTISRDNAKNSLYLQMNSLRAEDTALYYCARGRYSDVWGQGTTVTVSS | 246 | QSALTQPASVSGSPGQSITISCSGSSSDIGGYNYVSWYQQHPGKAPKLMIYDVTDRPSGVSNRFSGSKSGNTASLTISGLQAEDEADYYCGSYSNNNFYVFGTGTKVTVLG |
| A21-4B04 | 104 | EVQLVESGGGLVQPGRSLRLSCAASGFTFDAYGMHWVRQAPGKGLEWVSGISYDAGNIAYADSVRGRFTISRDNAKNSLYLQMNSLRAEDTALYYCARGRYSDVWGQGTTVTVSS | 248 | QSALTQPASVSGSPGQSITISCAGTSSNIGGYNYVSWYQQHPGKAPKLMIYDVSNRPSGVSNRFSGSKSGNTASLTISGLQAEDEADYYCASYSSNTFYVFGTGTKVTVLG |
| A23-4C12 | 106 | EVQLVESGGGLVQPGRSLRLSCAASGFTFDAYGMNWVRQAPGKGLEWVSGVSYNSGNKAYADSVRGRFTISRDNAKNSLYLQMNSLRAEDTALYYCARGRYSDVWGQGTTVTVSS | 250 | QSALTQPASVSGSPGQSITISCSGTSSDVGGYNYVSWYQQHPGKAPKLMIYDVTKRPSGVSNRFSGSKSGNTASLTISGLQAEDEADYYCGSYSSNTFYVFGTGTKVTVLG |
| A21-4G06 | 108 | EVQLVESGGGLVQPGRSLRLSCAASGFTFDTYGMNWVRQAPGKGLEWVSGISYNAGTKAYADSVRGRFTISRDNAKNSLYLQMNSLRAEDTALYYCARGRYSDVWGQGTTVTVSS | 252 | QSALTQPASVSGSPGQSITISCAGSSSNVGGYNYVSWYQQHPGKAPKLMIYDVTKRPSGVSNRFSGSKSGNTASLTISGLQAEDEADYYCGSYSNSNFYVFGTGTKVTVLG |
| A23-3E04 | 110 | EVQLVESGGGLVQPGRSLRLSCAASGFTFDEYGMHWVRQAPGKGLEWVSGVSWNSGSIAYADSVRGRFTISRDNAKNSLYLQMNSLRAEDTALYYCARGRYSDVWGQGTTVTVSS | 254 | QSALTQPASVSGSPGQSITISCTGSSSDVGGYNYVSWYQQHPGKAPKLMIYDVTKRPSGVSNRFSGSKSGNTASLTISGLQAEDEADYYCSSYSSSTFYVFGTGTKVTVLG |
| A24-1C09 | 112 | EVQLVESGGGLVQPGRSLRLSCAASGFTFDAYGMNWVRQAPGKGLEWVSGISYNGGNKAYADSVRGRFTISRDNAKNSLYLQMNSLRAEDTALYYCARGRYSDVWGQGTTVTVSS | 256 | QSALTQPASVSGSPGQSITISCTGTSSNVGSYNYVSWYQQHPGKAPKLMIYDVNDRPSGVSNRFSGSKSGNTASLTISGLQAEDEADYYCGSYDSNTFYVFGTGTKVTVLG |

TABLE 14-continued

Amino acid sequences of heavy-chain and light-chain variable regions of selected antibodies

| Antibody name | Heavy-chain variable regions SEQ ID NO: | Amino acid sequences | Light-chain variable regions SEQ ID NO: | Amino acid Sequences |
|---|---|---|---|---|
| A24-1C04 | 114 | EVQLVESGGGLVQPGRSLRLSCAASGFTFDGYGMHWVRQAPGKGLEWVSGISYNSGSTAYADSVRGRFTISRDNAKNSLYLQMNSLRAEDTALYYCARGRYSDVWGQGTTVTVSS | 258 | QSALTQPASVSGSPGQSITISCTGTSSNIGGYNYVSWYQQHPGKAPKLMIYDVTKRPSGVSNRFSGSKSGNTASLTISGLQAEDEADYYCGSYSNSNFYVFGTGTKVTVLG |
| A25-1H10 | 116 | EVQLVESGGGLVQPGRSLRLStABLE 14ASGFTFDAYGMHWVRQAPGKGLEWVSGVSYNAGTTAYADSVRGRFTISRDNAKNSLYLQMNSLRAEDTALYYCAKGRSMDVWGQGTTVTVSS | 260 | QSALTQPASVSGSPGQSITISCGGSSSDVGGYNYVSWYQQHPGKAPKLMIYEVSNRPSGVSNRFSGSKSGNTASLTISGLQAEDEADYYCGSYSNSNFYVFGTGTKVTVLG |
| A21-4D08 | 118 | EVQLVESGGGLVQPGRSLRLSCAASGFTFDTYGMHWVRQAPGKGLEWVSGVSYNSGNKAYADSVKGRFTISRDNAKNSLYLQMNSLRAEDTALYYCARGRYSDVWGQGTTVTVSS | 262 | QSALTQPASVSGSPGQSITISCGGTSSDVGGYNYVSWYQQHPGKAPKLMIYDVNDRPSGVSNRFSGSKSGNTASLTISGLQAEDEADYYCGSYSNNNFYVFGTGTKVTVLG |
| A24-1D08 | 120 | EVQLVESGGGLVQPGRSLRLSCAASGFTFDNYGMHWVRQAPGKGLEWVSGVSYNSGNTGYADSVRGRFTISRDNAKNSLYLQMNSLRAEDTALYYCARGRYSDVWGQGTTVTVSS | 264 | QSALTQPASVSGSPGQSITISCAGSSSNVVSYNYVSWYQQHPGKAPKLMIYDVNKRPSGVSNRFSGSKSGNTASLTISGLQAEDEADYYCGSYDSNTFYVFGTGTKVTVLG |
| A24-1A08 | 122 | EVQLVESGGGLVQPGRSLRLSCAASGFTFDAYGMHWVRQAPGKGLEWVSGISYDAGNTAYADSVRGRFTISRDNAKNSLYLQMNSLRAEDTALYYCARGRYSDVWGQGTTVTVSS | 266 | QSALTQPASVSGSPGQSITISCTGSSSNIGGYNYVSWYQQHPGKAPKLMIYEVNNRPSGVSNRFSGSKSGNTASLTISGLQAEDEADYYCASYSSNTFYVFGTGTKVTVLG |
| A21-4A07 | 124 | EVQLVESGGGLVQPGRSLRLSCAASGFTFDTYGMHWVRQAPGKGLEWVSGVSYNSGSKAYADSVKGRFTISRDNAKNSLYLQMNSLRAEDTALYYCARGRYSDVWGQGTTVTVSS | 268 | QSALTQPASVSGSPGQSITISCAGSSSNIGGYNYVSWYQQHPGKAPKLMIYDVNDRPSGVSNRFSGSKSGNTASLTISGLQAEDEADYYCGSYSNSNFYVFGTGTKVTVLG |
| A24-1B09 | 126 | EVQLVESGGGLVQPGRSLRLSCAASGFTFDRYGMHWVRQAPGKGLEWVSGVSYDGGTTAYADSVRGRFTISRDNAKNSLYLQMNSLRAEDTALYYCARGRYSDVWGQGTTVTVSS | 270 | QSALTQPASVSGSPGQSITISCTGTSSNIGSYNYVSWYQQHPGKAPKLMIYDVNKRPSGVSNRFSGSKSGNTASLTISGLQAEDEADYYCGSYDSNTFYVFGTGTKVTVLG |
| A24-1E07 | 128 | EVQLVESGGGLVQPGRSLRLSCAASGFTFDEYGMHWVRQAPGKGLEWVSGISYDAGSTAYADSVRGRFTISRDNAKNSLYLQMNSLRAEDTALYYCARGRYSDVWGQGTTVTVSS | 272 | QSALTQPASVSGSPGQSITISCAGSSSNVGGYNYVSWYQQHPGKAPKLMIYEVSNRPSGVSNRFSGSKSGNTASLTISGLQAEDEADYYCGSYDSNTFYVFGTGTKVTVLG |
| H21-3A07 | 130 | QVQLVESGGGVVQPGRSLRLSCAASGFTFSNYYMNWVRQAPGKGLEWVTVSYDSGNKYYADSVKGRFTISRDNSKNTLYLQMNSLRAEDTAVYYCARGSRRDAFDVWGQGTMVTVSSA | 274 | DIQMTQSPSTLSASVGDRVTITCRASQSISNRLAWYQQKPGKAPKLLIYKASNLESGVPSRFSGSGSGTEFTLTISSLQPDDFATYYCQQTNSFPLTFGGGTKVEIKRTV |

TABLE 14-continued

Amino acid sequences of heavy-chain and light-chain variable regions of selected antibodies

| Antibody name | Heavy-chain variable regions | | Light-chain variable regions | |
|---|---|---|---|---|
| | SEQ ID NO: | Amino acid sequences | SEQ ID NO: | Amino acid Sequences |
| H21-4D11 | 132 | QVQLVESGGGVVQPGRSLRLSCAASGFTFSNYAMNWVRQAPGKGLEWVIISYDSSKYYADSVKGRFTISRDNSKNTLYLQMNSLRAEDTAVYYCARGSGKRDAFDVWGQGTMVTVSSA | 276 | DIQMTQSPSTLSASVGDRVTITCQASQGISNRLAWYQQKPGKAPKLLIYKASNLQSGVPSRFSGSGSGTEFTLTISSLQPDDFATYYCQQTNSFPLTFGGGTKVEIKRTV |
| H21-3C11 | 134 | QVQLVESGGGVVQPGRSLRLSCAASGFTFSNYAMHWVRQAPGKGLEWVVSYDGGNIYYADSVKGRFTISRDNSKNTLYLQMNSLRAEDTAVYYCARGSGRRDAFDVWGQGTMVTVSSA | 278 | DIQMTQSPSTLSASVGDRVTITCRASQSISNRLAWYQQKPGKAPKLLIYKASSLQSGVPSRFSGSGSGTEFTLTISSLQPDDFATYYCQQTNSFPLTFGGGTKVEIKRTV |
| H21-3A09 | 136 | QVQLVESGGGVVQPGRSLRLSCAASGFTFSNYDIHWVRQAPGKGLEWVVSYDGSNTYYADSVKGRFTISRDNSKNTLYLQMNSLRAEDTAVYYCARGSGKRDAFDVWGQGTMVTVSSA | 280 | DIQMTQSPSTLSASVGDRVTITCRASQSISNRLAWYQQKPGKAPKLLIYKASNLQSGVPSRFSGSGSGTEFTLTISSLQPDDFATYYCQQTNSFPLTFGGGTKVEIKRTV |
| H21-4H04 | 138 | QVQLVESGGGVVQPGRSLRLSCAASGFTFSSYAIHWVRQAPGKGLEWVVVSYDGGSKYYADSVKGRFTISRDNSKNTLYLQMNSLRAEDTAVYYCARGSGRRDAFDVWGQGTMVTVSSA | 282 | DIQMTQSPSTLSASVGDRVTITCQASQSISSRLAWYQQKPGKAPKLLIYKASSLQSGVPSRFSGSGSGTEFTLTISSLQPDDFATYYCQQTNSFPLTFGGGTKVEIKRTV |
| H23-3D08 | 140 | QVQLVESGGGVVQPGRSLRLSCAASGFTFSDYDMHWVRQAPGKGLEWVVISYDGGSKYYADSVKGRFTISRDNSKNTLYLQMNSLRAEDTAVYYCARGSGQRDAFDVWGQGTMVTVSSA | 284 | DIQMTQSPSTLSASVGDRVTITCQASQGISNRLAWYQQKPGKAPKLLIYKASNLETGVPSRFSGSGSGTEFTLTISSLQPDDFATYYCQQTNSFPLTFGGGTKVEIKRTV |
| H21-4D09 | 142 | QVQLVESGGGVVQPGRSLRLSCAASGFTFSNYYINWVRQAPGKGLEWVSVSYDGGSIYYADSVKGRFTISRDNSKNTLYLQMNSLRAEDTAVYYCARGSGRRDAFDVWGQGTMVTVSSA | 286 | DIQMTQSPSTLSASVGDRVTITCQASQGIRNRLAWYQQKPGKAPKLLIYKASNLQSGVPSRFSGSGSGTEFTLTISSLQPDDFATYYCQQTNSFPLTFGGGTKVEIKRTV |
| H24-1D11 | 144 | QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCARGSGGRDAFDVWGQGTMVTVSSA | 288 | DIQMTQSPSTLSASVGDRVTITCRASQSISSRLAWYQQKPGKAPKLLIYKASSLETGVPSRFSGSGSGTEFTLTISSLQPDDFATYYCQQTNSFPLTFGGGTKVEIKRTV |

TABLE 15

Polynucleotide sequences of heavy-chain and light-chain
variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| A11-C07 | 17 | GAAGTGCAGCTGGTCGAG AGTGGGGGAGGCTTGGTA CAACCTGGAAGATCCCTT AGACTCTCTTGCGCAGCA AGCGGGTTCACCTTTGAC GAATATGGCATGCACTGG GTGAGACAGGCTCCAGGG AAGGGTCTGGAGTGGGTG TCTGGCGTTTCATGGAAT TCTGGTAGCATTGCGTAC GCTGACTCTGTGAGAGGC AGATTCACTATCTCCAGA GATAACGCCAAAAACAGC TTATACCTGCAGATGAAT TCACTGAGAGCCGAGGAC ACAGCCCTGTACTATTGT GCTAGAGGAAGATATTCG GATGTGTGGGGCCAGGGA ACTACAGTTACCGTCTCC TCA | 161 | CAGTCTGCACTTACTCA GCCAGCCAGTGTGTCTG GGAGTCCTGGACAGTC GATCACCATTTCCTGCA CGGGATCAAGTAGCGA TGTGGGTGGCTATAATT ATGTGTCCTGGTACCAG CAGCACCCAGGCAAGG CCCCCAAACTGATGATT TACGACGTAACAAAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGCTTCTTACTCTA GCAACACTTTTTACGTT TTCGGAACCGGGACAA AGGTGACCGTCTTGGGC |
| A11-G06 | 19 | GAAGTGCAGCTGGTCGAG AGTGGGGGAGGCTTGGTA CAACCTGGAAGATCCCTT AGACTCTCTTGCGCAGCA AGCGGGTTCACCTTTGAC GAATATGGCATGCACTGG GTGAGACAGGCTCCAGGG AAGGGTCTGGAGTGGGTG TCTGGCGTTTCATGGAAT TCTGGTAGCATTGCGTAC GCTGACTCTGTGAGAGGC AGATTCACTATCTCCAGA GATAACGCCAAAAACAGC TTATACCTGCAGATGAAT TCACTGAGAGCCGAGGAC ACAGCCCTGTACTATTGT GCTAAAGGAAGAATGTTG GATGTGTGGGGCCAGGGA ACTACAGTTACCGTCTCC TCA | 163 | CAGTCTGCACTTACTCA GCCAGCCAGTGTGTCTG GGAGTCCTGGACAGTC GATCACCATTTCCTGCA CGGGATCAAGTAGCGA TGTGGGTGGCTATAATT ATGTGTCCTGGTACCAG CAGCACCCAGGCAAGG CCCCCAAACTGATGATT TACGACGTAACAAAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGGTTCTTACAATA ACAACACTTTTTACGTT TTCGGAACCGGGACAA AGGTGACCGTCTTGGGC |
| A12-C09 | 21 | GAAGTGCAGCTGGTCGAG AGTGGGGGAGGCTTGGTA CAACCTGGAAGATCCCTT AGACTCTCTTGCGCAGCA AGCGGGTTCACCTTTGAC GAATATGGCATGCACTGG GTGAGACAGGCTCCAGGG AAGGGTCTGGAGTGGGTG TCTGGCGTTTCATGGAAT TCTGGTAGCATTGCGTAC GCTGACTCTGTGAGAGGC AGATTCACTATCTCCAGA GATAACGCCAAAAACAGC TTATACCTGCAGATGAAT TCACTGAGAGCCGAGGAC ACAGCCCTGTACTATTGT GCTAAAGGAAGAACGAT GGATGTGTGGGGCCAGGG AACTACAGTTACCGTCTC CTCA | 165 | CAGTCTGCACTTACTCA GCCAGCCAGTGTGTCTG GGAGTCCTGGACAGTC GATCACCATTTCCTGCA CGGGATCAAGTAGCGA TGTGGGTGGCTATAATT ATGTGTCCTGGTACCAG CAGCACCCAGGCAAGG CCCCCAAACTGATGATT TACGACGTAACAAAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGGTTCTTACTCTA GCAACACTTTTTACGTT TTCGGAACCGGGACAA AGGTGACCGTCTTGGGC |
| A12-E05 | 23 | GAAGTGCAGCTGGTCGAG AGTGGGGGAGGCTTGGTA CAACCTGGAAGATCCCTT AGACTCTCTTGCGCAGCA AGCGGGTTCACCTTTGAC GAATATGGCATGCACTGG GTGAGACAGGCTCCAGGG AAGGGTCTGGAGTGGGTG | 167 | CAGTCTGCACTTACTCA GCCAGCCAGTGCGTCTG GGAGTCCTGGACAGTC GATCACCATTTCCTGCA CGGGATCAAGTAGCGA TGTGGGTGGCTATAATT ATGTGTCCTGGTACCAG CAGCACCCAGGCAAGG |

TABLE 15-continued

Polynucleotide sequences of heavy-chain and light-chain variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | TCTGGCGTTTCATGGAAT TCTGGTAGCATTGCGTAC GCTGACTCTGTGAGAGGC AGATTCACTATCTCCAGA GATAACGCCAAAAACAGC TTATACCTGCAGATGAAT TCACTGAGAGCCGAGGAC ACAGCCCTGTACTATTGT GCTAGAGGAAGAATGATC GATGTGTGGGGCCAGGGA ACTACAGTTACCGTCTCC TCA | | CCCCCAAACTGATGATT TACGACGTAACAAAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGGTTCTTACAATA GCAACACTTTTTACGTT TTCGGAACCGGGACAA AGGTGACCGTCTTGGGC |
| A12-E01 | 25 | GAAGTGCAGCTGGTCGAG AGTGGGGGAGGCTTGGTA CAACCTGCAAGATCCCTT AGACTCTCTTGCGCAGCA AGCGGGTTCACCTTTGAC GAATATGGCATGCACTGG GTGAGACAGGCTCCAGGG AAGGGTCTGGAGTGGGTG TCTGGCGTTTCATGGAAT TCTGGTAGCATTGCGTAC GCTGACTCTGTGAGAGGC AGATTCACTATCTCCAGA GATAACGCCAAAAACAGC TTATACCTGCAGATGAAT TCACTGAGAGCCGAGGAC ACAGCCCTGTACTATTGT GCTAAAGGAAGACTTTTG GATGTGTGGGGCCAGGGA ACTACAGTTACCGTCTCC TCA | 169 | CAGTCTGCACTTACTCA GCCAGCCAGTGTGTCTG GGAGTCCTGGACAGTC GATCACCATTTCCTGCA CGGGATCAAGTAGCGA TGTGGGTGGCTATAATT ATGTGTCCTGGTACCAG CAGCACCCAGGCAAGG CCCCCAAACTGATGATT TACGACGTAACAAAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTTCTTCTTACTCTA ACAACACTTTTTACGTT TTCGGAACCGGGACAA AGGTGACCGTCTTGGGC |
| A12-E04 | 27 | GAAGTGCAGCTGGTCGAG AGTGGGGGAGGCTTGGTA CAACCTGGAAGATCCCTT AGACTCTCTTGCGCAGCA AGCGGGTTCACCTTTGAC GAATATGGCATGCACTGG GTGAGACAGGCTCCAGGG AAGGGTCTGGAGTGGGTG TCTGGCGTTTCATGGAAT TCTGGTAGCATTGCGTAC GCTGACTCTGTGAGAGGC AGATTCACTATCTCCAGA GATAACGCCAAAAACAGC TTATACCTGCAGATGAAT TCACTGAGAGCCGAGGAC ACAGCCCTGTACTATTGT GCTAAAGGAAGAATGATG GATGTGTGGGGCCAGGGA ACTACAGTTACCGTCTCC TCA | 171 | CAGTCTGCACTTACTCA GCCAGCCAGTGTGTCTG GGAGTCCTGGACAGTC GATCACCATTTCCTGCA CGGGATCAAGTAGCGA TGTGGGTGGCTATAATT ATGTGTCCTGGTACCAG CAGCACCCAGGCAAGG CCCCCAAACTGATGATT TACGACGTAACAAAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGCTTCTTACAATA ACTCCACTTTTTACGTT TTCGGAACCGGGACAA AGGTGACCGTCTTGGGC |
| A12-F02 | 29 | GAAGTGCAGCTGGTCGAG AGTGGGGGAGGCTTGGTA CAACCTGGAAGATCCCTT AGACTCTCTTGCGCAGCA AGCGGGTTCACCTTTGAC GAATATGGCATGCACTGG GTGAGACAGGCTCCAGGG AAGGGTCTGGAGTGGGTG TCTGGCGTTTCATGGAAT TCTGGTAGCATTGCGTAC GCTGACTCTGTGAGAGGC AGATTCACTATCTCCAGA GATAACGCCAAAAACAGC TTATACCTGCAGATGAAT TCACTGAGAGCCGAGGAC ACAGCCCTGTACTATTGT | 173 | CAGTCTGCACTTACTCA GCCAGCCAGTGTGTCTG GGAGTCCTGGACAGTC GATCACCATTTCCTGCA CGGGATCAAGTAGCGA TGTGGGTGGCTATAATT ATGTGTCCTGGTACCAG CAGCACCCAGGCAAGG CCCCCAAACTGATGATT TACGACGTAACAAAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA |

TABLE 15-continued

Polynucleotide sequences of heavy-chain and light-chain
variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | GCTAAAGGAAGATATTTG<br>GATGTGTGGGCCAGGGA<br>ACTACAGTTACCGTCTCC<br>TCA | | TTGTGGTTCTTACGATA<br>GCAACACTTTTTACGTT<br>TTCGGAACCGGGACAA<br>AGGTGACCGTCTTGGGC |
| A12-H04 | 31 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>GAATATGGCATGCACTGG<br>GTGAGACAGGCTCCAGGG<br>AAGGGTCTGGAGTGGGTG<br>TCTGGCGTTTCATGGAAT<br>TCTGGTAGCATTGCGTAC<br>GCTGACTCTGTGAGAGGC<br>AGATTCACTATCTCCAGA<br>GATAACGCCAAAAACAGC<br>TTATACCTGCAGATGAAT<br>TCACTGAGAGCCGAGGAC<br>ACAGCCCTGTACTATTGT<br>GCTAAAGGAAGACTTTTG<br>GATGTGTGGGCCAGGGA<br>ACTACAGTTACCGTCTCC<br>TCA | 175 | CAGTCTGCACTTACTCA<br>GCCAGCCAGTGTGTCTG<br>GGAGTCCTGGACAGTC<br>GATCACCATTTCCTGCA<br>CGGGATCAAGTAGCGA<br>TGTGGGTGGCTATAATT<br>ATGTGTCCTGGTACCAG<br>CAGCACCCAGGCAAGG<br>CCCCCAAACTGATGATT<br>TACGACGTAACAAAGC<br>GCCCCTCAGGGGTCTCC<br>AATCGCTTTTCTGGCAG<br>TAAAAGCGGAAACACA<br>GCCTCCCTGACTATCAG<br>CGGCCTCCAGGCTGAA<br>GACGAGGCTGATTATTA<br>TTGTGGTGCTTACTCTA<br>ACACCAATTTTTACGTT<br>TTCGGAACCGGGACAA<br>AGGTGACCGTCTTGGGC |
| A23-3H04 | 33 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>ACCTATGGGATGAACTGG<br><u>G</u>TGAGACAGGCTCCAGGG<br>A<u>A</u>GGGTCTGGAGTGGGTG<br>TCTGGCATTTCATATAAT<br>GGTGGTACCACAGCGTAC<br>GCTGACTCTGTGAGAGGC<br>AGATTCACTATCTCCAGA<br>GATAACGCCAAAAACAGC<br>TTATACCTGCAGATGAAT<br>TCACTGAGAGCCGAGGAC<br>ACAGCCCTGTACTATTGT<br>GCTAGAGGAAGATATTCG<br>GATGTGTGGGCCAGGGA<br>ACTACAGTTACCGTCTCC<br>TCA | 177 | CAGTCTGCACTTACTCA<br>GCCAGCCAGTGTGTCTG<br>GGAGTCCTGGACAGTC<br>GATCACCATTTCCTGCG<br>GCGGATCAAGTAGCGA<br>TGTCGGTGGCTATAATT<br>ATGTGTCCTGGTACCAG<br>CAGCACCCAGGCAAGG<br>CCCCCAAACTGATGATT<br>TACGACGTTAACAAGC<br>GCCCCTCAGGGGTCTCC<br>AATCGCTTTTCTGGCAG<br>TAAAAGCGGAAACACA<br>GCCTCCCTGACTATCAG<br>CGGCCTCCAAGCTGAA<br>GACGAGGCTGATTATTA<br>TTGTGGTTCTTACGATA<br>GCAACACTTTTTACGTT<br>TTCGGAACCGGGACAA<br>AGGTGACCGTCTTGGGC |
| A21-4C03 | 35 | GAAGTGCAGCTGGTCGAG<br>AGTGGGGAGGCTTGGTAC<br>AACCTGGAAGATCCCTTA<br>GACTCTCTTGCGCAGCAA<br>GCGGGTTCACCTTTGACG<br>CATATGGGATGAACGGGT<br>GAGACAGGCTCCAGGAA<br>GGGTCTGGAGTGGGTGTC<br>TGGCATTTCATATAATTCT<br>GGTACCATAGCGTACGCT<br>GACTCTGTGAAAGGCAGA<br>TTCACTATCTCCAGAGAT<br>AACGCCAAAAACAGCTTA<br>TACCTGCAGATGAATTCA<br>CTGAGAGCCGGGACACAG<br>CCCTGTACTATTGTGCTA<br>GAGGAAGATATTCGGATG<br>TGTGGGCCAGGGAACTA<br>CAGTTACCGTCTCCTCA | 179 | CAGTCTGCACTTACTCA<br>GCCAGCCAGTGTGTCTG<br>GGAGTCCTGGACAGTC<br>GATCACCATTTCCTGCA<br>CCGGATCAAGTAGCGA<br>TATCGGTGGCTATAATT<br>ATGTGTCCTGGTACCAG<br>CAGCACCCAGGCAAGG<br>CCCCCAAACTGATGATT<br>TACGACGTTAGCGATCG<br>CCCCTCAGGGGTCTCCA<br>ATCGCTTTTCTGGCAGT<br>AAAAGCGGAAACACAG<br>CCTCCCTGACTATCAGC<br>GGCCTCCAAGCTGAAG<br>ACGAGGCTGATTATTAT<br>TGTGGTTCTTACTCTAG<br>CAACACTTTTTACGTTT<br>TCGGAACCGGGACAAA<br>GGTGACCGTCTTGGGC |
| A24-1G10 | 37 | GAAGTGCAGCTGGTCGAG<br>AGTGGGGGAGGCTTGGTA<br>CAACCTGGAAGATCCCTT | 181 | CAGTCTGCACTTACTCA<br>GCCAGCCAGTGTGTCTG<br>GGAGTCCTGGACAGTC |

TABLE 15-continued

Polynucleotide sequences of heavy-chain and light-chain
variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | AGACTCTCTTGCGCAGCA<br>AGCGGGTTCACCTTTGAC<br>GCCTATGGGATGCACTGG<br>GTGAGACAGGCTCCAGGG<br>AAGGGTCTGGAGTGGGTG<br>TCTGGCATTTCATATAATT<br>CTGGTACCAAAGCGTACG<br>CTGACTCTGTGAAAGGCA<br>GATTCACTATCTCCAGAG<br>ATAACGCCAAAAACAGCT<br>TATACCTGCAGATGAATT<br>CACTGAGAGCCGAGGACA<br>CAGCCCTGTACTATTgTGC<br>TAGAGGAAGATATTCGGA<br>TGTGTGGGGCCAGGGAAC<br>TACAGTTACCGTCTCCTCA | | GATCACCATTTCCTGCG<br>GCGGATCAAGTAGCAA<br>TATCGGTGGCTATAATT<br>ATGTGTCCTGGTACCAG<br>CAGCACCCAGGCAAGG<br>CCCCCAAACTGATGATT<br>TACGACGTTAACAAGC<br>GCCCCTCAGGGGTCTCC<br>AATCGCTTTTCTGGCAG<br>TAAAAGCGGAAACACA<br>GCCTCCCTGACTATCAG<br>CGGCCTCCAAGCTGAA<br>GACGAGGCTGATTATTA<br>TTGTGCTTCTTACTCTA<br>ACTCCAATTTTTACGTT<br>TTCGGAACCGGGACAA<br>AGGTGACCGTCTTGGGC |
| A24-1F07 | 39 | GAAGTGCAGCTGGTCGAG<br>AGTGGGGGAGGCTTGGTA<br>CAACCTGgAAGATCCCTT<br>AGACTCTCTTGCGCAGCA<br>AGCGGGTTCACCTTTGAC<br>GCCTATGGGATGCACTGG<br>GTGAGACAGGCTCCAGGG<br>AAGGGTCTGGAGTGGGTG<br>TCTGGCGTTTCATATAATT<br>CTGGTACCACAGCGTACG<br>CTGACTCTGTGAGAGGCA<br>GATTCACTATCTCCAGAG<br>ATAACGCCAAAAACAGCT<br>TATACCTGCAGATGAATT<br>CACTGAGAGCCGAGGACA<br>CAGCCCTGTACTATTGTG<br>CTAGAGGAAGATATTCGG<br>ATGTGTGGGGCCAGGGAA<br>CTACAGTTACCGTCTCCTCA | 183 | CAGTCTGCACTTACTCA<br>GCCAGCCAGTGTGTCTG<br>GGAGTCCTGGACAGTC<br>GATCACCATTTCCTGCA<br>GCGGATCAAGTAGCAA<br>TGTCGGTAGCTATAATT<br>ATGTGTCCTGGTACCAG<br>CAGCACCCAGGCAAGG<br>CCCCCAAACTGATGATT<br>TACGACGTTACCAAGC<br>GCCCCTCAGGGGTCTCC<br>AATCGCTTTTCTGGCAG<br>TAAAAGCGGAAACACA<br>GCCTCCCTGACTATCAG<br>CGGCCTCCAAGCTGAA<br>GACGAGGCTGATTATTA<br>TTGTGGTTCTTACTCTA<br>ACTCCAATTTTTACGTT<br>TTCGGAACCGGGACAA<br>AGGTGACCGTCTTGGGC |
| A21-4B10 | 41 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>GAATATGGGATGCACTGG<br>GTGAGACAGGCTCCAGGG<br>AAGGGTCTGGAGTGGGTG<br>TCTGGCATTTCATATAATT<br>CTGGTAACAAAGCGTACG<br>CTGACTCTGTGAGAGGCA<br>GATTCACTATCTCCAGAG<br>ATAACGCCAAAAACAGCT<br>TATACCTGCAGATGAATT<br>CACTGAGAGCCGAGGACA<br>CAGCCCTGTACTATTGTG<br>CTAGAGGAAGATATTCGG<br>ATGTGTGGGGCCAGGGAA<br>CTACAGTTACCGTCTCCTCA | 185 | CAGTCTGCACTTACTCA<br>GCCAGCCAGTGTGTCTG<br>GGAGTCCTGGACAGTC<br>GATCACCATTTCCTGCA<br>GCGGATCAAGTAGCAA<br>TATCGGTGGCTATAATT<br>ATGTGTCCTGGTACCAG<br>CAGCACCCAGGCAAGG<br>CCCCCAAACTGATGATT<br>TACGACGTTAGCAAGC<br>GCCCCTCAGGGGTCTCC<br>AATCGCTTTTCTGGCAG<br>TAAAAGCGGAAACACA<br>GCCTCCCTGACTATCAG<br>CGGCCTCCAAGCTGAA<br>GACGAGGCTGATTATTA<br>TTGTGGTTCTTACGATA<br>GCAACACTTTTTACGTT<br>TTCGGAACCGGGACAA<br>AGGTGACCGTCTTGGGC |
| A21-4G04 | 43 | GAAGTGCAGCTGGTC<br>GAGAGTGGGGGAGGCTTG<br>GTACAACCTG<br>GAAGATCCCTTAG<br>ACTCTCTTGCGCAGCAAG<br>CGGGTTCACCTTTGACAG<br>CTATGGGATGCACTGGGT<br>GAGACAGGCTCCAGGGA<br>AGGGTCTGGAGTGGGTGT<br>CTGGCATTTCATATAATG<br>GTGGTAACACAGCGTACG | 187 | CAGTCTGCACTTACTCA<br>GCCAGCCAGTGTGTCTG<br>GGAGTCCTGGACAGTC<br>GATCACCATTTCCTGCA<br>GCGGATCAAGTAGCAA<br>TATCGGTGGCTATAATT<br>ATGTGTCCTGGTACCAG<br>CAGCACCCAGGCAAGG<br>CCCCCAAACTGATGATT<br>TACGACGTTAACGAGC<br>GCCCCTCAGGGGTCTCC |

TABLE 15-continued

Polynucleotide sequences of heavy-chain and light-chain
variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | CTGACTCTGTGAGAGGCA<br>GATTCACTATCTCCAGAG<br>ATAACGCCAAAAACAGCT<br>TATACCTGCAGATGAATT<br>CACTGAGAGCCGAGGACA<br>CAGCCCTGTACTATTGTG<br>CTAGAGGAAGATATTCGG<br>ATGTGTGGGGCCAGGGAA<br>CTACAGTTACCGTCTCTTCA | | AATCGCTTTTCTGGCAG<br>TAAAAGCGGAAACACA<br>GCCTCCCTGACTATCAG<br>CGGCCTCCAAGCTGAA<br>GACGAGGCTGATTATTA<br>TTGTGGTTCTTACTCTA<br>ACAACAATTTTTACGTT<br>TTCGGAACCGGGACAA<br>AGGTGACCGTCTTGGGC |
| A23-3H05 | 45 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>GCATATGGGATGAACTGG<br>GTGAGACAGGCTCCAGGG<br>AAGGGTCTGGAGTGGGTG<br>TCTGGCATTTCATATAATT<br>CTGGTACCATAGCGTACG<br>CTGACTCTGTGAAAGGCA<br>GATTCACTATCTCCAGAG<br>ATAACGCCAAAAACAGCT<br>TATACCTGCAGATGAATT<br>CACTGAGAGCCGAGGACA<br>CAGCCCTGTACTATTGTG<br>CTAGAGGAAGATATTCGG<br>ATGTGTGGGGCCAGGGAA<br>CTACAGTTACCGTCTCCTCA | 189 | CAGTCTGCACTTACTCA<br>GCCAGCCAGTGTGTCTG<br>GGAGTCCTGGACAGTC<br>GATCACCATTTCCTGCG<br>GCGGATCAAGTAGCAA<br>TGTCGGTGGCTATAATT<br>ATGTGTCCTGGTACCAG<br>CAGCACCCAGGCAAGG<br>CCCCCAAACTGATGATT<br>TACGACGTTAGCAATCG<br>CCCCTCAGGGGTCTCCA<br>ATCGCTTTTCTGGCAGT<br>AAAAGCGGAAACACAG<br>CCTCCCTGACTATCAGC<br>GGCCTCCAAGCTGAAG<br>ACGAGGCTGATTATTAT<br>TGTGGTTCTTACTCTAA<br>CTCCAATTTTTACGTTT<br>TCGGAACCGGGACAAA<br>GGTGACCGTCTTGGGC |
| A21-3A09 | 47 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>AACTATGGGATGAACTGG<br>GTGAGACAGGCTCCAGGG<br>AAGGGTCTGGAGTGGGTG<br>TCTGGCATTTCATATAATT<br>CTGGTACCAAAGCGTACG<br>CTGACTCTGTGAAAGGCA<br>GATTCACTATCTCCAGAG<br>ATAACGCCAAAAACAGCT<br>TATACCTGCAGATGAATT<br>CACTGAGAGCCGAGGACA<br>CAGCCCTGTACTATTGTG<br>CTAGAGGAAGATATTCGG<br>ATGTGTGGGGCCAGGGAA<br>CTACAGTTACCGTCTCCTCA | 191 | CAGTCTGCACTTACTCA<br>GCCAGCCAGTGTGTCTG<br>GGAGTCCTGGACAGTC<br>GATCACCATTTCCTGCA<br>GCGGATCAAGTAGCGA<br>TATCGGTGGCTATAATT<br>ATGTGTCCTGGTACCAG<br>CAGCACCCAGGCAAGG<br>CCCCCAAACTGATGATT<br>TACGACGTTAACAAGC<br>GCCCCTCAGGGGTCTCC<br>AATCGCTTTTCTGGCAG<br>TAAAAGCGGAAACACA<br>GCCTCCCTGACTATCAG<br>CGGCCTCCAAGCTGAA<br>GACGAGGCTGATTATTA<br>TTGTGCTTCTTACTCTA<br>GCAACACTTTTTACGTT<br>TTCGGAACCGGGACAA<br>AGGTGACCGTCTTGGGC |
| A21-4B06 | 49 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>AGCTATGGGATGCACTGG<br>GTGAGACAGGCTCCAGGG<br>AAGGGTCTGGAGTGGGTG<br>TCTGGCATTTCATATAAT<br>GGTGGTAGCAAAGCGTAC<br>GCTGACTCTGTGAGAGGC<br>AGATTCACTATCTCCAGA<br>GATAACGCCAAAAACAGC<br>TTATACCTGCAGATGAAT<br>TCACTGAGAGCCGAGGAC<br>ACAGCCCTGTACTATTGT | 193 | CAGTCTGCACTTACTCA<br>GCCAGCCAGTGTGTCTG<br>GGAGTCCTGGACAGTC<br>GATCACCATTTCCTGCA<br>GCGGATCAAGTAGCAA<br>TATCGGTAGCTATAATT<br>ATGTGTCCTGGTACCAG<br>CAGCACCCAGGCAAGG<br>CCCCCAAACTGATGATT<br>TACGACGTTACCGATCG<br>CCCCTCAGGGGTCTCCA<br>ATCGCTTTTCTGGCAGT<br>AAAAGCGGAAACACAG<br>CCTCCCTGACTATCAGC<br>GGCCTCCAAGCTGAAG<br>ACGAGGCTGATTATTAT |

TABLE 15-continued

Polynucleotide sequences of heavy-chain and light-chain variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | GCTAGAGGAAGATATTCG GATGTGTGGGCCAGGGA ACTACAGTTACCGTCTCC TCA | | TGTGGTTCTTACTCTAG CAACACTTTTTACGTTT TCGGAACCGGGACAAA GGTGACCGTCTTGGGC |
| A24-1B05 | 51 | GAAGTGCAGCTGGTCGAG AGTGGGGGAGGCTTGGTA CAACCTGGAAGATCCCTT AGACTCTCTTGCGCAGCA AGCGGGTTCACCTTTGAC AAATATGGGATGAACTGG GTGAGACAGGCTCCAGGG AAGGGTCTGGAGTGGGTG TCTGGCATTTCATATAATT CTGGTAACACAGCGTACG CTGACTCTGTGAGAGGCA GATTCACTATCTCCAGAG ATAACGCCAAAAACAGCT TATACCTGCAGATGAATT CACTGAGAGCCGAGGACA CAGCCCTGTACTATTGTG CTAGAGGAAGATATTCGG ATGTGTGGGGCCAGGGAA CTACAGTTACCGTCTCCTCA | 195 | CAGTCTGCACTTACTCA GCCAGCCAGTGTGTCTG GGAGTCCTGGACAGTC GATCACCATTTCCTGCG CCGGATCAAGTAGCGA TATCGGTGGCTATAATT ATGTGTCCTGGTACCAG CAGCACCCAGGCAAGG CCCCCAAACTGATGATT TACGACGTTAGCAAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGGTTCTTACGATA GCAACACTTTTTACGTT TTCGGAACCGGGACAA AGGTGACCGTCTTGGGC |
| A23-3A08 | 53 | GAAGTGCAGCTGGTCGAG AGTGGGGGAGGCTTGGTA CAACCTGGAAGATCCCTT AGACTCTCTTGCGCAGCA AGCGGGTTCACCTTTGAC GCATATGGGATGCACTGG GTGAGACAGGCTCCAGGG AAGGGTCTGGAGTGGGTG TCTGGCATTTCATATAATT CTGGTACCACAGCGTACG CTGACTCTGTGAAAGGCA GATTCACTATCTCCAGAG ATAACGCCAAAAACAGCT TATACCTGCAGATGAATT CACTGAGAGCCGAGGACA CAGCCCTGTACTATTGTG CTAGAGGAAGATATTCGG ATGTGTGGGGCCAGGGAA CTACAGTTACCGTCTCCTCA | 197 | CAGTCTGCACTTACTCA GCCAGCCAGTGTGTCTG GGAGTCCTGGACAGTC GATCACCATTTCCTGCG CCGGATCAAGTAGCAA TATCGGTGGCTATAATT ATGTGTCCTGGTACCAG CAGCACCCAGGCAAGG CCCCCAAACTGATGATT TACGACGTTAGCAAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGGTTCTTACTCTA ACTCCAATTTTTACGTT TTCGGAACCGGGACAA AGGTGACCGTCTTGGGC |
| A21-4C08 | 55 | GAAGTGCAGCTGGTCGAG AGTGGGGGAGGCTTGGTA CAACCTGGAAGATCCCTT AGACTCTCTTGCGCAGCA AGCGGGTTCACCTTTGAC ACATATGGGATGCACTGG GTGAGACAGGCTCCAGGG AAGGGTCTGGAGTGGGTG TCTGGCATTTCATATAAT GCCGGTAACAAAGCGTAC GCTGACTCTGTGAGAGGC AGATTCACTATCTCCAGA GATAACGCCAAAAACAGC TTATACCTGCAGATGAAT TCACTGAGAGCCGAGGAC ACAGCCCTGTACTATTGT GCTAGAGGAAGATATTCG GATGTGTGGGCCAGGGA ACTACAGTTACCGTCTCC TCA | 199 | CAGTCTGCACTTACTCA GCCAGCCAGTGTGTCTG GGAGTCCTGGACAGTC GATCACCATTTCCTGCA GCGGATCAAGTAGCAA TGTCGGTAGCTATAATT ATGTGTCCTGGTACCAG CAGCACCCAGGCAAGG CCCCCAAACTGATGATT TACGACGTTAACAATCG CCCCTCAGGGGTCTCCA ATCGCTTTTCTGGCAGT AAAAGCGGAAACACAG CCTCCCTGACTATCAGC GGCCTCCAAGCTGAAG ACGAGGCTGATTATTAT TGTGGTTCTTACTCTAG CAACACTTTCTACGTTT TCGGAACCGGGACAAA GGTGACCGTCTTGGGC |
| A23-4D09 | 57 | GAAGTGCAGCTGGTCGAG AGTGGGGGAGGCTTGGTA CAACCTGGAAGATCCCTT | 201 | CAGTCTGCACTTACTCA GCCAGCCAGTGTGTCTG GGAGTCCTGGACAGTC |

TABLE 15-continued

Polynucleotide sequences of heavy-chain and light-chain variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | AGACTCTCTTGCGCAGCA<br>AGCGGGTTCACCTTTGAC<br>GCCTATGGGATGCACTGG<br>GTGAGACAGGCTCCAGGG<br>AAGGGTCTGGAGTGGGTG<br>TCTGGCGTTTCATATGAT<br>GCTGGTAACACAGCGTAC<br>GCTGACTCTGTGAGAGGC<br>AGATTCACTATCTCCAGA<br>GATAATGCCAAAAACAGC<br>TTATACCTGCAGATGAAT<br>TCACTGAGAGCCGAGGAC<br>ACAGCCCTGTACTATTGT<br>GCTAGAGGAAGATATTCG<br>GATGTGTGGGGCCAGGGA<br>ACTACAGTTACCGTCTCC<br>TCA | | GATCACCATTTCCTGCA<br>GCGGATCAAGTAGCAA<br>TATCGGTAGCTATAATT<br>ATGTGTCCTGGTACCAG<br>CAGCACCCAGGCAAGG<br>CCCCCAAACTGATGATT<br>TACGACGTTACCGATCG<br>CCCCTCAGGGGTCTCCA<br>ATCGCTTTTCTGGCAGT<br>AAAAGCGGAAACACAG<br>CCTCCCTGACTATCAGC<br>GGCCTCCAAGCTGAAG<br>ACGAGGCTGATTATTAT<br>TGTGGTTCTTACTCTAG<br>CAACACTTTTTACGTTT<br>TCGGAACCGGGACAAA<br>GGTGACCGTCTTGGGC |
| A23-3D03 | 59 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>GCATATGGGATGAACTGG<br>GTGAGACAGGCTCCAGGG<br>AAGGGTCTGGAGTGGGTG<br>TCTGGCATTTCATATAAT<br>GCTGGTAGCACAGCGTAC<br>GCTGACTCTGTGAGAGGC<br>AGATTCACTATCTCCAGA<br>GATAACGCCAAAAACAGC<br>TTATACCTGCAGATGAAT<br>TCACTGAGAGCCGAGGAC<br>ACAGCCCTGTACTATTGT<br>GCTAGAGGAAGATATTCG<br>GATGTGTGGGGCCAGGGA<br>ACTACAGTTACCGTCTCC<br>TCA | 203 | CAGTCTGCACTTACTCA<br>GCCAGCCAGTGTGTCTG<br>GGAGTCCTGGACAGTC<br>GATCACCATTTCCTGCA<br>CCGGATCAAGTAGCGA<br>TGTCGGTGGCTATAATT<br>ATGTGTCCTGGTACCAG<br>CAGCACCCAGGCAAGG<br>CCCCCAAACTGATGATT<br>TACGACGTTACCAATCG<br>CCCCTCAGGGGTCTCCA<br>ATCGCTTTTCTGGCAGT<br>AAAAGCGGAAACACAG<br>CCTCCCTGACTATCAGC<br>GGCCTCCAAGCTGAAG<br>ACGAGGCTGATTATTAT<br>TGTGGTTCTTACGATAG<br>CAACACTTTTTACGTTT<br>TCGGAACCGGGACAAA<br>GGTGACCGTCTTGGGC |
| A21-4B03 | 61 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>GCATATGGGATGAACTGG<br>GTGAGACAGGCTCCAGGG<br>AAGGGTCTGGAGTGGGTG<br>TCTGGCATTTCATATAAT<br>GCTGGTAACAAAGCGTAC<br>GCTGACTCTGTGAGAGGC<br>AGATTCACTATCTCCAGA<br>GATAACGCCAAAAACAGC<br>TTATACCTGCAGATGAAT<br>TCACTGAGAGCCGAGGAC<br>ACAGCCCTGTACTATTGT<br>GCTAGAGGAAGATATTCG<br>GATGTGTGGGGCCAGGGA<br>ACTACAGTTACCGTCTCC<br>TCA | 205 | CAGTCTGCACTTACTCA<br>GCCAGCCAGTGTGTCTG<br>GGAGTCCTGGACAGTC<br>GATCACCATTTCCTGCA<br>GCGGATCAAGTAGCAA<br>TATCGGTAGCTATAATT<br>ATGTGTCCTGGTACCAG<br>CAGCACCCAGGCAAGG<br>CCCCCAAACTGATGATT<br>TACGACGTTAACAAGC<br>GCCCCTCAGGGGTCTCC<br>AATCGCTTTTCTGGCAG<br>TAAAAGCGGAAACACA<br>GCCTCCCTGACTATCAG<br>CGGCCTCCAAGCTGAA<br>GACGAGGCTGATTATTA<br>TTGTGCTTCTTACTCTA<br>GCAACACTTTTTACGTT<br>TTCGGAACCGGGACAA<br>AGGTGACCGTCTTGGGC |
| A21-3D10 | 63 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>AACTATGGGATGCACTGG<br>GTGAGACAGGCTCCAGGG<br>AAGGGTCTGGAGTGGGTG<br>TCTGGCATTTCATATGAT<br>GCTGGTACCACAGCGTAC<br>GCTGACTCTGTGAAAGGC | 207 | CAGTCTGCACTTACTCA<br>GCCAGCCAGTGTGTCTG<br>GGAGTCCTGGACAGTC<br>GATCACCATTTCCTGCG<br>GCGGAACAAGTAGCAA<br>TATCGGTGGCTATAATT<br>ATGTGTCCTGGTACCAG<br>CAGCACCCAGGCAAGG<br>CCCCCAAACTGATGATT<br>TACGACGTTACCAATCG<br>CCCCTCAGGGGTCTCCA |

TABLE 15-continued

Polynucleotide sequences of heavy-chain and light-chain variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | AGATTCACTATCTCCAGA GATAACGCCAAAAACAGC TTATACCTGCAGATGAAT TCACTGAGAGCCGAGGAC ACAGCCCTGTACTATTGT GCTAAAGGAAGATATTCG GATGTGTGGGCCAGGGA ACTACAGTTACCGTCTCC TCA | | ATCGCTTTTCTGGCAGT AAAAGCGGAAACACAG CCTCCCTGACTATCAGC GGCCTCCAAGCTGAAG ACGAGGCTGATTATTAT TGTGGTTCTTACTCTAA CACCAATTTTTACGTTT TCGGAACCGGGACAAA GGTGACCGTCTTGGGC |
| A21-3A10 | 65 | GAAGTGCAGCTGGTCGAG AGTGGGGGAGGCTTGGTA CAACCtGGAAGATCCCTTA GACTCTCTTGCGCAGCAA GCGGGTTCACCTTTGACG CATATGGGATGCACTGGG TGAGACAGGCTCCAGGGA AGGGTCTGGAGTGGGTGT CTGGCATTTCATATAATG CTGGTAACAAAGCGTACG CTGACTCTGTGAGAGGCA GATTCACTATCTCCAGAG ATAACGCCAAAAACAGCT TATACCTGCAGATGAATT CACTGAGAGCCGAGGACA CAGCCCTGTACTATTGTG CTAGAGGAAGATATTCGG ATGTGTGGGCCAGGGAA CTACAGTTACCGTCTCCTCA | 209 | CAGTCTGCACTTACTCA GCCAGCCAGTGTGTCTG GGAGTCCTGGACAGTC GATCACCATTTCCTGCG CCGGATCAAGTAGCAA TATCGGTGGCTATAATT ATGTGTCCTGGTACCAG CAGCACCCAGGCAAGG CCCCCAAACTGATGATT TACGACGTTAGCAAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGGTTCTTACTCTA ACTCCAATTTTTACGTT TTCGGAACCGGGACAA AGGTGACCGTCTTGGGC |
| A21-4H04 | 67 | GAAGTGCAGCTGGTCGAG AGTGGGGGAGGCTTGGTA CAACCtggaAGATCCCTTAG ACTCTCTTGCGCAGCAAG CGGGTTCACCTTTGACAG CTATGGGATGCACTGGGT GAGACAGGCTCCAGGGA AGGGTCTGGAGTGGGTGT CCGGCATTTCATATAATT CTGGTAACAAAGCGTACG CTGACTCTGTGAAAGGCA GATTCACTATCTCCAGAG ATAACGCCAAAAACAGCT TATACCTGCAGATGAATT CACTGAGAGCCGAGGACA CAGCCCTGTACTATTGTG CTAGAGGAAGATATTCGG ATGTGTGGGCCAGGGAA CTACAGTTACCGTCTCCTCA | 211 | CAGTCTGCACTTACTCA GCCAGCCAGTGTGTCTG GGAGTCCTGGACAGTC GATCACCATTTCCTGCA GCGGAACAAGTAGCGA TATCGGTGGCTATAATT ATGTGTCCTGGTACCAG CAGCACCCAGGCAAGG CCCCCAAACTGATGATT TACGACGTTAGCAAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGGTTCTTACTCTA ACAACAATTTTTACGTT TTCGGAACCGGGACAA AGGTGACCGTCTTGGGC |
| A21-4F11 | 69 | GAAGTGCAGCTGGTCGAG AGTGGGGGAGGCTTGGTA CAACCTGGAAGATCCCTT AGACTCTCTTGCGCAGCA AGCGGGTTCACCTTTGAC GCATATGGGATGAACTGG GTGAGACAGGCTCCAGGG AAGGGTCTGGAGTGGGTG TCTGGCATTTCATATAAT GGTGGTACCAAAGCGTAC GCTGACTCTGTGAGAGGC AGATTCACTATCTCCAGA GATAACGCCAAAAACAGC TTATACCTGCAGATGAAT TCACTGAGAGCCGAGGAT ACAGCCCTGTACTATTGT | 213 | CAGTCTGCACTTACTCA GCCAGCCAGTGTGTCTG GGAGTCCTGGACAGTC GATCACCATTTCCTGCG GCGGAACAAGTAGCAA TATCGGTGGCTATAATT ATGTGTCCTGGTACCAG CAGCACCCAGGCAAGG CCCCCAAACTGATGATT TACGACGTTAACGATCG CCCCTCAGGGGTCTCCA ATCGCTTTTCTGGCAGT AAAAGCGGAAACACAG CCTCCCTGACTATCAGC GGCCTCCAAGCTGAAG ACGAGGCTGATTATTAT |

TABLE 15-continued

Polynucleotide sequences of heavy-chain and light-chain
variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | GCTAGAGGAAGATATTCG GATGTGTGGGCCAGGGA ACTACAGTTACCGTCTCC TCA | | TGTGCTTCTTACTCTAG CAACACTTTTTACGTTT TCGGAACCGGGACAAA GGTGACCGTCTTGGGC |
| A23-3G05 | 71 | GAAGTGCAGCTGGTCGAG AGTGGGGGAGGCTTGGTA CAACCTGGAAGATCCCTT AGACTCTCTTGCGCAGCA AGCGGGTTCACCTTTGAC ACATATGGGATGCACTGG GTGAGACAGGCTCCAGGG AAGGGTCTGGAGTGGGTG TCTGGCATTTCATATAATT CTGGTACCATAGCGTACG CTGACTCTGTGAGAGGCA GATTCACTATCTCCAGAG ATAACGCCAAAAACAGCT TATACCTGCAGATGAATT CACTGAGAGCCGAGGACA CAGCCCTGTACTATTGTG CTAGAGGAAGATATTCGG ATGTGTGGGGCCAGGGAA CTACAGTTACCGTCTCCTCA | 215 | CAGTCTGCACTTACTCA GCCAGCCAGTGTGTCTG GGAGTCCTGGACAGTC GATCACCATTTCCTGCG CCGGATCAAGTAGCAA TATCGGTAGCTATAATT ATGTGTCCTGGTACCAG CAGCACCCAGGCAAGG CCCCCAAACTGATGATT TACGACGTTAGCAATCG CCCCTCAGGGGTCTCCA ATCGCTTTTCTGGCAGT AAAAGCGGAAACACAG CCTCCCTGACTATCAGC GGCCTCCAAGCTGAAG ACGAGGCTGATTATTAT TGTGGTTCTTACGATAG CAACACTTTTTACGTTT TCGGAACCGGGACAAA GGTGACCGTCTTGGGC |
| A23-3A10 | 73 | GAAGTGCAGCTGGTCGAG AGTGGGGGAGGCTTGGTA CAACCTGGAAGATCCCTT AGACTCTCTTGCGCAGCA AGCGGGTTCACCTTTGAC AAATATGGGATGCACTGG GTGAGACAGGCTCCAGGG AAGGGTCTGGAGTGGGTG TCTGGCATTTCATATAAT GCTGGTAGCAAAGCGTAC GCTGACTCTGTGAAAGGC AGATTCACTATCTCCAGA GATAACGCCAAAAACAGC TTATACCTGCAGATGAAT TCACTGAGAGCCGAGGAC ACAGCCCTGTACTATTGT GCTAGAGGAAGATATTCG GATGTGTGGGCCAGGGA ACTACAGTTACCGTCTCC TCA | 217 | CAGTCTGCACTTACTCA GCCAGCCAGTGTGTCTG GGAGTCCTGGACAGTC GATCACCATTTCCTGCG CCGGATCAAGTAGCAA TATCGGTGGCTATAATT ATGTGTCCTGGTACCAG CAGCACCCAGGCAAGG CCCCCAAACTGATGATT TACGACGTTAGCGATCG CCCCTCAGGGGTCTCCA ATCGCTTTTCTGGCAGT AAAAGCGGAAACACAG CCTCCCTGACTATCAGC GGCCTCCAAGCTGAAG ACGAGGCTGATTATTAT TGTGGTTCTTACGATAG CAACACTTTTTACGTTT TCGGAACCGGGACAAA GGTGACCGTCTTGGGC |
| A25-1H04 | 75 | GAAGTGCAGCTGGTCGAG AGTGGGGGAGGCTTGGTA CAACCTGGAAGATCCCTT AGACTCTCTTGCGCAGCA AGCGGGTTCACCTTTGAC GCATATGGGATGAACTGG GTGAGACAGGCTCCAGGG AAGGGTCTGGAGTGGGTG TCTGGCATTTCATATAATT CTGGTAACACAGCGTACG CTGACTCTGTGAGAGGCA GATTCACTATCTCCAGAG ATAACGCCAAAAACAGCT TATACCTGCAGATGAATT CACTGAGAGCCGAGGACA CAGCCCTGTACTATTGTG CTAGAGGAAGATATTCGG ATGTGTGGGGCCAGGGAA CTACAGTTACCGTCTCCTCA | 219 | CAGTCTGCACTTACTCA GCCAGCCAGTGTGTCTG GGAGTCCTGGACAGTC GATCACCATTTCCTGCG CCGGATCAAGTAGCGA TATCGGTGGCTATAATT ATGTGTCCTGGTACCAG CAGCACCCAGGCAAGG CCCCCAAACTGATGATT TACGACGTTAGCGAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGGTTCTTACGATA GCAACACTTTTTACGTT TTCGGAACCGGGACAA AGGTGACCGTCTTGGGC |
| A23-3B06 | 77 | GAAGTGCAGCTGGTCGAG AGTGGGGGAGGCTTGGTA CAACCTGGAAGATCCCTT | 221 | CAGTCTGCACTTACTCA GCCAGCCAGTGTGTCTG GGAGTCCTGGACAGTC |

TABLE 15-continued

Polynucleotide sequences of heavy-chain and light-chain
variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | AGACTCTCTTGCGCAGCA<br>AGCGGGTTCACCTTTGAC<br>GCCTATGGGATGCACTGG<br>GTGAGACAGGCTCCAGGG<br>AAGGGTCTGGAGTGGGTG<br>TCTGGCATTTCATATAATT<br>CTGGTAGCAAAGCGTACG<br>CTGACTCTGTGAAAGGCA<br>GATTCACTATCTCCAGAG<br>ATAACGCCAAAAACAGCT<br>TATACCTGCAGATGAATT<br>CACTGAGAGCCGAGGACA<br>CAGCCCTGTACTATTGTG<br>CTAGAGGAAGATATTCGG<br>ATGTGTGGGGCCAGGGAA<br>CTACAGTTACCGTCTCCTCA | | GATCACCATTTCCTGCA<br>GCGGATCAAGTAGCGA<br>TGTCGGTGGCTATAATT<br>ATGTGTCCTGGTACCAG<br>CAGCACCCAGGCAAGG<br>CCCCCAAACTGATGATT<br>TACGACGTTAGCGAGC<br>GCCCCTCAGGGGTCTCC<br>AATCGCTTTTCTGGCAG<br>TAAAAGCGGAAACACA<br>GCCTCCCTGACTATCAG<br>CGGCCTCCAAGCTGAA<br>GACGAGGCTGATTATTA<br>TTGTGGTTCTTACGATA<br>GCAACACTTTTTACGTT<br>TTCGGAACCGGGACAA<br>AGGTGACCGTCTTGGGC |
| A23-4A09 | 79 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>AACTATGGGATGAACTGG<br>GTGAGACAGGCTCCAGGG<br>AAGGGTCTGGAGTGGGTG<br>TCTGGCATTTCATATGATT<br>CTGGTAACAAAGCGTACG<br>CTGACTCTGTGAAAGGCA<br>GATTCACTATCTCCAGAG<br>ATAACGCCAAAAACAGCT<br>TATACCTGCAGATGAATT<br>CACTGAGAGCCGAGGACA<br>CAGCCCTGTACTATTGTG<br>CTAGAGGAAGATATTCGG<br>ATGTGTGGGGCCAGGGAA<br>CTACAGTTACCGTCTCCTCA | 223 | CAGTCTGCACTTACTCA<br>GCCAGCCAGTGTGTCTG<br>GGAGTCCTGGACAGTC<br>GATCACCATTTCCTGCG<br>GCGGATCAAGTAGCAA<br>TATCGGTGGCTATAATT<br>ATGTGTCCTGGTACCAG<br>CAGCACCCAGGCAAGG<br>CCCCCAAACTGATGATT<br>TACGACGTTACCAAGC<br>GCCCCTCAGGGGTCTCC<br>AATCGCTTTTCTGGCAG<br>TAAAAGCGGAAACACA<br>GCCTCCCTGACTATCAG<br>CGGCCTCCAAGCTGAA<br>GACGAGGCTGATTATTA<br>TTGTGCTTCTTACTCTA<br>GCAACACTTTTTACGTT<br>TTCGGAACCGGGACAA<br>AGGTGACCGTCTTGGGC |
| A25-1D09 | 81 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTTAC<br>GCATATGGGATGCACTGG<br>GTGAGACAGGCTCCAGGG<br>AAGGGTCTGGAGTGGGTG<br>TCTGGCATTTCATATAAT<br>GGTGGTACCATAGCGTAC<br>GCTGACTCTGTGAAAGGC<br>AGATTCACTATCTCCAGA<br>GATAACGCCAAAAACAGC<br>TTATACCTGCAGATGAAT<br>TCACTGAGAGCCGAGGAC<br>ACAGCCCTGTACTATTGT<br>GCTAGAGGAAGATATTCG<br>GATGTGTGGGGCCAGGGA<br>ACTACAGTTACCGTCTCC<br>TCA | 225 | CAGTCTGCACTTACTCA<br>GCCAGCCAGTGTGTCTG<br>GGAGTCCTGGACAGTC<br>GATCACCATTTCCTGCG<br>GCGGAACAAGTAGCGA<br>TGTCGGTAGCTATAATT<br>ATGTGTCCTGGTACCAG<br>CAGCACCCAGGCAAGG<br>CCCCCAAACTGATGATT<br>TACGACGTTAACAAGC<br>GCCCCTCAGGGGTCTCC<br>AATCGCTTTTCTGGCAG<br>TAAAAGCGGAAACACA<br>GCCTCCCTGACTATCAG<br>CGGCCTCCAAGCTGAA<br>GACGAGGCTGATTATTA<br>TTGTGGTTCTTACTCTA<br>ACTCCAATTTTTACGTT<br>TTCGGAACCGGGACAA<br>AGGTGACCGTCTTGGGC |
| A21-4E10 | 83 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>GCCTATGGGATGAACTGG<br>GTGAGACAGGCTCCAGGG<br>AAGGGTCTGGAGTGGGTG<br>TCTGGCGTTTCATATAAC<br>GCTGGTAACAAAGCGTAC<br>GCTGACTCTGTGAGAGGC | 227 | CAGTCTGCACTTACTCA<br>GCCAGCCAGTGTGTCTG<br>GGAGTCCTGGACAGTC<br>GATCACCATTTCCTGCA<br>CCGGATCAAGTAGCAA<br>TGTCGGTGGCTATAATT<br>ATGTGTCCTGGTACCAG<br>CAGCACCCAGGCAAGG<br>CCCCCAAACTGATGATT<br>TACGACGTTAGCAAGC<br>GCCCCTCAGGGGTCTCC |

TABLE 15-continued

Polynucleotide sequences of heavy-chain and light-chain
variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | AGATTCACTATCTCCAGA GATAACGCCAAAAACAGC TTATACCTGCAGATGAAT TCACTGAGAGCCGAGGAC ACAGCCCTGTACTATTGT GCTAGAGGAAGATATTCG GATGTGTGGGGCCAGGGA ACTACAGTTACCGTCTCC TCA | | AATCGCTTTTCTGGCAG TAAAAGCGGAAACACA GCCTCCCTGACTATCAG CGGCCTCCAAGCTGAA GACGAGGCTGATTATTA TTGTGGTTCTTACTCTA GCAACACTTTTTACGTT TTCGGAACCGGGACAA AGGTGACCGTCTTGGGC |
| A23-3C04 | 85 | GAAGTGCAGCTGGTCGAG AGTGGGGGAGGCTTGGTA CAACCTGGAAGATCC CTTAGACTCTCTTGCGCA GCAAGCGGGTTCACCTTT GACACATATGGGATGCAC TGGGTGAGACAGGCTCCA GGGAAGGGTCTGGAGTGG GTGTCTGGCATTTCATAT GATTCTGGTACCACAGCG TACGCTGACTCTGTGAAA GGCAGATTCACTATCTCC AGAGATAACGCCAAAAA CAGCTTATACCTGCAGAT GAATTCACTGAGAGCCGA GGACACAGCCCTGTACTA TTGTGCTAGAGGAAGATA TTCGGATGTGTGGGGCCA GGGAACTACAGTTACCGT CTCCTCA | 229 | CAGTCTGCACTTACTCA GCCAGCCAGTGTGTCTG GGAGTCCTGGACAGTC GATCACCATTTCCTGCA GCGGAACAAGTAGCGA TATCGGTGGCTATAATT ATGTGTCCTGGTACCAG CAGCACCCAGGCAAGG CCCCCAAACTGATGATT TACGACGTTACCGAGCC CCCCTCAGGGGTCTCCA ATCGCTTTTCTGGCAGT AAAAGCGGAAACACAG CCTCCCTGACTATCAGC GGCCTCCAAGCTGAAG ACGAGGCTGATTATTAT TGTGCTTCTTACTCTAG CAACACTTTTTACGTTT TCGGAACCGGGACAAA GGTGACCGTCTTGGGC |
| A23-3G06 | 87 | GAAGTGCAGCTGGTCGAG AGTGGGGGAGGCTTGGTA CAACCTGGAAGATCC CTTAGACTCTCTTGCGCA GCAAGCGGGTTCACCTTT GACGCATATGGGATGAAC TGGGTGAGACAGGCTCCA GGGAAGGGTCTGGAGTGG GTGTCTGGCATTTCATAT AATTCTGGTAACATAGCG TACGCTGACTCTGTGAGA GGCAGATTCACTATCTCC AGAGATAACGCCAAAAA CAGCTTATACCTGCAGAT GAATTCACTGAGAGCCGA GGACACAGCCCTGTACTA TTGTGCTAGAGGAAGATA TTCGGATGTGTGGGGCCA GGGAACTACAGTTACCGT CTCCTCA | 231 | CAGTCTGCACTTACTCA GCCAGCCAGTGTGTCTG GGAGTCCTGGACAGTC GATCACCATTTCCTGCG CCGGAACAAGTAGCAA TATCGGTGGCTATAATT ATGTGTCCTGGTACCAG CAGCACCCAGGCAAGG CCCCCAAACTGATGATT TACGACGTTAACGATCG CCCCTCAGGGGTCTCCA ATCGCTTTTCTGGCAGT AAAAGCGGAAACACAG CCTCCCTGACTATCAGC GGCCTCCAAGCTGAAG ACGAGGCTGATTATTAT TGTGGTTCTTACGATAG CAACACTTTTTACGTTT TCGGAACCGGGACAAA GGTGACCGTCTTGGGC |
| A24-1E09 | 89 | GAAGTGCAGCTGGTCGAG AGTGGGGGAGGCTTGGTA CAACCTGGAAGATCCCTT AGACTCTCTTGCGCAGCA AGCGGGTTCACCTTTGAC AAATATGGGATGCACTGG GTGAGACAGGCTCCAGGG AAGGGTCTGGAGTGGGTG TCTGGCGTTTCATATAAT GCTGGTACCACAGCGTAC GCTGACTCTGTGAGAGGC AGATTCACTATCTCCAGA GATAACGCCAAAAACAGC TTATACCTGCAGATGAAT TCACTGAGAGCCGAGGAC ACAGCCCTGTACTATTGT | 233 | CAGTCTGCACTTACTCA GCCAGCCAGTGTGTCTG GGAGTCCTGGACAGTC GATCACCATTTCCTGCA CCGGATCAAGTAGCAA TATCGGTGGCTATAATT ATGTGTCCTGGTACCAG CAGCACCCAGGCAAGG CCCCCAAACTGATGATT TACGACGTTACCAATCG CCCCTCAGGGGTCTCCA ATCGCTTTTCTGGCAGT AAAAGCGGAAACACAG CCTCCCTGACTATCAGC GGCCTCCAAGCTGAAG ACGAGGCTGATTATTAT |

TABLE 15-continued

Polynucleotide sequences of heavy-chain and light-chain variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | GCTAGAGGAAGATATTCG GATGTGTGGGCCAGGGA ACTACAGTTACCGTCTCC TCA | | TGTGGTTCTTACTCTAA CTCCAATTTTTACGTTT TCGGAACCGGGACAAA GGTGACCGTCTTGGGC |
| A23-3F03 | 91 | GAAGTGCAGCTGGTCGAG AGTGGGGGAGGCTTGGTA CAACCTGGAAGATCCCTT AGACTCTCTTGCGCAGCA AGCGGGTTCACCTTTGAC ACATATGGGATGCACTGG GTGAGACAGGCTCCAGGG AAGGGTCTGGAGTGGGTG TCTGGCATTTCATATAATT CTGGTAACATAGCGTACG CTGACTCTGTGAAAGGCA GATTCACTATCTCCAGAG ATAACGCCAAAAACAGCT TATACCTGCAGATGAATT CACTGAGAGCCGAGGACA CAGCCCTGTACTATTGTG CTAGAGGAAGATATTCGG ATGTGTGGGGCCAGGGAA CTACAGTTACCGTCTCCTCA | 235 | CAGTCTGCACTTACTCA GCCAGCCAGTGTGTCTG GGAGTCCTGGACAGTC GATCACCATTTCCTGCG GCGGATCAAGTAGCAA TATCGGTAGCTATAATT ATGTGTCCTGGTACCAG CAGCACCCAGGCAAGG CCCCCAAACTGATGATT TACGACGTAACAAAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGGTTCTTACGATA GCAACACTTTTTACGTT TTCGGAACCGGGACAA AGGTGACCGTCTTGGGC |
| A21-4F07 | 93 | GAAGTGCAGCTGGTCGAG AGTGGGGGAGGCTTGGTA CAACCTGGAAGATCCCTT AGACTCTCTTGCGCAGCA AGCGGGTTCACCTTTGAC GCCTATGGGATGAACTGG GTGAGACAGGCTCCAGGG AAGGGTCTGGAGTGGGTG TCTGGCATTTCATATAAT GCTGGTAACAAAGCGTAC GCTGACTCTGTGAAAGGC AGATTCACTATCTCCAGA GATAACGCCAAAAACAGC TTATACCTGCAGATGAAT TCACTGAGAGCCGAGGAC ACAGCCCTGTACTATTGT GCTAGAGGAAGATATTCG GATGTGTGGGCCAGGGA ACTACAGTTACCGTCTCC TCA | 237 | CAGTCTGCACTTACTCA GCCAGCCAGTGTGTCTG GGAGTCCTGGACAGTC GATCACCATTTCCTGCA GCGGAACAAGTAGCAA TGTCGGTGGCTATAATT ATGTGTCCTGGTACCAG CAGCACCCAGGCAAGG CCCCCAAACTGATGATT TACGACGTTAGCGATCG CCCCTCAGGGGTCTCCA ATCGCTTTTCTGGCAGT AAAAGCGGAAACACAG CCTCCCTGACTATCAGC GGCCTCCAAGCTGAAG ACGAGGCTGATTATTAT TGTGGTTCTTACTCTAA CTCCAATTTTTACGTTT TCGGAACCGGGACAAA GGTGACCGTCTTGGGC |
| A24-1A03 | 95 | GAAGTGCAGCTGGTCGAG AGTGGGGGAGGCTTGGTA CAACCTGGAAGATCCCTT AGACTCTCTTGCGCAGCA AGCGGGTTCACCTTTGAC GCATATGGGATGAACTGG GTGAGACAGGCTCCAGGG AAGGGTCTGGAGTGGGTG TCTGGCATTTCATATAAT GCTGGTAACACAGCGTAC GCTGACTCTGTGAAAGGC AGATTCACTATCTCCAGA GATAACGCCAAAAACAGC TTATACCTGCAGATGAAT TCACTGAGAGCCGAGGAC ACAGCCCTGTACTATTGT GCTAGAGGAAGATATTCG GATGTGTGGGCCAGGGA ACTACAGTTACCGTCTCC TCA | 239 | CAGTCTGCACTTACTCA GCCAGCCAGTGTGTCTG GGAGTCCTGGACAGTC GATCACCATTTCCTGCG GCGGATCAAGTAGCAA TGTCGGTGGCTATAATT ATGTGTCCTGGTACCAG CAGCACCCAGGCAAGG CCCCCAAACTGATGATT TACGACGTTAGCAAGC GCCCCTCAGGGGTCTC AATCGCTTTTCTGGCAG TAAAAGCGGAAACACA GCCTCCCTGACTATCAG CGGCCTCCAAGCTGAA GACGAGGCTGATTATTA TTGTGGTTCTTACTCTA ACTCCAATTTTTACGTT TTCGGAACCGGGACAA AGGTGACCGTCTTGGGC |
| A24-1H11 | 97 | GAAGTGCAGCTGGTCGAG AGTGGGGGAGGCTTGGTA CAACCTGGAAGATCCCTT | 241 | CAGTCTGCACTTACTCA GCCAGCCAGTGTGTCTG GGAGTCCTGGACAGTC |

TABLE 15-continued

Polynucleotide sequences of heavy-chain and light-chain
variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | AGACTCTCTTGCGCAGCA<br>AGCGGGTTCACCTTTGAC<br>GCATATGGGATGCACTGG<br>GTGAGACAGGCTCCAGGG<br>AAGGGTCTGGAGTGGGTG<br>TCTGGCATTTCATATAATT<br>CTGGTACCACAGCGTACG<br>CTGACTCTGTGAGAGGCA<br>GATTCACTATCTCCAGAG<br>ATAACGCCAAAAACAGCT<br>TATACCTGCAGATGAATT<br>CACTGAGAGCCGAGGACA<br>CAGCCCTGTACTATTGTG<br>CTAGAGGAAGATATTCGG<br>ATGTGTGGGGCCAGGGAA<br>CTACAGTTACCGTCTCCTCA | | GATCACCATTTCCTGCA<br>CCGGATCAAGTAGCGA<br>TGTCGGTGGCTATAATT<br>ATGTGTCCTGGTACCAG<br>CAGCACCCAGGCAAGG<br>CCCCCAAACTGATGATT<br>TACGAAGTTAACAAGC<br>GCCCCTCAGGGGTCTCC<br>AATCGCTTTTCTGGCAG<br>TAAAAGCGGAAACACA<br>GCCTCCCTGACTATCAG<br>CGGCCTCCAAGCTGAA<br>GACGAGGCTGATTATTA<br>TTGTGCTTCTTACTCTA<br>GCAACACTTTTTACGTT<br>TTCGGAACCGGGACAA<br>AGGTGACCGTCTTGGGC |
| A21-3D09 | 99 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>AACTATGGGATGAACTGG<br>GTGAGACAGGCTCCAGGG<br>AAGGGTCTGGAGTGGGTG<br>TCTGGCATTTCATATAATT<br>CTGGTACCAAAGCGTACG<br>CTGACTCTGTGAAAGGCA<br>GATTCACTATCTCCAGAG<br>ATAACGCCAAAAACAGCT<br>TATACCTGCAGATGAATT<br>CACTGAGAGCCGAGGACA<br>CAGCCCTGTACTATTGTG<br>CTAGAGGAAGATATTCGG<br>ATGTGTGGGGCCAGGGAA<br>CTACAGTTACCGTCTCCTCA | 243 | CAGTCTGCACTTACTCA<br>GCCAGCCAGTGTGTCTG<br>GGAGTCCTGGACAGTC<br>GATCACCATTTCCTGCA<br>GCGGAACAAGTAGCAA<br>TGTCGGTGGCTATAATT<br>ATGTGTCCTGGTACCAG<br>CAGCACCCAGGCAAGG<br>CCCCCAAACTGATGATT<br>TACGACGTTAACAAGC<br>GCCCCTCAGGGGTCTCC<br>AATCGCTTTTCTGGCAG<br>TAAAAGCGGAAACACA<br>GCCTCCCTGACTATCAG<br>CGGCCTCCAAGCTGAA<br>GACGAGGCTGATTATTA<br>TTGTGGTTCTTACTCTA<br>ACTCCAATTTTTACGTT<br>TTCGGAACCGGGACAA<br>AGGTGACCGTCTTGGGC |
| A24-1D10 | 101 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>AACTATGGGATGCACTGG<br>GTGAGACAGGCTCCAGGG<br>AAGGGTCTGGAGTGGGTG<br>TCTGGCATTTCATATAATT<br>CTGGTAACAAAGCGTACG<br>CTGACTCTGTGAAAGGCA<br>GATTCACTATCTCCAGAG<br>ATAACGCCAAAAACAGCT<br>TATACCTGCAGATGAATT<br>CACTGAGAGCCGAGGACA<br>CAGCCCTGTACTATTGTG<br>CTAGAGGAAGATATTCGG<br>ATGTGTGGGGCCAGGGAA<br>CTACAGTTACCGTCTCCTCA | 245 | CAGTCTGCACTTACTCA<br>GCCAGCCAGTGTGTCTG<br>GGAGTCCTGGACAGTC<br>GATCACCATTTCCTGCA<br>GCGGATCAAGTAGCGA<br>TATCGGTGGCTATAATT<br>ATGTGTCCTGGTACCAG<br>CAGCACCCAGGCAAGG<br>CCCCCAAACTGATGATT<br>TACGACGTTACCGATCG<br>CCCCTCAGGGGTCTCCA<br>ATCGCTTTTCTGGCAGT<br>AAAAGCGGAAACACAG<br>CCTCCCTGACTATCAGC<br>GGCCTCCAAGCTGAAG<br>ACGAGGCTGATTATTAT<br>TGTGGTTCTTACTCTAA<br>CAACAATTTTTACGTTT<br>TCGGAACCGGGACAAA<br>GGTGACCGTCTTGGGC |
| A21-4B04 | 103 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>GCCTATGGGATGCACTGG<br>GTGAGACAGGCTCCAGGG<br>AAGGGTCTGGAGTGGGTG<br>TCTGGCATTTCATATGAT<br>GCTGGTAACATAGCGTAC<br>GCTGACTCTGTGAGAGGC | 247 | CAGTCTGCACTTACTCA<br>GCCAGCCAGTGTGTCTG<br>GGAGTCCTGGACAGTC<br>GATCACCATTTCCTGCG<br>CCGGAACAAGTAGCAA<br>TATCGGTGGCTATAATT<br>ATGTGTCCTGGTACCAG<br>CAGCACCCAGGCAAGG<br>CCCCCAAACTGATGATT<br>TACGACGTTAGCAATCG<br>CCCCTCAGGGGTCTCCA |

TABLE 15-continued

Polynucleotide sequences of heavy-chain and light-chain variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | AGATTCACTATCTCCAGA<br>GATAACGCCAAAAACAGC<br>TTATACCTGCAGATGAAT<br>TCACTGAGAGCCGAGGAC<br>ACAGCCCTGTACTATTGT<br>GCTAGAGGAAGATATTCG<br>GATGTGTGGGGCCAGGGA<br>ACTACAGTTACCGTCTCC<br>TCA | | ATCGCTTTTCTGGCAGT<br>AAAAGCGGAAACACAG<br>CCTCCCTGACTATCAGC<br>GGCCTCCAAGCTGAAG<br>ACGAGGCTGATTATTAT<br>TGTGCTTCTTACTCTAG<br>CAACACTTTTTACGTTT<br>TCGGAACCGGGACAAA<br>GGTGACCGTCTTGGGC |
| A23-4C12 | 105 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>GCATATGGGATGAACTGG<br>GTGAGACAGGCTCCAGGG<br>AAGGGTCTGGAGTGGGTG<br>TCTGGCGTTTCATATAATT<br>CTGGTAACAAAGCGTACG<br>CTGACTCTGTGAGAGGCA<br>GATTCACTATCTCCAGAG<br>ATAACGCCAAAAACAGCT<br>TATACCTGCAGATGAATT<br>CACTGAGAGCCGAGGACA<br>CAGCCCTGTACTATTGTG<br>CTAGAGGAAGATATTCGG<br>ATGTGTGGGGCCAGGGAA<br>CTACAGTTACCGTCTCCTCA | 249 | CAGTCTGCACTTACTCA<br>GCCAGCCAGTGTGTCTG<br>GGAGTCCTGGACAGTC<br>GATCACCATTTCCTGCA<br>GCGGAACAAGTAGCGA<br>TGTCGGTGGCTATAATT<br>ATGTGTCCTGGTACCAG<br>CAGCACCCAGGCAAGG<br>CCCCCAAACTGATGATT<br>TACGACGTTACCAAGC<br>GCCCCTCAGGGGTCTCC<br>AATCGCTTTTCTGGCAG<br>TAAAAGCGGAAACACA<br>GCCTCCCTGACTATCAG<br>CGGCCTCCAAGCTGAA<br>GACGAGGCTGATTATTA<br>TTGTGGTTCTTACTCTA<br>GCAACACTTTTTACGTT<br>TTCGGAACCGGGACAA<br>AGGTGACCGTCTTGGGC |
| A21-4G06 | 107 | GAAGTGCAGCTGGTCGAG<br>AGTGGGGGAGGCTTGGTA<br>CAACCTGGAAGATCCCTT<br>AGACTCTCTTGCGCAGCA<br>AGCGGGTTCACCTTTGAC<br>ACATATGGGATGAACTGG<br>GTGAGACAGGCTCCAGGG<br>AAGGGTCTGGAGTGGGTG<br>TCTGGCATTTCATATAAT<br>GCTGGTACCAAAGCGTAC<br>GCTGACTCTGTGAGAGGC<br>AGATTCACTATCTCCAGA<br>GATAACGCCAAAAACAGC<br>TTATACCTGCAGATGAAT<br>TCACTGAGAGCCGAGGAC<br>ACAGCCCTGTACTATTGT<br>GCTAGAGGAAGATATTCG<br>GATGTGTGGGGCCAGGGA<br>ACTACAGTTACCGTCTCC<br>TCA | 251 | CAGTCTGCACTTACTCA<br>GCCAGCCAGTGTGTCTG<br>GGAGTCCTGGACAGTC<br>GATCACCATTTCCTGCG<br>CCGGATCAAGTAGCAA<br>TGTCGGTGGCTATAATT<br>ATGTGTCCTGGTACCAA<br>CAGCACCCAGGCAAGG<br>CCCCCAAACTGATGATT<br>TACGACGTAACAAAGC<br>GCCCCTCAGGGGTCTCC<br>AATCGCTTTTCTGGCAG<br>TAAAAGCGGAAACACA<br>GCCTCCCTGACTATCAG<br>CGGCCTCCAAGCTGAA<br>GACGAGGCTGATTATTA<br>TTGTGGTTCTTACTCTA<br>ACTCCAATTTTTACGTT<br>TTCGGAACCGGGACAA<br>AGGTGACCGTCTTGGGC |
| A23-3E04 | 109 | GAAGTGCAGCTGGTCGAG<br>AGTGGGGGAGGCTTGGTA<br>CAACCTGGAAGAT<br>CCCTTAGACTCTCTTGCGC<br>AGCAAGCGGGTTCACCTT<br>TGACAAATATGGGATGCA<br>CTGGGTGAGACAGGCTCC<br>AGGGAAGGGTCTGGAGTG<br>GGTGTCTGGCATTTCATA<br>TAATGCTGGTACCACAGC<br>GTACGCTGACTCTGTGAA<br>AGGCAGATTCACTATCTC<br>CAGAGATAACGCCAAAA<br>ACAGCTTATACCTGCAGA<br>TGAATTCACTGAGAGCCG<br>AGGACACAGCCCTGTACT | 253 | CAGTCTGCACTTACTCA<br>GCCAGCCAGTGTGTCTG<br>GGAGTCCTGGACAGTC<br>GATCACCATTTCCTGCA<br>CCGGATCAAGTAGCGA<br>TGTCGGTGGCTATAATT<br>ATGTGTCCTGGTACCAG<br>CAGCACCCAGGCAAGG<br>CCCCCAAACTGATGATT<br>TACGACGTTACCGATCG<br>CCCCTCGGGGTCTCCA<br>ATCGCTTTTCTGGCAGT<br>AAAAGCGGAAACACAG<br>CCTCCCTGACTATCAGC<br>GGCCTCCAAGCTGAAG<br>ACGAGGCTGATTATTAT |

TABLE 15-continued

Polynucleotide sequences of heavy-chain and light-chain
variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | ATTGTGCTAGAGGAAGAT ATTCGGATGTGTGGGGCC AGGGAACTACAGTTACCG TCTCCTCA | | TGTGGTTCTTACTCTAA CTCCAATTTTTACGTTT TCGGAACCGGGACAAA GGTGACCGTCTTGGGC |
| A24-1C09 | 111 | GAAGTGCAGCTGGTCGAG AGTGGGGGAGGCTTGGTA CAACCTGGAAGATCCCTT AGACTCTCTTGCGCAGCA AGCGGGTTCACCTTTGAC GCATATGGGATGAACTGG GTGAGACAGGCTCCAGGG AAGGGTCTGGAGTGGGTG TCTGGCATTTCATATAAT GGTGGTAACAAAGCGTAC GCTGACTCTGTGAGAGGC AGATTCACTATCTCCAGA GATAACGCCAAAAACAGC TTATACCTGCAGATGAAT TCACTGAGAGCCGAGGAC ACAGCCCTGTACTATTGT GCTAGAGGAAGATATTCG GATGTGTGGGGCCAGGGA ACTACAGTTACCGTCTCC TCA | 255 | CAGTCTGCACTTACTCA GCCAGCCAGTGTGTCTG GGAGTCCTGGACAGTC GATCACCATTTCCTGCA CCGGAACAAGTAGCAA TGTCGGTAGCTATAATT ATGTGTCCTGGTACCAG CAGCACCCAGGCAAGG CCCCCAAACTGATGATT TACGACGTTAACGATCG CCCCTCAGGGGTCTCCA ATCGCTTTTCTGGCAGT AAAAGCGGAAACACAG CCTCCCTGACTATCAGC GGCCTCCAAGCTGAAG ACGAGGCTGATTATTAT TGTGGTTCTTACGATAG CAACACTTTTTACGTTT TCGGAACCGGGACAAA GGTGACCGTCTTGGGC |
| A24-1C04 | 113 | GAAGTGCAGCTGGTCGAG AGTGGGGGAGGCTTGGTA CAACCTGGAAGATCCCTT AGACTCTCTTGCGCAGCA AGCGGGTTCACCTTTGAC GGATATGGGATGCACTGG GTGAGACAGGCTCCAGGG AAGGGTCTGGAGTGGGTG TCTGGCATTTCATATAATT CTGGTAGCACAGCGTACG CTGACTCTGTGAGAGGCA GATTCACTATCTCCAGAG ATAACGCCAAAAACAGCT TATACCTGCAGATGAATT CACTGAGAGCCGAGGACA CAGCCCTGTACTATTGTG CTAGAGGAAGATATTCGG ATGTGTGGGGCCAGGGAA CTACAGTTACCGTCTCCTCA | 257 | CAGTCTGCACTTACTCA GCCAGCCAGTGTGTCTG GGAGTCCTGGACAGTC GATCACCATTTCCTGCA CCGGAACAAGTAGCAA TATCGGTGGCTATAATT ATGTGTCCTGGTACCAG CAGCACCCAGGCAAGG CCCCCAAACTGATGATT TACGACGTTACCAAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGGTTCTTACTCTA ACTCCAATTTTTACGTT TTCGGAACCGGGACAA AGGTGACCGTCTTGGGC |
| A25-1H10 | 115 | GAAGTGCAGCTGGTCGAG AGTGGGGGAGGCTTGGTA CAACCTGGAAGATC CCTTAGACTCTCTTGCGC AGCAAGCGGGTTCACCTT TGACGCCTATGGGATGCA CTGGGTGAGACAGGCTCC AGGGAAGGGTCTGGAGTG GGTGTCTGGCGTTTCATA TAATGCTGGTACCACAGC GTACGCTGACTCTGTGAG AGGCAGATTCACTATCTC CAGAGATAACGCCAAAA ACAGCTTATACCTGCAGA TGAATTCACTGAGAGCCG AGGACACAGCCCTGTACT ATTGTGCTAGAGGAAGAT ATTCGGATGTGTGGGGCC AGGGAACTACAGTTACCG TCTCCTCA | 259 | CAGTCTGCACTTACTCA GCCAGCCAGTGTGTCTG GGAGTCCTGGACAGTC GATCACCATTTCCTGCG GCGGATCAAGTAGCGA TGTCGGTGGCTATAATT ATGTGTCCTGGTACCAG CAGCACCCAGGCAAGG CCCCCAAACTGATGATT TACGAAGTTAGCAATC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGGTTCTTACTCTA ACTCCAATTTTTACGTT TTCGGAACCGGGACAA AGGTGACCGTCTTGGGC |
| A21-4D08 | 117 | GAAGTGCAGCTGGTCGAG AGTGGGGGAGGCTTGGTA CAACCTGGAAGATCCCTT | 261 | CAGGCGGAGGTGGGTC CGGCGGTGGCGGATCG CAGTCTGCACTTACTCA |

TABLE 15-continued

Polynucleotide sequences of heavy-chain and light-chain variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | AGACTCTCTTGCGCAGCA AGCGGGTTCACCTTTGAC ACATATGGGATGCACTGG GTGAGACAGGCTCCAGGG AAGGGTCTGGAGTGGGTG TCTGGCGTTTCATATAATT CTGGTAACAAAGCGTACG CTGACTCTGTGAAAGGCA GATTCACTATCTCCAGAG ATAACGCCAAAAACAGCT TATACCTGCAGATGAATT CACTGAGAGCCGAGGACA CAGCCCTGTACTATTGTG CTAGAGGAAGATATTCGG ATGTGTGGGGCCAGGGAA CTACAGTTACCGTCTCCTCA | | GCCAGCCAGTGTGTCTG GGAGTCCTGGACAGTC GATCACCATTTCCTGCG GCGGAACAAGTAGCGA TGTCGGTGGCTATAATT ATGTGTCCTGGTACCAG CAGCACCCAGGCAAGG CCCCCAAACTGATGATT TACGACGTTAACGATCG CCCCTCAGGGGTCTCCA ATCGCTTTTCTGGCAGT AAAAGCGGAAACACAG CCTCCCTGACTATCAGC GGCCTCCAAGCTGAAG ACGAGGCTGATTATTAT TGTGGTTCTTACTCTAA CAACAATTTTTACGTTT TCGGAACCGGGACAAA GGTGACCGTCTTGGGC |
| A24-1D08 | 119 | GAAGTGCAGCTGGTCGAG AGTGGGGGAGGCTTGGTA CAACCTGGAAGATCCCTT AGACTCTCTTGCGCAGCA AGCGGGTTCACCTTTGAC AACTATGGGATGCACTGG GTGAGACAGGCTCCAGGG AAGGGTCTGGAGTGGGTG TCTGGCATTTCATATAATT CTGGTAACACAGGGTACG CTGACTCTGTGAGAGGCA GATTCACTATCTCCAGAG ATAACGCCAAAAACAGCT TATACCTGCAGATGAATT CACTGAGAGCCGAGGACA CAGCCCTGTACTATTGTG CTAGAGGAAGATATTCGG ATGTGTGGGGCCAGGGAA CTACAGTTACCGTCTCCTCA | 263 | CAGGCGGAGGTGGGTC CGGCGGTGGCGGATCG CAGTCTGCACTTACTCA GCCAGCCAGTGTGTCTG GGAGTCCTGGACAGTC GATCACCATTTCCTGCG CCGGATCAAGTAGCAA TGTCGTGAGCTATAATT ATGTGTCCTGGTACCAG CAGCACCCAGGCAAGG CCCCCAAACTGATGATT TACGACGTTAACAAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGGTTCTTACGATA GCAACACTTTTTACGTT TTCGGAACCGGGACAA AGGTGACCGTCTTGGGC |
| A24-1A08 | 121 | GAAGTGCAGCTGGTCGAG AGTGGGGGAGGCTTGGTA CAACCTGGAAGATCCCTT AGACTCTCTTGCGCAGCA AGCGGGTTCACCTTTGAC GCATATGGGATGCACTGG GTGAGACAGGCTCCAGGG AAGGGTCTGGAGTGGGTG TCTGGCATTTCATATGAT GCTGGTAACACAGCGTAC GCTGACTCTGTGAGAGGC AGATTCACTATCTCCAGA GATAACGCCAAAAACAGC TTATACCTGCAGATGAAT TCACTGAGAGCCGAGGAC ACAGCCCTGTACTATTGT GCTAGAGGAAGATATTCG GATGTGTGGGGCCAGGGA ACTACAGTTACCGTCTCC TCA | 265 | CAGTCTGCACTTACTCA GCCAGCCAGTGTGTCTG GGAGTCCTGGACAGTC GATCACCATTTCCTGCA CCGGATCAAGTAGCAA TATCGGTGGCTATAATT ATGTGTCCTGGTACCAG CAGCACCCAGGCAAGG CCCCCAAACTGATGATT TACGAAGTTAACAATC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGCTTCTTACTCTA GCAACACTTTTTACGTT TTCGGAACCGGGACAA AGGTGACCGTCTTGGGC |
| A21-4A07 | 123 | GAAGTGCAGCTGGTCGAG AGTGGGGGAGGCTTGGTA CAACCTGGAAGATCCCTT AGACTCTCTTGCGCAGCA AGCGGGTTCACCTTTGAC ACCTATGGGATGCACTGG GTGAGACAGGCTCCAGGG | 267 | CAGTCTGCACTTACTCA GCCAGCCAGTGTGTCTG GGAGTCCTGGACAGTC GATCACCATTTCCTGCG CCGGATCAAGTAGCAA TATCGGTGGCTATAATT ATGTGTCCTGGTACCAG |

TABLE 15-continued

Polynucleotide sequences of heavy-chain and light-chain
variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | AAGGGTCTGGAGTGGGTG TCTGGCGTTTCATATAATT CTGGTAGCAAAGCGTACG CTGACTCTGTGAAAGGCA GATTCACTATCTCCAGAG ATAACGCCAAAAACAGCT TATACCTGCAGATGAATT CACTGAGAGCCGAGGACA CAGCCCTGTACTATTGTG CTAGAGGAAGATATTCGG ATGTGTGGGGCCAGGGAA CTACAGTTACCGTCTCCTCA | | CAGCACCCAGGCAAGG CCCCCAAACTGATGATT TACGACGTTAACGATCG CCCCTCAGGGGTCTCCA ATCGCTTTTCTGGCAGT AAAAGCGGAAACACAG CCTCCCTGACTATCAGC GGCCTCCAAGCTGAAG ACGAGGCTGATTATTAT TGTGGTTCTTACTCTAA CTCCAATTTTTACGTTT TCGGAACCGGGACAAA GGTGACCGTCTTGGGC |
| A24-1B09 | 125 | GAAGTGCAGCTGGTCGAG AGTGGGGGAGGCTTGGTA CAACCTGGAAGATCCCTT AGACTCTCTTGCGCAGCA AGCGGGTTCACCTTTGAC AGATATGGGATGCACTGG GTGAGACAGGCTCCAGGG AAGGGTCTGGAGTGGGTG TCTGGCGTTTCATATGAT GGTGGTACCACAGCGTAC GCTGACTCTGTGAGAGGC AGATTCACTATCTCCAGA GATAACGCCAAAAACAGC TTATACCTGCAGATGAAT TCACTGAGAGCCGAGGAC ACAGCCCTGTACTATTGT GCTAGAGGAAGATATTCG GATGTGTGGGGCCAGGGA ACTACAGTTACCGTCTCC TCA | 269 | CAGTCTTCACTTACTCA GCCAGCCAGTGTGTCTG GGAGTCCTGGACAGTC GATCACCATTTCCTGCA CCGGAACAAGTAGCAA TATCGGTAGCTATAATT ATGTGTCCTGGTACCAG CAGCACCCAGGCAAGG CCCCCAAACTGATGATT TACGACGTTAACAAGC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGGTTCTTACGATA GCAACACTTTTTACGTT TTCGGAACCGGGACAA AGGTGACCGTCTTGGGC |
| A24-1E07 | 127 | GAAGTGCAGCTGGTCGAG AGTGGGGGAGGCTTGGTA CAACCTGGAAGATCCCTT AGACTCTCTTGCGCAGCA AGCGGGTTCACCTTTGAC GAATATGGGATGCACTGG GTGAGACAGGCTCCAGGG AAGGGTCTGGAGTGGGTG TCTGGCATTTCATATGAT GCTGGTAGCACAGCGTAC GCTGACTCTGTGAGAGGC AGATTCACTATCTCCAGA GATAACGCCAAAAACAGC TTATACCTGCAGATGAAT TCACTGAGAGCCGAGGAC ACAGCCCTGTACTATTGT GCTAGAGGAAGATATTCG GATGTGTGGGGCCAGGGA ACTACAGTTACCGTCTCC TCA | 271 | CAGTCTGCACTTACTCA GCCAGCCAGTGTGTCTG GGAGTCCTGGACAGTC GATCACCATTTCCTGCG CCGGATCAAGTAGCAA TGTCGGTGGCTATAATT ATGTGTCCTGGTACCAG CAGCACCCAGGCAAGG CCCCCAAACTGATGATT TACGAAGTTAGCAATC GCCCCTCAGGGGTCTCC AATCGCTTTTCTGGCAG TAAAAGCGGAAACACA GCCTCCCTGACTATCAG CGGCCTCCAAGCTGAA GACGAGGCTGATTATTA TTGTGGTTCTTACGATA GCAACACTTTTTACGTT TTCGGAACCGGGACAA AGGTGACCGTCTTGGGC |
| H21-3A07 | 129 | CAAGTGCAGCTGGTGGAG TCTGGCGGAGGTGTGGTC CAACCCGGTAAGTCTCTG AGACTCTCCTGCGCAGCC TCTGGCTTTACATTCAGTA ACTACTACATGAATTGGG TCAGACAGGCTCCAGGAA AAGGCTTGGAGTGGTGG CCACTGTTTCTTACGATA GCGGCAACAAATACTATG CAGATTCTGTGAAAGGGC GATTCACCATTTCCAGAG ACAACTCTAAGAACACTC TTTATCTGCAGATGAATA GCCTGAGAGCTGAAGACA | 273 | GACATCCAGATGACCC AGTCTCCTTCCACCCTG TCTGCATCTGTAGGAGA CAGAGTCACCATCACTT GTCGAGCTAGTCAGAG TATTAGTAACCGGTTGG CTTGGTATCAGCAGAA ACCAGGGAAAGCCCCT AAGCTCCTGATCTATAA GGCATCTAACTTAGAA AGTGGGGTCCCATCAA GGTTCAGCGGCAGTGG ATCTGGGACAGAATTC ACTCTCACCATCAGCAG CCTGCAGCCTGATGATT |

TABLE 15-continued

Polynucleotide sequences of heavy-chain and light-chain variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | CTGCCGTTTACTATTGTGC GAGGGGGAGTTGAAGAC GGGATGCTTTTGACGTGT GGGGCCAGGGCACAATG GTCACCGTATCATCA | | TTGCAACTTACTATTGT CAACAGACGAACAGTT TCCCTCTCACTTTCGGC GGAGGGACCAAGGTGG AGATCAAA |
| H21-4D11 | 131 | CAAGTGCAGCTGGTGGAG TCTGGCGGAGGTGTGGTC CAACCTGGAAGGTCTCTG AGACTCTCCTGCGCAGCC TCTGGATTTACATTCAGT AACTACGCCATGAATTGG GTCAGACAGGCTCCAGGA AAAGGCTTGGAGTGGGTG GCCATTATTTCTTACGATA GCAGCAGCAAATACTATG CAGATTCTGTGAAAGGGC GATTCACCATTTCCAGAG ACAACTCTAAGAACACTC TTTATCTGCAGATGAATA GCCTGAGAGCTGAAGACA CTGCCGTTTACTATTGTGC GAGGGGGAGTGGGAAGC GGGATGCTTTTGACGTGT GGGGCCAGGGCACAATG GTCACCGTATCATCA | 275 | GACATCCAGATGACCC AGTCTCCTTCCACCCTG TCTGCATCTGTAGGAGA CAGAGTCACCATCACTT GTCAAGCTAGTCAGGG TATTAGTAACCGGTTGG CTTGGTATCAGCAGAA ACCAGGGAAAGCCCCT AAGCTCCTGATCTATAA GGCATCTAACTTACAAA GTAGGGTCCCATCAAG GTTCAGCGGCAGTGGA TCTGGGACAGAATTCAC TCTCACCATCAGCAGCC TGCAGCCTGATGATTTT GCAACTTACTATTGTCA ACAGACGAACAGTTTC CCTCTCACTTTCGGCGG AGGGACCAAGGTGGAG ATCAAA |
| H21-3C11 | 133 | CAAGTGCAGCTGGTGGAG TCTGGCGGAGGTGTGGTC CAACCTGGAAGGTCTCTG AGACTCTCCTGCGCAGCC TCTGGCTTTACATTCAGTA ACTACGCCATGCATTGGG TCAGACAGGCTCCAGGAA AAGGCTTGGAGTGGGTGG CCGTTGTTTCTTACGATGG CGGCAACATATACTATGC AGATTCTGTGAAAGGGCG ATTCACCATTTCCAGAGA CAACTCTAAGAACACTCT TTATCTGCAGATGAATAG CCTGAGAGCTGAAGACAC TGCCGTTTACTATTGTGCG AGGGGGAGTGGGCGGCG GGATGCTTTTGACGTGTG GGGCCAGGGCACAATGGT CACCGTATCATCA | 277 | GACATCCAGATGACCC AGTCTCCTTCCACCCTG TCTGCATCTGTAGGAGA CAGAGTCACCATCACTT GTCGAGCTAGTCAGAG TATTAGTAACCGGTTGG CTTGGTATCAGCAGAA ACCAGGGAAAGCCCCT AAGCTCCTGATCTATAA GGCATCTAGCTTACAAA GTGGGGTCCCATCAAG GTTCAGCGGCAGTGGA TCTGGGACAGAATTCAC TCTCACCATCAGCAGCC TGCAGCCTGATGATTTT GCAACTTACTATTGTCA ACAGACGAACAGTTTC CCTCTCACTTTCGGCGG AGGGACCAAGGTGGAG ATCAAA |
| H21-3A09 | 135 | CAAGTGCAGCTGGTGGAG TCTGGCGGAGGTGTGGTC CAACCTGGAAGGTCTCTG AGACTCTCCTGCGCAGCC TCTGGCTTTACATTCAGTA ACTACGACATTCATTGGG TCAGACAGGCTCCAGGAA AAGGCTTGGAGTGGGTGG CCGTTGTTTCTTACGATGG CAGCAACACATACTATGC AGATTCTGTGAAAGGGCG ATTCACCATTTCCAGAGA CAACTCTAAGAACACTCT TTATCTGCAGATGAATAG CCTGAGAGCTGAAGACAC TGCCGTTTACTATTGTGCG AGGGGGAGTGGGAAGCG GGATGCTTTTGACGTGTG GGGCCAGGGCACAATGGT CACCGTATCATCA | 279 | GACATCCAGATGACCC AGTCTCCTTCCACCCTG TCTGCATCTGTAGGAGA CAGAGTCACCATCACTT GTCGAGCTAGTCAGAG TATTAGTAACCGGTTGG CTTGGTATCAGCAGAA ACCAGGGAAAGCCCCT AAGCTCCTGATCTATAA GGCATCTAACTTACAAA GTGGGGTCCCATCAAG GTTCAGCGGCAGTGGA TCTGGGAAAGAATTCA CTCTCACCATCAGCAGC CTGCAGCCTGATGATTT TGCAACTTACTATTGTC AACAGACGAACAGTTT CCCTCTCACTTTCGGCG GAGGGACCAAGGTGGA GATCAAA |
| H21-4H04 | 137 | CAAGTGCAGCTGGTGGAG TCTGGCGGAGGTGTGGTC | 281 | GACATCCAGATGACCC AGTCTCCTTCCACCCTG |

TABLE 15-continued

Polynucleotide sequences of heavy-chain and light-chain variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | CAACCCGTTTAAGTCTCT GAGACTCTCCTGCGCAGC CTCTGGCTTTACACTTAGT AGCTACGCCATTCATTGG GTCAGACAGGCTCCAGGA AAAGGCTTGGAGTGGGTG GCCGTTGTTTCTTACGATG GCGGCAGCAAATACTATG CAGATTCTGTGAAAGGGC GATTCACCATTTCCAGAG ACAACTCTAAGAACACTC TTTATCTGCAGATGAATA GCCTGAGAGCTGAAGACA CTGCCGTTTACTATTGTGC GAGGGGGAGTGGGAGGC GGGATGCTTTTGACGTGT GGGGCCAGGGCACAATG GTCACCGTATCATCA | | TCTGCATCTGTAGGAGA CAGAGTCACCATCACTT GTCAAGCTAGTCAGAG TATTAGTAGCCGGTTGG CTTGGTATCAGCAGAA ACCAGGGAAAGCCCCT AAGCTCCTGATCTATAA GGCATCTAGCTTACAAA GTGGGGTCCCATCAAG GTTCAGCGGCGGTGGA TCTGGGACAGAATTCAC TCTCACCATCAGCAGCC TGCAGCCTGATGATTTT GCAACTTACTATTGTCA ACAGACGAACAGTTTC CCTCTCACTTTCGGCGG AGGGACCAAGGTGGAG ATCAAA |
| H23-3D08 | 139 | CAAGTGCAGCTGGTGGAG TCTGGCGGAGGTGTGGTC CAACCTGGAAGGTCTCTG AGACTCTCCTGCGCAGAC TCTGGCTTTACATTCAGTG ACTACGACATGCATTGGG TCAGACAGGCTCCAGGAA AAGGCTTGGAGTGGGTGG CCGTTATTTCTTACGATGG CGGCAGCAAATACTATGC AGATTCTGTGAAAGGGCG ATTCACCATTTCCAGAGA CAACTCTAAGAACACTCT TTATCTGCAGATGAATAG CCTGAGAGCTGAAGACAC TGCCGTTTACTATTGTGCG AGGGGGAGTGGGCAGCG GGATGCTTTTGACGTGTG GGGCCAGGGCACAATGGT CACCGTATCATCA | 283 | GACATCCAGATGACCC AGTCTCCTTCCACCCTG TCTGCATCTGTAGGAGA CAGAGTCACCATCACTT GTCAAGCTAGTCAGGG TATTAGTAACCGGTTGG CTTGGTATCAGCAGAA ACCAGGGAAAGCCCCT AAGCTCCTGATCTATAA GGCATCTAACTTAGAA ACTGGGGTCCCATCAA GGTTCAGCGGCAGTGG ATCTGGGACAGAATTC ACTCTCACCATCAGCAG CCTGCAGCCTGATGATT TTGCAACTTACTATTGT CAACAGACGAACAGTT TCCCTCTCACTTTCGGC GGAGGGACCAAGGTGG AGATCAAA |
| H21-4D09 | 141 | CAAGTGCAGCTGGTGGAG TCTGGCGGAGGTGTGGTC CAACCTGGAAGGTCTCTG AGACTCTCCTGCGCAGCC TCTGGCTTTACATTCAGTA ACTACTACATTAATTGGG TCAGACAGGCTCCAGGAA AAGGCTTGGAGTGGGTGG CCAGTGTTTCTTACGATG GCGGCAGCATATACTATG CAGATTCTGTGAAAGGGC GATTCACCATTTCCAGAG ACAACTCTAAGAACACTC TTTATCTGCAGATGAATA GCCTGAGAGCTGAAGACA CTGCCGTTTACTATTGTGC GAGGGGGAGTGGGAGGC GGGATGCTTTTGACGTGT GGGGCCAGGGCACAATG GTCACCGTATCATCA | 285 | GACATCCAGATGACCC AGTCTCCTTCCACCCTG TCTGCATCTGTAGGAGA CAGAGTCACCATCACTT GTCAAGCTAGTCAGGG TATTCGTAACCGGTTGG CTTGGTATCAGCAGAA ACCAGGGAAAGCCCCT AAGCTCCTGATCTATAA GGCATCTAACTTACAAA GTGGGGTCCCATCAAG GTTCAGCGGCAGTGGA TCTGGGACAGAATTCAC TCTCACCATCAGCAGCC TGCAGCCTGATGATTTT GCAACTTACTATTGTCA ACAGACGAACAGTTTC CCTCTCACTTTCGGCGG AGGGACCAAGGTGGAG ATCAAA |
| H24-1D11 | 143 | CAAGTGCAGCTGGTGGAG TCTGGCGGAGGTGTGGTC CAACCTGGAAGGTCTCTG AGACTCTCCTGCGCAGCC TCTGGCTTTACATTCAGTA GCTACGCCATGCACTGGG TCAGACAGGCTCCAGGAA AAGGCTTGGAGTGGGTGG CCGTTATCTCTTACGATG GTAGCAATAAGTACTATG | 287 | GACATCCAGATGACCC AGTCTCCTTCCACCCTG TCTGCATCTGTAGGAGA CAGAGTCACCATCACTT GCCGGGCCAGTCAGAG TATTAGTAGCCGGTTGG CCTGGTATCAGCAGAA ACCAGGGAAAGCCCCT AAGCTCCTGATCTATAA GGCATCTAGCTTAGAA |

TABLE 15-continued

Polynucleotide sequences of heavy-chain and light-chain variable regions of selected antibodies

| Antibody name | heavy-chain variable regions | | light-chain variable regions | |
|---|---|---|---|---|
| | SEQ ID NO: | Polynucleotide sequences | SEQ ID NO: | Polynucleotide sequences |
| | | CAGATTCTGTGAAAGGGC GATTCACCATTTCCAGAG ACAACTCTAAGAACACTC TTTATCTGCAGATGAATA GCCTGAGAGCTGAAGACA CTGCCGTTTACTATTGTGC GAGGGGGAGTGGGGGAC GGGATGCTTTTGACGTGT GGGGCCAGGGCACAATG GTCACCGTATCATCA | | ACTGGGGTCCCATCAA GGTTCAGCGGCAGTGG ATCTGGGACAGAATTC ACTCTCACCATCAGCAG CCTGCAGCCTGATGATT TTGCAACTTACTATTGT CAACAGACGAACAGTT TCCCTCTCACTTTCGGC GGAGGGACCAAGGTGG AGATCAAA |

TABLE 16

CDR3 sequences of heavy-chain and light-chain variable regions of selected antibodies

| Clone name | Heavy-chain variable regions | | | | Light-chain variable regions | | | |
|---|---|---|---|---|---|---|---|---|
| | SEQ ID NO: | CDR1 | CDR2 | CDR3 | SEQ ID NO: | CDR1 | CDR2 | CDR3 |
| A11-C07 | 18 | EYGMH SEQ ID NO: 293 | GVSWNSGS IAYADSVRG SEQ ID NO: 313 | GRYSDV SEQ ID NO: 362 | 162 | TGSSSDVG GYNYVS SEQ ID NO: 374 | DVTKRPS SEQ ID NO: 406 | ASYSSNT FYV SEQ ID NO: 426 |
| A11-G06 | 20 | EYGMH SEQ ID NO: 293 | GVSWNSGS IAYADSVRG SEQ ID NO: 313 | GRMLDV SEQ ID NO: 363 | 164 | TGSSSDVG GYNYVS SEQ ID NO: 374 | DVTKRPS SEQ ID NO: 406 | GSYNNNT FYV SEQ ID NO: 427 |
| A12-C09 | 22 | EYGMH SEQ ID NO: 293 | GVSWNSGS IAYADSVRG SEQ ID NO: 313 | GRTMDV SEQ ID NO: 364 | 166 | TGSSSDVG GYNYVS SEQ ID NO: 374 | DVTKRPS SEQ ID NO: 406 | GSYSSNT FYV SEQ ID NO: 428 |
| A12-E05 | 24 | EYGMH SEQ ID NO: 293 | GVSWNSGS IAYADSVRG SEQ ID NO: 313 | GRSLDV SEQ ID NO: 365 | 168 | TGSSSDVG GYNYVS SEQ ID NO: 374 | DVTKRPS SEQ ID NO: 406 | ASYSSNT FYV SEQ ID NO: 426 |
| A12-E01 | 26 | EYGMH SEQ ID NO: 293 | GVSWNSGS IAYADSVRG SEQ ID NO: 313 | GRLLDV SEQ ID NO: 366 | 170 | TGSSSDVG GYNYVS SEQ ID NO: 374 | DVTKRPS SEQ ID NO: 406 | GSYSNNN FYV SEQ ID NO: 429 |
| A12-E04 | 28 | EYGMH SEQ ID NO: 293 | GVSWNSGS IAYADSVRG SEQ ID NO: 313 | GRLFDV SEQ ID NO: 367 | 172 | TGSSSDVG GYNYVS SEQ ID NO: 374 | DVTKRPS SEQ ID NO: 406 | GSYSNSN FYV SEQ ID NO: 430 |
| A12-F02 | 30 | EYGMH SEQ ID NO: 293 | GVSWNSGS IAYADSVRG SEQ ID NO: 313 | GRYLDV SEQ ID NO: 368 | 174 | TGSSSDVG GYNYVS SEQ ID NO: 374 | DVTKRPS SEQ ID NO: 406 | GSYDSNT FYV SEQ ID NO: 431 |
| A12-H04 | 32 | EYGMH SEQ ID NO: 293 | GVSWNSGS IAYADSVRG SEQ ID NO: 313 | GRLLDV SEQ ID NO: 366 | 176 | TGSSSDVG GYNYVS SEQ ID NO: 374 | DVTKRPS SEQ ID NO: 406 | GAYSNTN FYV SEQ ID NO: 432 |

TABLE 17

CDR sequences of heavy-chain and light-chain variable regions of selected antibodies

| Clone name | heavy-chain variable regions SEQ ID NO: | CDR1 | CDR2 | CDR3 | light-chain variable regions SEQ ID NO: | CDR1 | CDR2 | CDR3 |
|---|---|---|---|---|---|---|---|---|
| A23-3H04 | 34 | TYGMN SEQ ID NO: 294 | GISYNGGTT AYADSVRG SEQ ID NO: 314 | GRYSDV SEQ ID NO: 362 | 178 | GGSSSDVG GYNYVS SEQ ID NO: 375 | DVNKRPS SEQ ID NO: 407 | GSYDSNT FYV SEQ ID NO: 431 |
| A24-1G10 | 38 | AYGMH SEQ ID NO: 295 | GISYNSGTK AYADSVKG SEQ ID NO: 315 | GRYSDV SEQ ID NO: 362 | 182 | GGSSSNIG GYNYVS SEQ ID NO: 376 | DVNKRPS SEQ ID NO: 407 | ASYSNSN FYV SEQ ID NO: 430 |
| A24-1F07 | 40 | AYGMH SEQ ID NO: 295 | GVSYNSGTT AYADSVRG SEQ ID NO: 316 | GRYSDV SEQ ID NO: 362 | 184 | SGSSSNVG SYNYVS SEQ ID NO: 377 | DVTKRPS SEQ ID NO: 406 | GSYSNSN FYV SEQ ID NO: 369 |
| A21-4B10 | 42 | EYGMH SEQ ID NO: 293 | GISYNSGNK AYADSVRG SEQ ID NO: 317 | GRYSDV SEQ ID NO: 362 | 186 | SGSSSNIG GYNYVS SEQ ID NO: 378 | DVSKRPS SEQ ID NO: 408 | GSYDSNT FYV SEQ ID NO: 431 |
| A21-4G04 | 44 | SYGMH SEQ ID NO: 296 | GISYNGGNT AYADSVRG SEQ ID NO: 318 | GRYSDV SEQ ID NO: 362 | 188 | SGSSSNIG GYNYVS SEQ ID NO: 378 | DVNERPS SEQ ID NO: 409 | GSYSNNN FYV SEQ ID NO: 429 |
| A23-3H05 | 46 | AYGMN SEQ ID NO: 297 | GISYNSGTI AYADSVKG SEQ ID NO: 319 | GRYSDV SEQ ID NO: 362 | 190 | GGSSSNVG GYNYVS SEQ ID NO: 379 | DVSNRPS SEQ ID NO: 410 | GSYSNSN FYV SEQ ID NO: 430 |
| A21-3A09 | 48 | NYGMN SEQ ID NO: 298 | GISYNSGTK AYADSVKG SEQ ID NO: 315 | GRYSDV SEQ ID NO: 362 | 192 | SGSSSDIG GYNYVS SEQ ID NO: 380 | DVNKRPS SEQ ID NO: 407 | ASYSSNT FYV SEQ ID NO: 426 |
| A21-4B06 | 50 | SYGMH SEQ ID NO: 296 | GISYNGGSK AYADSVRG SEQ ID NO: 320 | GRYSDV SEQ ID NO: 362 | 194 | SGSSSNIG SYNYVS SEQ ID NO: 381 | DVTDRPS SEQ ID NO: 411 | GSYSSNT FYV SEQ ID NO: 428 |
| A24-1B05 | 52 | KYGMN SEQ ID NO: 299 | GISYNSGNT AYADSVRG SEQ ID NO: 321 | GRYSDV SEQ ID NO: 362 | 196 | AGSSSDIG GYNYVS SEQ ID NO: 382 | DVSKRPS SEQ ID NO: 408 | GSYDSNT FYV SEQ ID NO: 431 |
| A23-3A08 | 54 | AYGMH SEQ ID NO: 295 | GISYNSGTT AYADSVKG SEQ ID NO: 322 | GRYSDV SEQ ID NO: 362 | 198 | AGSSSNIG GYNYVS SEQ ID NO: 383 | DVSKRPS SEQ ID NO: 408 | GSYSNSN FYV SEQ ID NO: 430 |
| A21-4C08 | 56 | TYGMH SEQ ID NO: 300 | GISYNAGNK AYADSVRG SEQ ID NO: 323 | GRYSDV SEQ ID NO: 362 | 200 | SGSSSNVG SYNYVS SEQ ID NO: 377 | DVNNRPS SEQ ID NO: 412 | GSYSSNT FYV SEQ ID NO: 428 |
| A23-4D09 | 58 | AYGMH SEQ ID NO: 295 | GVSYDAGNT AYADSVRG SEQ ID NO: 324 | GRYSDV SEQ ID NO: 362 | 202 | SGSSSNIG SYNYVS SEQ ID NO: 381 | DVTDRPS SEQ ID NO: 411 | GSYSSNT FYV SEQ ID NO: 428 |
| A23-3D03 | 60 | AYGMN SEQ ID NO: 297 | GISYNAGST AYADSVRG SEQ ID NO: 325 | GRYSDV SEQ ID NO: 362 | 204 | TGSSSDVG GYNYVS SEQ ID NO: 374 | DVTNRPS SEQ ID NO: 413 | GSYDSNT FYV SEQ ID NO: 431 |
| A21-4B03 | 62 | AYGMN SEQ ID NO: 297 | GISYNAGNK AYADSVRG SEQ ID NO: 323 | GRYSDV SEQ ID NO: 362 | 206 | SGSSSNIG SYNYVS SEQ ID NO: 381 | DVNKRPS SEQ ID NO: 407 | ASYSSNT FYV SEQ ID NO: 426 |

TABLE 17-continued

CDR sequences of heavy-chain and light-chain variable regions of selected antibodies

| Clone name | heavy-chain variable regions SEQ ID NO: | CDR1 | CDR2 | CDR3 | light-chain variable regions SEQ ID NO: | CDR1 | CDR2 | CDR3 |
|---|---|---|---|---|---|---|---|---|
| A21-3D10 | 64 | NYGMH SEQ ID NO: 301 | GISYDAGTT AYADSVKG SEQ ID NO: 326 | GRYSDV SEQ ID NO: 362 | 208 | GGTSSNIG GYNYVS SEQ ID NO: 384 | DVTNRPS SEQ ID NO: 413 | GSYSNTN FYV SEQ ID NO: 434 |
| A21-3A10 | 66 | AYGMH SEQ ID NO: 295 | GISYNAGNK AYADSVRG SEQ ID NO: 323 | GRYSDV SEQ ID NO: 362 | 210 | AGSSSNIG GYNYVS SEQ ID NO: 383 | DVSKRPS SEQ ID NO: 408 | GSYSNSN FYV SEQ ID NO: 430 |
| A21-4H04 | 68 | SYGMH SEQ ID NO: 296 | GISYNSGNK AYADSVKG SEQ ID NO: 327 | GRYSDV SEQ ID NO: 362 | 212 | SGTSSDIG GYNYVS SEQ ID NO: 386 | DVSKRPS SEQ ID NO: 408 | GSYSNNN FYV SEQ ID NO: 429 |
| A21-4F11 | 70 | AYGMN SEQ ID NO: 297 | GISYNGGTK AYADSVRG SEQ ID NO: 328 | GRYSDV SEQ ID NO: 362 | 214 | GGTSSNIG GYNYVS SEQ ID NO: 384 | DVNDRPS SEQ ID NO: 414 | ASYSSNT FYV SEQ ID NO: 426 |
| A23-3G05 | 72 | TYGMH SEQ ID NO: 300 | GISYNSGTI AYADSVRG SEQ ID NO: 329 | GRYSDV SEQ ID NO: 362 | 216 | AGSSSNIG SYNYVS SEQ ID NO: 385 | DVSNRPS SEQ ID NO: 410 | GSYDSNT FYV SEQ ID NO: 431 |
| A23-3A10 | 74 | KYGMH SEQ ID NO: 302 | GISYNAGSK AYADSVKG SEQ ID NO: 330 | GRYSDV SEQ ID NO: 362 | 218 | AGSSSNIG GYNYVS SEQ ID NO: 383 | DVSDRPS SEQ ID NO: 415 | GSYDSNT FYV SEQ ID NO: 431 |
| A25-1H04 | 76 | AYGMN SEQ ID NO: 297 | GISYNSGNT AYADSVRG SEQ ID NO: 321 | GRYSDV SEQ ID NO: 362 | 220 | AGSSSDIG GYNYVS SEQ ID NO: 382 | DVSERPS SEQ ID NO: 416 | GSYDSNT FYV SEQ ID NO: 431 |
| A23-3B06 | 78 | AYGMH SEQ ID NO: 295 | GISYNSGSK AYADSVKG SEQ ID NO: 331 | GRYSDV SEQ ID NO: 362 | 222 | SGSSSDVG GYNYVS SEQ ID NO: 387 | DVSERPS SEQ ID NO: 416 | GSYDSNT FYV SEQ ID NO: 431 |
| A23-4A09 | 80 | NYGMN SEQ ID NO: 298 | GISYDSGNK AYADSVKG SEQ ID NO: 332 | GRYSDV SEQ ID NO: 362 | 224 | GGSSSNIG GYNYVS SEQ ID NO: 376 | DVTKRPS SEQ ID NO: 406 | ASYSSNT FYV SEQ ID NO: 426 |
| A25-1D09 | 82 | AYGMH SEQ ID NO: 295 | GISYNGGTI AYADSVKG SEQ ID NO: 333 | GRYSDV SEQ ID NO: 362 | 226 | GGTSSDVG SYNYVS SEQ ID NO: 388 | DVNKRPS SEQ ID NO: 407 | GSYSNSN FYV SEQ ID NO: 430 |
| A21-4E10 | 84 | AYGMN SEQ ID NO: 297 | GVSYNAGNK AYADSVRG SEQ ID NO: 334 | GRYSDV SEQ ID NO: 362 | 228 | TGSSSNVG GYNYVS SEQ ID NO: 389 | DVSKRPS SEQ ID NO: 408 | GSYSSNT FYV SEQ ID NO: 428 |
| A23-3C04 | 86 | TYGMH SEQ ID NO: 300 | GISYDSGTT AYADSVKG SEQ ID NO: 335 | GRYSDV SEQ ID NO: 362 | 230 | SGTSSDIG GYNYVS SEQ ID NO: 386 | DVTEPPS SEQ ID NO: 417 | ASYSSNT FYV SEQ ID NO: 426 |
| A23-3G06 | 88 | AYGMN SEQ ID NO: 297 | GISYNSGNI AYADSVRG SEQ ID NO: 336 | GRYSDV SEQ ID NO: 362 | 232 | AGTSSNIG GYNYVS SEQ ID NO: 390 | DVNDRPS SEQ ID NO: 414 | GSYDSNT FYV SEQ ID NO: 431 |
| A24-1E09 | 90 | KYGMH SEQ ID NO: 302 | GVSYNAGTT AYADSVRG SEQ ID NO: 337 | GRYSDV SEQ ID NO: 362 | 234 | TGSSSNIG GYNYVS SEQ ID NO: 391 | DVTNRPS SEQ ID NO: 413 | GSYSNSN FYV SEQ ID NO: 430 |

TABLE 17-continued

CDR sequences of heavy-chain and light-chain variable regions of selected antibodies

| Clone name | heavy-chain variable regions SEQ ID NO: | CDR1 | CDR2 | CDR3 | light-chain variable regions SEQ ID NO: | CDR1 | CDR2 | CDR3 |
|---|---|---|---|---|---|---|---|---|
| A23-3F03 | 92 | TYGMH SEQ ID NO: 300 | GISYNSGNI AYADSVKG SEQ ID NO: 338 | GRYSDV SEQ ID NO: 362 | 236 | GGSSSNIG SYNYVS SEQ ID NO: 392 | DVTKRPS SEQ ID NO: 406 | GSYDSNT FYV SEQ ID NO: 431 |
| A21-4F07 | 94 | AYGMN SEQ ID NO: 297 | GISYNAGNK AYADSVKG SEQ ID NO: 339 | GRYSDV SEQ ID NO: 362 | 238 | SGTSSNVG GYNYVS SEQ ID NO: 393 | DVSDRPS SEQ ID NO: 415 | GSYSNSN FYV SEQ ID NO: 430 |
| A24-1A03 | 96 | AYGMN SEQ ID NO: 297 | GISYNAGNT AYADSVKG SEQ ID NO: 340 | GRYSDV SEQ ID NO: 362 | 240 | GGSSNVG GYNYVS SEQ ID NO: 379 | DVSKRPS SEQ ID NO: 408 | GSYSNSN FYV SEQ ID NO: 430 |
| A24-1H11 | 98 | AYGMH SEQ ID NO: 295 | GISYNSGTT AYADSVRG SEQ ID NO: 341 | GRYSDV SEQ ID NO: 362 | 242 | TGSSSDVG GYNYVS SEQ ID NO: 374 | EVNKRPS SEQ ID NO: 418 | ASYSSNT FYV SEQ ID NO: 426 |
| A21-3D09 | 100 | NYGMN SEQ ID NO: 298 | GISYNSGTK AYADSVKG SEQ ID NO: 315 | GRYSDV SEQ ID NO: 362 | 244 | SGTSSNVG GYNYVS SEQ ID NO: 393 | DVNKRPS SEQ ID NO: 407 | GSYSNSN FYV SEQ ID NO: 430 |
| A24-1D10 | 102 | NYGMH SEQ ID NO: 301 | GISYNSGNK AYADSVKG SEQ ID NO: 327 | GRYSDV SEQ ID NO: 362 | 246 | SGSSSDIG GYNYVS SEQ ID NO: 380 | DVTDRPS SEQ ID NO: 411 | GSYSNNN FYV SEQ ID NO: 429 |
| A21-4B04 | 104 | AYGMH SEQ ID NO: 295 | GISYDAGNI AYADSVRG SEQ ID NO: 342 | GRYSDV SEQ ID NO: 362 | 248 | AGTSSNIG GYNYVS SEQ ID NO: 390 | DVSNRPS SEQ ID NO: 410 | ASYSSNT FYV SEQ ID NO: 426 |
| A23-4C12 | 106 | AYGMN SEQ ID NO: 297 | GVSYNSGNK AYADSVRG SEQ ID NO: 343 | GRYSDV SEQ ID NO: 362 | 250 | SGTSSDVG GYNYVS SEQ ID NO: 394 | DVTKRPS SEQ ID NO: 406 | GSYSSNT FYV SEQ ID NO: 428 |
| A21-4G06 | 108 | TYGMN SEQ ID NO: 294 | GISYNAGTK AYADSVRG SEQ ID NO: 344 | GRYSDV SEQ ID NO: 362 | 252 | AGSSSNVG GYNYVS SEQ ID NO: 395 | DVTKRPS SEQ ID NO: 406 | GSYSNSN FYV SEQ ID NO: 430 |
| A23-3E04 | 110 | KYGMH SEQ ID NO: 302 | GISYNAGTT AYADSVKG SEQ ID NO: 345 | GRYSDV SEQ ID NO: 362 | 254 | TGSSSDVG GYNYVS SEQ ID NO: 374 | DVTDRPS SEQ ID NO: 411 | GSYSNSN FYV SEQ ID NO: 430 |
| A24-1C09 | 112 | AYGMN SEQ ID NO: 297 | GISYNGGNK AYADSVRG SEQ ID NO: 346 | GRYSDV SEQ ID NO: 362 | 256 | TGTSSNVG SYNYVS SEQ ID NO: 396 | DVNDRPS SEQ ID NO: 414 | GSYDSNT FYV SEQ ID NO: 431 |
| A24-1C04 | 114 | GYGMH SEQ ID NO: 303 | GISYNSGST AYADSVRG SEQ ID NO: 347 | GRYSDV SEQ ID NO: 362 | 258 | TGTSSNIG GYNYVS SEQ ID NO: 397 | DVTKRPS SEQ ID NO: 406 | GSYSNSN FYV SEQ ID NO: 430 |
| A25-1H10 | 116 | AYGMH SEQ ID NO: 295 | GVSYNAGTT AYADSVRG SEQ ID NO: 337 | GRYSDV SEQ ID NO: 362 | 260 | GGSSSDVG GYNYVS SEQ ID NO: 375 | EVSNRPS SEQ ID NO: 419 | GSYSNSN FYV SEQ ID NO: 430 |
| A21-4D08 | 118 | TYGMH SEQ ID NO: 300 | GVSYNSGNK AYADSVKG SEQ ID NO: 348 | GRYSDV SEQ ID NO: 362 | 262 | GGTSSDVG GYNYVS SEQ ID NO: 398 | DVNDRPS SEQ ID NO: 414 | GSYSNNN FYV SEQ ID NO: 429 |

TABLE 17-continued

CDR sequences of heavy-chain and light-chain
variable regions of selected antibodies

| Clone name | heavy-chain variable regions | | | | light-chain variable regions | | | |
|---|---|---|---|---|---|---|---|---|
| | SEQ ID NO: | CDR1 | CDR2 | CDR3 | SEQ ID NO: | CDR1 | CDR2 | CDR3 |
| A24-1D08 | 120 | NYGMH SEQ ID NO: 301 | GISYNSGNT GYADSVRG SEQ ID NO: 349 | GRYSDV SEQ ID NO: 362 | 264 | AGSSSNVV SYNYVS SEQ ID NO: 399 | DVNKRPS SEQ ID NO: 407 | GSYDSNT FYV SEQ ID NO: 431 |
| A24-1A08 | 122 | AYGMH SEQ ID NO: 295 | GISYDAGNT AYADSVRG SEQ ID NO: 350 | GRYSDV SEQ ID NO: 362 | 266 | TGSSSNIG GYNYVS SEQ ID NO: 391 | EVNNRPS SEQ ID NO: 420 | ASYSSNT FYV SEQ ID NO: 426 |
| A21-4A07 | 124 | TYGMH SEQ ID NO: 300 | GVSYNSGSK AYADSVKG SEQ ID NO: 351 | GRYSDV SEQ ID NO: 362 | 268 | AGSSSNIG GYNYVS SEQ ID NO: 383 | DVNDRPS SEQ ID NO: 414 | GSYSNSN FYV SEQ ID NO: 430 |
| A24-1B09 | 126 | RYGMH SEQ ID NO: 304 | GVSYDGGTT AYADSVRG SEQ ID NO: 352 | GRYSDV SEQ ID NO: 362 | 270 | TGTSSNIG SYNYVS SEQ ID NO: 400 | DVNKRPS SEQ ID NO: 407 | GSYDSNT FYV SEQ ID NO: 431 |
| A24-1E07 | 128 | EYGMH SEQ ID NO: 293 | GISYDAGST AYADSVRG SEQ ID NO: 353 | GRYSDV SEQ ID NO: 362 | 272 | AGSSSNVG GYNYVS SEQ ID NO: 395 | EVSNRPS SEQ ID NO: 419 | GSYDSNT FYV SEQ ID NO: 431 |
| A21-4C03 | 36 | | | GRYSDV SEQ ID NO: 362 | 180 | | | |
| H21-3A07 | 130 | NYYMN SEQ ID NO: 305 | TVSYDSGNK YYADSVKG SEQ ID NO: 354 | GSRR DAFDV SEQ ID NO: 369 | 274 | RASQSISN RLA SEQ ID NO: 401 | KASNLES SEQ ID NO: 421 | QQTNSFP LT SEQ ID NO: 435 |
| H21-4D11 | 132 | NYAMN SEQ ID NO: 306 | IISYDSSSK YYADSVKG SEQ ID NO: 355 | GSGKRD AFDV SEQ ID NO: 370 | 276 | QASQGISN RLA SEQ ID NO: 402 | KASNLQS SEQ ID NO: 422 | QQTNSFP LT SEQ ID NO: 435 |
| H21-3C11 | 134 | NYAMH SEQ ID NO: 307 | VVSYDGGNI YYADSVKG SEQ ID NO: 356 | GSGRRD AFDV SEQ ID NO: 371 | 278 | RASQSISN RLA SEQ ID NO: 401 | KASSLQS SEQ ID NO: 423 | QQTNSFP LT SEQ ID NO: 435 |
| H21-3A09 | 136 | NYDIH SEQ ID NO: 308 | VVSYDGSNT YYADSVKG SEQ ID NO: 357 | GSGKRD AFDV SEQ ID NO: 370 | 280 | RASQSISN RLA SEQ ID NO: 401 | KASNLQS SEQ ID NO: 422 | QQTNSFP LT SEQ ID NO: 435 |
| H21-4H04 | 138 | SYAIH SEQ ID NO: 309 | VVSYDGGSK YYADSVKG SEQ ID NO: 358 | GSGRRD AFDV SEQ ID NO: 371 | 282 | QASQSISS RLA SEQ ID NO: 403 | KASSLQS SEQ ID NO: 423 | QQTNSFP LT SEQ ID NO: 435 |
| H23-3D08 | 140 | DYDMH SEQ ID NO: 310 | VISYDGGSK YYADSVKG SEQ ID NO: 359 | GSGQRD AFDV SEQ ID NO: 372 | 284 | QASQGISN RLA SEQ ID NO: 402 | KASNLET SEQ ID NO: 424 | QQTNSFP LT SEQ ID NO: 435 |
| H21-4D09 | 142 | NYYIN SEQ ID NO: 311 | SVSYDGGSI YYADSVKG SEQ ID NO: 360 | GSGRRD AFDV SEQ ID NO: 371 | 286 | QASQGIRN RLA SEQ ID NO: 404 | KASNLQS SEQ ID NO: 422 | QQTNSFP LT SEQ ID NO: 435 |
| H24-1D11 | 144 | SYAMH SEQ ID NO: 312 | VISYDGSNK YYADSVKG SEQ ID NO: 361 | GSGGRD AFDV SEQ ID NO: 373 | 288 | RASQSISS RLA SEQ ID NO: 405 | KASSLET SEQ ID NO: 425 | QQTNSFP LT SEQ ID NO: 435 |

The invention claimed is:

1. A FcRn-specific antibody comprising a heavy-chain variable region and a light-chain variable region selected from among the following heavy-chain and light-chain variable regions (1) to (15), or a FcRn-binding fragment thereof:
   (1) a heavy-chain variable region, which comprises CDR1, CDR2 and CDR3 contained in an amino acid sequence of SEQ ID NO: 54, and a light-chain variable region, which comprises CDR1, CDR2 and CDR3 contained in an amino acid sequence of SEQ ID NO: 198;
   (2) a heavy-chain variable region, which comprises CDR1, CDR2 and CDR3 contained in an amino acid sequence of SEQ ID NO: 48, and a light-chain variable region, which comprises CDR1, CDR2 and CDR3 contained in an amino acid sequence of SEQ ID NO: 192;
   (3) a heavy-chain variable region, which comprises CDR1, CDR2 and CDR3 contained in an amino acid sequence of SEQ ID NO: 56, and a light-chain variable region, which comprises CDR1, CDR2 and CDR3 contained in an amino acid sequence of SEQ ID NO: 200;
   (4) a heavy-chain variable region, which comprises CDR1, CDR2 and CDR3 contained in an amino acid sequence of SEQ ID NO: 66, and a light-chain variable region, which comprises CDR1, CDR2 and CDR3 contained in an amino acid sequence of SEQ ID NO: 210;
   (5) a heavy-chain variable region, which comprises CDR1, CDR2 and CDR3 contained in an amino acid sequence of SEQ ID NO: 38, and a light-chain variable region, which comprises CDR1, CDR2 and CDR3 contained in an amino acid sequence of SEQ ID NO: 182;
   (6) a heavy-chain variable region, which comprises CDR1, CDR2 and CDR3 contained in an amino acid sequence of SEQ ID NO: 40, and a light-chain variable region, which comprises CDR1, CDR2 and CDR3 contained in an amino acid sequence of SEQ ID NO: 184;
   (7) a heavy-chain variable region, which comprises CDR1, CDR2 and CDR3 contained in an amino acid sequence of SEQ ID NO: 42, and a light-chain variable region, which comprises CDR1, CDR2 and CDR3 contained in an amino acid sequence of SEQ ID NO: 186;
   (8) a heavy-chain variable region, which comprises CDR1, CDR2 and CDR3 contained in an amino acid sequence of SEQ ID NO: 36, and a light-chain variable region, which comprises CDR1, CDR2 and CDR3 contained in an amino acid sequence of SEQ ID NO: 180;
   (9) a heavy-chain variable region, which comprises CDR1, CDR2 and CDR3 contained in an amino acid sequence of SEQ ID NO: 46, and a light-chain variable region, which comprises CDR1, CDR2 and CDR3 contained in an amino acid sequence of SEQ ID NO: 190;
   (10) a heavy-chain variable region, which comprises CDR1, CDR2 and CDR3 contained in an amino acid sequence of SEQ ID NO: 18, and a light-chain variable region, which comprises CDR1, CDR2 and CDR3 contained in an amino acid sequence of SEQ ID NO: 162;
   (11) a heavy-chain variable region, which comprises CDR1, CDR2 and CDR3 contained in an amino acid sequence of SEQ ID NO: 64, and a light-chain variable region, which comprises CDR1, CDR2 and CDR3 contained in an amino acid sequence of SEQ ID NO: 208;
   (12) a heavy-chain variable region, which comprises CDR1, CDR2 and CDR3 contained in an amino acid sequence of SEQ ID NO: 58, and a light-chain variable region, which comprises CDR1, CDR2 and CDR3 contained in an amino acid sequence of SEQ ID NO: 202;
   (13) a heavy-chain variable region, which comprises CDR1, CDR2 and CDR3 contained in an amino acid sequence of SEQ ID NO: 78, and a light-chain variable region, which comprises CDR1, CDR2 and CDR3 contained in an amino acid sequence of SEQ ID NO: 222;
   (14) a heavy-chain variable region, which comprises CDR1, CDR2 and CDR3 contained in an amino acid sequence of SEQ ID NO: 52, and a light-chain variable region, which comprises CDR1, CDR2 and CDR3 contained in an amino acid sequence of SEQ ID NO: 196; and
   (15) a heavy-chain variable region, which comprises CDR1, CDR2 and CDR3 contained in an amino acid sequence of SEQ ID NO: 34, and a light-chain variable region, which comprises CDR1, CDR2 and CDR3 contained in an amino acid sequence of SEQ ID NO: 178.

2. The FcRn-specific antibody or FcRn-binding fragment thereof according to claim 1, comprising a heavy-chain variable region and a light-chain variable region selected from among the following heavy-chain and light-chain variable regions (1) to (10):
   (1) a heavy-chain variable region, which comprises CDR1, CDR2 and CDR3 contained in an amino acid sequence of SEQ ID NO: 54, and a light-chain variable region, which comprises CDR1, CDR2 and CDR3 contained in an amino acid sequence of SEQ ID NO: 198;
   (2) a heavy-chain variable region, which comprises CDR1, CDR2 and CDR3 contained in an amino acid sequence of SEQ ID NO: 48, and a light-chain variable region, which comprises CDR1, CDR2 and CDR3 contained in an amino acid sequence of SEQ ID NO: 192;
   (3) a heavy-chain variable region, which comprises CDR1, CDR2 and CDR3 contained in an amino acid sequence of SEQ ID NO: 56, and a light-chain variable region, which comprises CDR1, CDR2 and CDR3 contained in an amino acid sequence of SEQ ID NO: 200;
   (4) a heavy-chain variable region, which comprises CDR1, CDR2 and CDR3 contained in an amino acid sequence of SEQ ID NO: 66, and a light-chain variable region, which comprises CDR1, CDR2 and CDR3 contained in an amino acid sequence of SEQ ID NO: 210;
   (5) a heavy-chain variable region, which comprises CDR1, CDR2 and CDR3 contained in an amino acid sequence of SEQ ID NO: 38, and a light-chain variable region, which comprises CDR1, CDR2 and CDR3 contained in an amino acid sequence of SEQ ID NO: 182;
   (6) a heavy-chain variable region, which comprises CDR1, CDR2 and CDR3 contained in an amino acid sequence of SEQ ID NO: 40, and a light-chain variable region, which comprises CDR1, CDR2 and CDR3 contained in an amino acid sequence of SEQ ID NO: 184;
(7) a heavy-chain variable region, which comprises CDR1, CDR2 and CDR3 contained in an amino acid sequence of SEQ ID NO: 42, and a light-chain variable region, which comprises CDR1, CDR2 and CDR3 contained in an amino acid sequence of SEQ ID NO: 186;
(8) a heavy-chain variable region, which comprises CDR1, CDR2 and CDR3 contained in an amino acid sequence of SEQ ID NO: 36, and a light-chain variable region, which comprises CDR1, CDR2 and CDR3 contained in an amino acid sequence of SEQ ID NO: 180;
(9) a heavy-chain variable region, which comprises CDR1, CDR2 and CDR3 contained in an amino acid sequence of SEQ ID NO: 46, and a light-chain variable region, which comprises CDR1, CDR2 and CDR3 contained in an amino acid sequence of SEQ ID NO: 190; and
(10) a heavy-chain variable region, which comprises CDR1, CDR2 and CDR3 contained in an amino acid sequence of SEQ ID NO: 18, and a light-chain variable region, which comprises CDR1, CDR2 and CDR3 contained in an amino acid sequence of SEQ ID NO: 162.

3. The FcRn-specific antibody or FcRn-binding fragment thereof according to claim 1, wherein the antibody or FcRn-binding fragment thereof is selected from among single-chain antibodies, diabodies, triabodies, tetrabodies, Fab fragments, F(ab')2 fragments, Fd, scFv, minibodies, IgD antibodies, IgE antibodies, IgM antibodies, IgG1 antibodies, IgG2 antibodies, IgG3 antibodies, and IgG4 antibodies.

4. A composition for detecting the presence of FcRn, comprising the FcRn-specific antibody or FcRn-binding fragment thereof according to claim 1.

5. A FcRn-specific antibody or a FcRn-binding fragment thereof, comprising a heavy-chain variable region of SEQ ID NO: 54, and a light-chain variable region of SEQ ID NO: 198.

* * * * *

UNITED STATES PATENT AND TRADEMARK OFFICE
CERTIFICATE OF CORRECTION

PATENT NO. : 10,280,207 B2
APPLICATION NO. : 14/899554
DATED : May 7, 2019
INVENTOR(S) : Kim et al.

Page 1 of 1

It is certified that error appears in the above-identified patent and that said Letters Patent is hereby corrected as shown below:

In the Specification

Column 1, Line 4, insert: -- CROSS-REFERENCE TO RELATED APPLICATIONS
This application is a U.S. national phase under the provisions of 35 U.S.C. § 371 of International Patent Application No. PCT/KR14/05495 filed June 20, 2014, which in turn claims priority of Korean Patent Application No. 10-2013-0071185 filed June 20, 2013. The disclosures of such international patent application and Korean priority patent application are hereby incorporated herein by reference in their respective entireties, for all purposes. --.

Column 35, Line 19: "(COST)" should be -- (COS7) --.

Column 42, Line 21: "FcRn a" should be -- FcRn α --.

Column 69, Line 54: "A11-007" should be -- A11-C07 --.

Column 69, Line 55: "A12-009" should be -- A12-C09 --.

Column 70, Line 14: "A11-007" should be -- A11-C07 --.

Column 70, Line 14: "A12-009" should be -- A12-C09 --.

Column 73, Line 45: "A11-007" should be -- A11-C07 --.

Column 76, Line 38, Table 14 "A11-007" should be -- A11-C07 --.

Signed and Sealed this
Eighteenth Day of June, 2019

Andrei Iancu
*Director of the United States Patent and Trademark Office*